United States Patent
Chung et al.

(10) Patent No.: US 9,850,253 B2
(45) Date of Patent: Dec. 26, 2017

(54) CONDENSED CYCLIC COMPOUND AND ORGANIC LIGHT EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Yeonsook Chung, Seoul (KR); Jhunmo Son, Yongin-si (KR); Yongsik Jung, Yongin-si (KR); Hyeonho Choi, Seoul (KR); Jongsoo Kim, Yongin-si (KR); Myungsun Sim, Seoul (KR); Hosuk Kang, Suwon-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 344 days.

(21) Appl. No.: 14/665,371

(22) Filed: Mar. 23, 2015

(65) Prior Publication Data

US 2015/0333271 A1    Nov. 19, 2015

(30) Foreign Application Priority Data

May 19, 2014   (KR) .................. 10-2014-0059967

(51) Int. Cl.
  *C07D 491/00*   (2006.01)
  *C07D 265/34*   (2006.01)
  (Continued)

(52) U.S. Cl.
  CPC ....... *C07D 491/147* (2013.01); *C07D 491/14* (2013.01); *C07D 495/04* (2013.01);
  (Continued)

(58) Field of Classification Search
  CPC   C07D 491/147; C07D 491/14; C07D 519/00; C07D 495/04; C07D 495/14; C07F 7/0896; H01L 51/5012; H01L 51/0071; H01L 51/0072; H01L 51/0096; H01L 51/0092; H01L 51/5056; H01L 51/5072;
  (Continued)

(56) References Cited

U.S. PATENT DOCUMENTS 9,564,601 B2 *   2/2017   Kim ................... H01L 51/0061

FOREIGN PATENT DOCUMENTS

JP      2010-135467 A   6/2010
JP        5604848 B2    4/2011
(Continued)

*Primary Examiner* — William Cheung
(74) *Attorney, Agent, or Firm* — Cantor Colburn LLP

(57) ABSTRACT

A condensed cyclic compound represented by Formula 1:

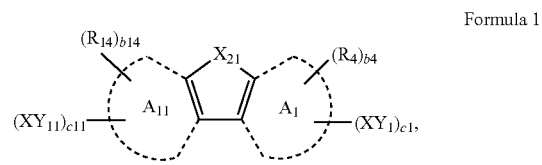

Formula 1 wherein in Formula 1, $A_1$, $A_{11}$, $X_{21}$, $XY_1$, $XY_{11}$, $R_4$, $R_{14}$, b4, b14, c1, and c11 are as described in the specification.

25 Claims, 4 Drawing Sheets

(51) Int. Cl.
| | |
|---|---|
| *C07D 239/00* | (2006.01) |
| *C07D 471/00* | (2006.01) |
| *H01L 29/08* | (2006.01) |
| *C07D 491/147* | (2006.01) |
| *H01L 51/00* | (2006.01) |
| *C07D 495/04* | (2006.01) |
| *H01L 51/50* | (2006.01) |
| *C07D 495/14* | (2006.01) |
| *C07D 519/00* | (2006.01) |
| *C07D 491/14* | (2006.01) |
| *C07F 7/08* | (2006.01) |

(52) U.S. Cl.
CPC ......... *C07D 495/14* (2013.01); *C07D 519/00* (2013.01); *C07F 7/0896* (2013.01); *H01L 51/0071* (2013.01); *H01L 51/0072* (2013.01); *H01L 51/5012* (2013.01); *H01L 51/0081* (2013.01); *H01L 51/0085* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/552* (2013.01)

(58) Field of Classification Search
CPC ............. H01L 51/5088; H01L 51/0081; H01L 51/0085; H01L 51/5016; H01L 2251/552
USPC ........ 257/40; 544/101, 251, 345; 546/83, 87
See application file for complete search history.

(56) References Cited

FOREIGN PATENT DOCUMENTS

| | | |
|---|---|---|
| JP | 2012-191031 A | 10/2012 |
| KR | 10-2012-0092908 A | 8/2012 |
| WO | 2012-090967 A1 | 7/2012 |
| WO | 2012-153780 A1 | 11/2012 |

* cited by examiner

CONDENSED CYCLIC COMPOUND AND ORGANIC LIGHT EMITTING DEVICE INCLUDING THE SAME

CROSS-REFERENCE TO RELATED APPLICATIONS

This application claims priority to Korean Patent Application No. 10-2014-0059967, filed on May 19, 2014, in the Korean Intellectual Property Office, and all the benefits accruing therefrom under 35 U.S.C. §119, the content of which is incorporated herein in its entirety by reference.

BACKGROUND

1. Field

The present disclosure relates to condensed cyclic compounds, and organic light-emitting devices including the same.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

A typical organic light-emitting device may include an anode, a cathode, and an emission layer disposed between the anode and the cathode. The organic light-emitting device may include a hole transport region between the anode and the emission layer, and an electron transport region between the emission layer and the cathode. Holes injected from the anode move to the emission layer via the hole transport region, while electrons injected from the cathode move to the emission layer via the electron transport region. Carriers such as the holes and electrons recombine in the emission layer to generate excitons. When the excitons drop from an excited state to a ground state, light is emitted.

Various types of organic light emitting devices are known. However, there still remains a need in OLEDs having low driving voltage, high efficiency, high brightness, and long lifespan.

SUMMARY

Provided are novel condensed cyclic compounds and organic light-emitting device including the same.

Additional aspects will be set forth in part in the description which follows and, in part, will be apparent from the description, or may be learned by practice of the presented embodiments.

According to an aspect, there is provided a condensed cyclic compound represented by Formula 1:

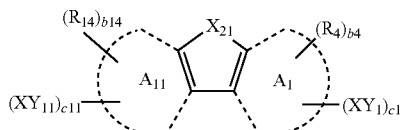

Formula 1

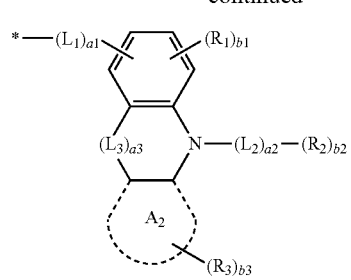

Formula 2-1

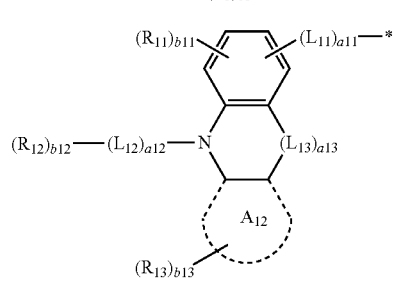

Formula 2-2 wherein, in Formulae 1, 2-1, and 2-2,
$X_{21}$ is selected from O, S, Se, and $Si(R_{21})(R_{22})$;
$XY_1$ is a group represented by Formula 2-1;
$XY_{11}$ is a group represented by Formula 2-2;
c1 and c11 are each independently an integer from 1 to 3;
$A_1$ is a 6-membered ring including at least one N as a ring-member atom;
$A_{11}$ is pyridine;
$A_2$ and $A_{12}$ are each independently selected from a benzene, a naphthalene, a pyridine, a pyrimidine, a pyrazine, a pyridazine, and a triazine;
$L_1$ and $L_{11}$ are each independently selected from
a phenylene group, a naphthylene group, a pyridinylene group, a pyrimidinylene group, a pyrazinylene group, a pyridazinylene group, and a triazinylene group; and
a phenylene group, a naphthylene group, a pyridinylene group, a pyrimidinylene group, a pyrazinylene group, a pyridazinylene group, and a triazinylene group, each substituted with at least one of a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a pyridinyl group, a pyrimidinyl group, a pyrazinyl group, a pyridazinyl group, and a triazinyl group;
$L_2$ and $L_{12}$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;
$L_3$ and $L_{13}$ are each independently selected from O, S, a substituted or unsubstituted $C_1$-$C_5$ alkylene group, and a substituted or unsubstituted $C_2$-$C_5$ alkenylene group;
a1 to a3, and a11 to a13 are each independently an integer selected from 0 to 3;

$R_1$ to $R_4$, $R_{11}$ to $R_{14}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b1, b2, b11, and b12 are each independently 1, 2, or 3;

b3 and b13 are each independently an integer selected from 1 to 6;

b4 is 1 or 2; and b14 is 0, 1, or 2, wherein at least one of substituents of the substituted $C_1$-$C_5$ alkylene group, the substituted $C_2$-$C_5$ alkenylene group, the substituted $C_3$-$C_{10}$ cycloalkylene group, the substituted $C_2$-$C_{10}$ heterocycloalkylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

According to another aspect, an organic light-emitting device includes:

a first electrode;

a second electrode; and an organic layer disposed between the first electrode and the second electrode, wherein the organic layer includes an emission layer and at least one condensed cyclic compounds represented by Formula 1.

The at least one condensed cyclic compounds represented by Formula 1 may be included in the emission layer.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
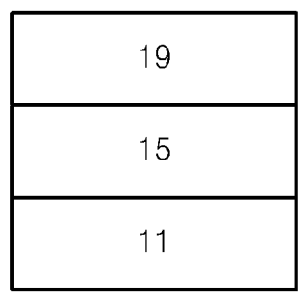
FIG. 1 is a schematic view of an organic light-emitting device according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an embodiment of the present disclosure, there is provided a condensed cyclic compound represented by Formula 1:

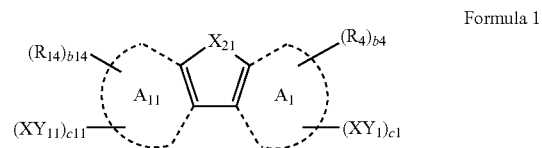

Formula 1

In Formula 1, $X_{21}$ may be selected from O, S, Se, and $Si(R_{21})(R_{22})$, wherein $R_{21}$ and $R_{22}$ may be the same as those defined herein.

In Formula 1, $XY_1$ may be a group represented by Formula 2-1;

$XY_{11}$ may be a group represented by Formula 2-2; and c1 and c11 may be each independently an integer from 1 to 3.

When c1 is 2 or more, two or more groups $XY_1$ may be identical or different. When c11 is 2 or more, two or more groups $XY_{11}$ may be identical or different.

Formula 2-1

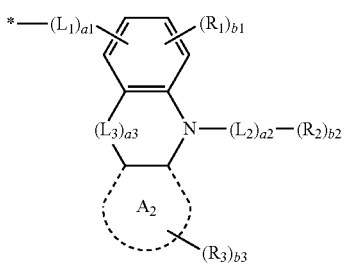

Formula 2-2

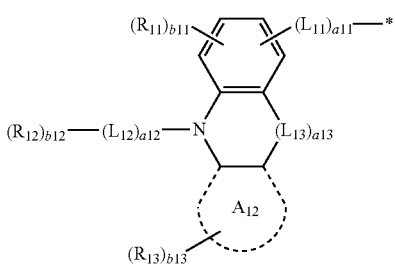

Substituents in Formulae 2-1 and 2-2 may be the same as those defined herein.

In Formulae 1, 2-1, and 2-2, $A_1$, $A_{11}$, $A_2$, and $A_{12}$ are rings condensed to adjacent rings sharing carbon with the adjacent ring.

In Formula 1, $A_1$ may be a 6-membered ring including at least one nitrogen (N) as a ring-member atom;

$A_{11}$ may be a pyridine; and $A_2$ and $A_{12}$ may be each independently selected from a benzene, a naphthalene, a pyridine, a pyrimidine, a pyrazine, a pyridazine, and a triazine.

In some embodiments, in Formula 1, $A_1$ may be selected from a pyridine, a pyrimidine, a pyrazine, a pyridazine, and a triazine. For example, $A_1$ in Formula 1 may be a pyridine. However, embodiments of the present disclosure are not limited thereto.

In some embodiments, in Formula 1, $A_2$ and $A_{12}$ may be each independently a benzene, a naphthalene, or a pyridine. In some other embodiments, $A_2$ and $A_{12}$ in Formula 1 may be both a benzene.

In some embodiments, the condensed cyclic compound of Formula 1 may be represented by one of Formulae 1(1) to 1(28):

Formula 1(1)

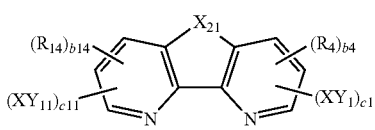

Formula 1(2)

Formula 1(3)

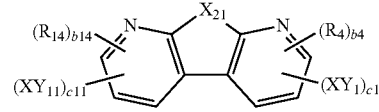

Formula 1(4)

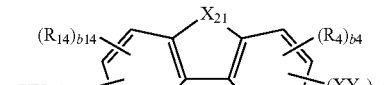

Formula 1(5)

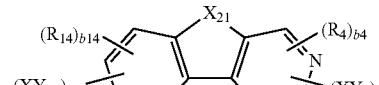

Formula 1(6)

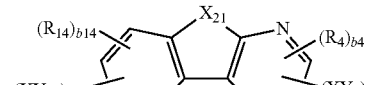

Formula 1(7)

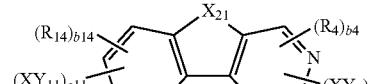

Formula 1(8)

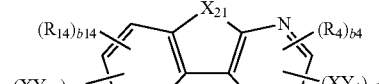

Formula 1(9)

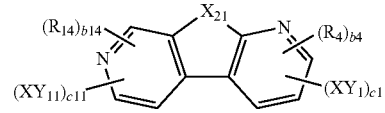

Formula 1(10)

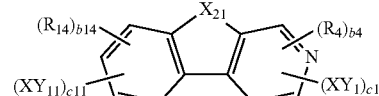

Formula 1(11)

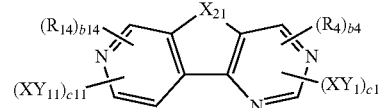

Formula 1(12)

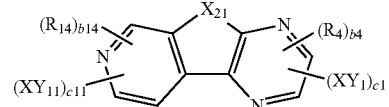

Formula 1(13)

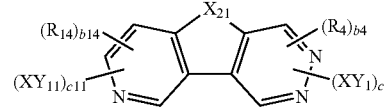

Formula 1(14)

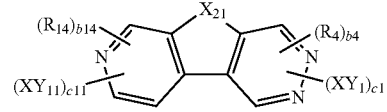

Formula 1(15)

-continued

Formula 1(16)
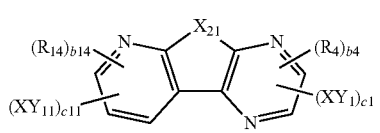

Formula 1(17)
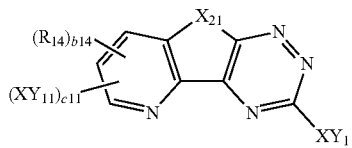

Formula 1(18)
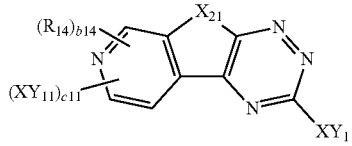

Formula 1(19)
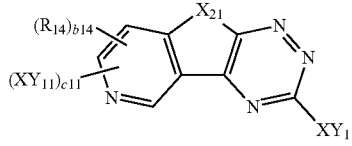

Formula 1(20)
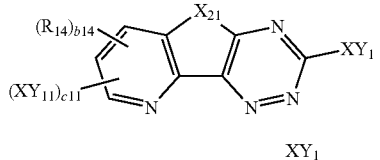

Formula 1(21)
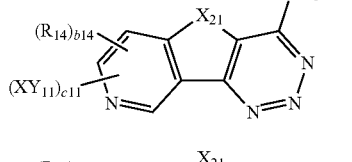

Formula 1(22)
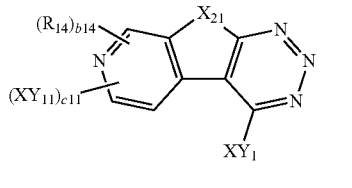

Formula 1(23)
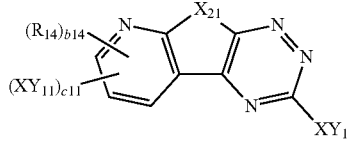

Formula 1(24)
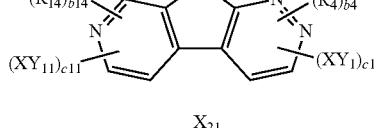

Formula 1(25)
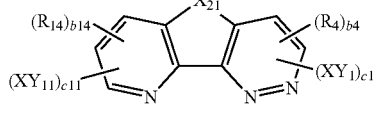

Formula 1(26)
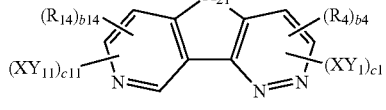

-continued

Formula 1(27)
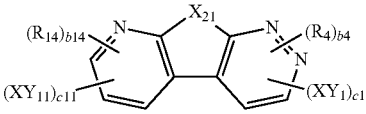

Formula 1(28)
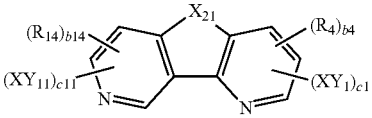

In Formulae 1(1) to 1(28), $X_{21}$, $XY_1$, $XY_{11}$, $L_1$ to $L_3$, $L_{11}$ to $L_{13}$, a1 to a3, a11 to a13, $R_1$ to $R_4$, $R_{11}$ to $R_{14}$, b1 to b4, and b11 to b14 are the same as defined herein below.

In some embodiments, the condensed cyclic compound of Formula 1 may be represented by one of Formulae 1-1 to 1-10:

Formula 1-1
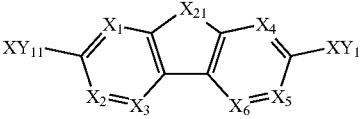

Formula 1-2
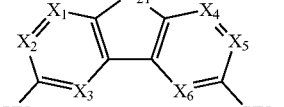

Formula 1-3
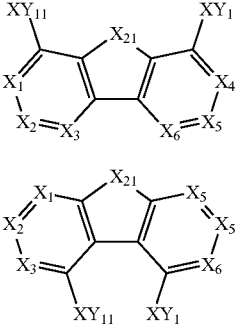

Formula 1-4
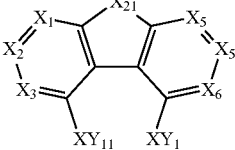

Formula 1-5
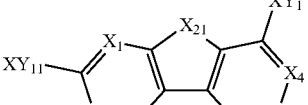

Formula 1-6
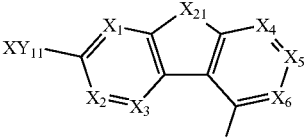

Formula 1-7
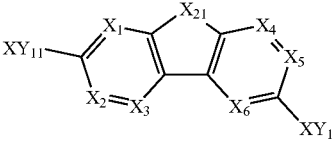

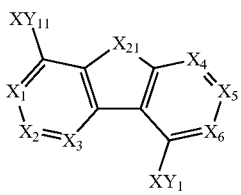

Formula 1-8

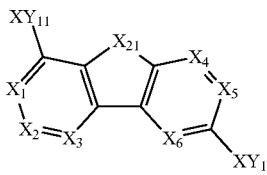

Formula 1-9

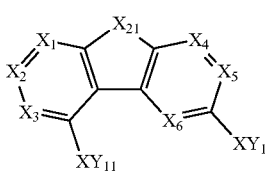

Formula 1-10

In Formulae 1-1 to 1-10, $X_{21}$, $XY_1$, and $XY_{11}$ may be the same as defined herein;

$X_1$ may be N or $C(R_{14a})$;
$X_2$ may be N or $C(R_{14b})$;
$X_3$ may be N or $C(R_{14c})$;
$X_4$ may be N or $C(R_{4a})$;
$X_5$ may be N or $C(R_{4b})$;
$X_6$ may be N or $C(R_{4c})$;
one of $X_1$ to $X_3$ may be N; and
at least one of $X_4$ to $X_6$ may be N;
$R_{14a}$ to $R_{14c}$ may be the same as defined for $R_{14}$ herein; and
$R_{4a}$ to $R_{4c}$ may be the same as defined for $R_4$ herein.

In Formula 1, $L_1$ and $L_{11}$ may be each independently selected from a phenylene group, a naphthylene group, a pyridinylene group, a pyrimidinylene group, a pyrazinylene group, a pyridazinylene group, and a triazinylene group; and a phenylene group, a naphthylene group, a pyridinylene group, a pyrimidinylene group, a pyrazinylene group, a pyridazinylene group, and a triazinylene group, each substituted with at least one of a hydrogen, a deuterium, a fluoro group (—F), a chloro group (—Cl), a bromo group (—Br), an iodo group (—I), a hydroxyl group, a cyano group, a nitro group, an amino group, an amidino group, a hydrazine group, a hydrazine group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a pyridinyl group, a pyrimidinyl group, a pyrazinyl group, a pyridazinyl group, and a triazinyl group.

For example, in Formula 1, $L_1$ and $L_{11}$ may be each independently selected from a phenylene group and a naphthylene group; and a phenylene group and a naphthylene group, each substituted with at least one of a hydrogen, a deuterium, —F, —Cl, —Br, —I, a hydroxyl group, a cyano group, a nitro group, an amino group, an amidino group, a hydrazine group, a hydrazine group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group. However, embodiments of the present disclosure are not limited thereto.

In Formula 1, a1, which indicates the number of groups $L_1$, may be an integer selected from 0 to 3. For example, a1 may be 0 or 1. When a1 is 0, -$(L_1)_{a1}$- may be a single bond. When a1 is 2 or more, a1 number of groups $L_1$ may be identical or different. In Formula 1, a11 may be understood based on the description of a1 and the structure of Formula 1.

In some embodiments, in Formula 1, a1 and a11 may be 0. That is, -$(L_1)_{a1}$- and -$(L_{11})_{a11}$- may be single bonds.

In Formula 1, $L_2$ and $L_{12}$ may be each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, in Formula 1, $L_2$ and $L_{12}$ may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, a $C_2$-$C_{60}$ heteroaryl group, a monovalent non-aromatic condensed polycyclic group, and a monovalent non-aromatic condensed heteropolycyclic group.

In some other embodiments, in Formula 1, $L_2$ and $L_{12}$ may be each independently selected from a phenylene group, a naphthylene group, a phenalenylene group, a phenanthrylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group; and a phenylene group, a naphthylene group, a phenalenylene group, a phenanthrylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group. However, embodiments of the present disclosure are not limited thereto.

In Formula 1, a2, which indicates the number of groups $L_2$, may be an integer selected from 0 to 3. For example, a2 may be 0, 1, or 2. When a2 is 0, -$(L_2)_{a2}$- may be a single bond. When a2 is 2 or more, a2 number of groups $L_2$ may be identical or different. In Formula 1, a12 may be understood based on the description of a2 and the structure of Formula 1.

In some embodiments, in Formula 1, a2 and a12 may be each independently 0 or 1.

In Formula 1, $L_3$ and $L_{13}$ may be each independently selected from O, S, a substituted or unsubstituted $C_1$-$C_5$ alkylene group, and a substituted or unsubstituted $C_2$-$C_5$ alkenylene group.

In some embodiments, in Formula 1, $L_3$ and $L_{13}$ may be each independently selected from O, S, a $C_1$-$C_5$ alkylene group, and a $C_2$-$C_5$ alkenylene group; and a $C_1$-$C_5$ alkylene group and a $C_2$-$C_5$ alkenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

In Formula 1, a3, which indicates the number of groups $L_3$, may be an integer selected from 0 to 3. When a3 is 0, -$(L_3)_{a3}$- may be a single bond. When a3 is 2 or more, a3 number of groups $L_3$ may be identical or different. In Formula 1, a13 may be understood based on the description of a3 and the structure of Formula 1.

In some embodiments, in Formula 1, a3 and a13 may be each independently 0 or 1.

In some embodiments, in Formula 1, -$(L_3)_{a3}$- and -$(L_{13})_{a13}$- may be each independently selected from a single bond, —O—, —S—, a $C_1$-$C_2$ alkylene group, and a $C_2$-$C_3$ alkenylene group; and a $C_1$-$C_2$ alkylene group and a $C_2$-$C_3$ alkenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{20}$ alkyl group. However, embodiments of the present disclosure are not limited thereto.

In Formula 1, $R_1$ to $R_4$, $R_{11}$ to $R_{14}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$).

In some embodiments, in Formula 1, $R_2$ and $R_{12}$ may be each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 1, $R_1$ to $R_4$, $R_{11}$ to $R_{14}$, and $R_{21}$ to $R_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a $C_1$-$C_{20}$ alkyl group, a $C_2$-$C_{20}$ alkenyl group, a $C_2$-$C_{20}$ alkynyl group, and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzofuranyl group, a dibenzothiophenyl group, a benzocarbazolyl group, a dibenzocarbazolyl group, an imidazopyrimidinyl group, and an imidazopyridinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{33}$)($Q_{34}$)($Q_{35}$); and —Si($Q_3$)($Q_4$)($Q_5$), wherein $Q_3$ to $Q_5$, and $Q_{33}$ to $Q_{35}$ are each independently a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group. However, embodiments of the present disclosure are not limited thereto.

In some other embodiments, in Formula 1, $R_2$ and $R_{12}$ may be each independently selected from groups represented by Formulae 5-1 to 5-36; and $R_1$, $R_3$, $R_4$, $R_{11}$, $R_{13}$, $R_{14}$, $R_{21}$, and $R_{22}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and the groups represented by Formulae 5-1 to 5-36. However, embodiments are not limited thereto.

Formula 5-1

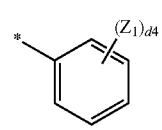

-continued
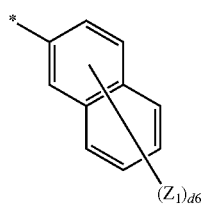
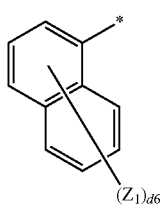
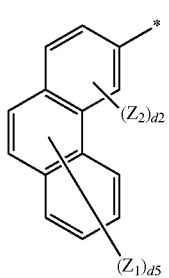
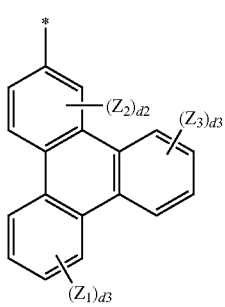
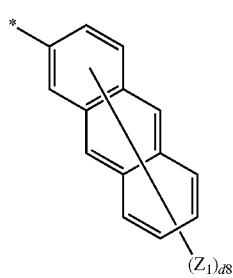
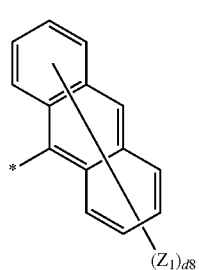
-continued
Formula 5-2
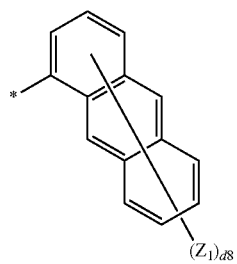
Formula 5-3
Formula 5-4
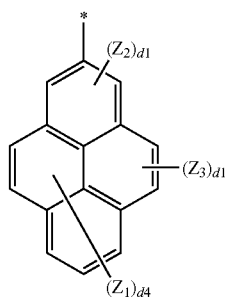
Formula 5-5
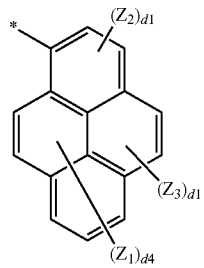
Formula 5-6
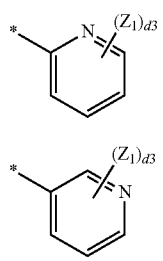
Formula 5-7
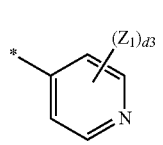
Formula 5-8
Formula 5-9
Formula 5-10
Formula 5-11
Formula 5-12
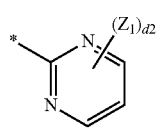
Formula 5-13
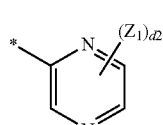
Formula 5-14
Formula 5-15
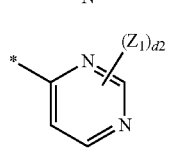
Formula 5-16

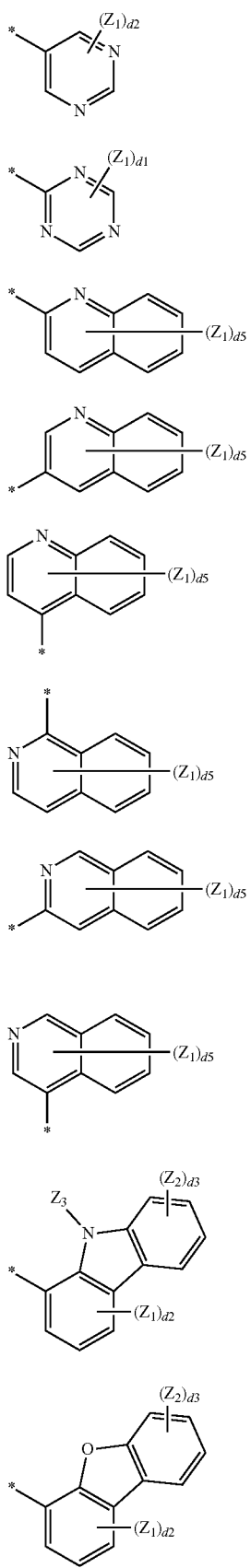
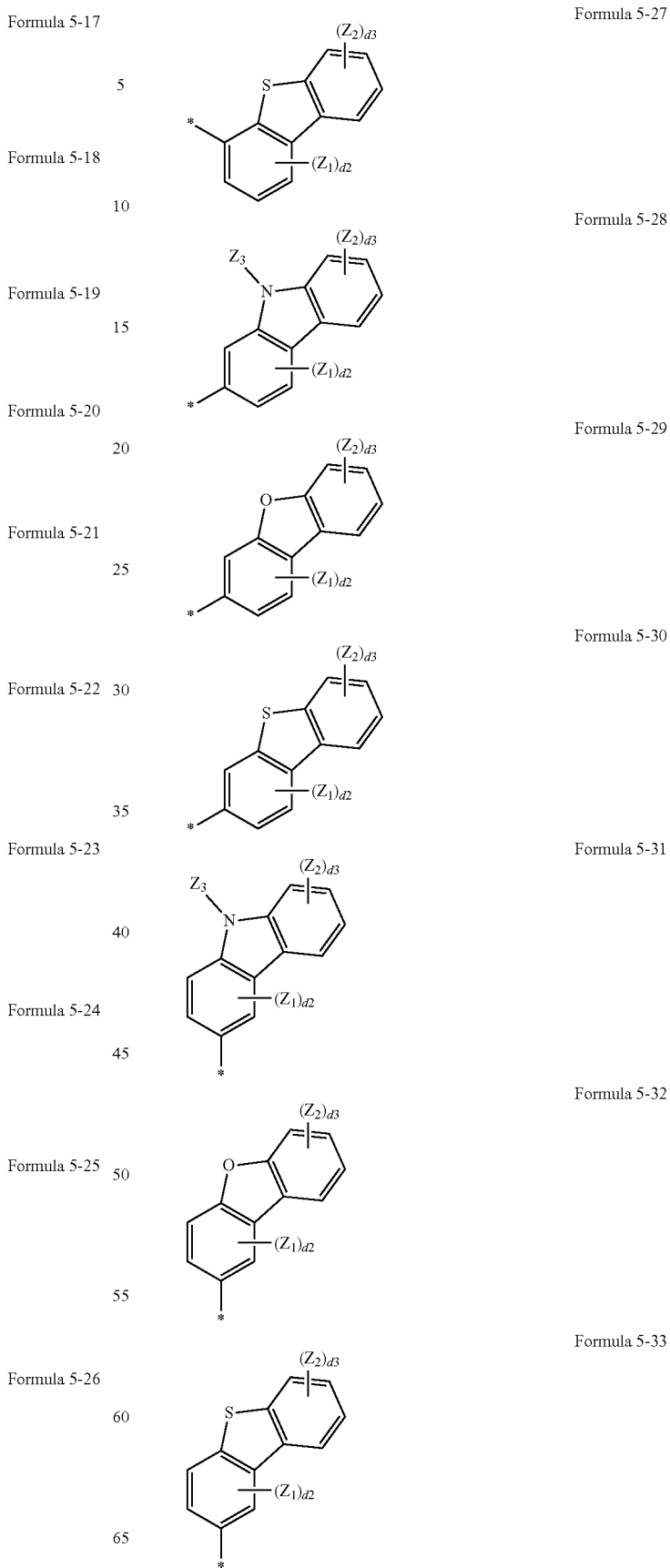

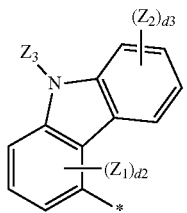

Formula 5-34

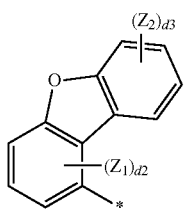

Formula 5-35

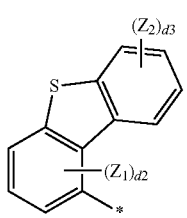

Formula 5-36

In Formulae 5-1 to 5-36, $Z_1$ to $Z_3$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 may be 1 or 2;
d2 may be an integer selected from 1 to 3;
d3 may be an integer selected from 1 to 4;
d4 may be an integer selected from 1 to 8;
d5 may be an integer selected from 1 to 6;
d6 may be an integer selected from 1 to 4;
d7 may be an integer selected from 1 to 8;
d8 may be an integer selected from 1 to 9; and
* indicates a binding site to an adjacent atom.

In some other embodiments, in Formula 1, $R_2$ and $R_{12}$ may be each independently selected from a phenyl group, a naphthyl group, an anthracenyl group, a pyrenyl group, a phenanthrenyl group, and a triphenylenyl group, and a phenyl group, a naphthyl group, an anthracenyl group, a pyrenyl group, a phenanthrenyl group, and a triphenylenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group; and $R_1$, $R_3$, $R_4$, $R_{11}$, $R_{13}$, $R_{14}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group. However, embodiments of the present disclosure are not limited thereto.

For example, in Formula 1, $R_1$, $R_3$, $R_4$, $R_{11}$, $R_{13}$, and $R_{14}$ may be hydrogen.

In Formula 1, b1, b2, b11, and b12, which indicate the number of groups $R_1$, the number of groups $R_2$, the number of groups $R_{11}$, and the number of groups $R_{12}$, respectively, may be each independently 1, 2, or 3. In Formula 1, b3 and b13, which indicate the number of groups $R_3$, and the number of groups $R_{13}$, respectively, may be each independently an integer selected from 1 to 6. In Formula 1, b4, which indicates the number of groups $R_4$, may be 1 or 2, and b14, which indicates the number of groups $R_{14}$, may be 0, 1, or 2. When b1 is 2 or more, b1 number of groups $R_1$ may be identical or different, which may also apply to b2 to b4, and b11 to b14.

In Formula 1, $XY_1$ may be represented by one of Formulae 2-1(1) to 2-1(6), and $XY_{11}$ may be represented by one of Formulae 2-2(1) to 2-2(6). However, embodiments of the present disclosure are not limited thereto.

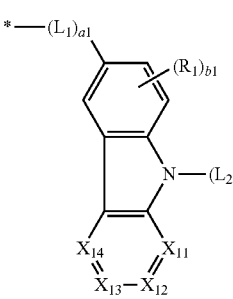

Formula 2-1(1)

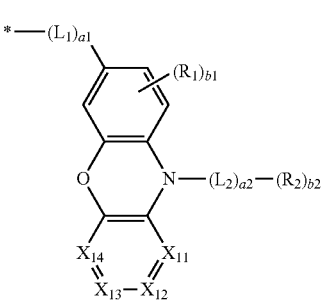

Formula 2-1(2)

Formula 2-1(3)
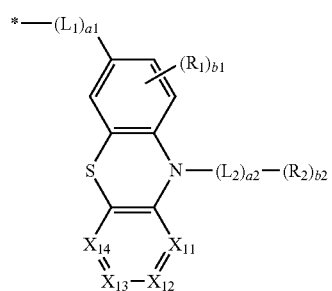
Formula 2-1(4)
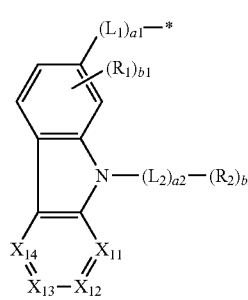
Formula 2-1(5)
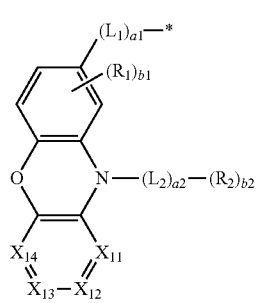
Formula 2-1(6)
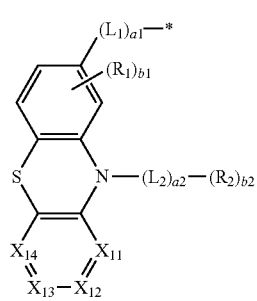
Formula 2-2(1)
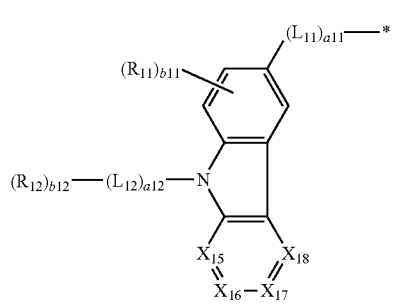
Formula 2-2(2)
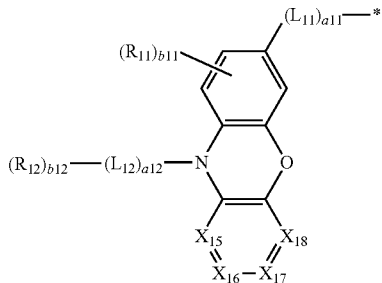
Formula 2-2(3)
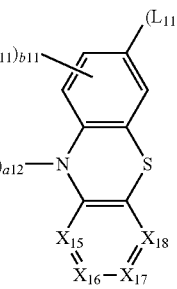
Formula 2-2(4)
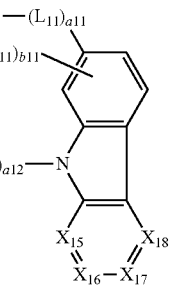
Formula 2-2(5)
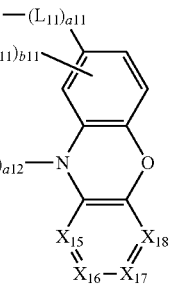
Formula 2-2(6)
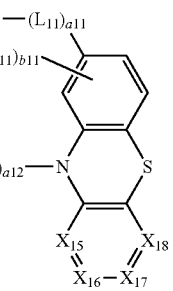
In Formulae 2-1(1) to 2-1(6) and Formulae 2-2(1) to 2-2(6),
$L_1$, $L_2$, $L_{11}$, $L_{12}$, a1, a2, a11, a12, $R_1$, $R_2$, $R_{11}$, $R_{12}$, b1, b2, b11, and b12 may be the same as defined herein,
$X_{11}$ may be N or $C(R_{3a})$,
$X_{12}$ may be N or $C(R_{3b})$,
$X_{13}$ may be N or $C(R_{3c})$, $X_{14}$ may be N or $C(R_{3d})$,
$X_{15}$ may be N or $C(R_{13a})$,
$X_{16}$ may be N or $C(R_{13b})$,
$X_{17}$ may be N or $C(R_{13c})$, and
$X_{18}$ may be N or $C(R_{13d})$,
$R_{3a}$ to $R_{3d}$ may be the same as defined for $R_3$ herein, and $R_{13a}$ to $R1_{3d}$ may be the same as defined for $R_{13}$ herein.

In some embodiments, in Formulae 2-1(1) to 2-1(6) and Formulae 2-2(1) to 2-2(6), $L_2$ and $L_{12}$ may be each independently selected from a phenylene group, a naphthylene group, a phenalenylene group, a phenanthrylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, and a phenylene group, a naphthylene group, a phenalenylene group, a phenanthrylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

a2 and a12 may be each independently 0 or 1; and
$R_2$ and $R_{12}$ may be each independently selected from
a phenyl group, a naphthyl group, an anthracenyl group, a pyrenyl group, a phenanthrenyl group, and a triphenylenyl group, and a phenyl group, a naphthyl group, an anthracenyl group, a pyrenyl group, a phenanthrenyl group, and a triphenylenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group; and $R_1$, $R_3$, to $R_{3d}$, $R_{11}$, and $R_{13a}$ to $R_{13d}$ may be each independently selected from a hydrogen, a deuterium, —F, —Cl, —Br, —I, a hydroxyl group, a cyano group, a nitro group, an amino group, an amidino group, a hydrazine group, a hydrazine group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group.

In some embodiments, the condensed cyclic compound of Formula 1 may be represented by one of Formulae 1(1) to 1(18), wherein, in Formulae 1(1) to 1(18), $XY_1$ may be represented by one of Formulae 2-1(1) to 2-1(6) and $XY_{11}$ may be represented by one of Formulae 2-2(1) to 2-2(6), $R_1$, $R_{3a}$ to $R_{3d}$, $R_4$, $R_{11}$, $R_{13a}$ to $R_{13d}$, $R_{14}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazine group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group;

b4 and b14 may be each independently 0, 1, or 2;

c1 and c11 may be each independently 1 or 2, for example, may be 1;

a1, a11, a2, and a12 may be each independently 0 or 1;

b1 and b11 may be each independently, 0, 1, or 2; and b2 and b12 may be 1.

In some other embodiments, the condensed cyclic compound of Formula 1 may be represented by one of Formulae 1-1 to 1-10, wherein, in Formulae 1-1 to 1-10, $XY_1$ may be represented by one of Formulae 2-1(1) to 2-1(6) and $XY_{11}$ may be represented by one of Formulae 2-2(1) to 2-2(6), $R_1$, $R_{3a}$ to $R_{3d}$, $R_{4a}$ to $R_{4c}$, $R_{11}$, $R_{13a}$ to $R_{13d}$, $R_{14a}$ to $R_{14c}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazine group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group;

a1, a11, a2, and a12 may be each independently 0 or 1;

b1 and b11 may be each independently, 0, 1, or 2; and b2 and b12 may be 1.

In some other embodiments, in Formula 1, i) $XY_1$=$XY_{11}$, or ii) $XY_1 \ne XY_{11}$.

In some embodiments, the condensed cyclic compound of Formula 1 may be one of Compounds 1 to 312. However, embodiments of the present disclosure are not limited thereto.

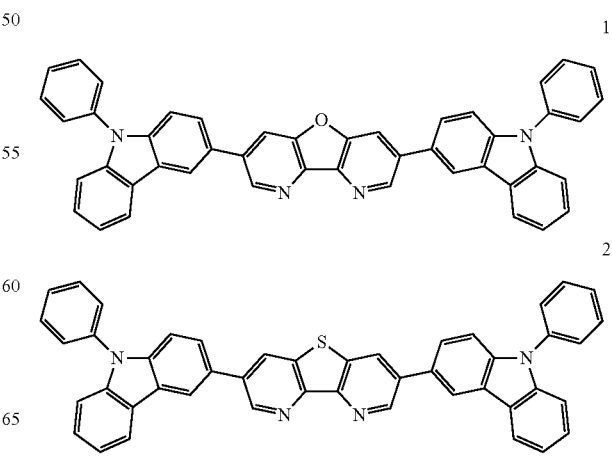

-continued
3
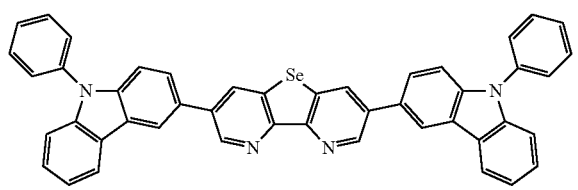
4
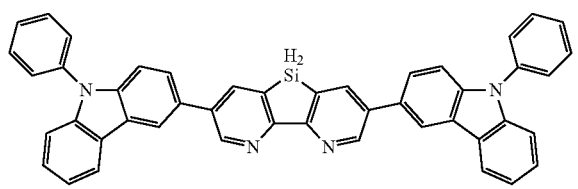
5
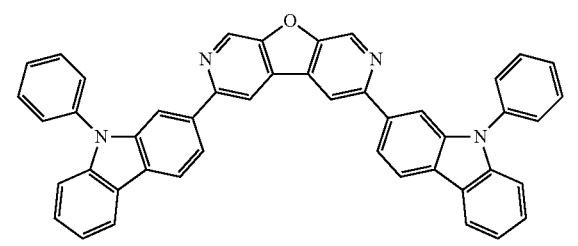
6
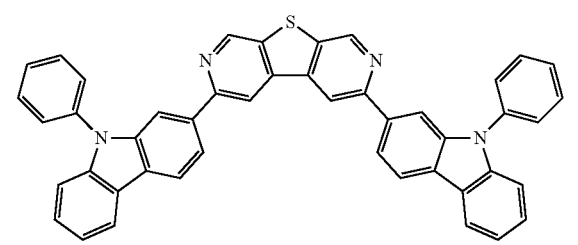
7
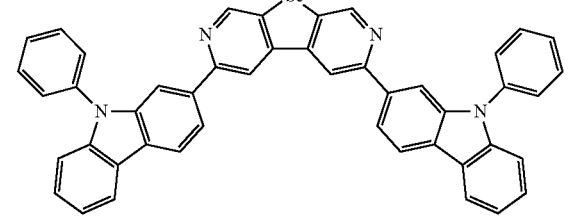
8
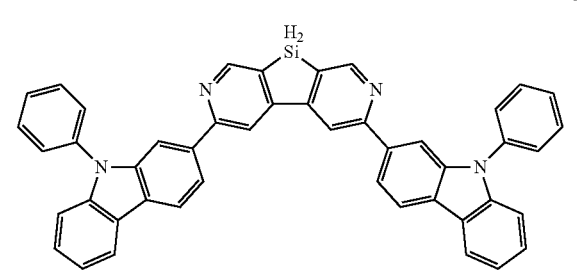
-continued
9
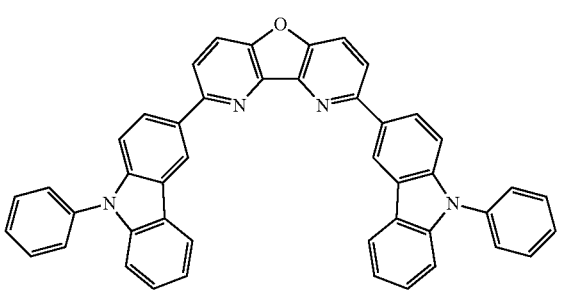
10
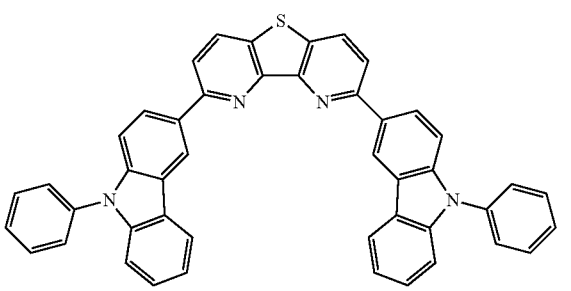
11
12
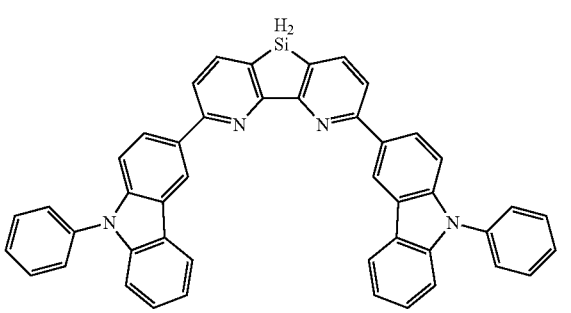
13
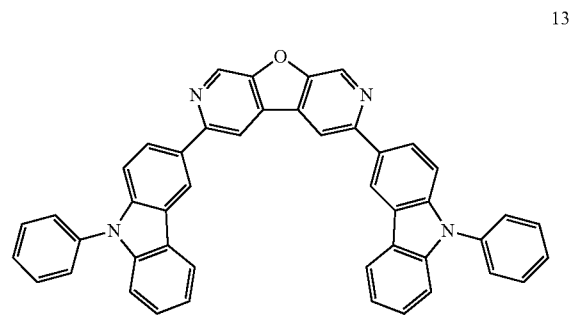

14
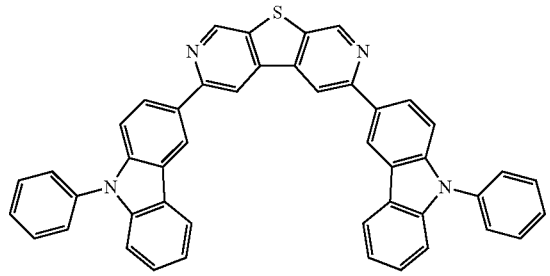
15
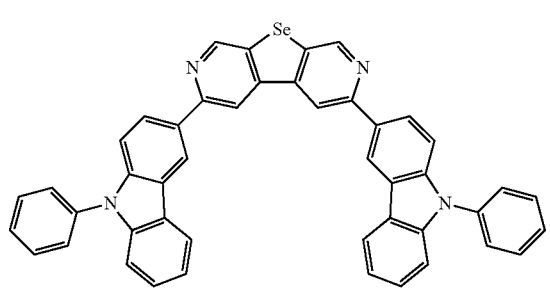
16
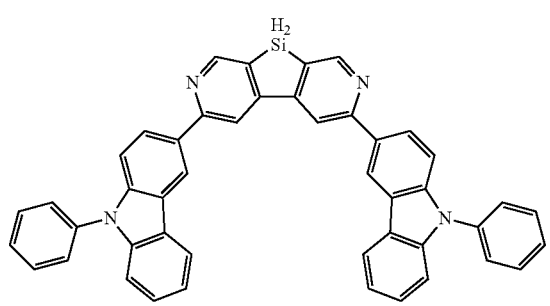
17
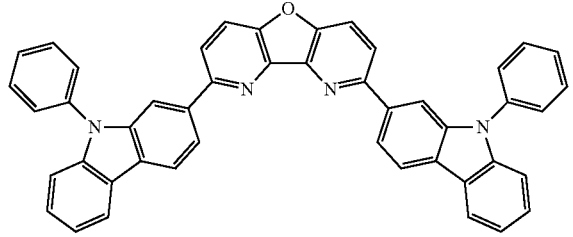
18
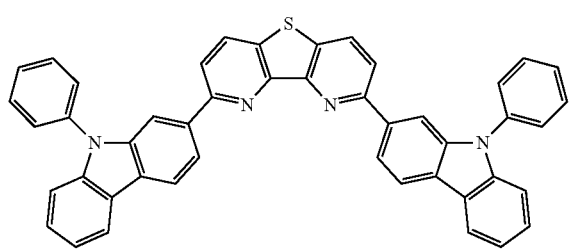
19
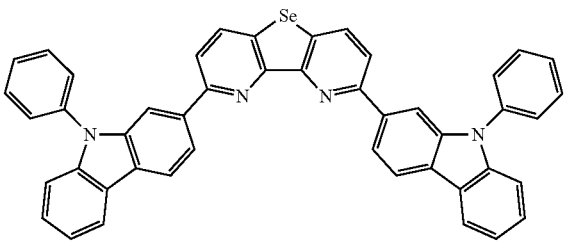
20
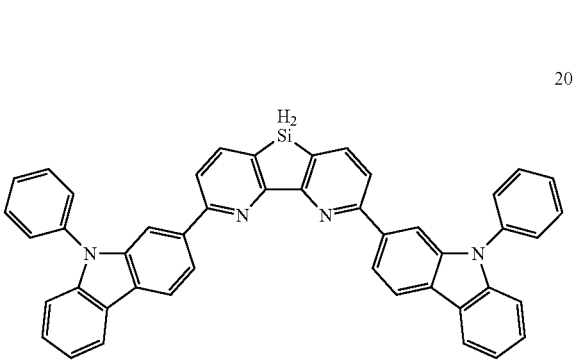
21
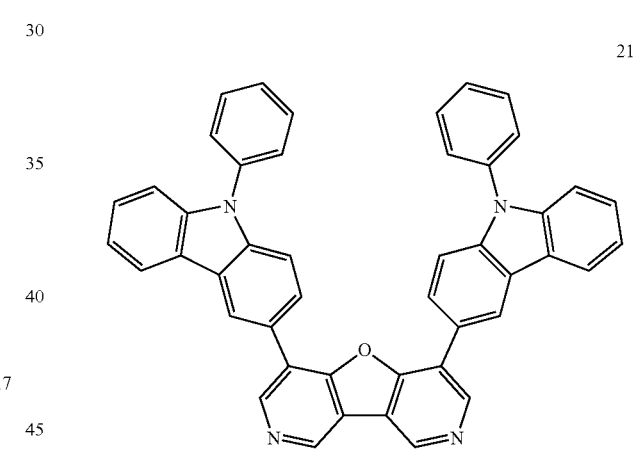
22
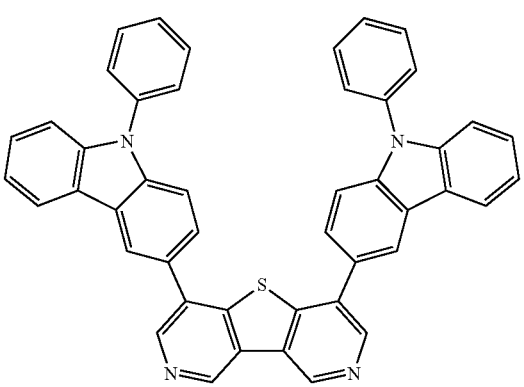

23
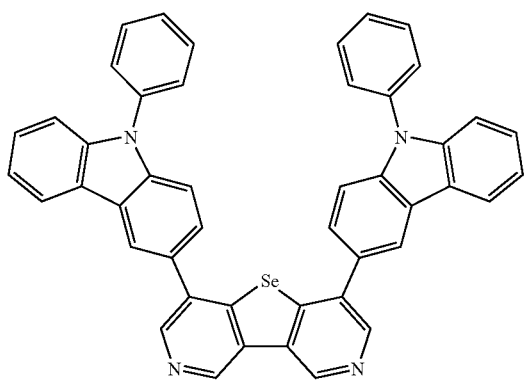
24
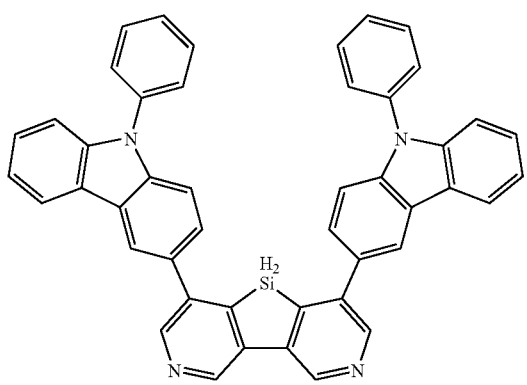
25
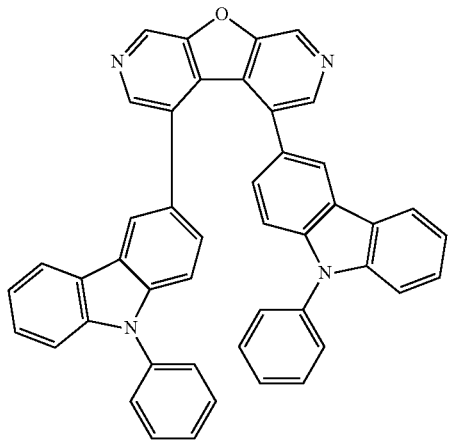
26
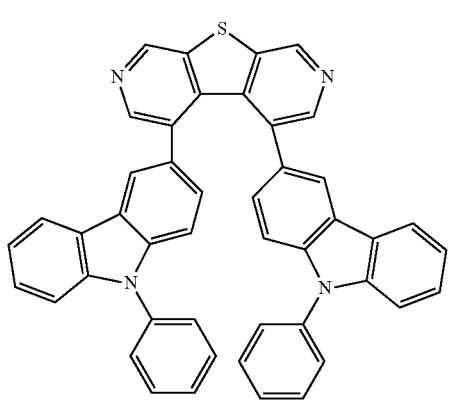
27
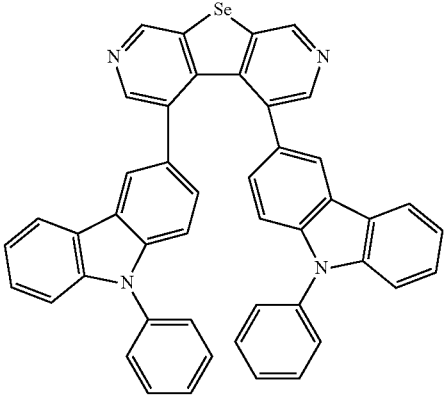
28
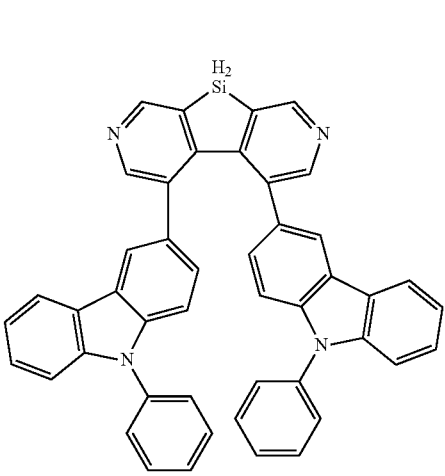
29
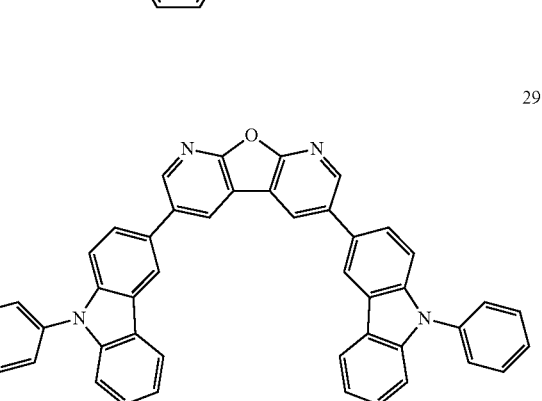
30
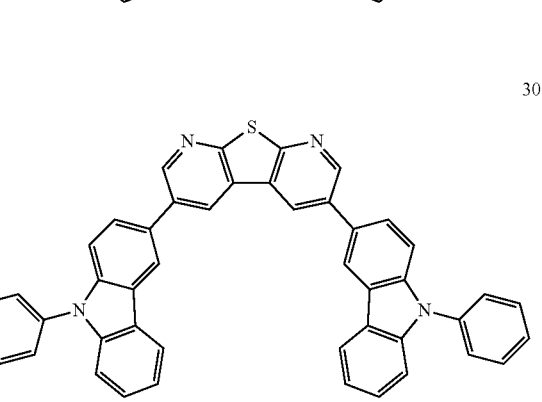

31
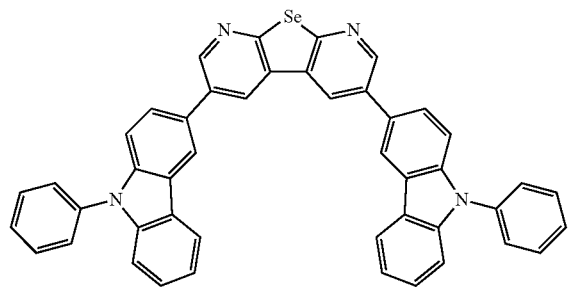
32
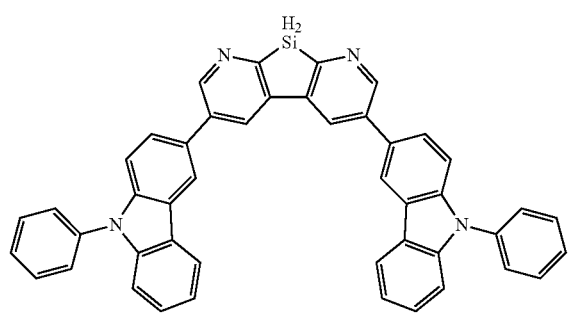
33
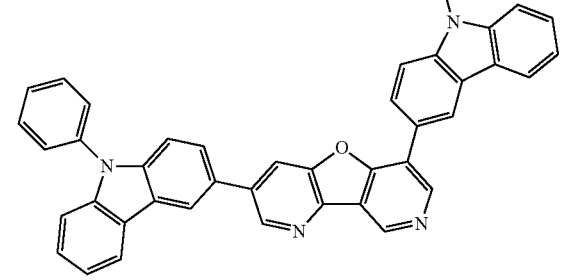
34
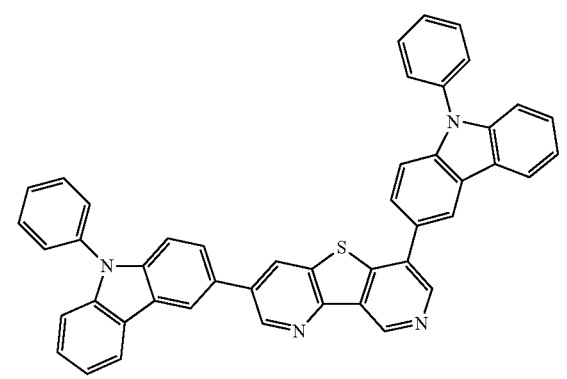
35
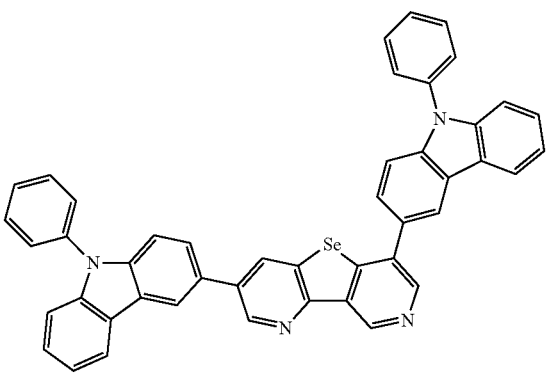
36
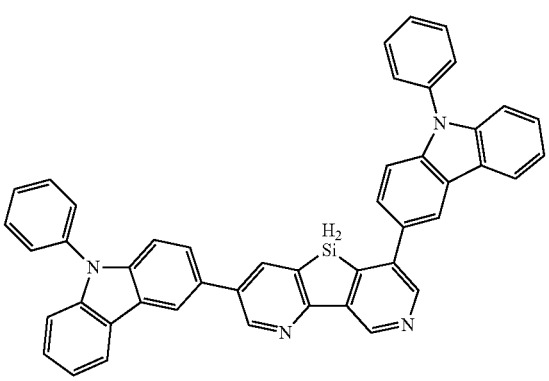
37

38
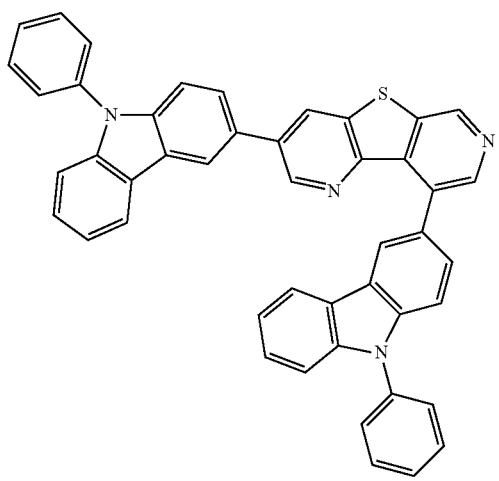
39
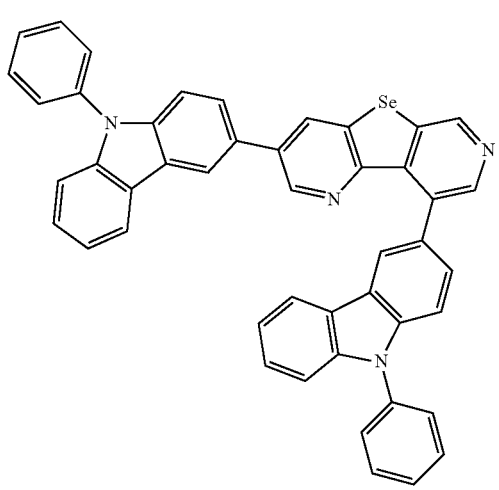
40
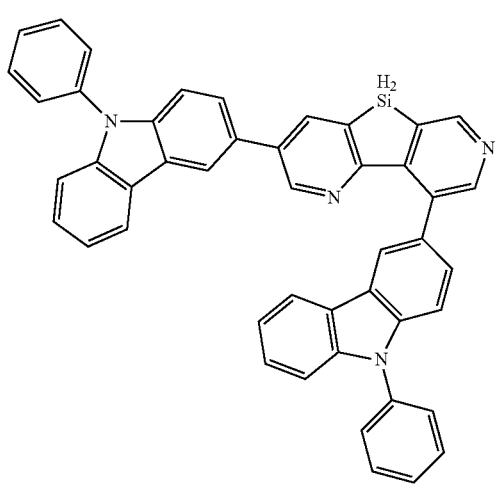
41
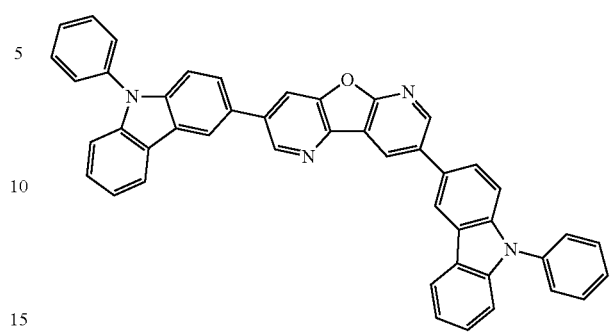
42
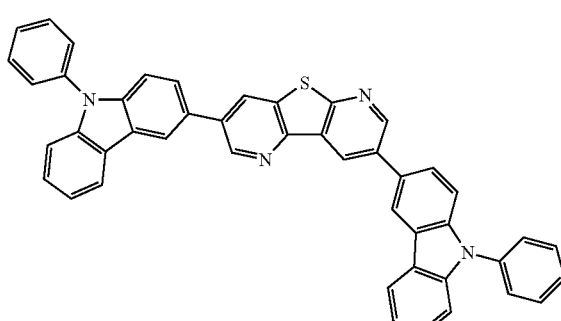
43
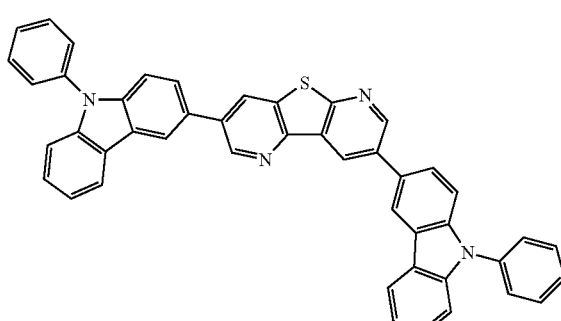
44
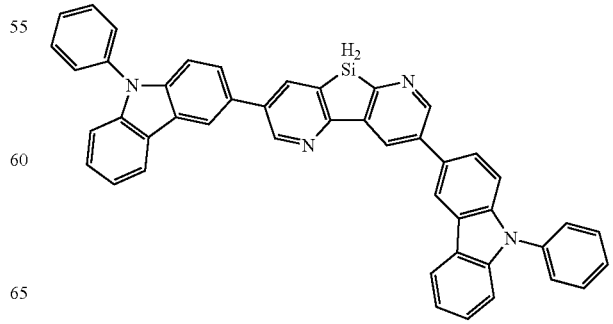

-continued
45
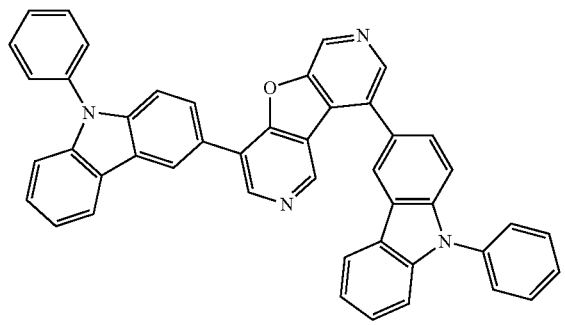
46
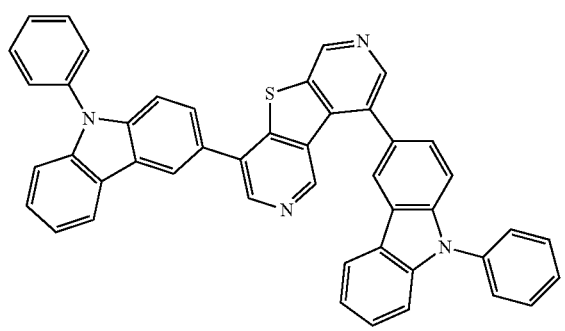
47
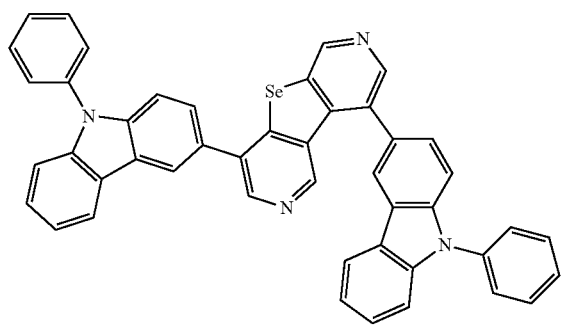
48
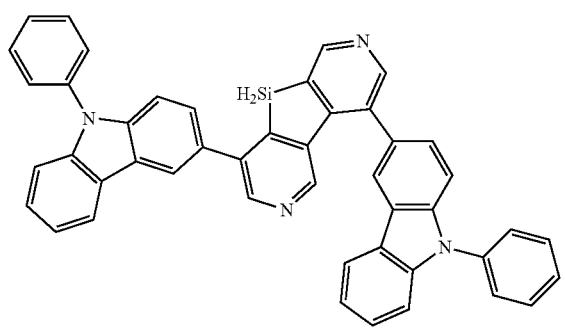
-continued
49
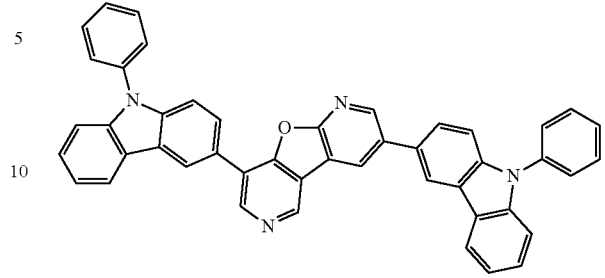
50
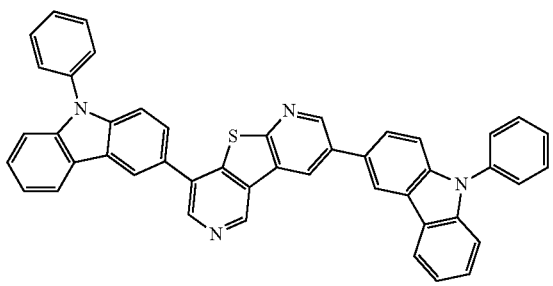
51
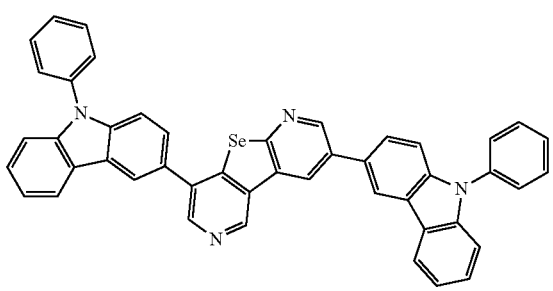
52
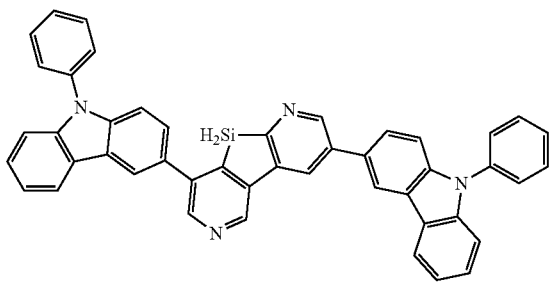
53
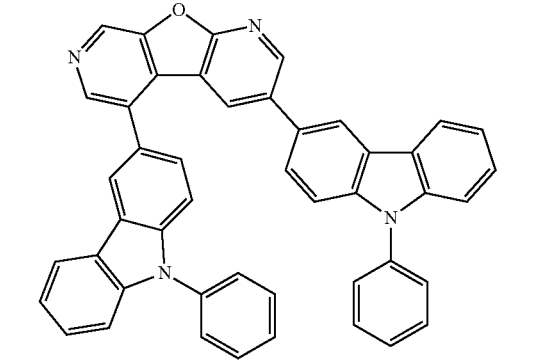

54
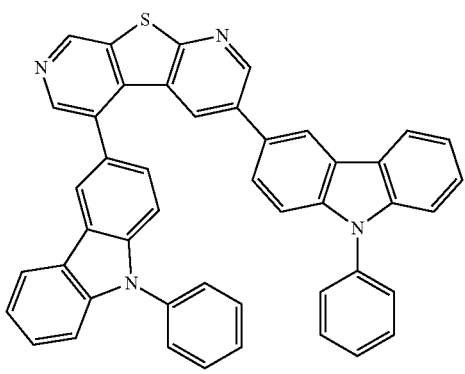
55
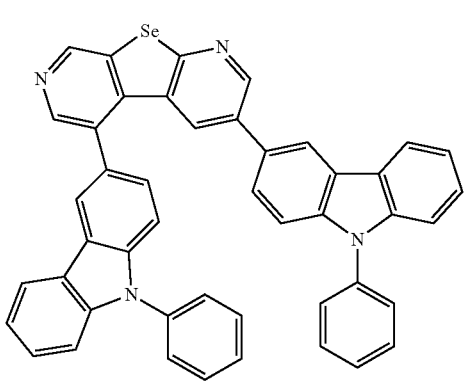
56
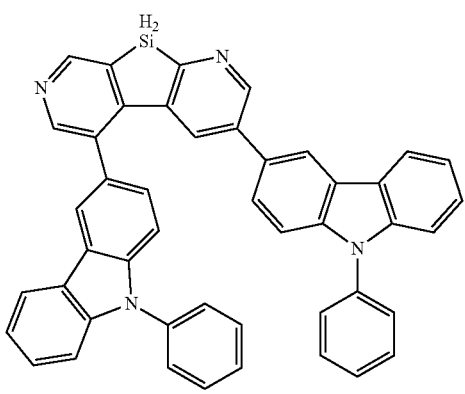
57
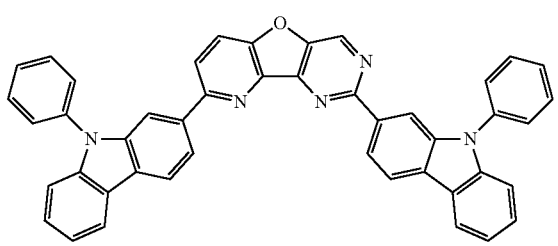
58
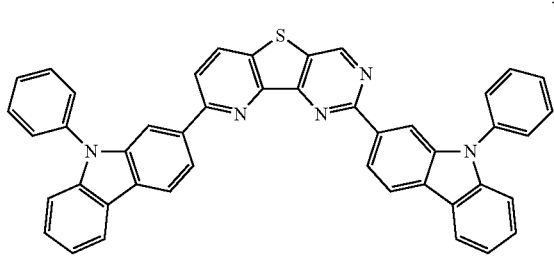
59
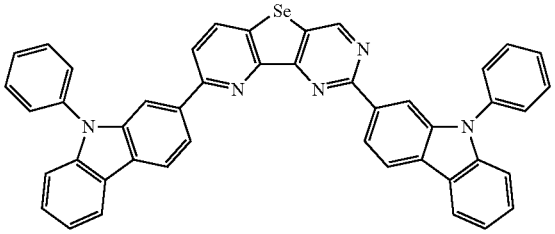
60
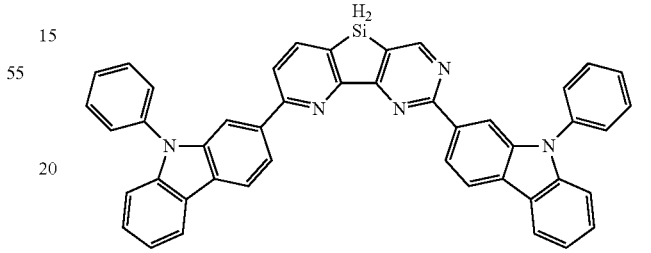
61
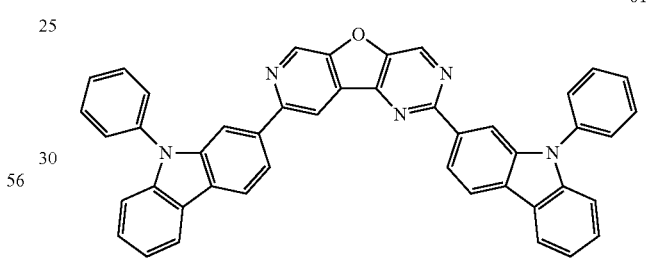
62
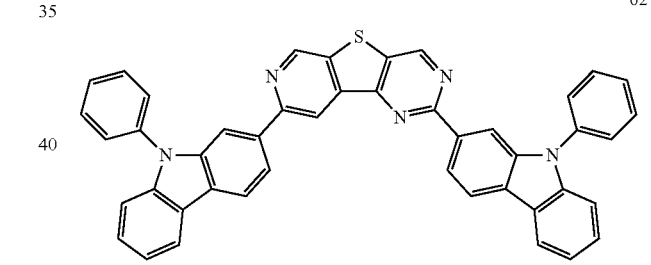
63
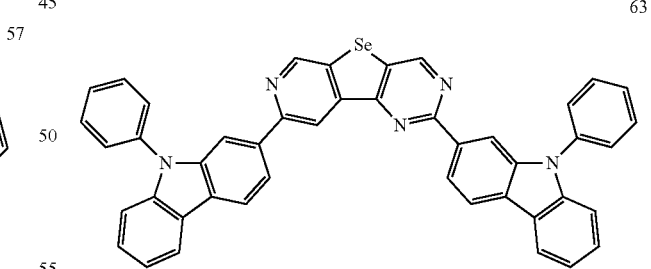
64
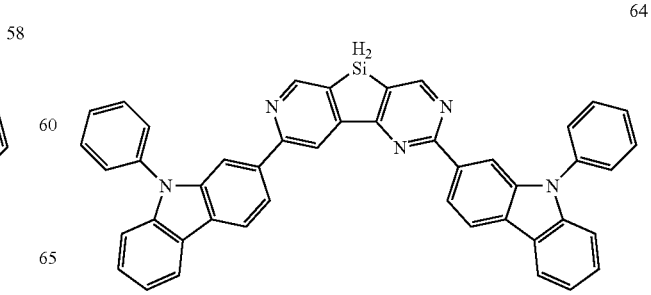

65
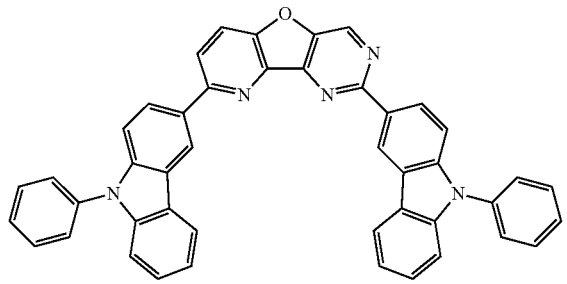
66
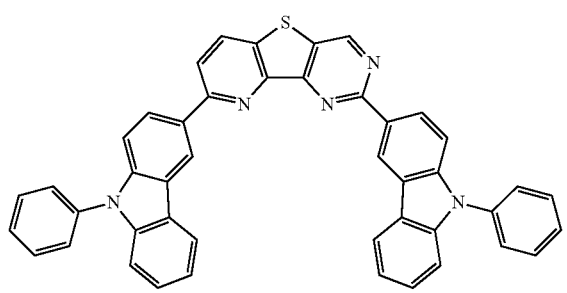
67
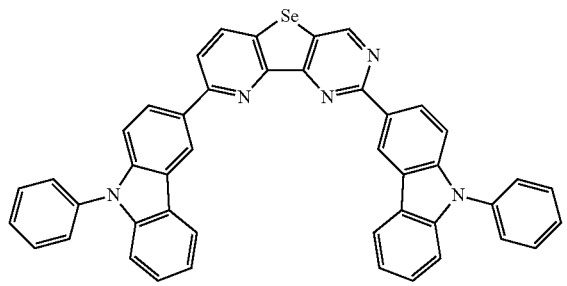
68
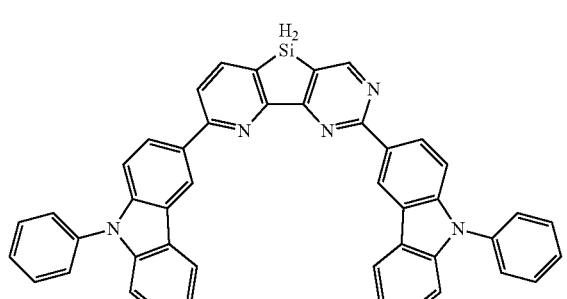
69
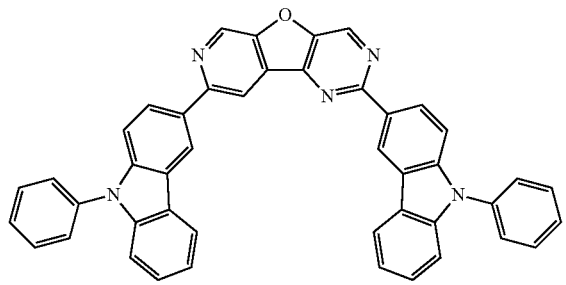
70
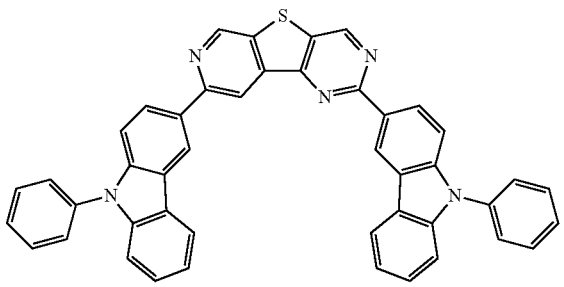
71
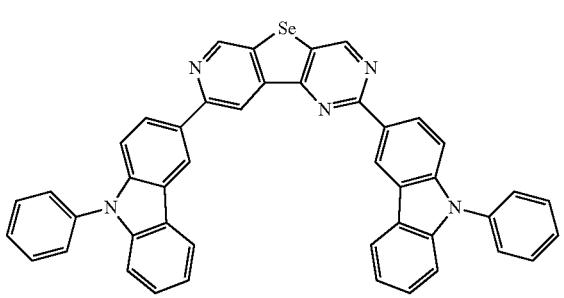
72
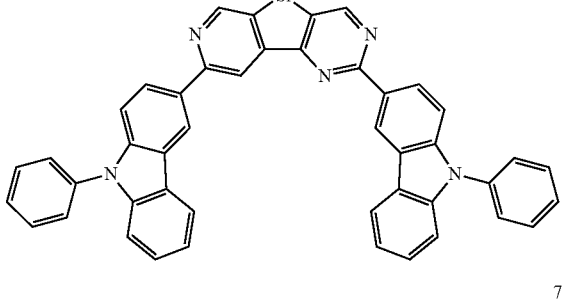
73
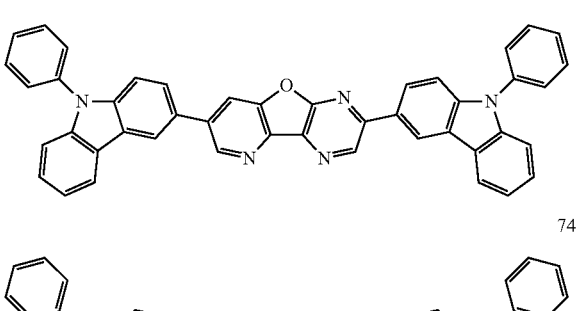
74
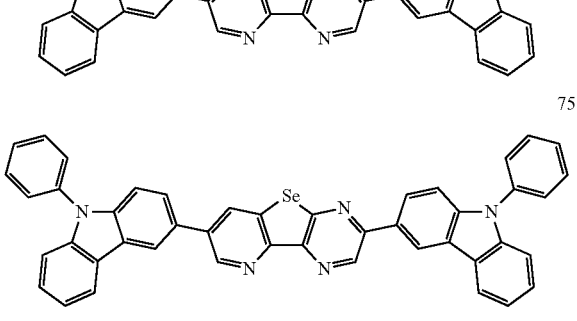
75

-continued
76
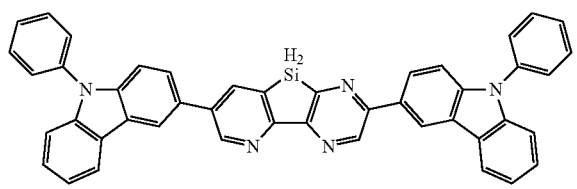
77
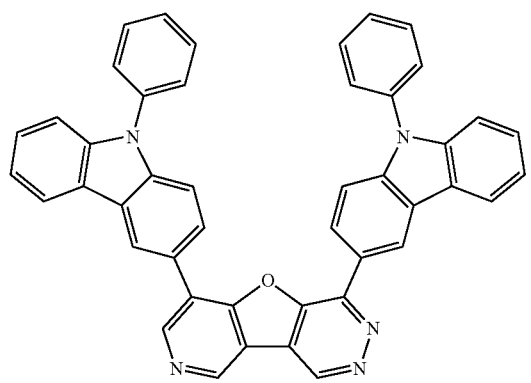
78
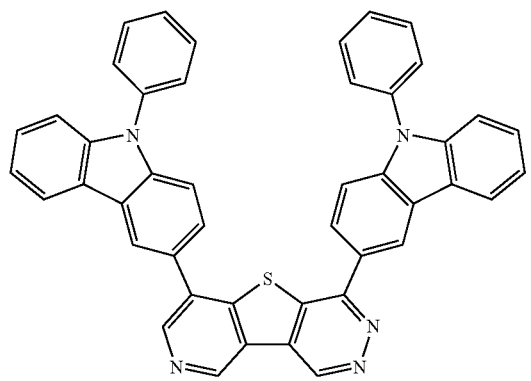
79
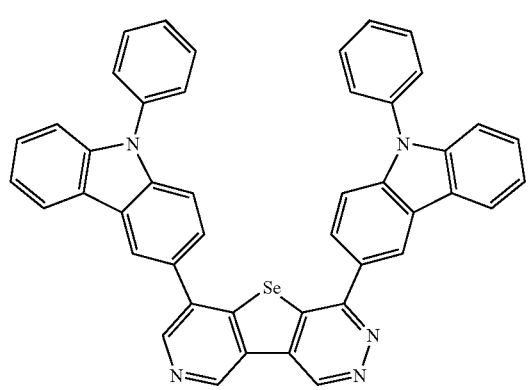
-continued
80
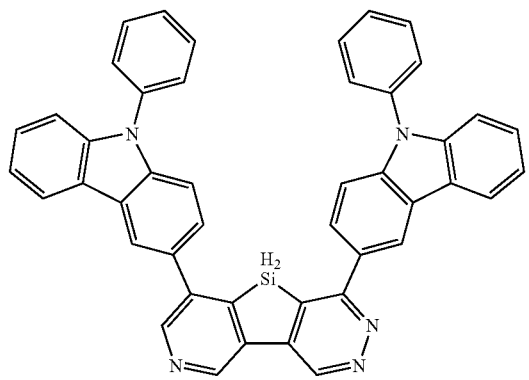
81
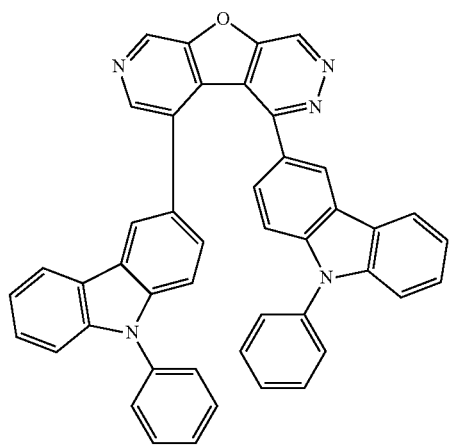
82
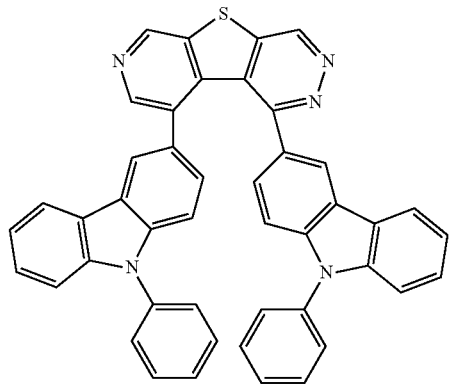
83
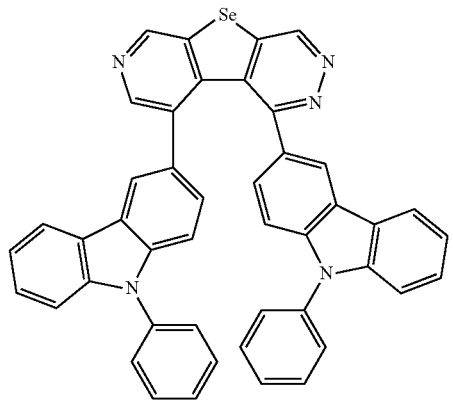

84
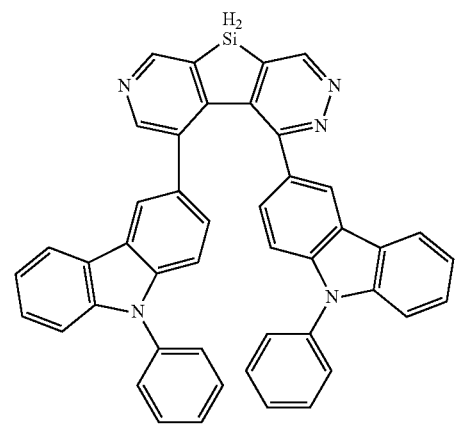
85
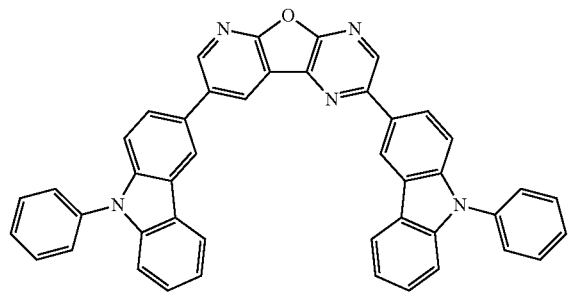
86
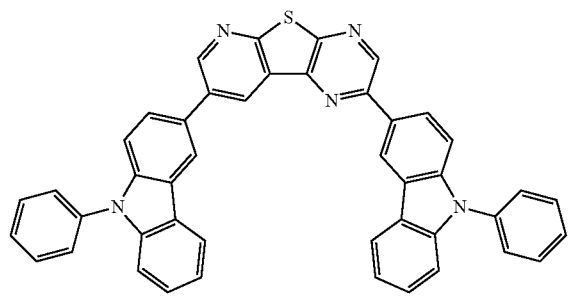
87
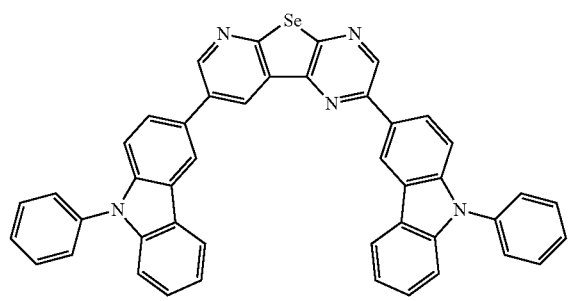
88
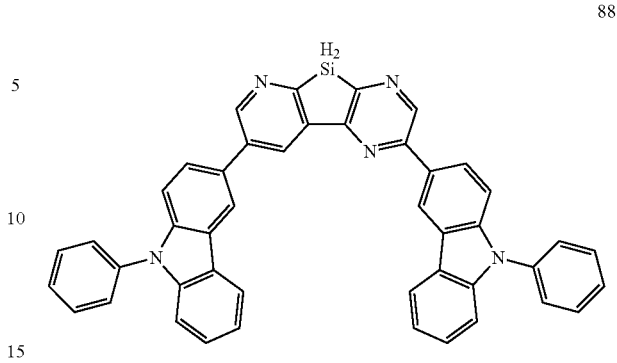
89
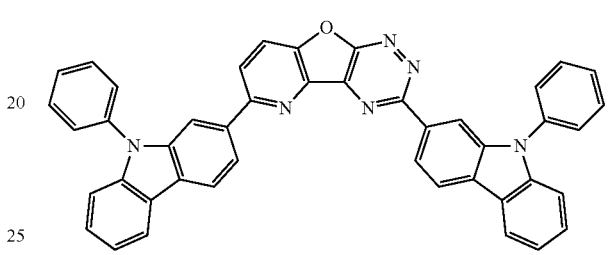
90
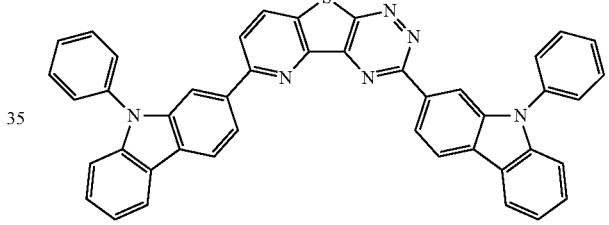
91
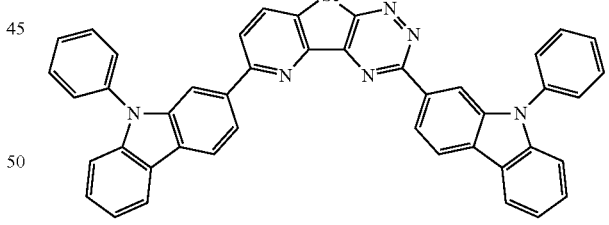
92
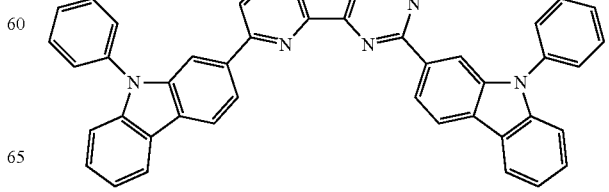

93
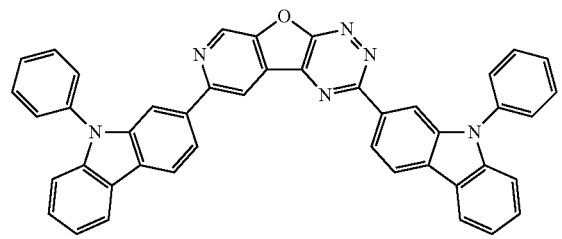
94
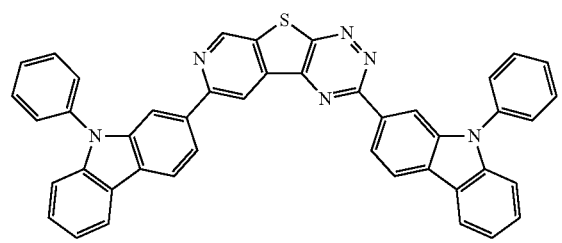
95
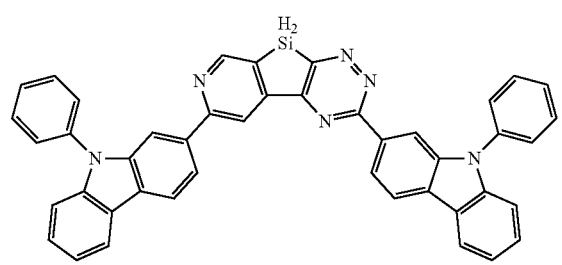
96
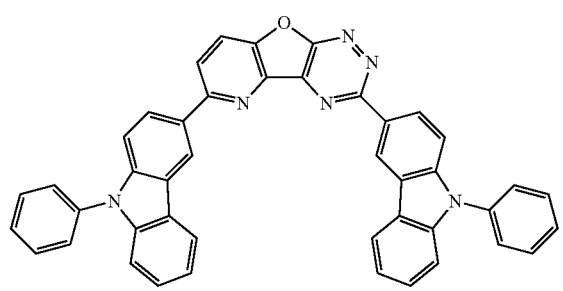
97
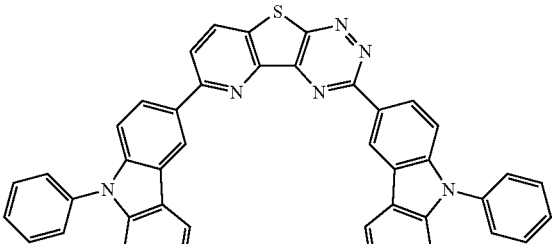
98
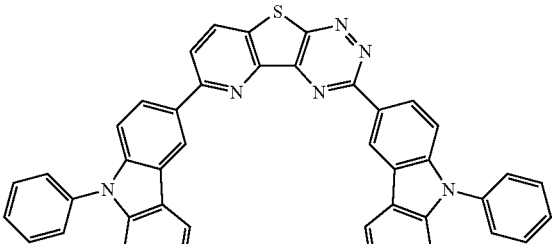
99
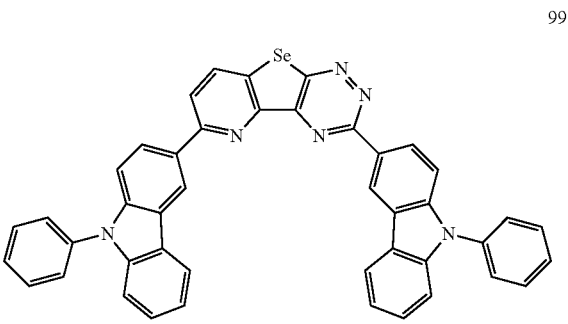
100
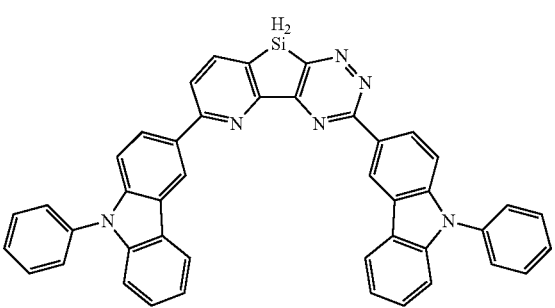
101
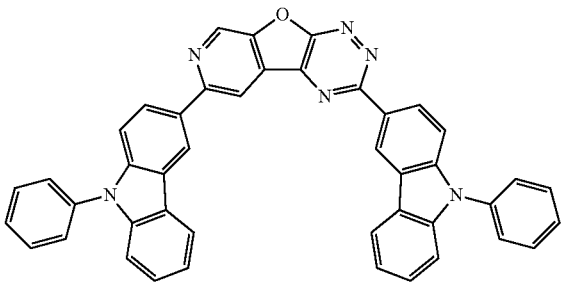
102
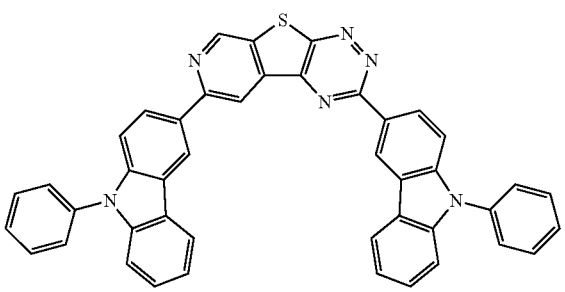

103
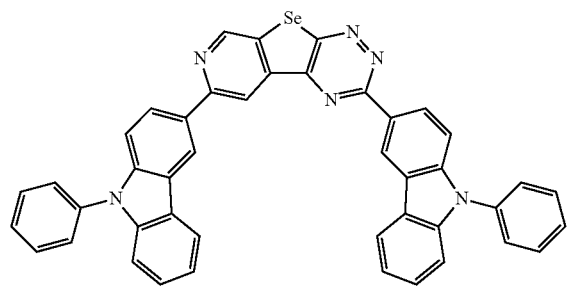
104
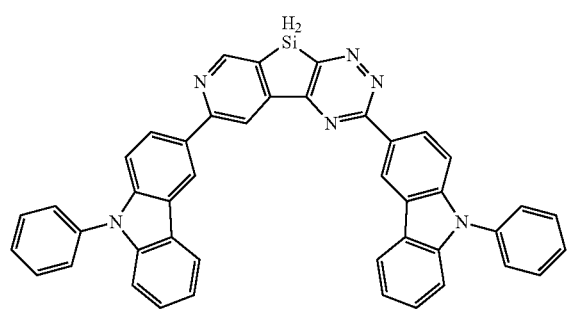
105
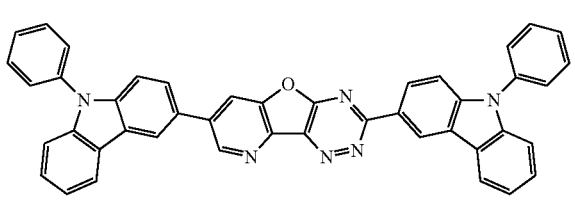
106
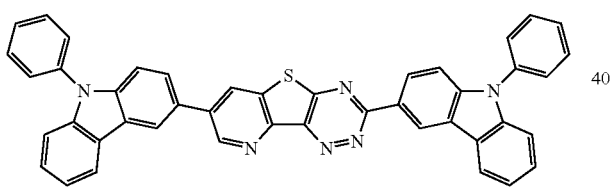
107
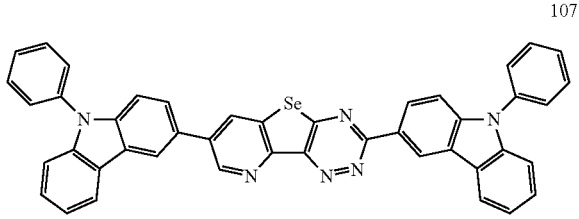
108
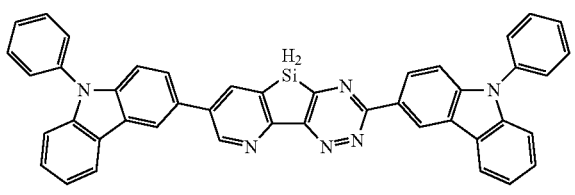
109
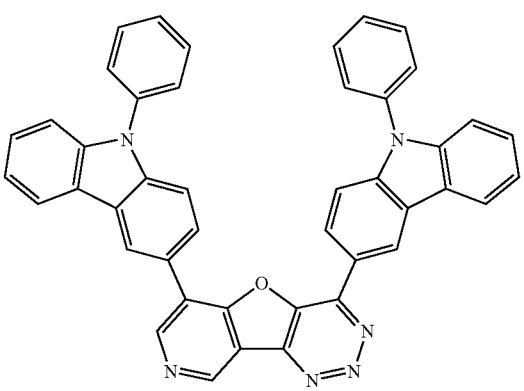
110
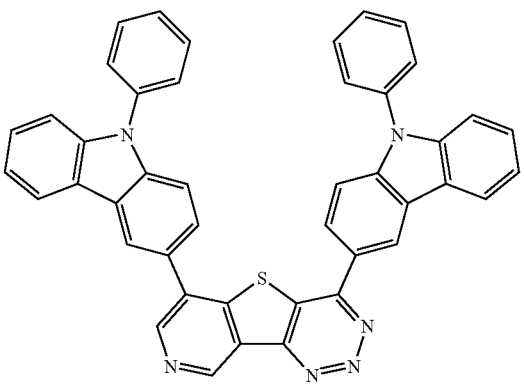
111
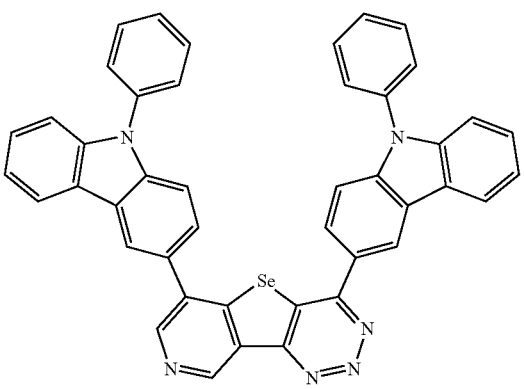
112
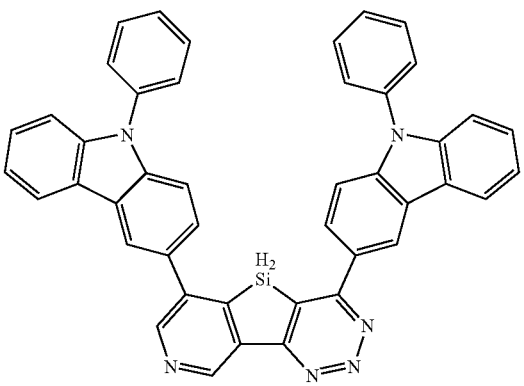

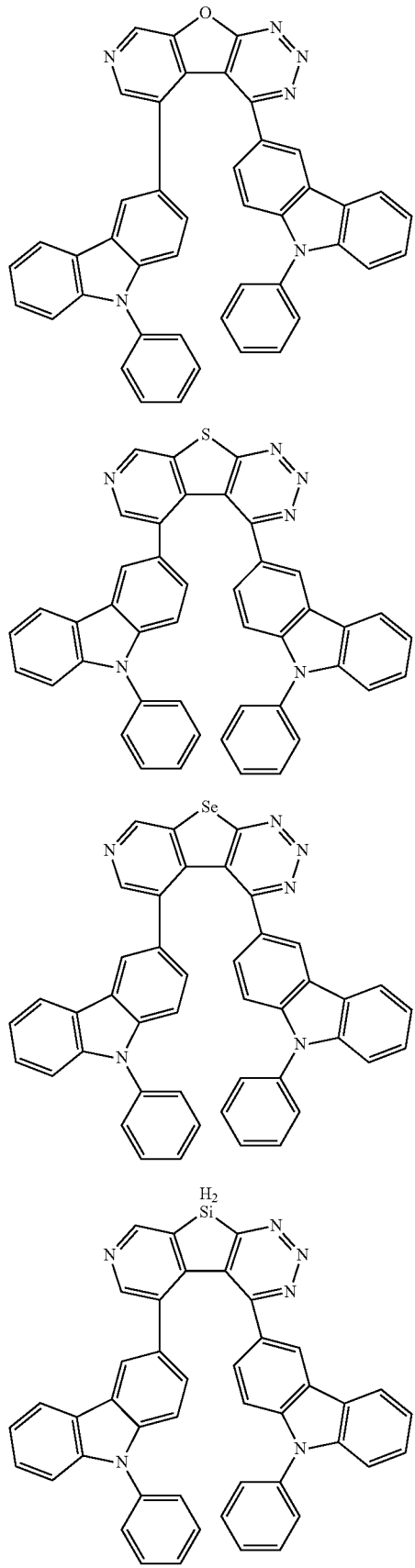
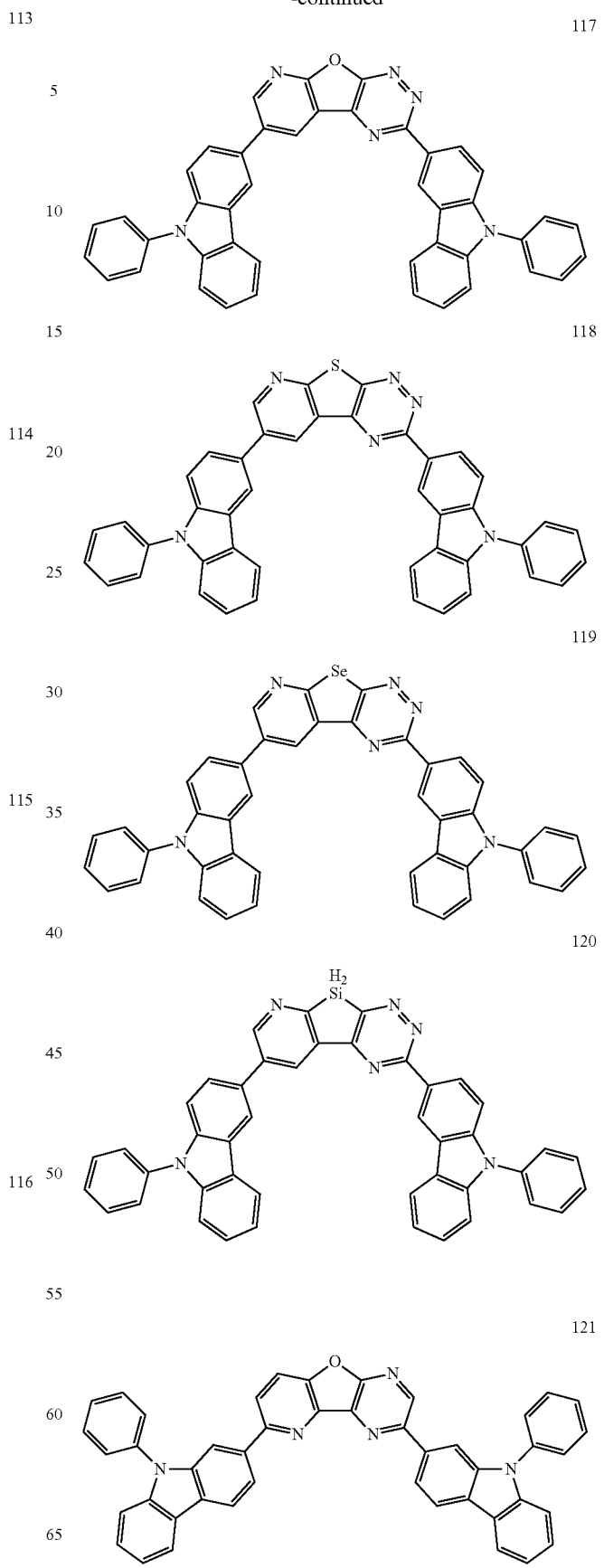

122
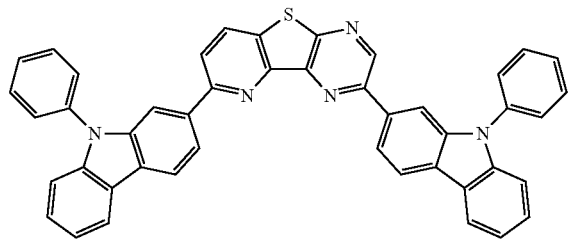
123
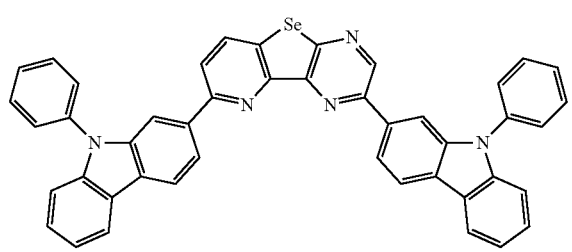
124
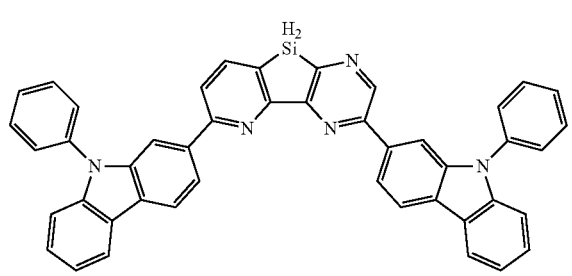
125
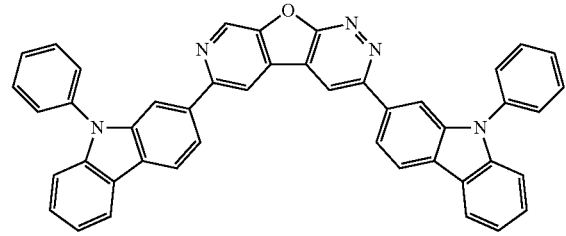
126
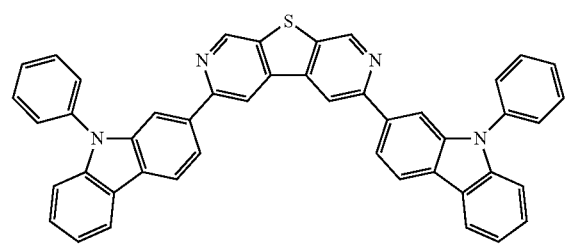
127
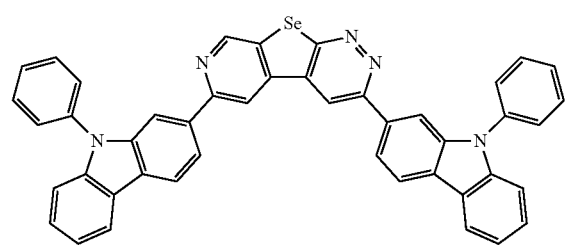
128
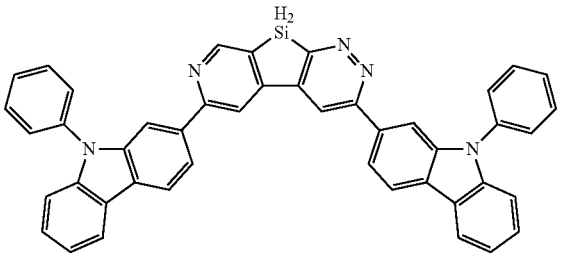
129
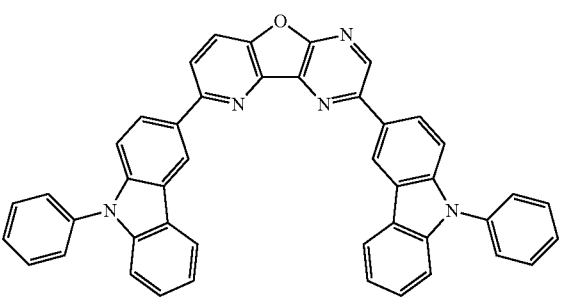
130
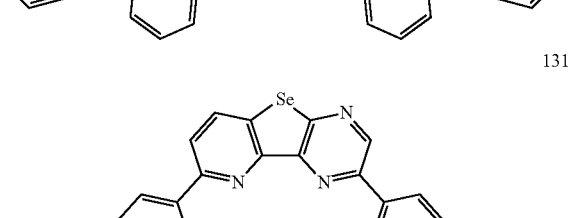
131
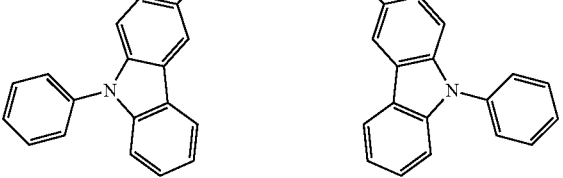
132
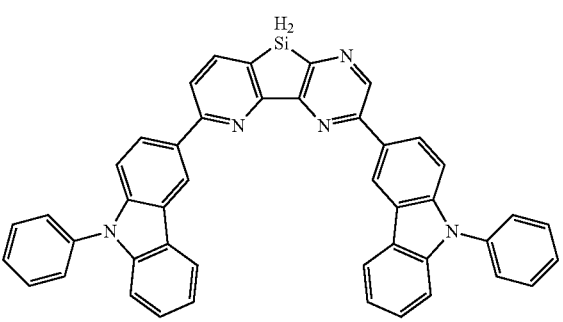

55
-continued

133

134

135

136

137

56
-continued

138

139

140

141

142

-continued
143
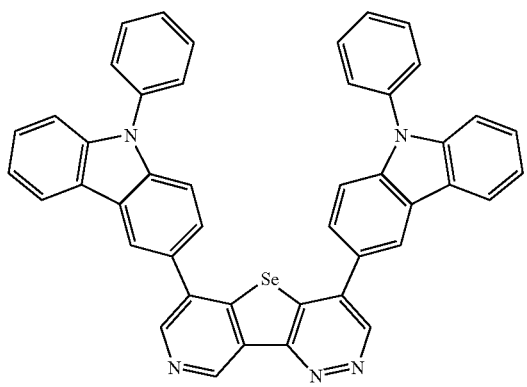
144
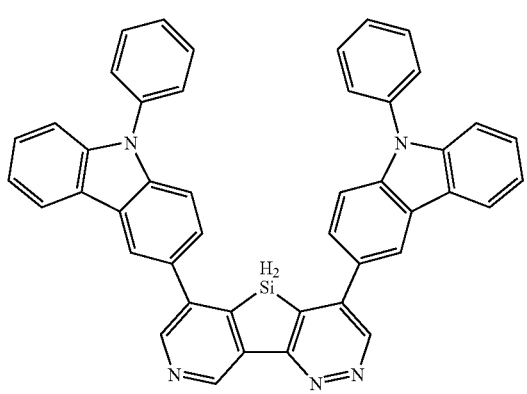
145
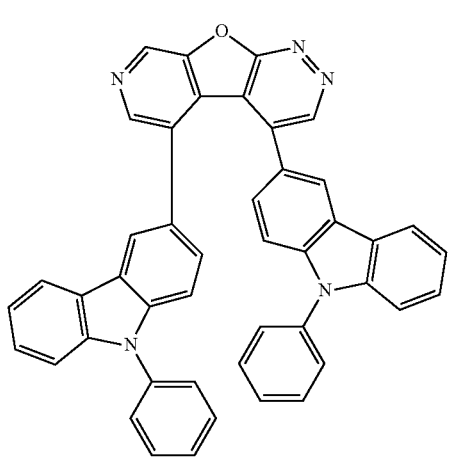
146
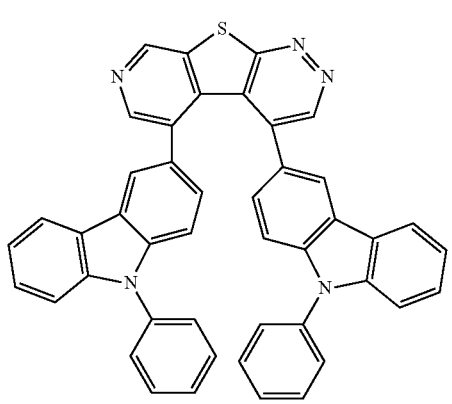
147
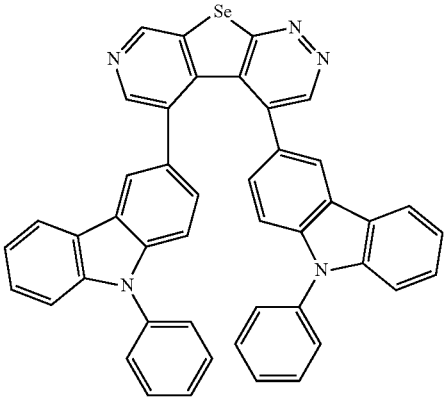
148
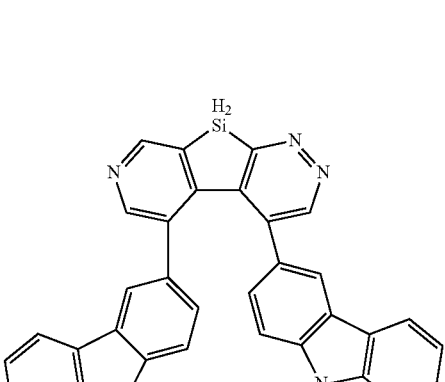
149
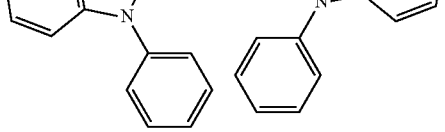
150
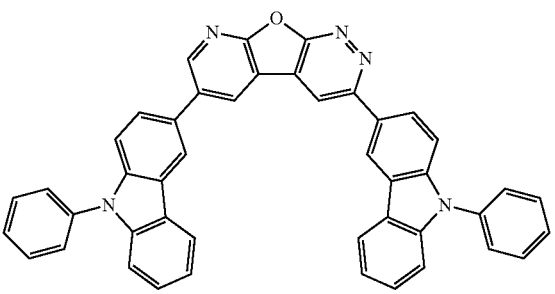

-continued
151
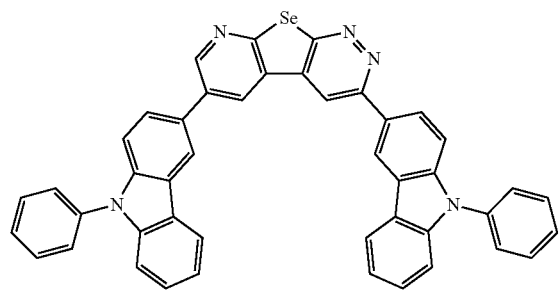
152
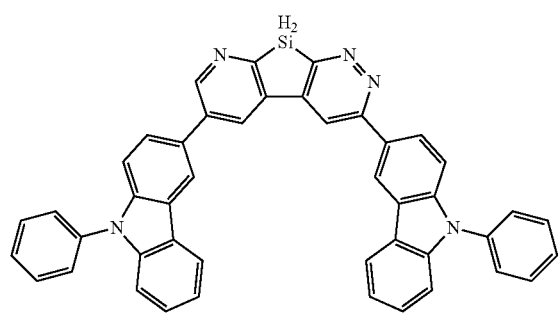
153
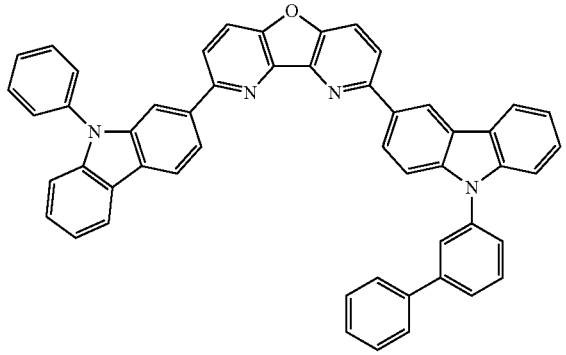
154
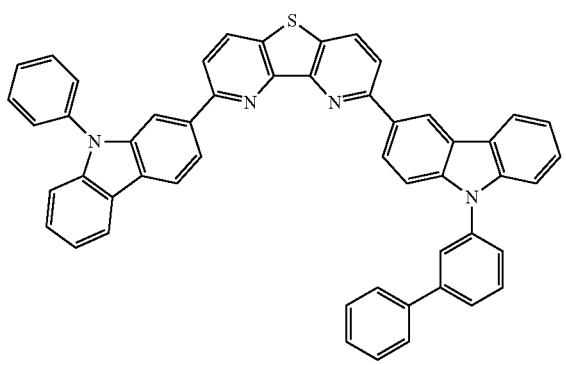
-continued
155
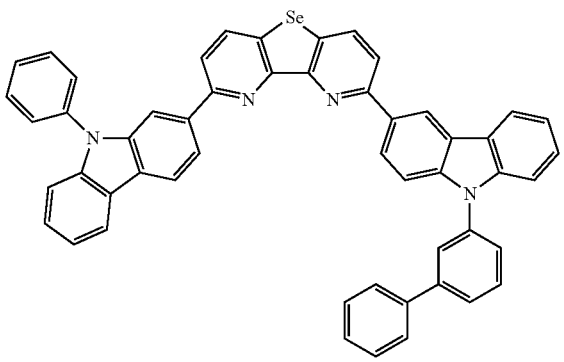
156
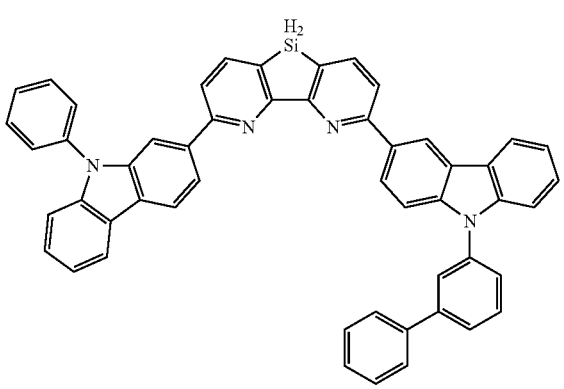
157
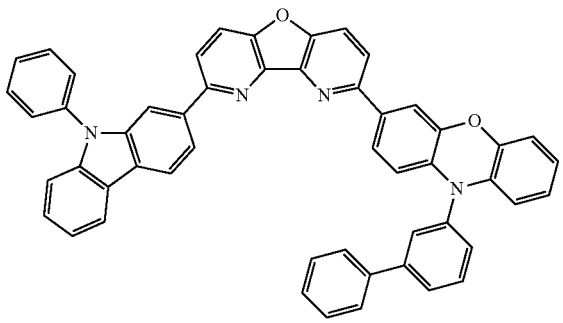
158
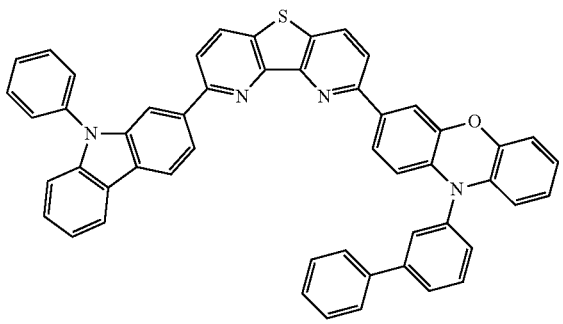

-continued
159
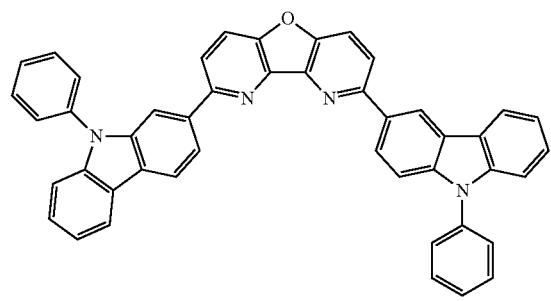
160
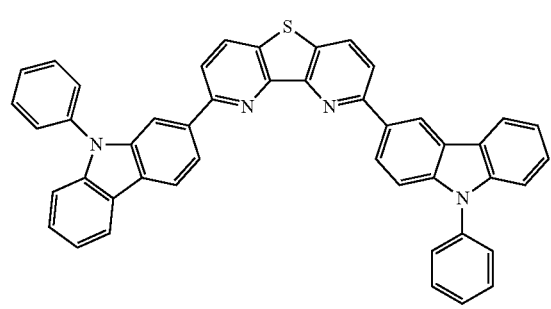
161
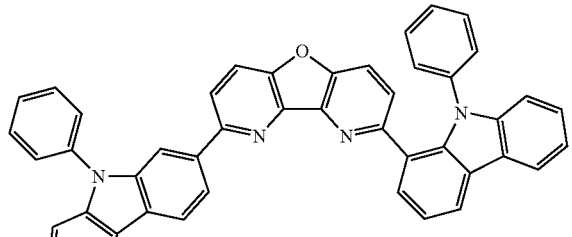
162
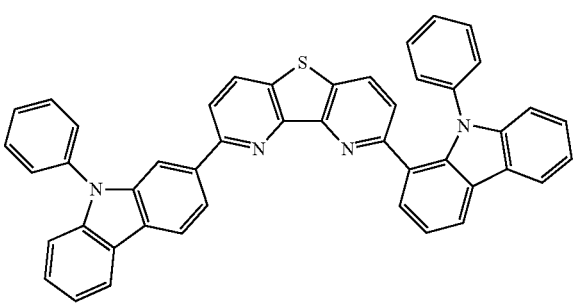
163
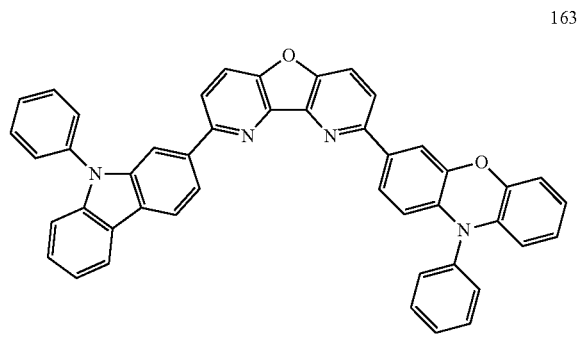
-continued
164
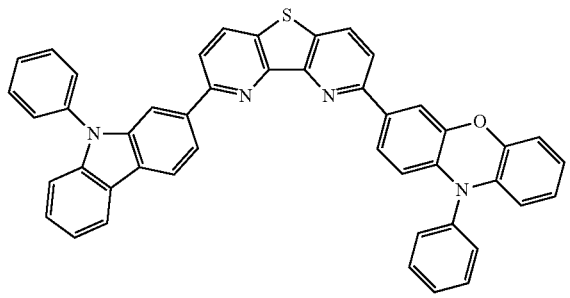
165
166
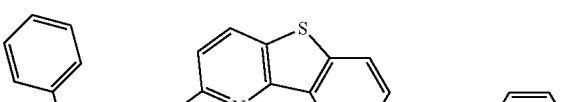
167
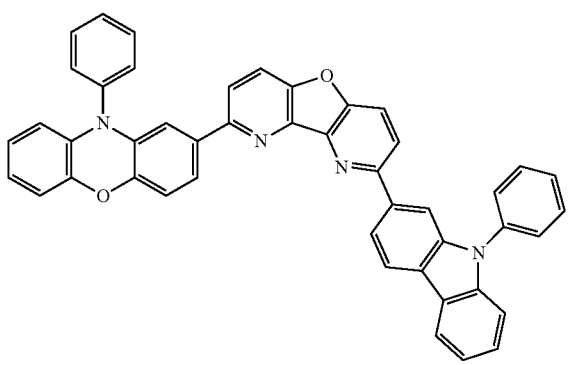

168
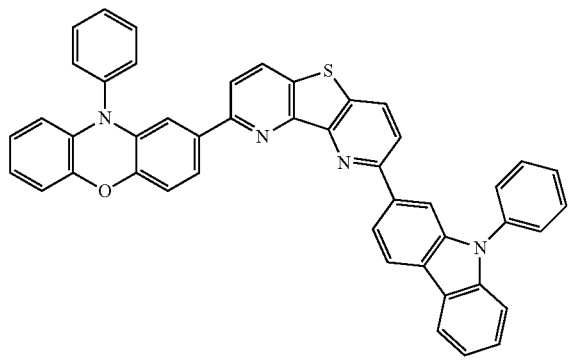
169
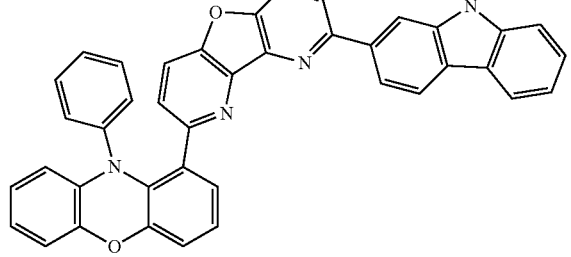
170
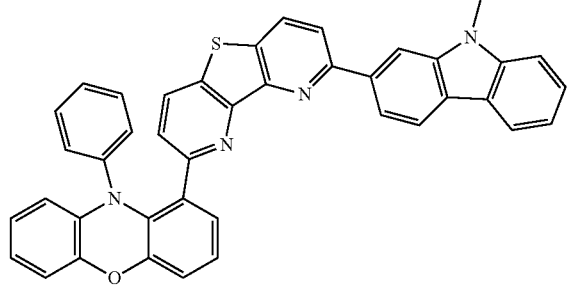
171
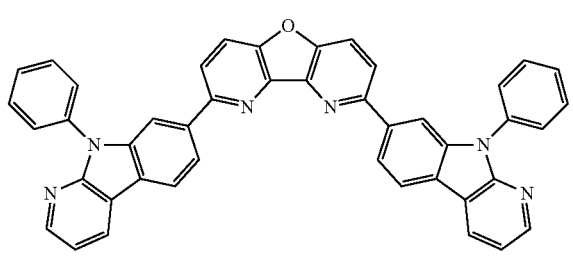
172
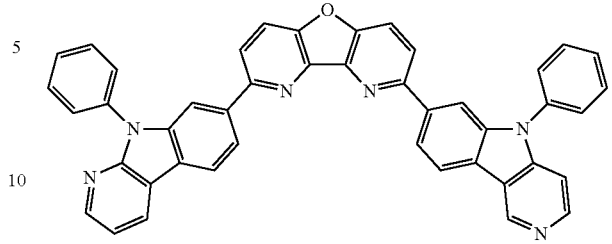
173
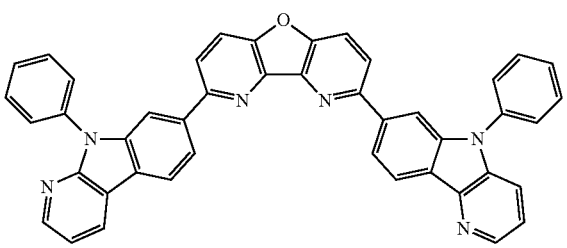
174
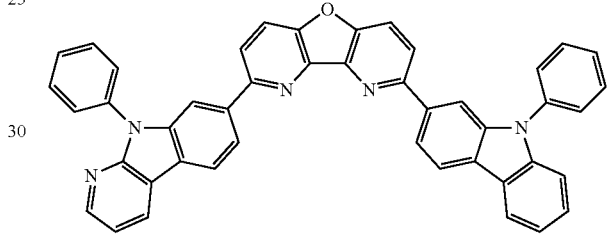
175
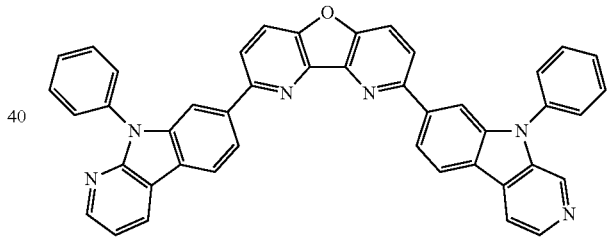
176
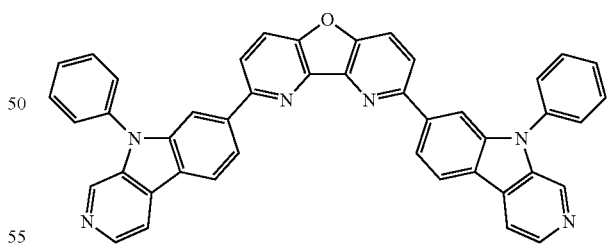
177
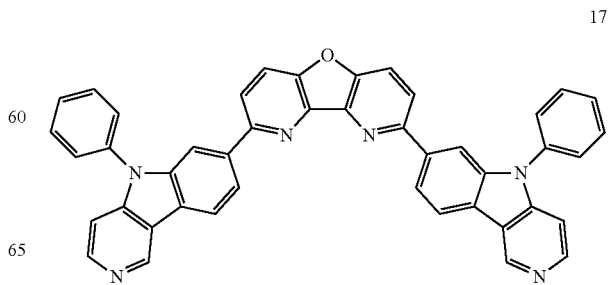

178
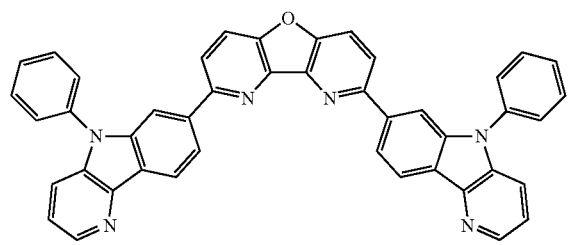
183
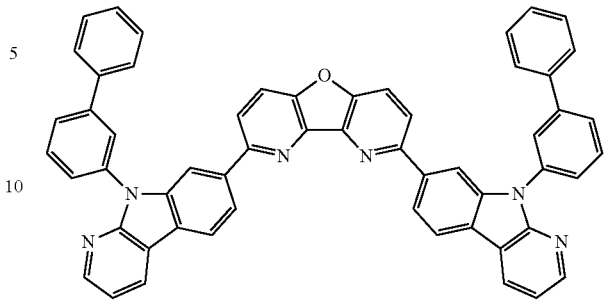
179
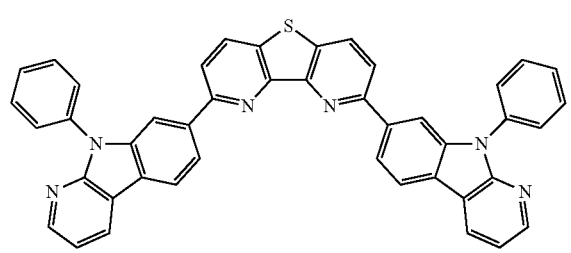
184
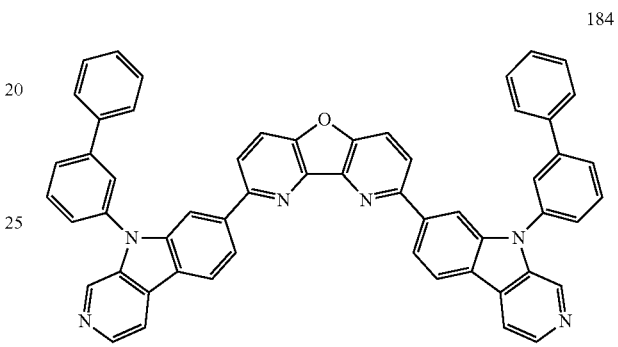
180
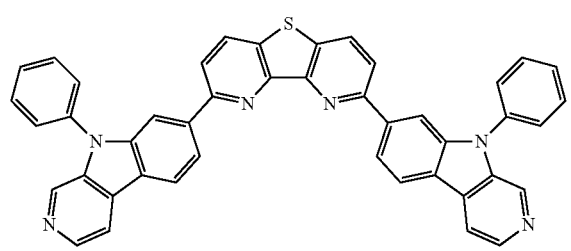
185
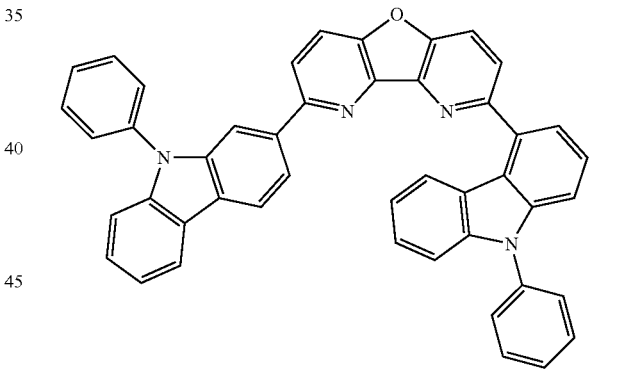
181
182
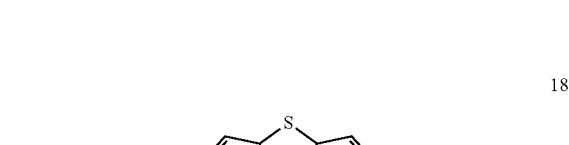
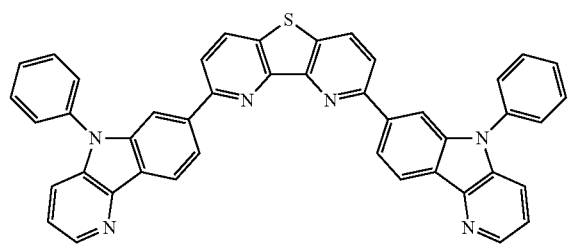
186
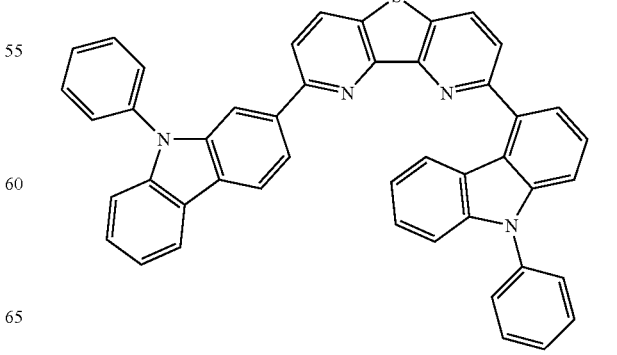
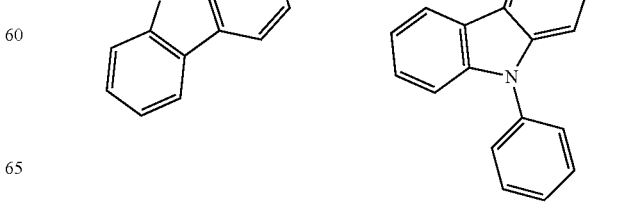

-continued
187
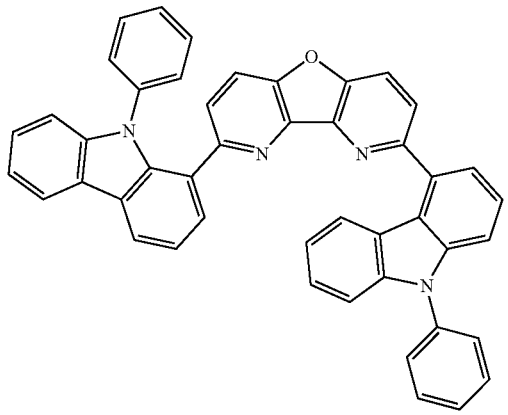
188
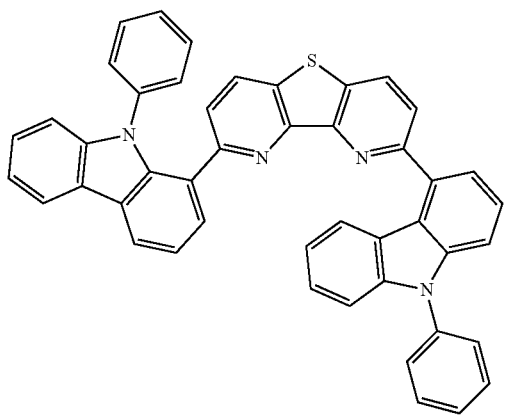
189
190
191
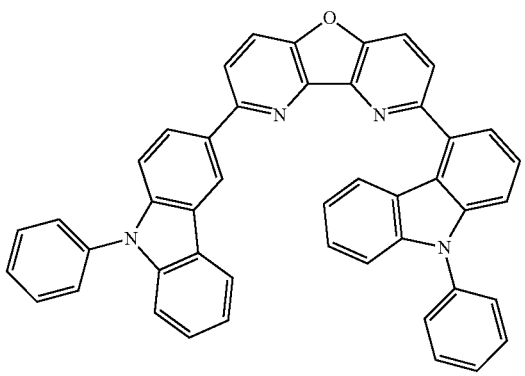
192
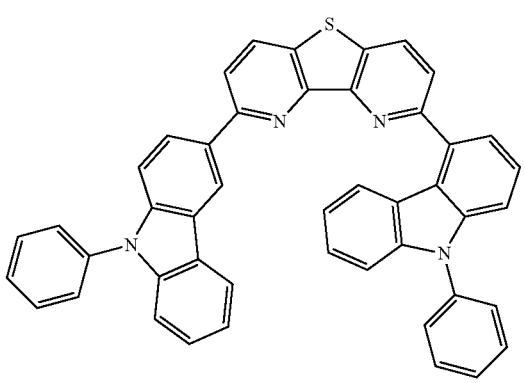
193
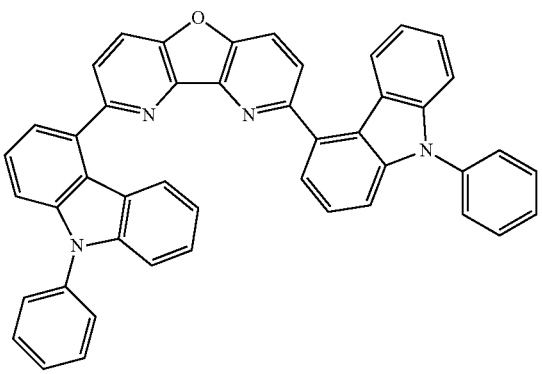
194
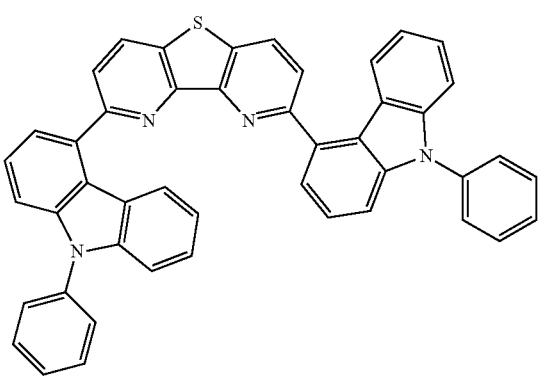

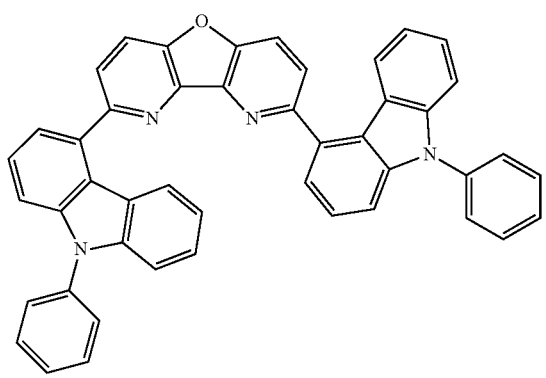
195
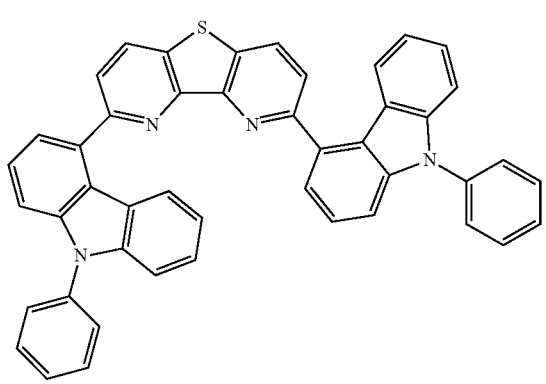
196
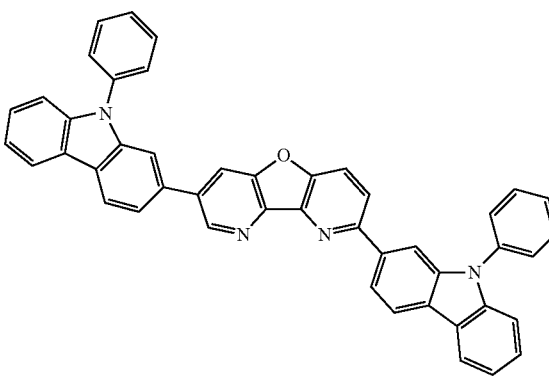
197
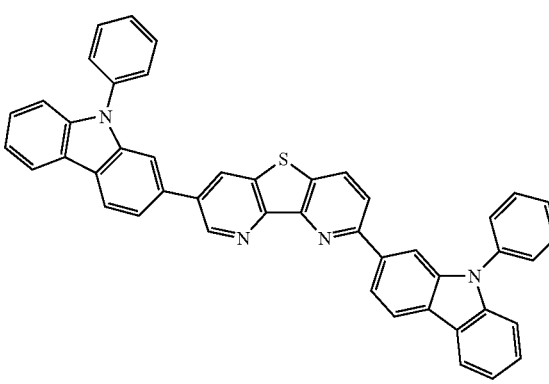
198
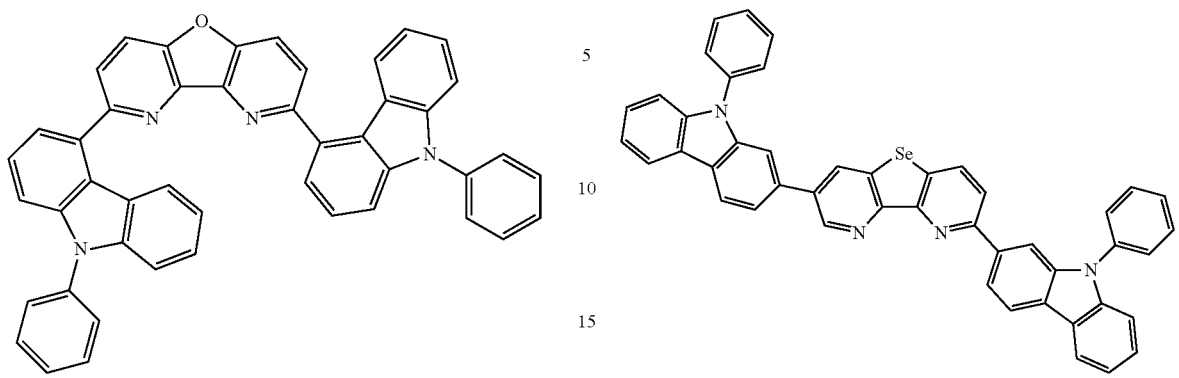
199
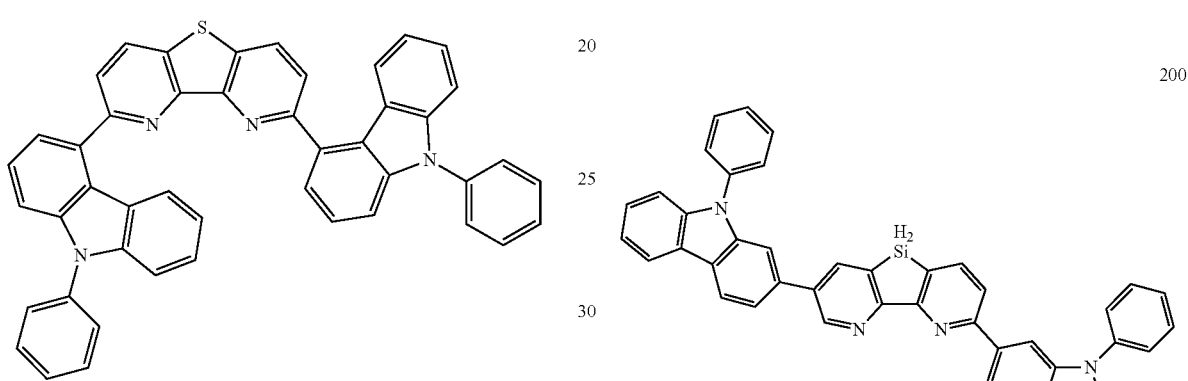
200
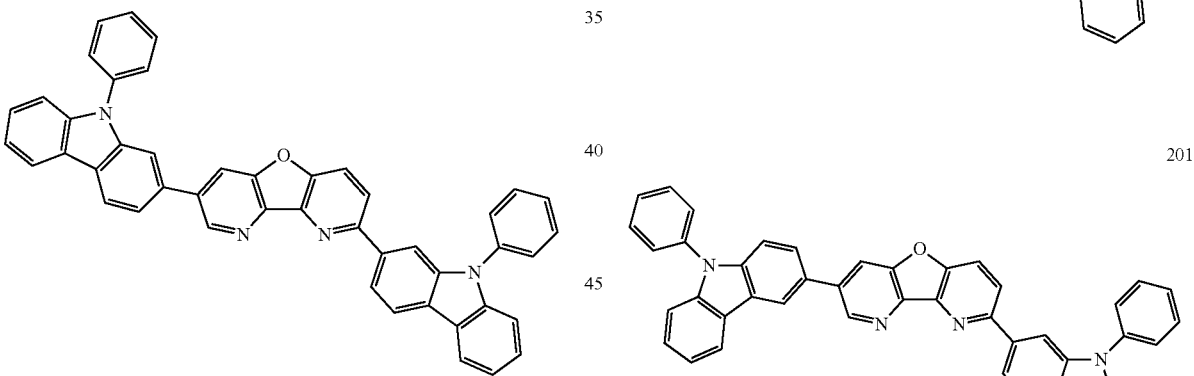
201
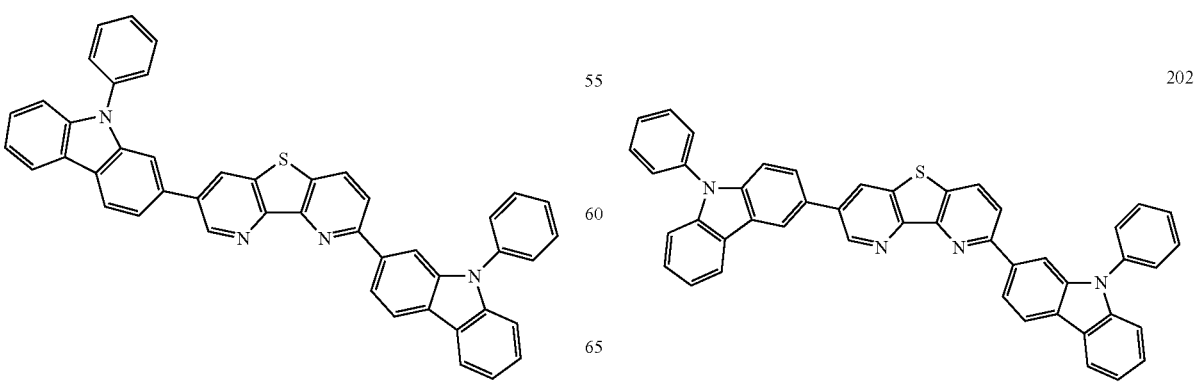
202

203
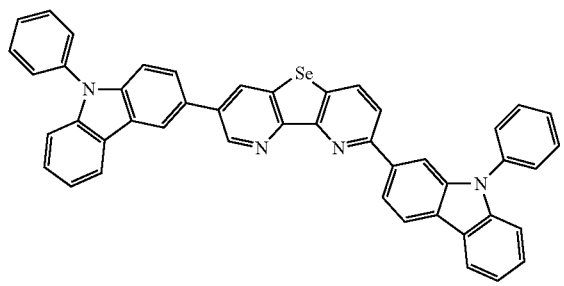
204
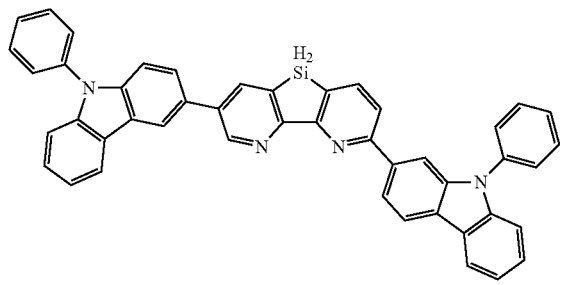
205
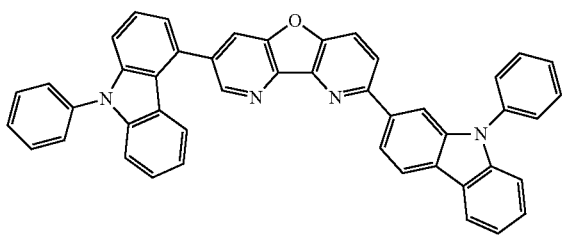
206
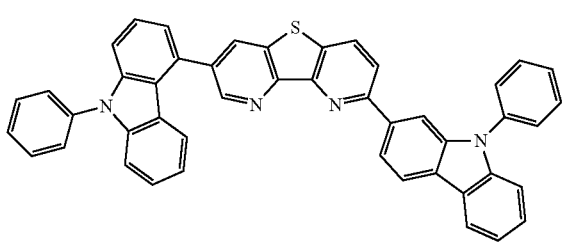
207
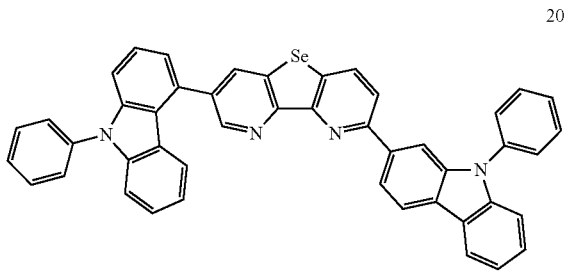
208
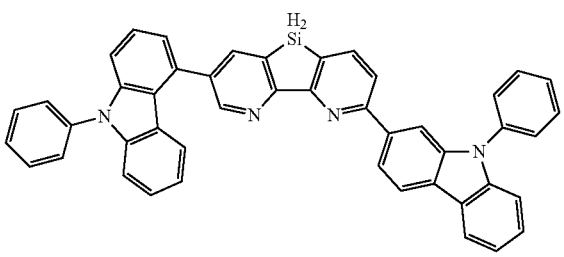
209
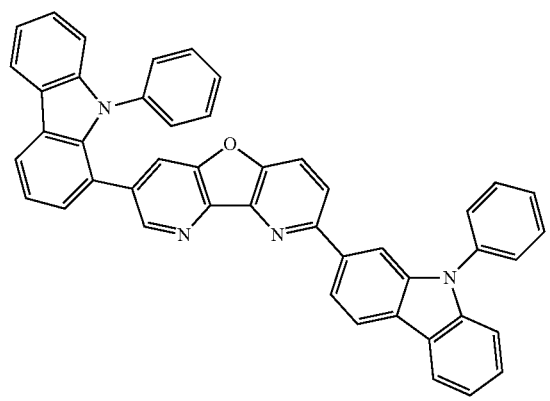
210
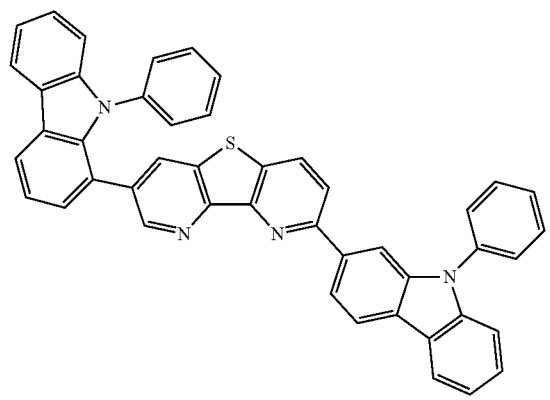
211
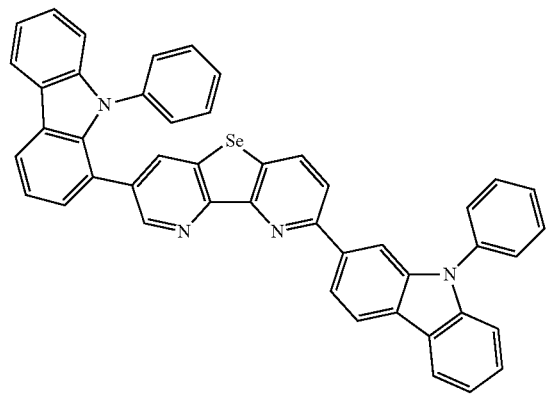

212
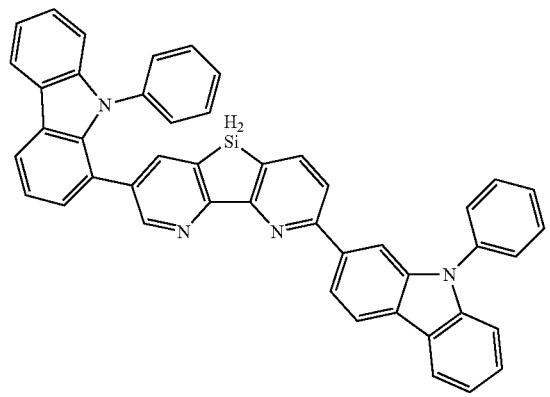
213
214
215
216
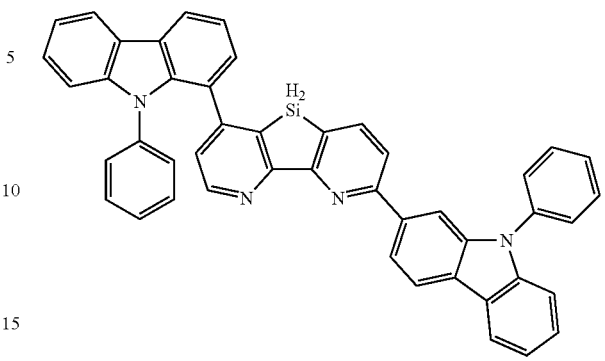
217
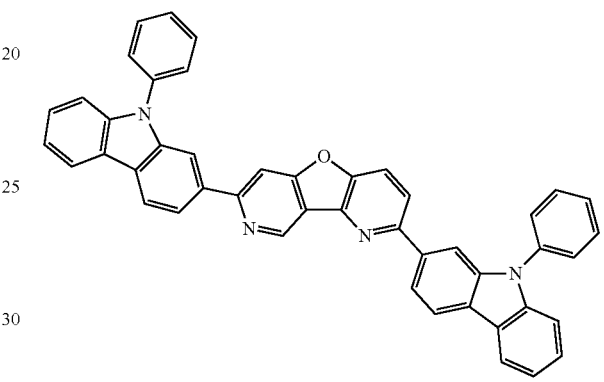
218
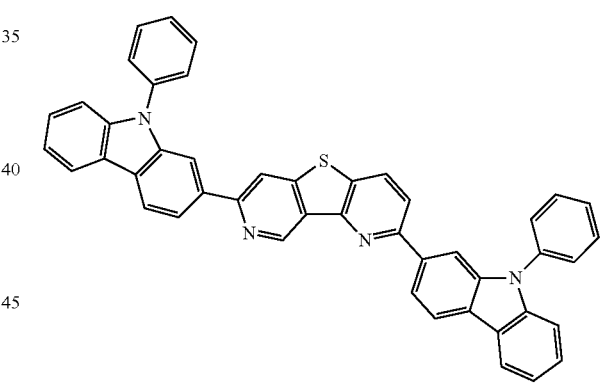
219
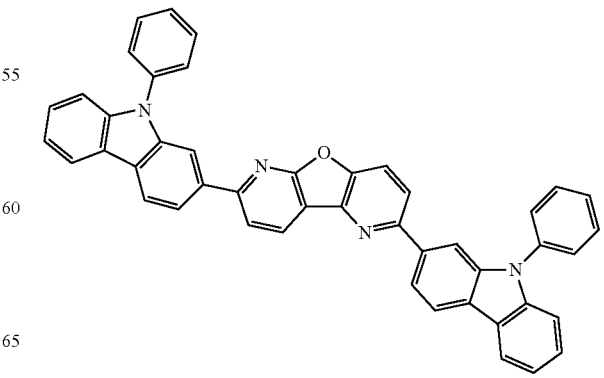

220
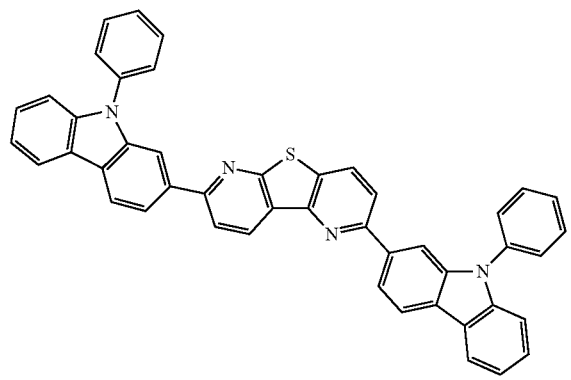
221
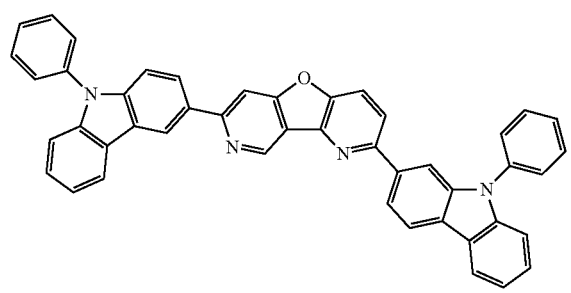
222
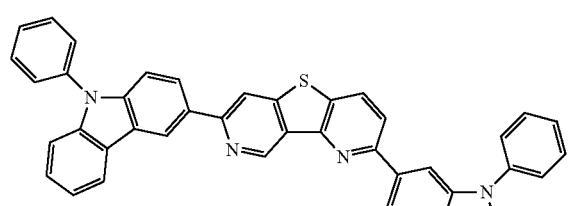
223
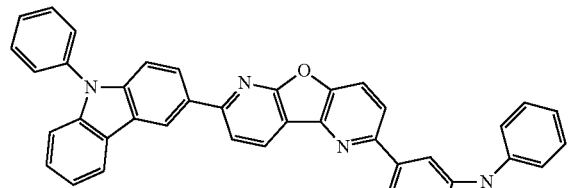
224
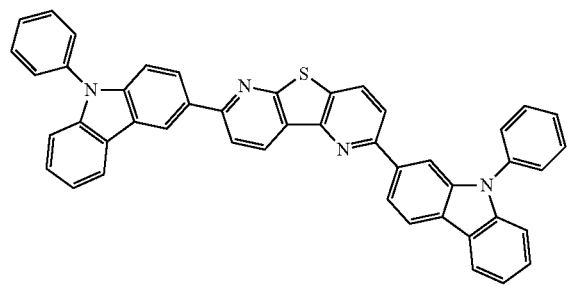
225
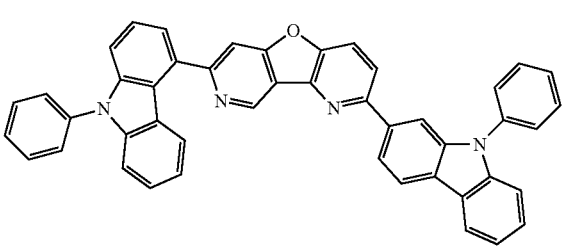
226
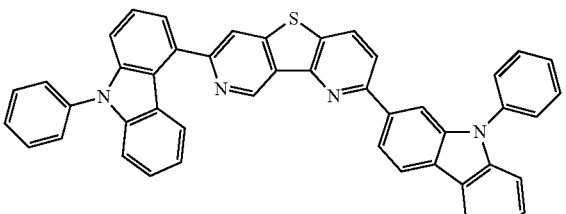
227
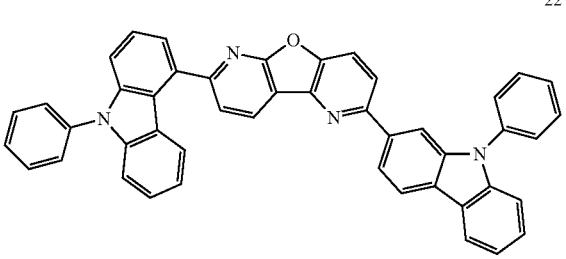
228
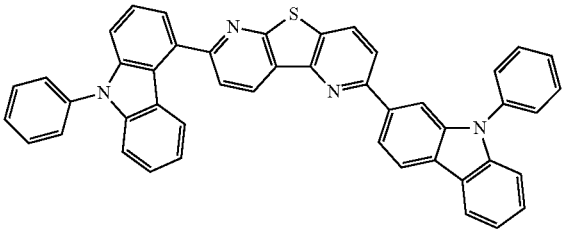
229
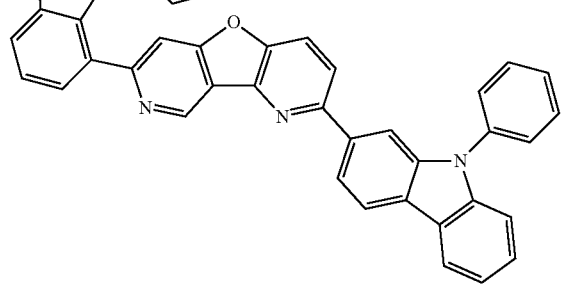

230
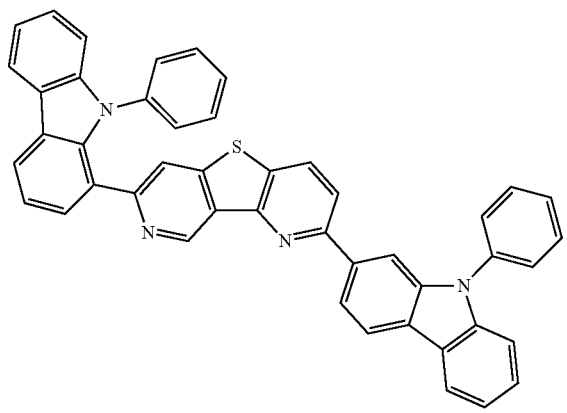
231
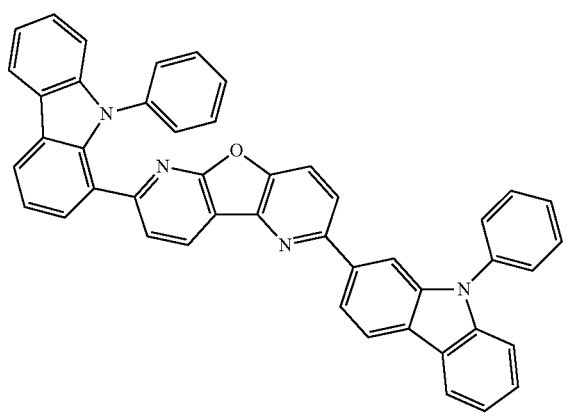
232
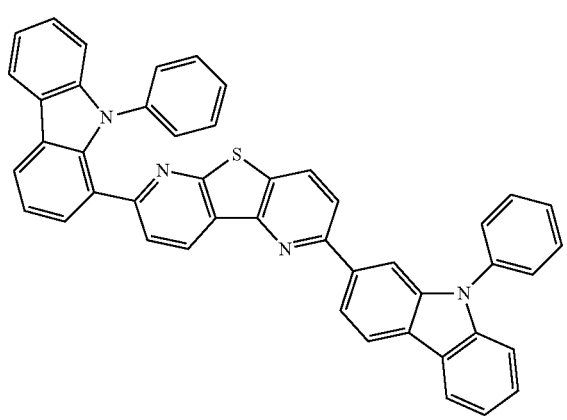
233
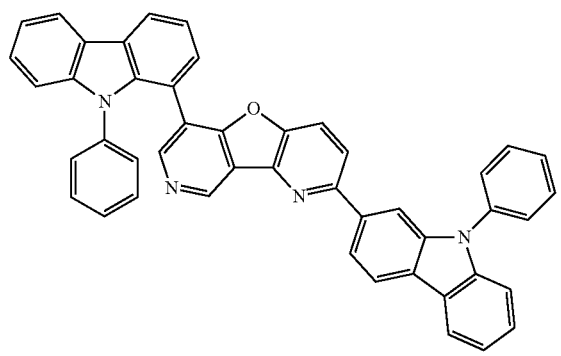
234
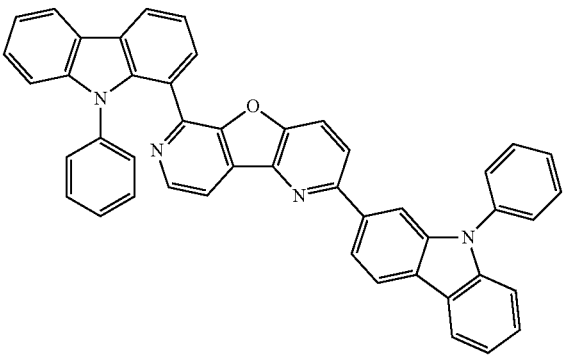
235
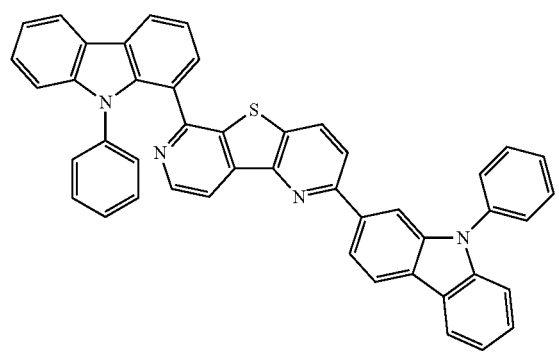
236

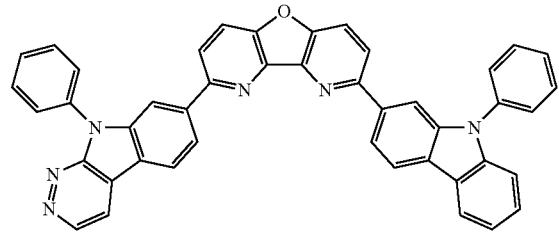
238
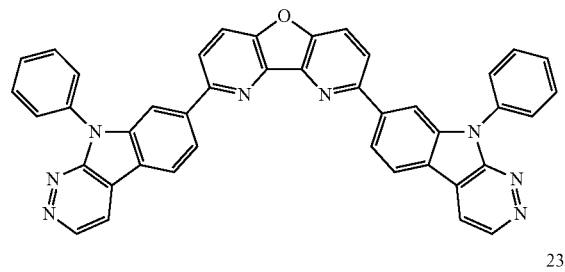
239
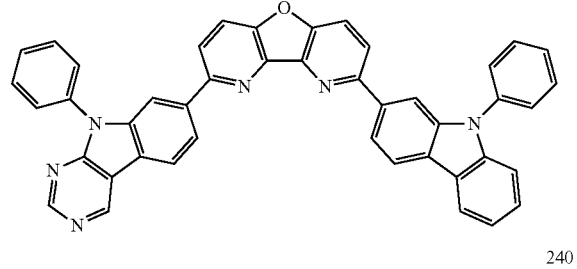
240
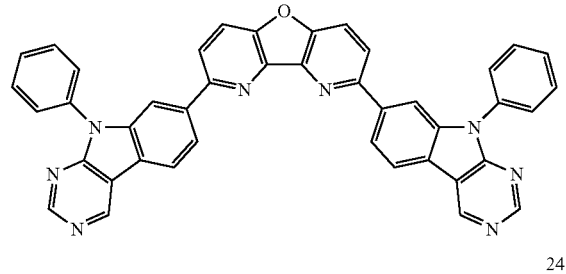
241
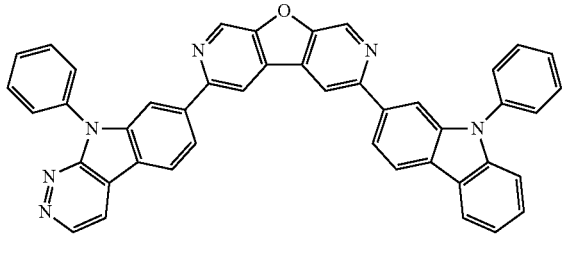
242
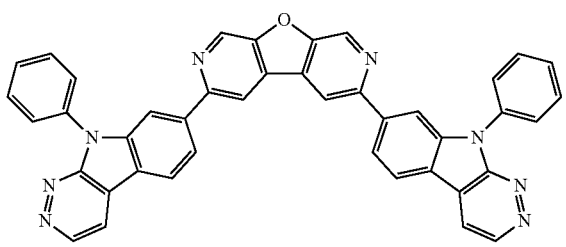
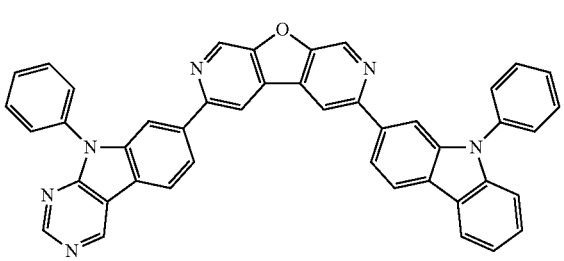
243
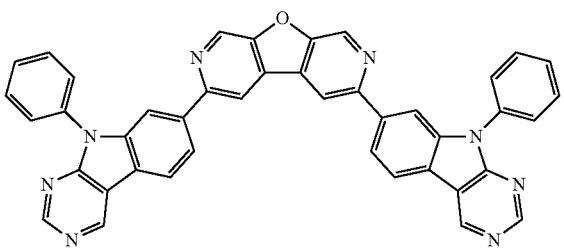
244
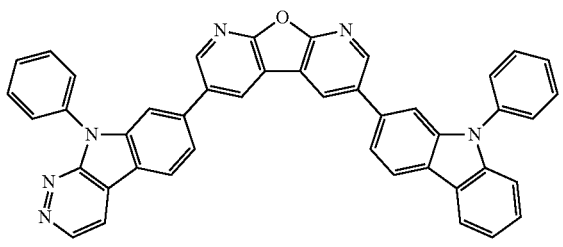
245
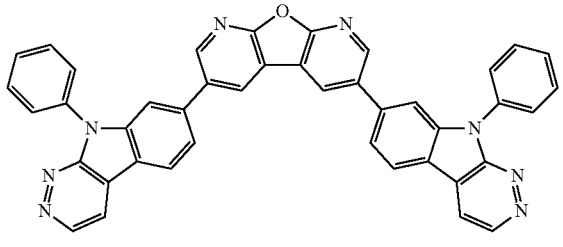
246
247
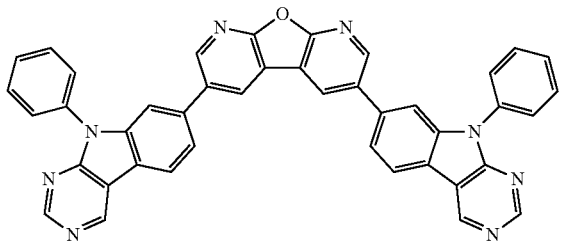
248

-continued
249
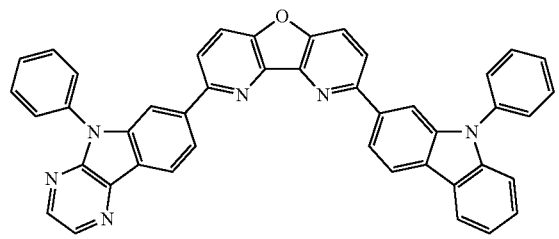
250
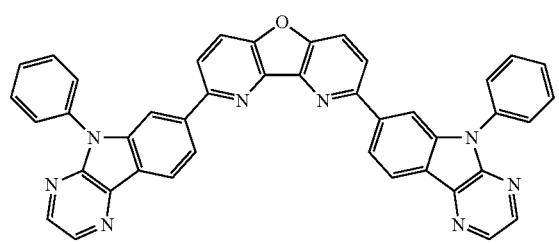
251
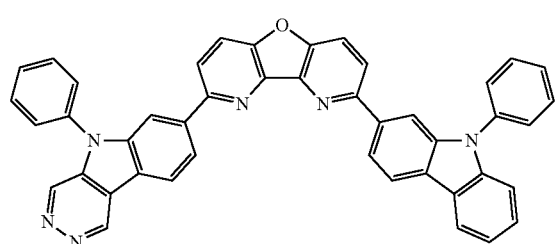
252
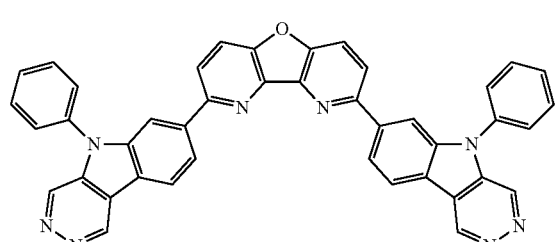
253
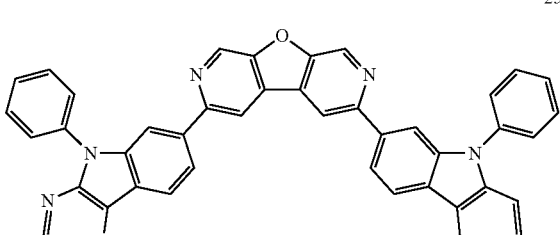
254
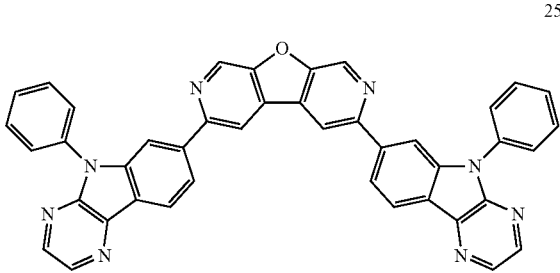
-continued
255
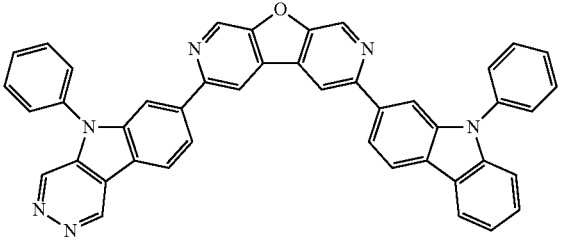
256
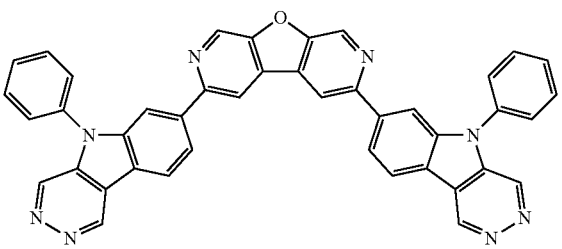
257
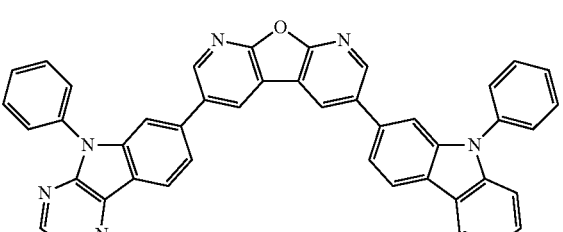
258
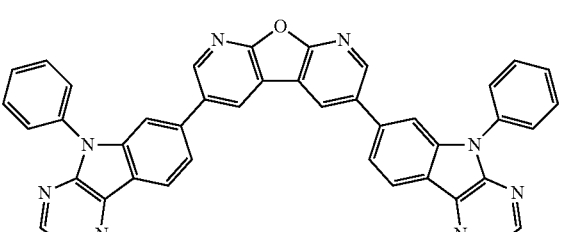
259
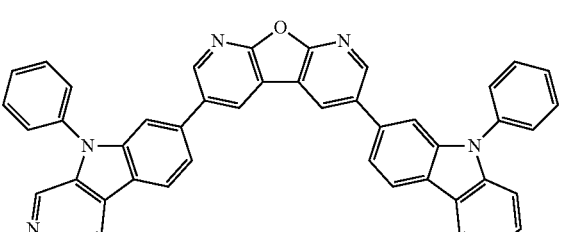
260
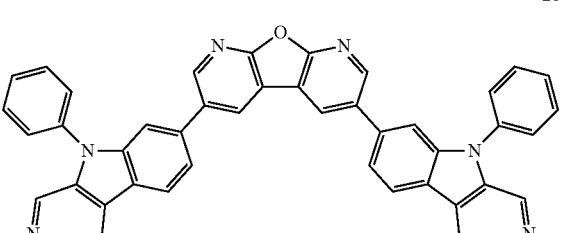

83
-continued
261
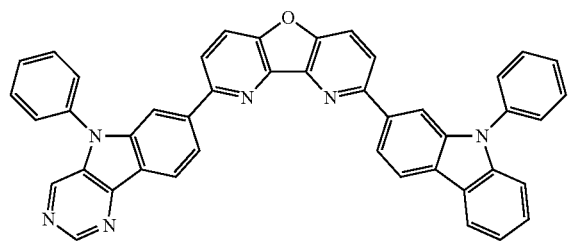
262
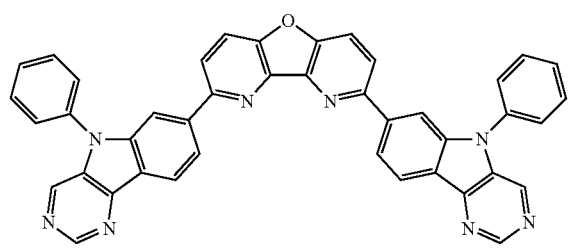
263
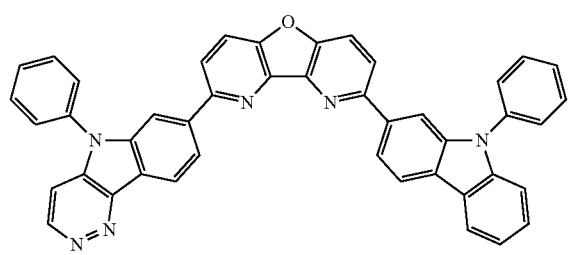
264
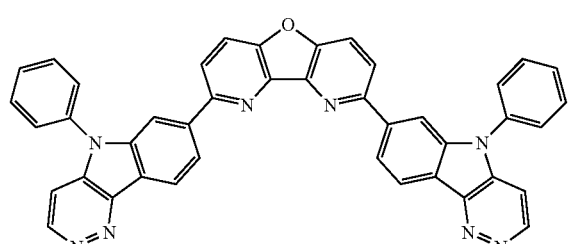
265
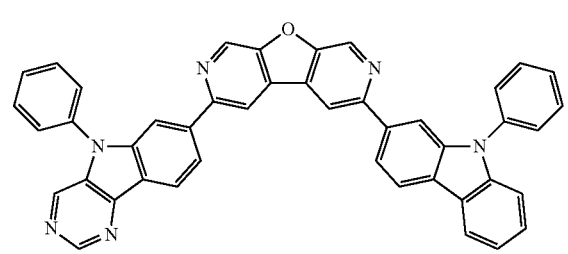
266
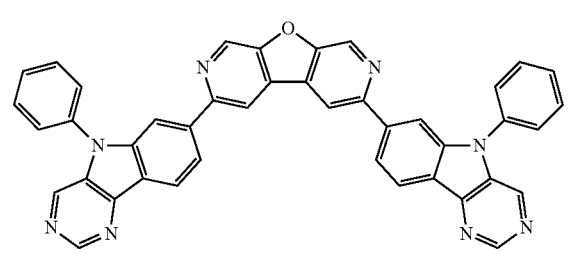
84
-continued
267
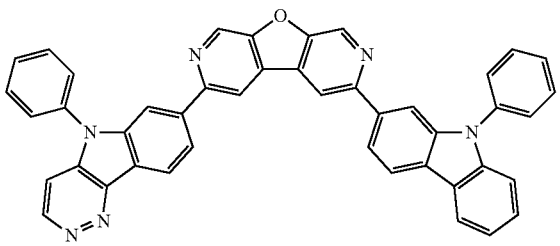
268
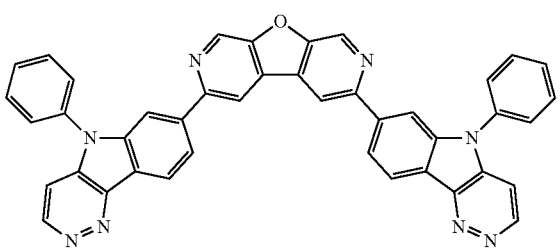
269
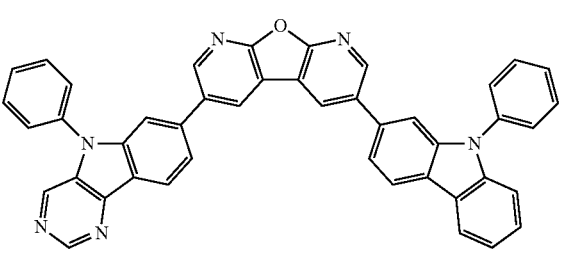
270
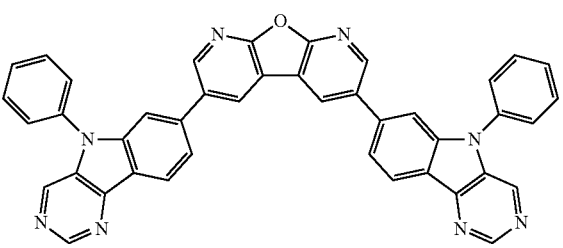
271
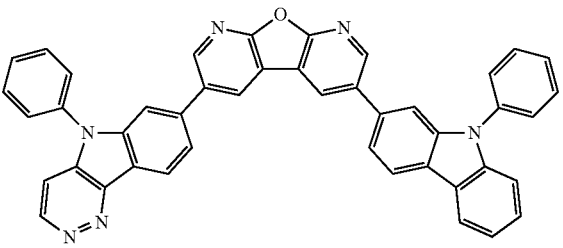
272
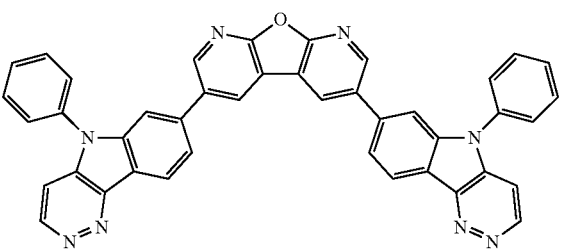

273
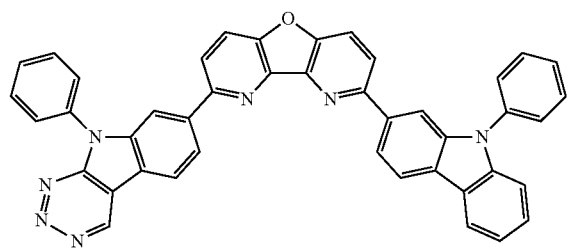
274
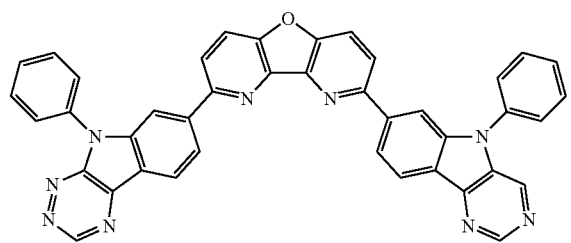
275
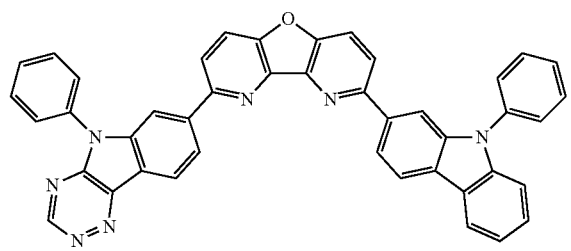
276
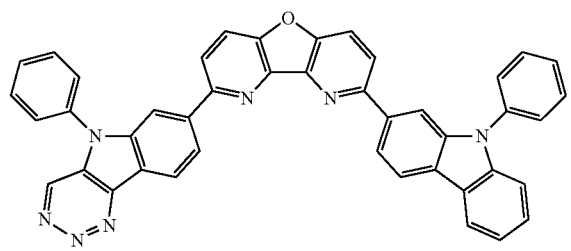
277
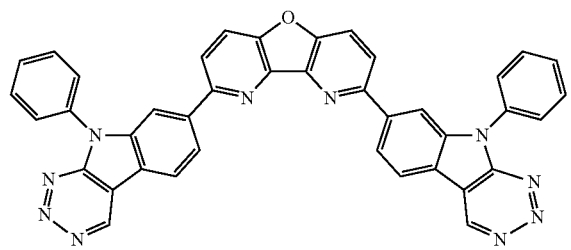
277
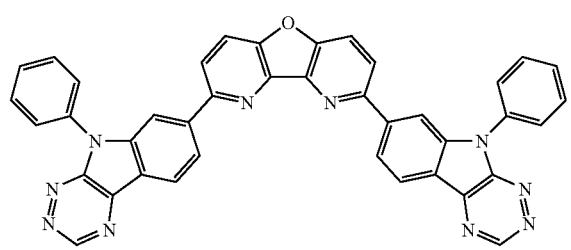
278
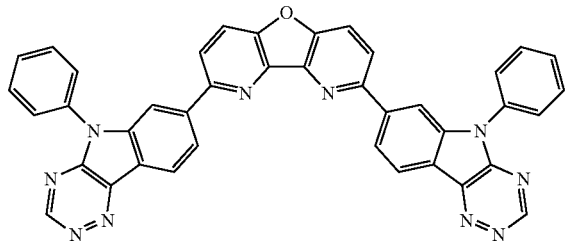
280
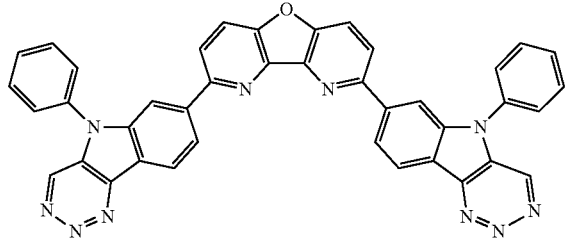
281
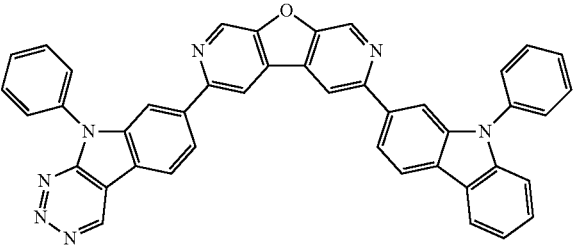
282
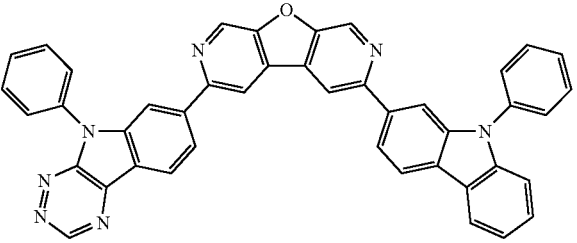
283
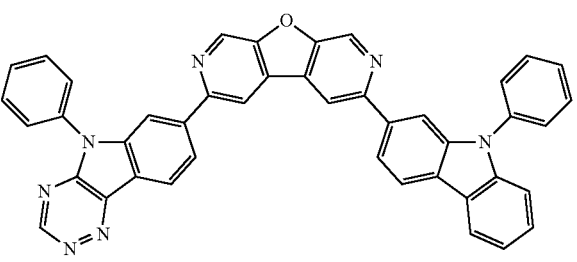
284
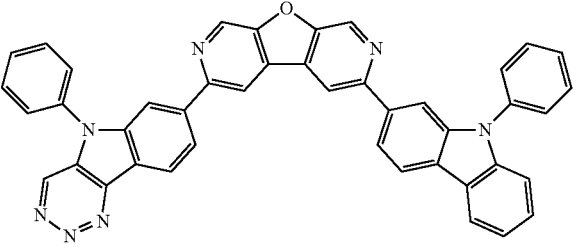

87
-continued
285
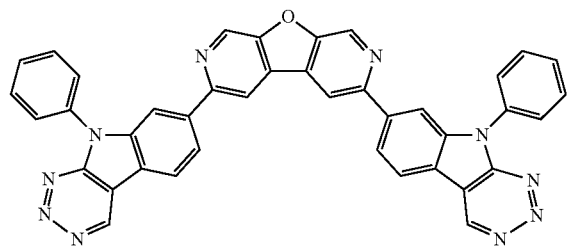
286
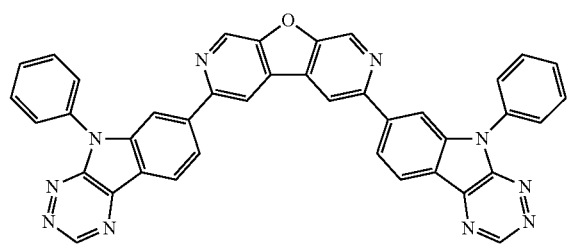
287
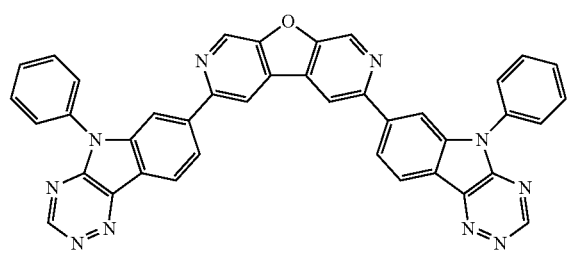
288
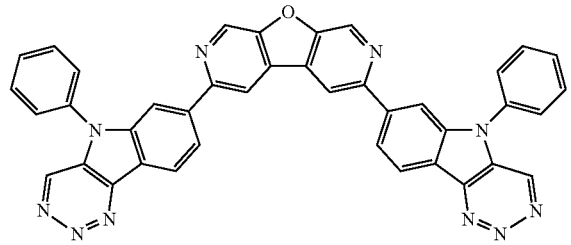
289
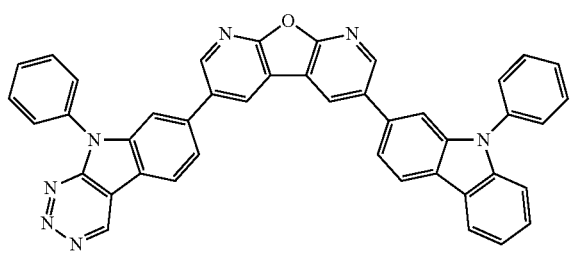
290
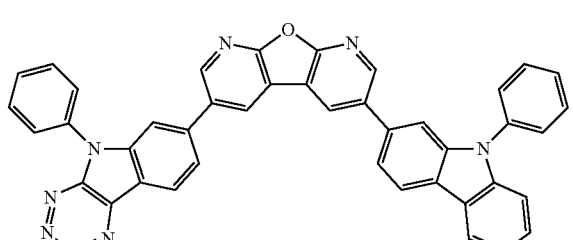
88
-continued
291
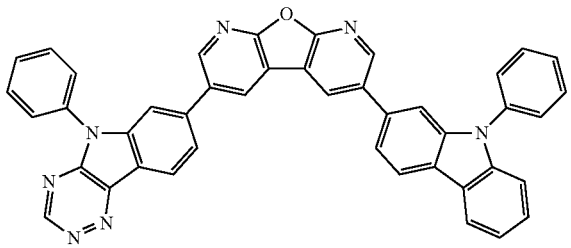
292
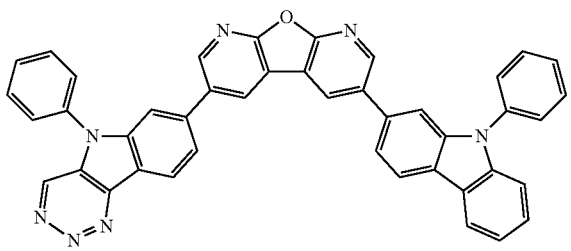
293
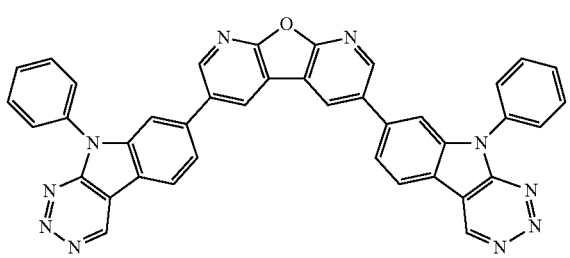
294
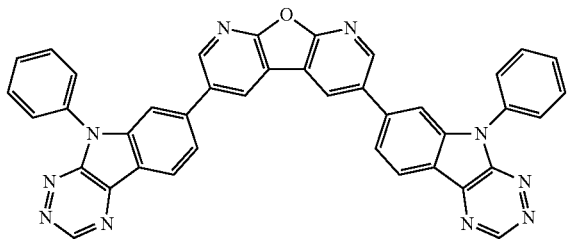
295
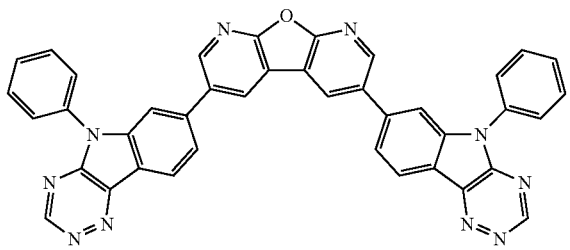
296
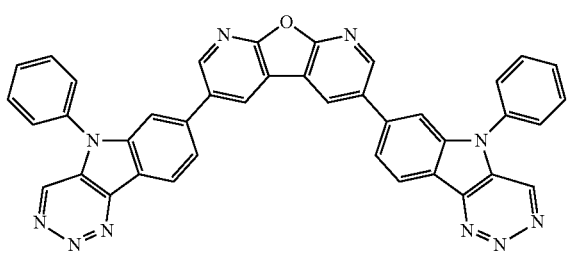

297
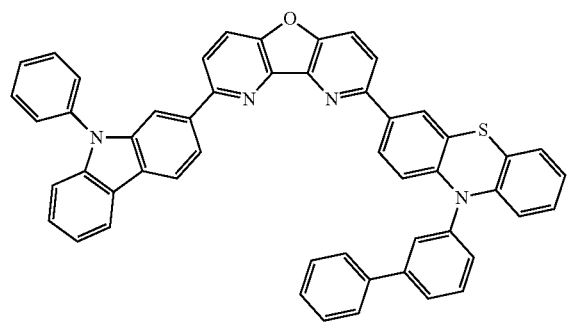
298
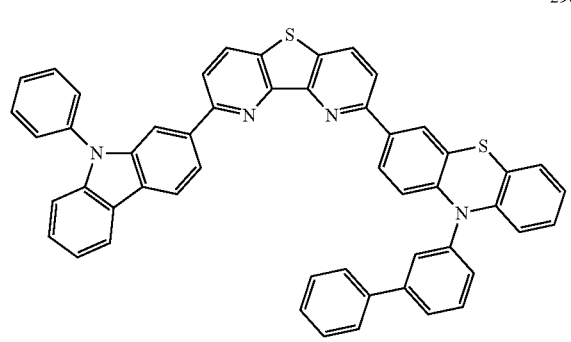
299
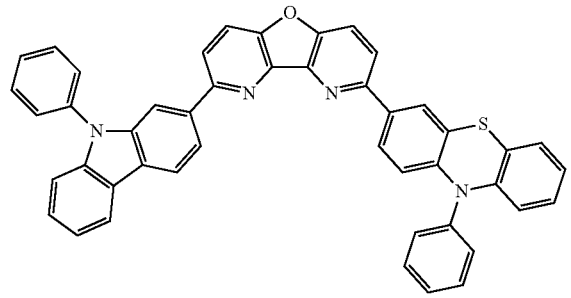
300
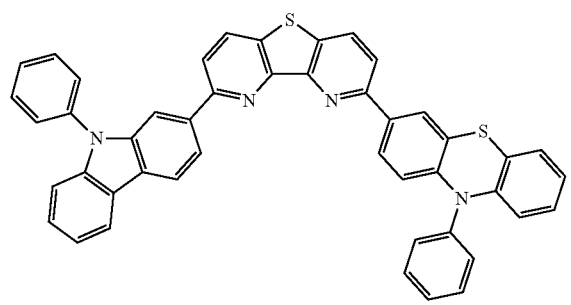
301
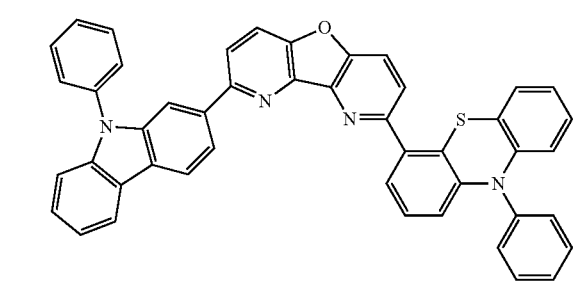
302
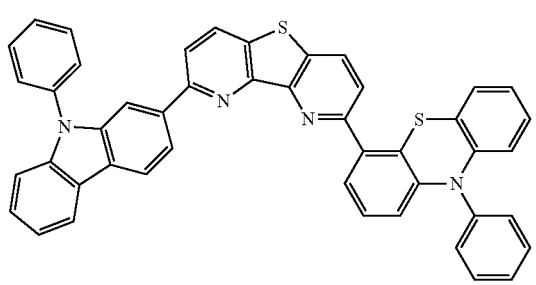
303
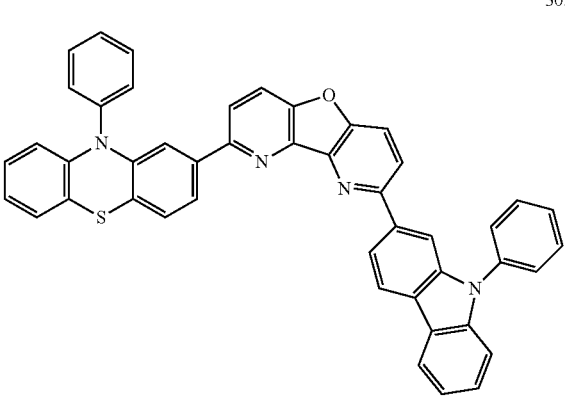
304
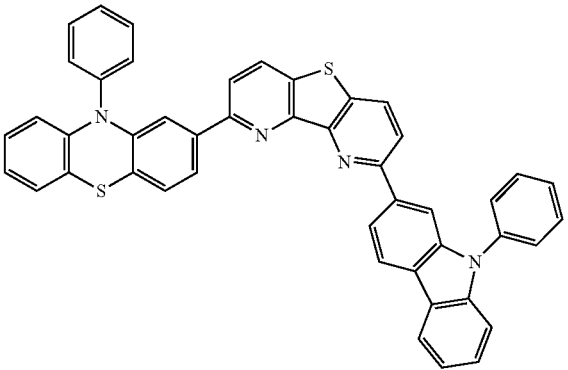
305
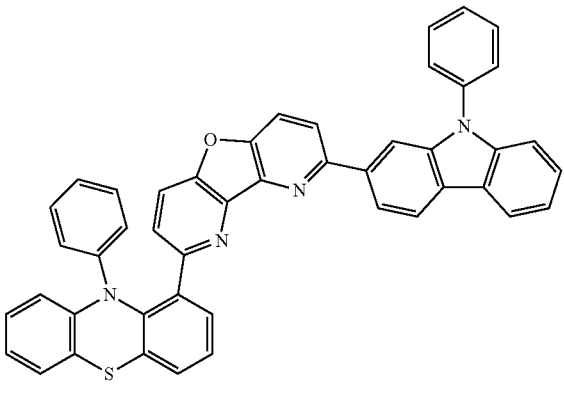

306

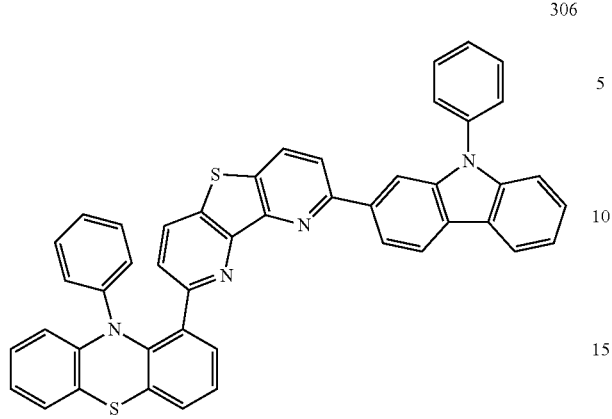

307

308

309

310

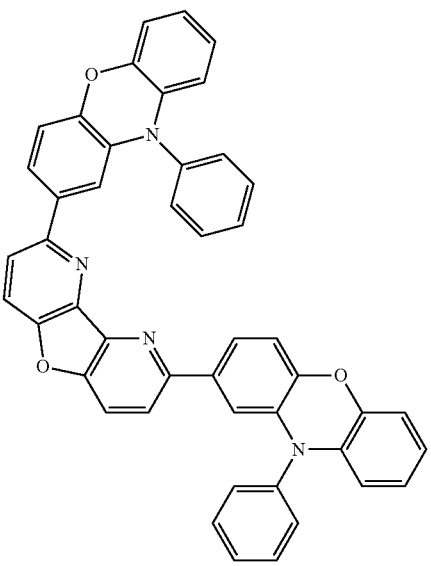

311

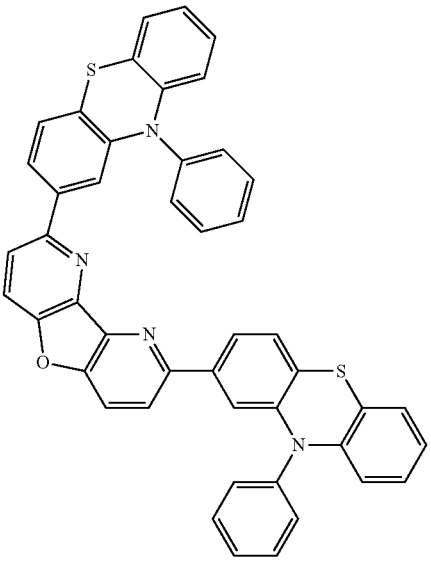

312

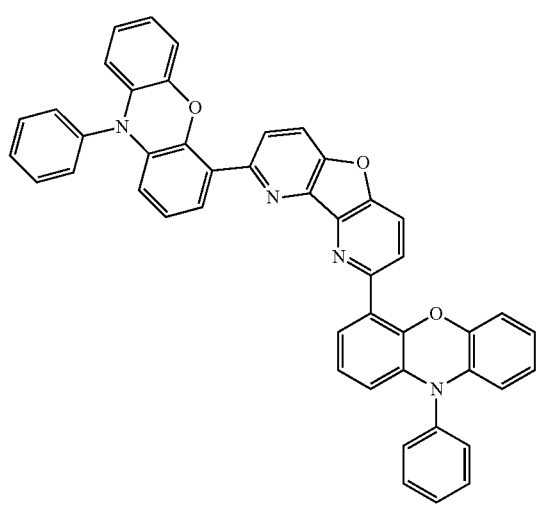

In Formula 1, $A_1$ may be a 6-membered ring including at least one nitrogen (N) as a ring-member atom, and $A_{11}$ may be a pyridine. That is, in Formula 1, $A_1$ may be a 6-membered ring including "at least one" nitrogen (N) as a ring-member atom, and $A_{11}$ may be a 6-membered ring including "one" nitrogen atom as a ring-member atom. Accordingly, the condensed cyclic compound of Formula 1 may have an improved electron transport ability, and thus form a bipolar structure which enables the whole molecule to transport both holes and electrons. Therefore, the condensed cyclic compound of Formula 1 may have improved electrical characteristics.

In the condensed cyclic compound of Formula 1, $XY_1$ and $XY_{11}$ may serve as hole transport units to enable the entire molecule to have a bipolar structure, and to improve thermal stability of the condensed cyclic compound.

In the condensed cyclic compound of Formula 1, i) $XY_1$ may be linked to $A_1$ via a "benzo ring" of the $XY_1$, and ii) $XY_{11}$ may be linked to $A_{11}$ via a "benzo ring" of the $XY_{11}$. Accordingly, the condensed cyclic compound of Formula 1 may have a high thermal decomposition temperature, and thus may have improved thermal stability.

For example, the condensed cyclic compound of Formula 1 may have a decomposition temperature higher than a sublimation temperature thereof at a vacuum level of about $10^{-8}$ torr to $10^{-3}$ torr. For example, the condensed cyclic compound of Formula 1 may have a decomposition temperature higher about 30° C. or greater than a sublimation temperature thereof at a vacuum level of about $10^{-8}$ torr to $10^{-3}$ torr. Thus, the condensed cyclic compound of Formula 1 may have improved process stability and improved film formation characteristics. Therefore, an organic light-emitting device including the condensed cyclic compound of Formula 1 may have improved stability during operation, and thus have a long lifetime.

In some embodiments, in the condensed cyclic compound of Formula 1, a gap between singlet ($S_1$) and triplet ($T_1$) energy levels may be about 0.3 electron volts (eV) or less. Therefore, the condensed cyclic compound of Formula 1 may be used as a thermally activated delayed fluorescence emitter, as described later.

Methods of synthesizing the condensed cyclic compound of Formula 1 may be understood by those of ordinary skill in the art based on the synthesis examples that will be described below.

The condensed cyclic compound of Formula 1 may be suitable for use as a material for an organic layer (for example, an emission layer) of an organic light-emitting device.

According to another embodiment of the present disclosure, an organic light-emitting device includes:

a first electrode, a second electrode disposed opposite to the first electrode, and an organic layer disposed between the first electrode and the second electrode, wherein the organic layer includes an emission layer and at least one of the condensed cyclic compounds of Formula 1.

Due to the presence of the organic layer including at least one of the condensed cyclic compounds of Formula 1, the organic light-emitting device may have a low driving voltage, a high efficiency, a high luminance, and a long lifetime.

At least one of the condensed cyclic compounds of Formula 1 may be disposed between a pair of electrodes of an organic light-emitting device. For example, the at least one of the condensed cyclic compounds of Formula 1 may be situated in one of the emission layer, a hole transport region disposed between the first electrode and the emission layer (for example, the hole transport region including at least one of a hole injection layer, a hole transport layer, and an electron blocking layer), and an electron transport region disposed between the emission layer and the second electrode (for example, the electron transport region including at least one of a hole blocking layer, an electron transport layer, and an electron injection layer). For example, the at least one of the condensed cyclic compounds of Formula 1 may be present in the emission layer.

In some embodiments, the emission layer may include the at least one of the condensed cyclic compounds of Formula 1, and may further include an organometallic compound. An amount of the at least one of the condensed cyclic compounds is greater than an amount of the organometallic compound. In this case, the at least one of the condensed cyclic compounds of Formula 1 may serve as a host, and the organometallic compound may serve as a dopant.

In some other embodiments, the at least one of the condensed cyclic compounds of Formula 1 present in the emission layer may serve as a thermally activated delayed fluorescence (TADF) emitter.

Excitons are generated upon recombination of electrons injected from the cathode and holes injected from the anode. This recombination of injected electrons and holes is called an excited state. Two spins of the excitons may be oriented in the opposite directions (spin 0, or singlet ($S_1$)) or may be oriented in the same direction (spin 1, or triplet ($T_1$)). Intersystem crossing (ISO) from $S_1$ to a triplet manifold ($T_1$ or a higher level than $T_1$) may be followed by second ISO from $T_1$ to $S_1$, resulting in fluorescence. This process is known as TADF mechanism. In other words, a TADF emitter refers to a material able to emit fluorescence through several times of repetition of the cycle $S_1 \rightarrow T_1 \rightarrow S_1$. The TADF emitter is a material able to emit fluorescent light via triplet state with an emission efficiency equivalent to the efficiency of a phosphorescent emitting material.

The condensed cyclic compound of Formula 1 may have a small gap of about 0.3 electron volt (eV) or less between $S_1$ (singlet) energy and $T_1$ (triplet) energy levels, and thus may emit fluorescence based on the TADF mechanism as described above. Thus, the at least one of the condensed cyclic compounds of Formula 1 in the emission layer may serve as a TADF emitter. The emission layer may include the at least one of the condensed cyclic compounds of Formula 1 only, or may further include a host, in addition to the at least one of the condensed cyclic compounds of Formula 1. The host may be any host that may be used in an emission layer of an organic light-emitting device.

As used herein, "(for example, the organic layer) including at least one condensed cyclic compound means that "(the organic layer) including one of the condensed cyclic compounds of Formula 1 above, or at least two different condensed cyclic compounds of Formula 1 above".

For example, the organic layer of the organic light-emitting device may include only Compound 1 as the condensed cyclic compound. For example, Compound 1 may be included in the EML of the organic light-emitting device. In some embodiments, the organic layer of the organic light-emitting device may include Compounds 1 and 2 as the condensed cyclic compound. For example, Compounds 1 and 2 may be included in the same layer (for example, in the EML) or in different layers.

The first electrode may be an anode as a hole injection electrode, and the second electrode may be a cathode as an electron injection electrode. In some embodiments, the first electrode may be a cathode as an electron injection electrode, and the second electrode may be a cathode as a hole injection electrode.

For example, the first electrode may be an anode, the second electrode may be a cathode, and the organic layer may include:

i) a hole transport region disposed between the first electrode and the emission layer, wherein the hole transport region includes at least one of a hole injection layer, a hole transport layer, and an electron blocking layer; and ii) an electron transport region disposed between the emission layer and the second electrode, wherein the electron transport region includes at least one of a hole blocking layer, an electron transport layer, and an electron injection layer.

The term "organic layer" as used herein refers to a single layer and/or a plurality of layers disposed between the first and second electrodes of the organic light-emitting device. The "organic layer" may include, for example, an organic compound or an organometallic complex including a metal.

FIG. 1 is a schematic view of an organic light-emitting device 10 according to an embodiment of the present disclosure. Hereinafter, a structure of an organic light-emitting device according to an embodiment of the present disclosure and a method of manufacturing the same will now be described with reference to FIG. 1. Referring to FIG. 1, the organic light-emitting device 10 has a structure in which a first electrode 11, an organic layer 15, and a second electrode 19 are sequentially stacked in this order.

A substrate (not shown) may be disposed under the first electrode 11 or on the second electrode 19 in FIG. 1. The substrate may be any substrate that is used in conventional organic light emitting devices. In some embodiments, the substrate may be a glass substrate or a transparent plastic substrate with strong mechanical strength, thermal stability, transparency, surface smoothness, ease of handling, and water resistance.

The first electrode 11 may be formed by depositing or sputtering a first electrode-forming material on the substrate 11. The first electrode 11 may be an anode. A material having a high work function may be selected as a material for the first electrode to facilitate hole injection. The first electrode 11 may be a reflective electrode, a semi-transmissive electrode, or a transmissive electrode. For example, the material for the first electrode 11 may be indium tin oxide (ITO), indium zinc oxide (IZO), tin oxide ($SnO_2$), or zinc oxide (ZnO). In some embodiments, the material for the first electrode 13 may be a metal, for example, magnesium (Mg), aluminum (Al), aluminum-lithium (Al—Li), calcium (Ca), magnesium-indium (Mg—In), magnesium-silver (Mg—Ag), or the like.

The first electrode 11 may have a single-layer structure or a multi-layer structure including at least two layers.

The organic layer 15 may be disposed on the first electrode 11.

The organic layer 15 may include at least one a hole transport region; an EML, and an electron transport region.

The hole transport region may be disposed between the first electrode 11 and the EML.

The hole transport region may include at least one of a hole injection layer (HIL), a hole transport layer (HTL), an electron blocking layer (EBL), and a buffer layer.

The hole transport region may include exclusively the HIL or the HTL. In some embodiments, the hole transport region may have a structure including a HIL/HTL or a HIL/HTL/EBL, wherein the layers forming the structure of the hole transport region may be sequentially stacked on the first electrode 11 in the stated order.

When the hole transport region includes the HIL, the HIL may be formed on the first electrode 11 by any of a variety of methods, for example, vacuum deposition, spin coating, casting, Langmuir-Blodgett (LB) deposition, or the like.

When the HIL is formed using vacuum deposition, vacuum deposition conditions may vary depending on the material that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Angstroms per second (A/sec). However, the deposition conditions are not limited thereto.

When the HIL is formed using spin coating, the coating conditions may vary depending on the material that is used to form the HIL, and the desired structure and thermal properties of the HIL to be formed. For example, the coating rate may be in the range of about 2,000 revolutions per minute (rpm) to about 5,000 rpm, and a temperature at which heat treatment is performed to remove a solvent after coating may be in a range of about 80° C. to about 200° C. However, the coating conditions are not limited thereto.

Conditions for forming the HTL and the EBL may be the same as those for the HIL described above.

In some embodiments, the hole transport region may include at least one of m-MTDATA, TDATA, 2-TNATA, NPB, 8-NPB, TPD, Spiro-TPD, Spiro-NPB, methylated NPB, TAPC, HMTPD, 4,4',4''-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201 below, and a compound represented by Formula 202 below.

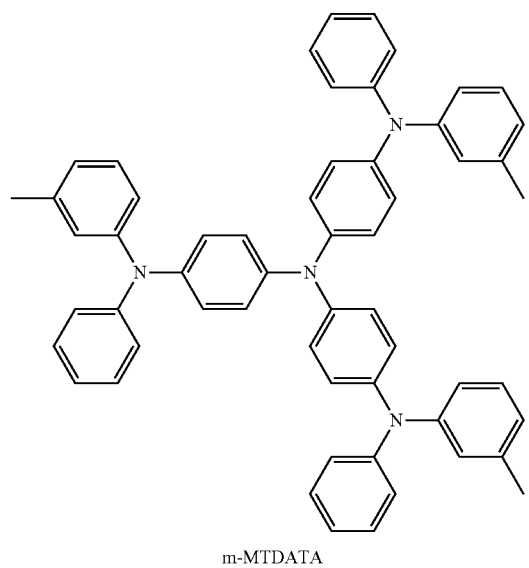

m-MTDATA

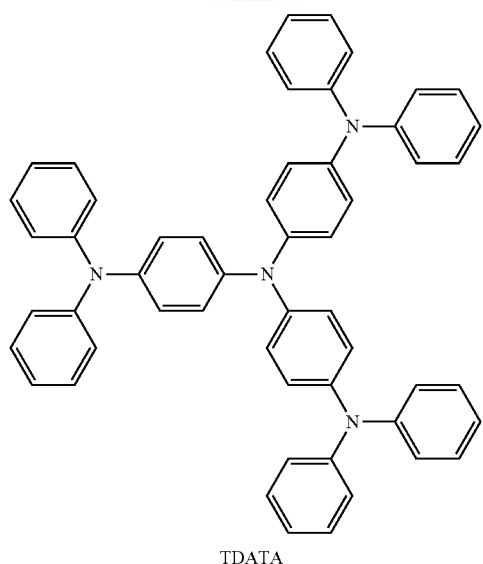
TDATA
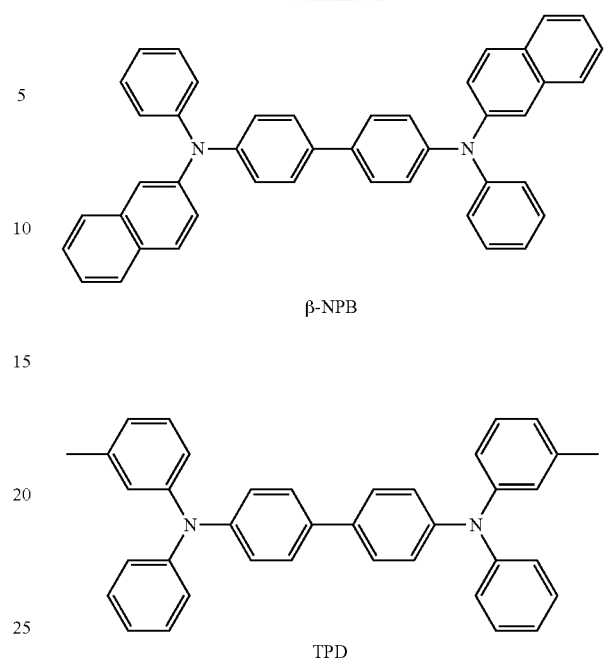
β-NPB
TPD
Spiro-TPD
Spiro-NPD
2-TNATA
NPB
methylated NPB

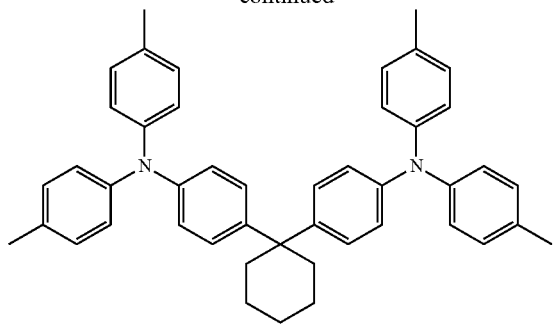

TAPC

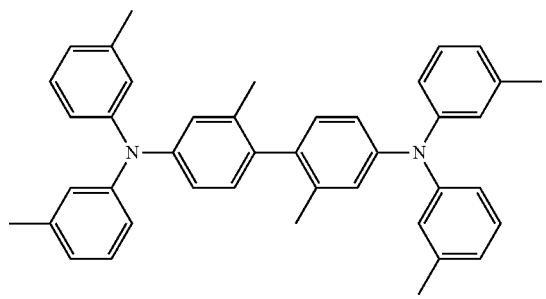

HMTPD

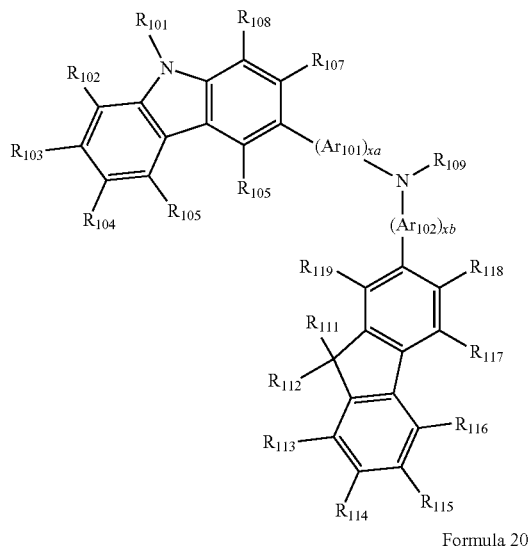

Formula 201

Formula 202

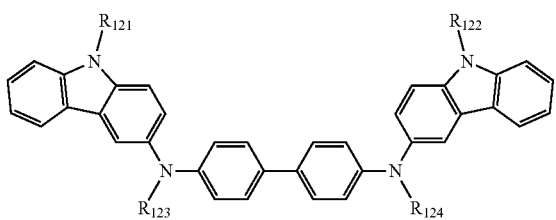

In Formula 201 above, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, or a pentacenylene group, and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, or a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may be each independently an integer from 0 to 5, for example, may be 0, 1, or 2. For example, xa may be 1, and xb may be 0, but are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, or the like), and a $C_1$-$C_{10}$ alkoxy group (for example, a methoxy group, an ethoxy group, a propoxy group, a butoxy group, a pentoxy group, or the like), a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a naphthyl group, an anthracenyl group, a fluorenyl group, and a pyrenyl group, and a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group. However, embodiments of the present disclosure are not limited thereto.

In Formula 201 above, $R_{109}$ may be selected from
a phenyl group, a naphthyl group, an anthracenyl group, and a pyridinyl group, and
a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

In some embodiments, the compound of Formula 201 may be a compound represented by Formula 201A, but is not limited thereto:

Formula 201A

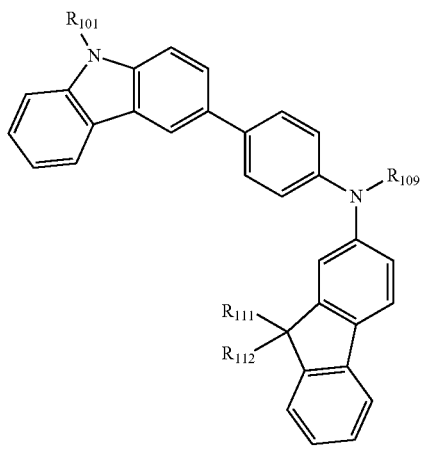

In Formula 201A, $R_{101}$, $R_{111}$, $R_{112}$, and $R_{109}$ may be the same as those defined above.

For example, the compound of Formula 201 and the compound of Formula 202 may be Compounds HT1 to HT20 below, but are not limited thereto:

HT1

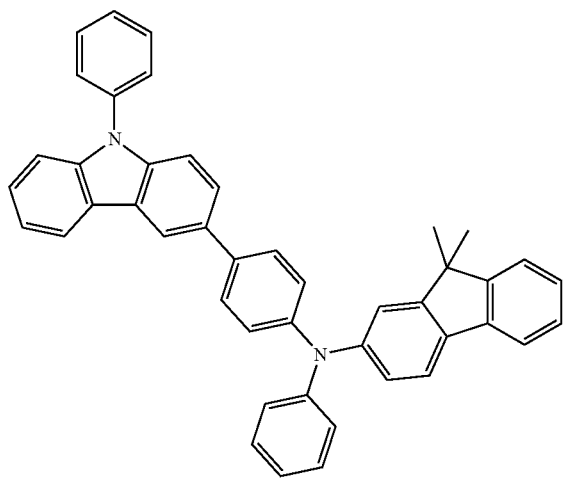

HT2

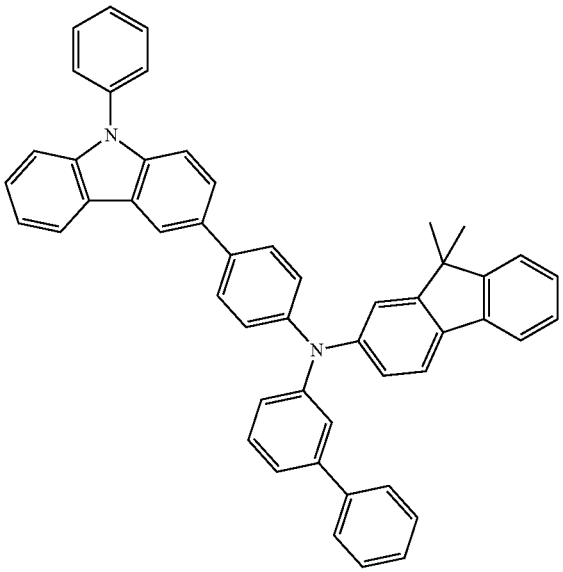

HT3

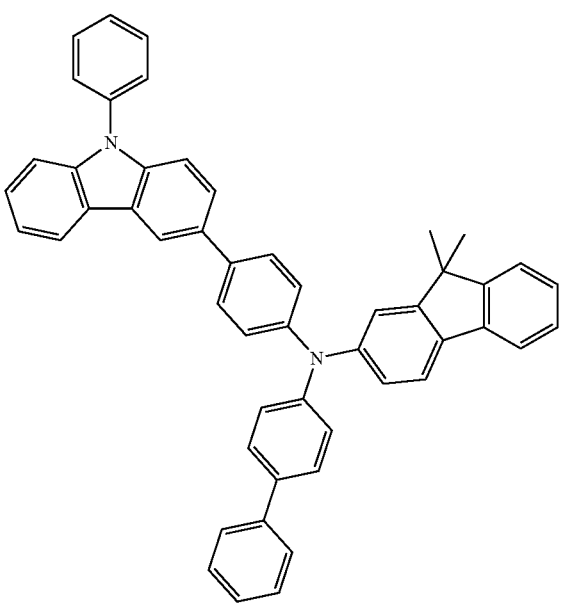

HT4
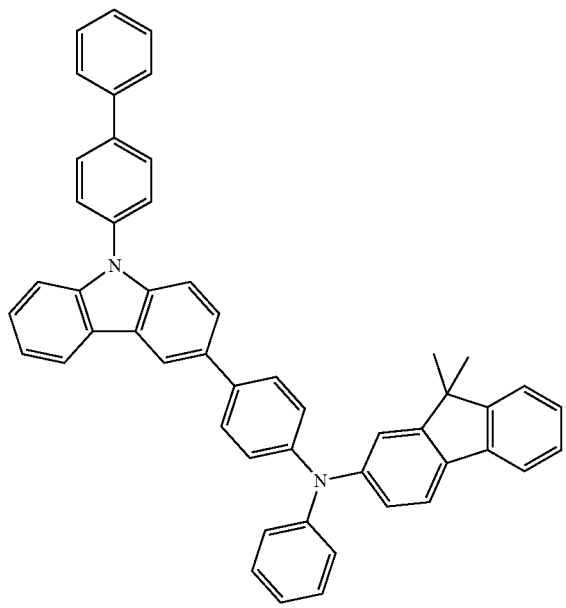
HT5
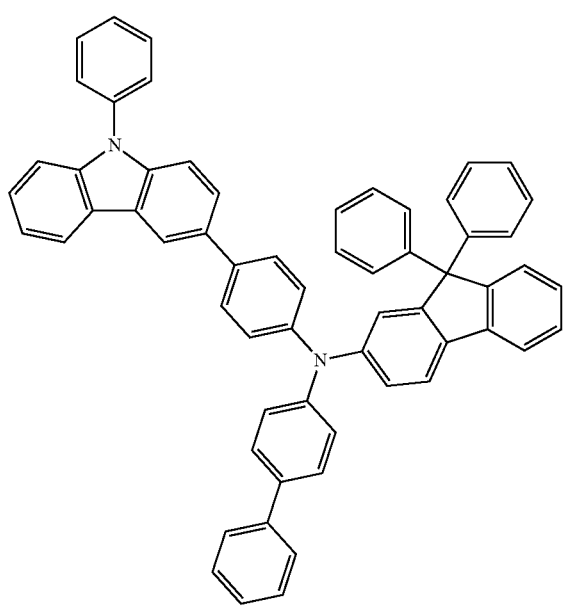
HT6
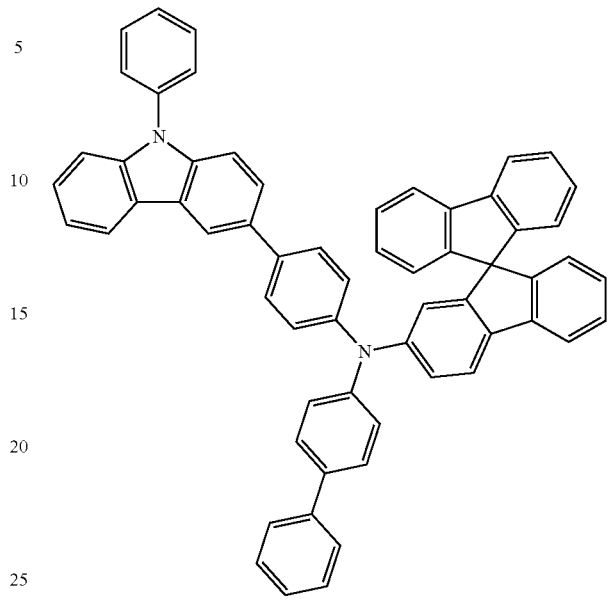
HT7
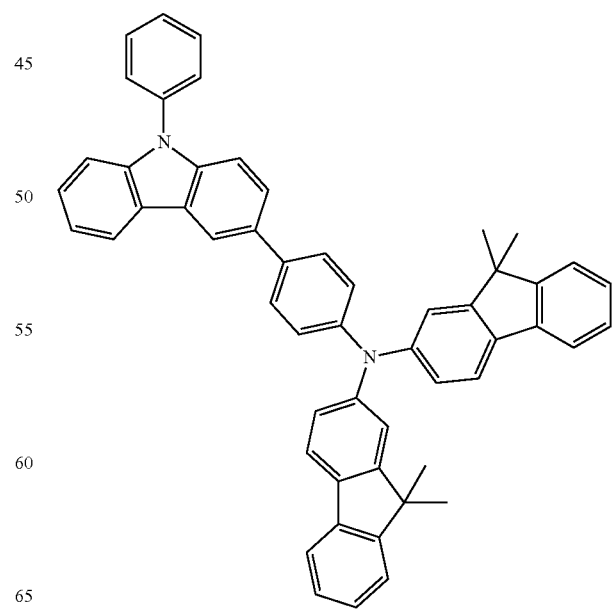

HT8
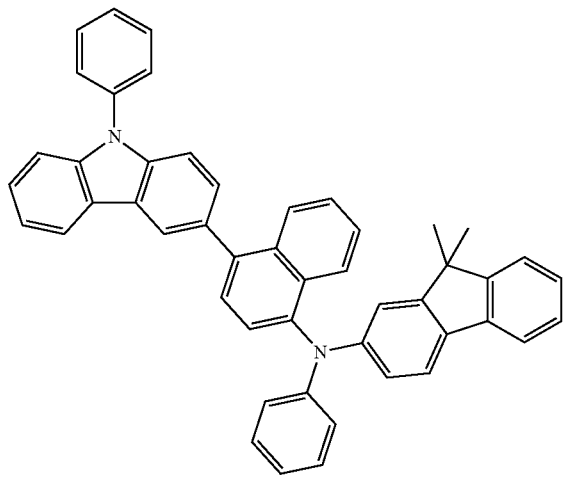
HT10
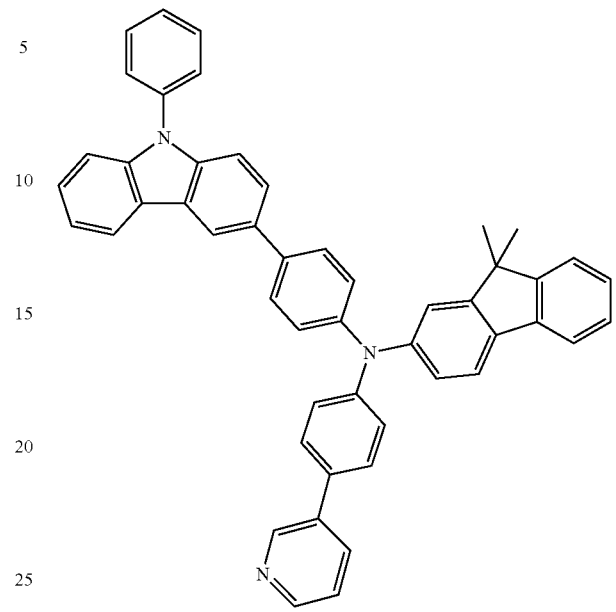
HT9
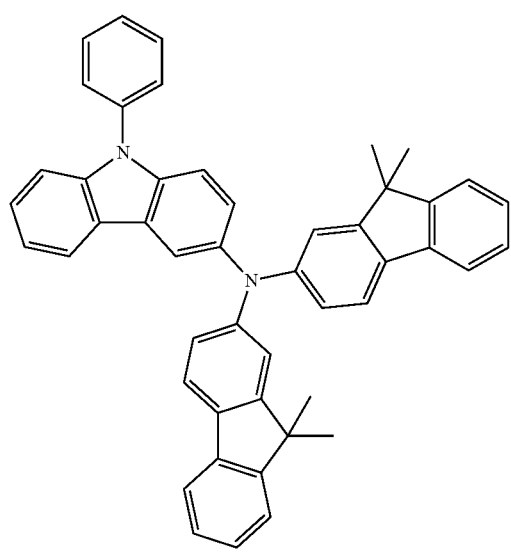
HT11
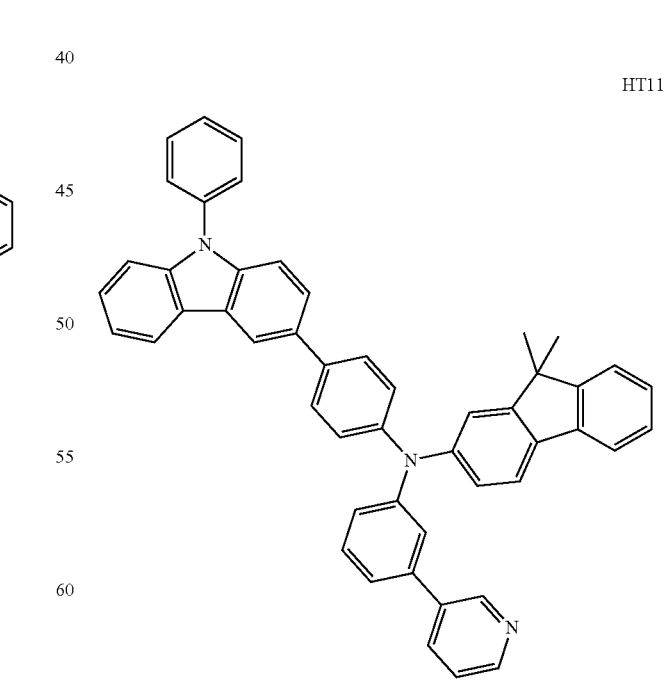

HT12
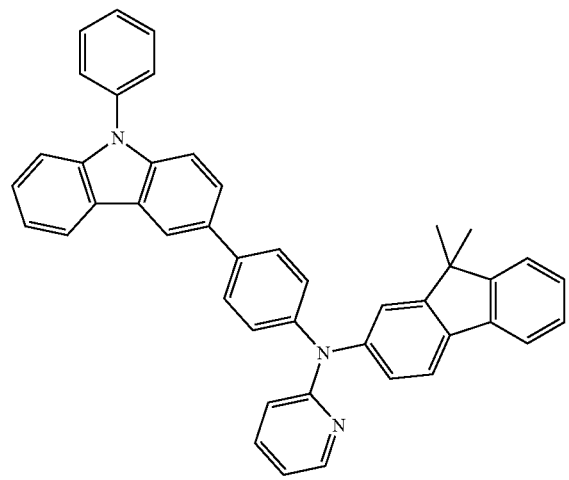
HT13
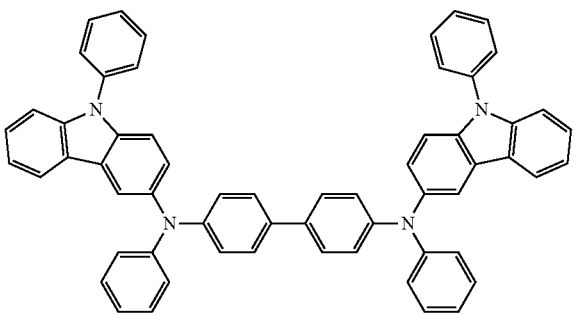
HT14
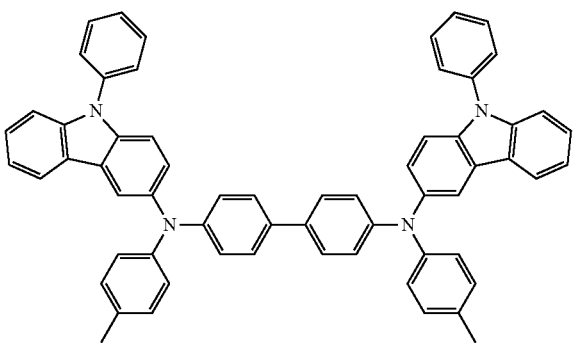
HT15
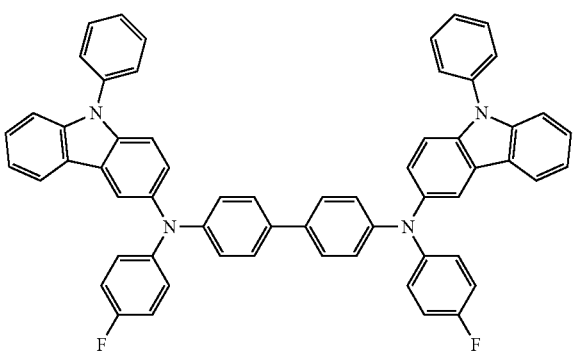
HT16
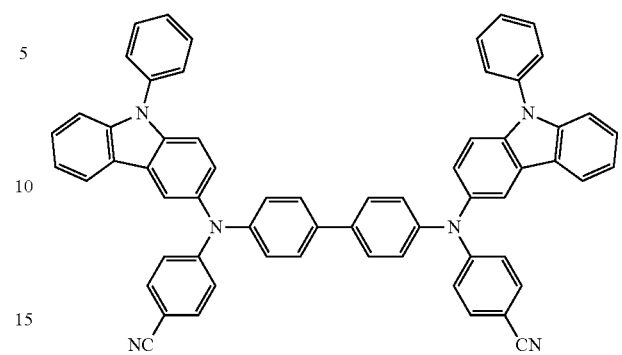
HT17
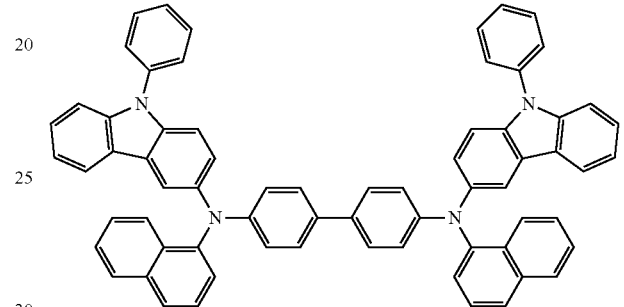
HT18
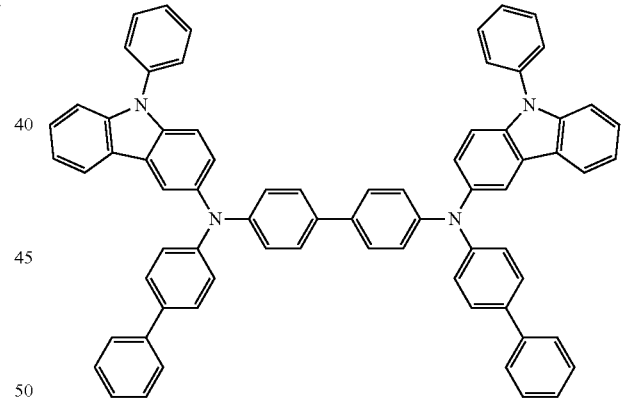
HT19
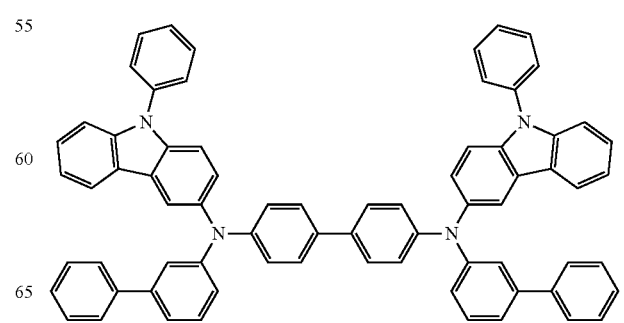

HT20

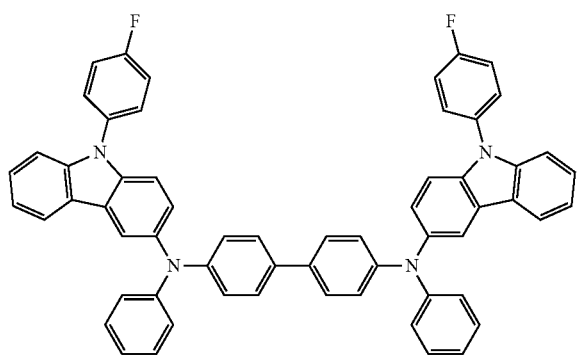

A thickness of the hole transport region may be from about 100 Angstrom (Å) to about 10,000 Å, and in some embodiments, from about 100 Å to about 1,000 Å. When the hole transport region includes a HIL and a HTL, a thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinone derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds Compound HT-D1.

Compound HT-D1

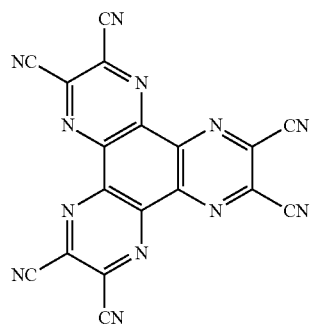

F4-TCNQ

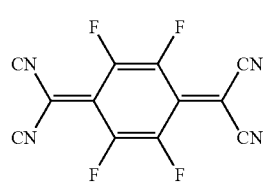

The hole transport region may further include a buffer layer.

The buffer layer may compensate for an optical resonance distance of light depending on a wavelength of the light emitted from the EML, and thus may increase efficiency.

The EML may be formed on the hole transport region by using vacuum deposition, spin coating, casting, LB deposition, or the like. When the EML is formed using vacuum deposition or spin coating, the conditions for deposition and coating may be similar to those for the formation of the HIL, though the conditions for the deposition and coating may vary depending on the material that is used to form the EML.

When the organic light-emitting device is a full color organic light-emitting device, the emission layer may be patterned into a red emission layer, a green emission layer, and a blue emission layer. In some embodiments, the EML may have a stack structure including a red emission layer, a green emission layer, and/or a blue emission layer that are stacked upon one another to emit white light, but is not limited thereto.

The EML may include at least one of the condensed cyclic compounds of Formula 1 only. In this case, the at least one of the condensed cyclic compounds of Formula 1 may serve as a TADF emitter.

In some other embodiments, the emission layer may include a host and a dopant. The host may include at least one of the condensed cyclic compounds of Formula 1, and the dopant may be any suitable dopant that may be used in an EML of an organic light-emitting device. For example, the dopant may include an organometallic compound including a transition metal, for example, iridium (Ir), platinum (Pt), osmium (Os), or rhodium (Rh).

In some embodiments, the dopant may be an organometallic compound represented by Formula 81:

Formula 81

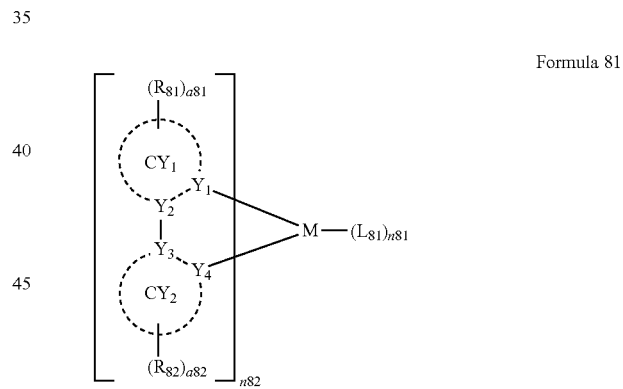

In Formula 81,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ may be each independently a carbon (C) or a nitrogen (N);

$CY_1$ and $CY_2$ may be each independently selected from benzene, naphthalene, fluorene, spiro-fluorene, indene, pyrrole, thiophene, furan, imidazole, pyrazole, thiazole, isothiazole, oxazole, isooxazole, pyridine, pyrazine, pyrimidine, pyridazine, quinoline, isoquinoline, benzoquinoline, quinoxaline, quinazoline, carbazole, benzoimidazole, benzofuran, benzothiophene, isobenzothiophene, benzooxazole, isobenzooxazole, triazole, tetrazole, oxadiazole, triazine, dibenzofuran, and dibenzothiophene, wherein $CY_1$ and $CY_2$ may be optionally linked to each other via a single bond or an organic linking group;

$R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), or —B(Q$_6$)(Q$_7$);

a81 and a82 may be each independently an integer selected from 1 to 5;

n81 may be an integer selected from 0 to 4;

n82 may be 1, 2, or 3;

L$_{81}$ may be selected from a monovalent organic ligand, a divalent organic ligand, and a trivalent organic ligand; and a bond between Y$_1$ and Y$_2$, and a bond between Y$_3$ and Y$_4$ may be each independently a single bond or a double bond.

For example, the phosphorescent dopant may include at least one of Compounds PD1 to PD74, but is not limited thereto. Compound PD1 is Ir(ppy)$_3$.

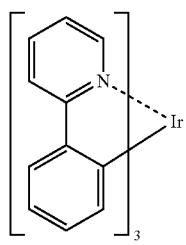

PD1

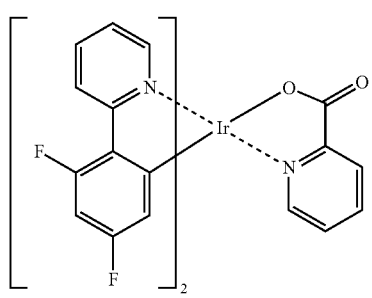

PD2

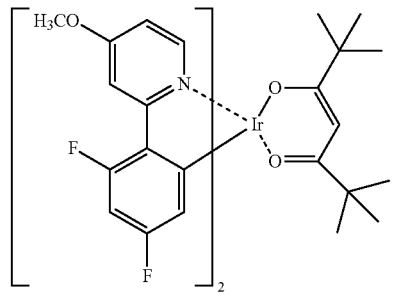

PD3

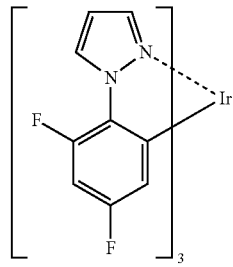

PD4

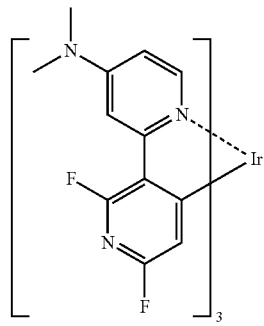

PD5

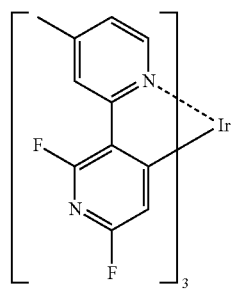

PD6

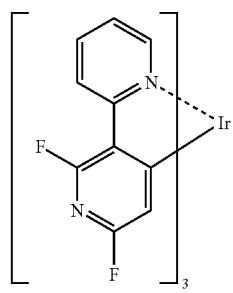

PD7

-continued
PD8
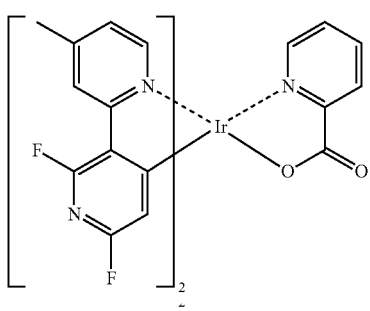
PD9
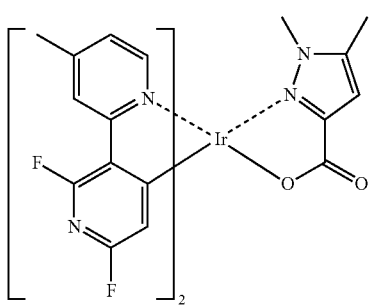
PD10
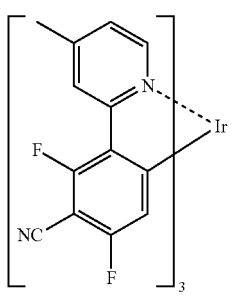
PD11
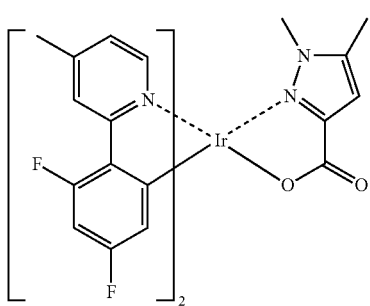
PD12
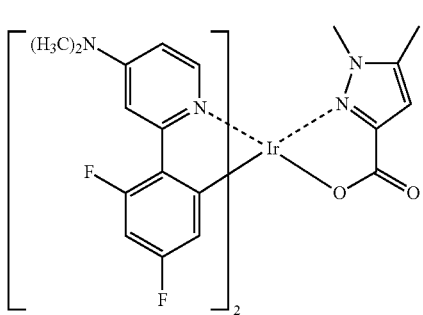
-continued
PD13
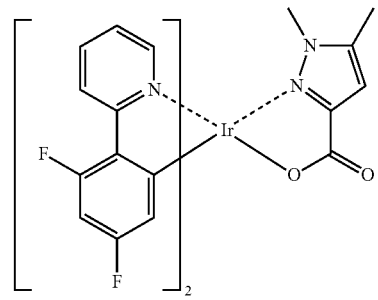
PD14
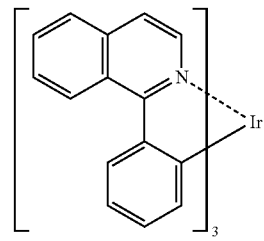
PD15
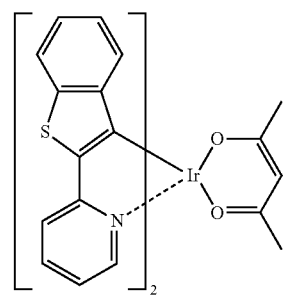
PD16
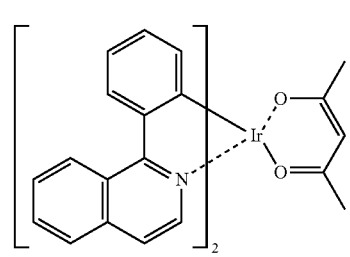
PD17
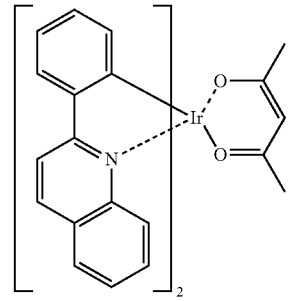

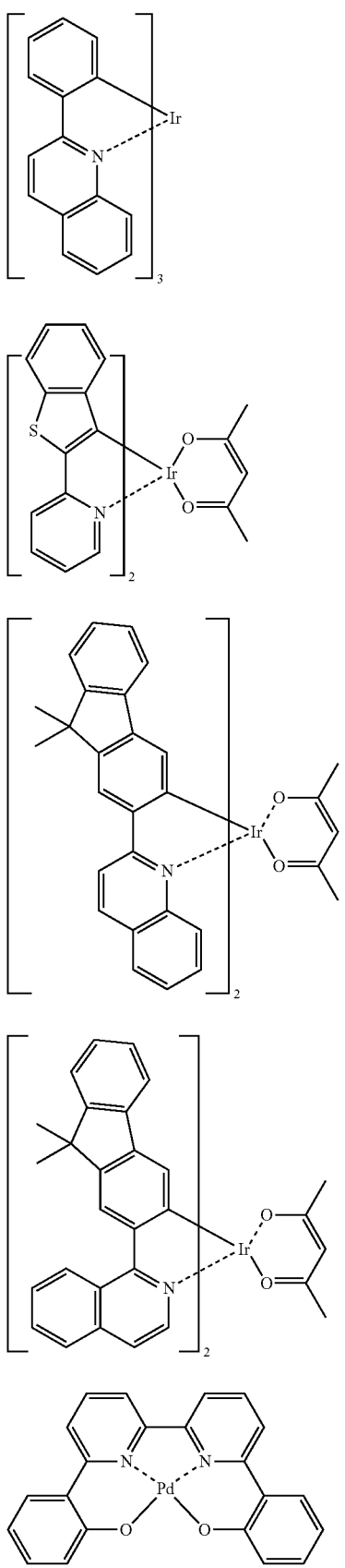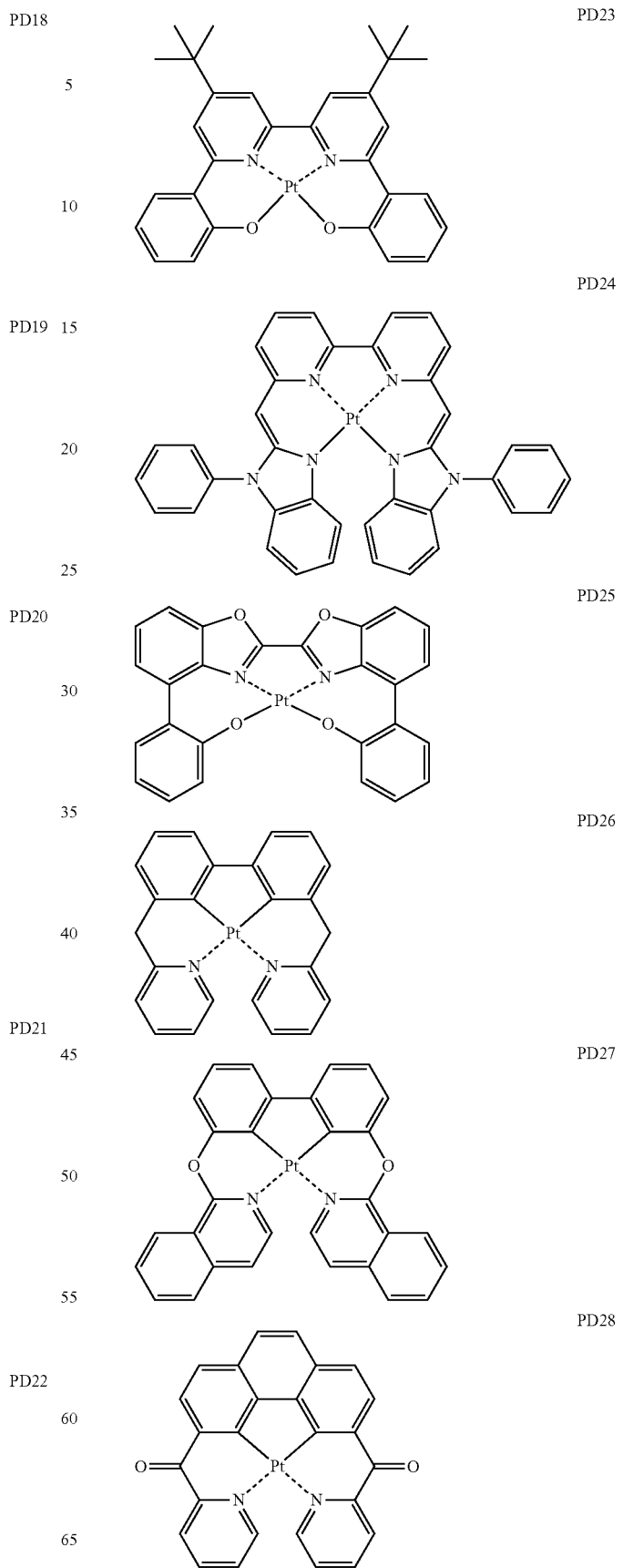

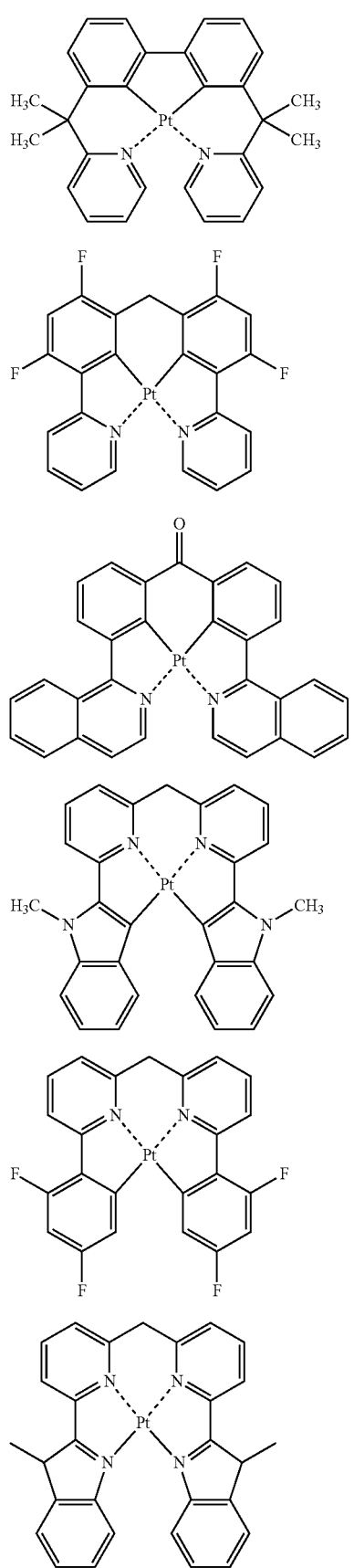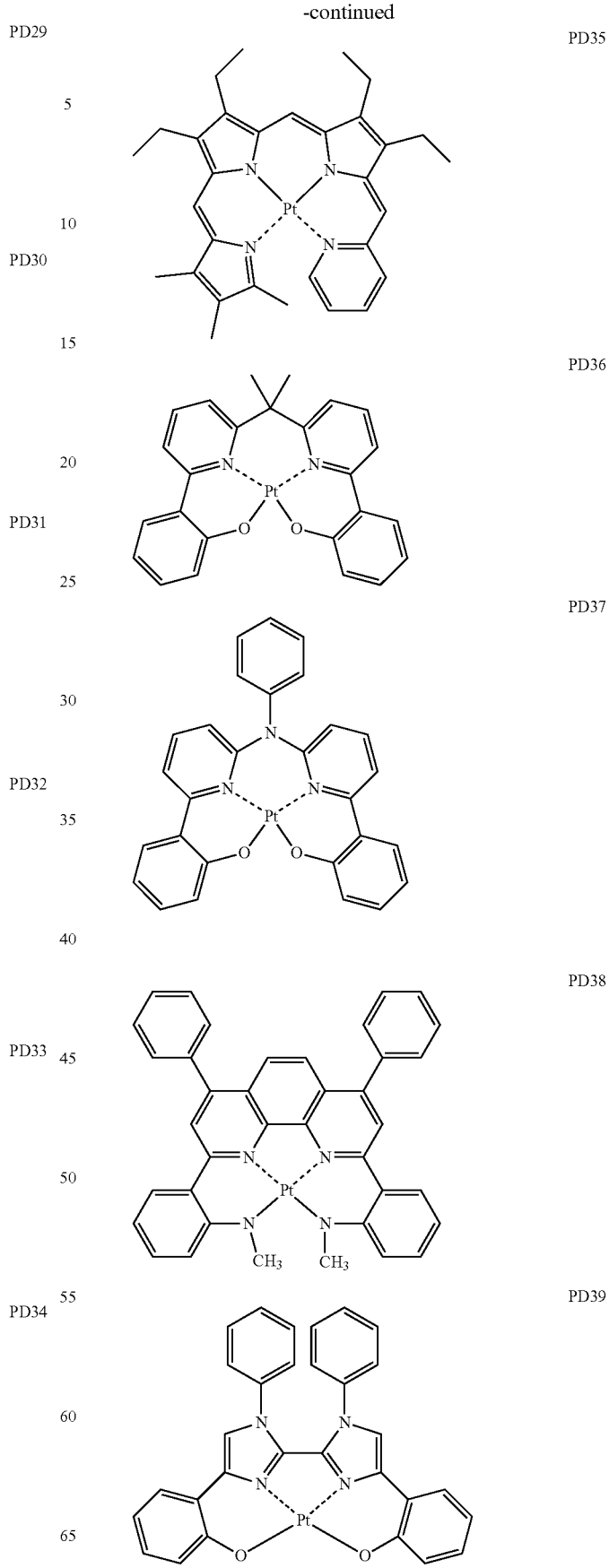

PD40
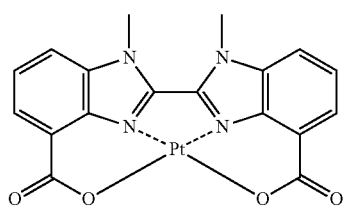
PD41
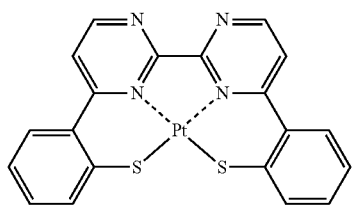
PD42
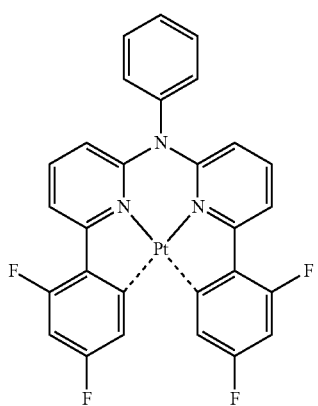
PD43
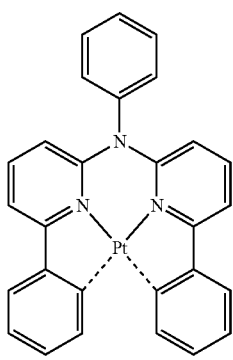
PD44
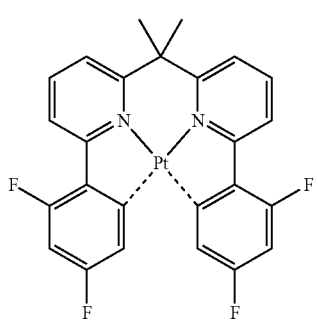
PD45
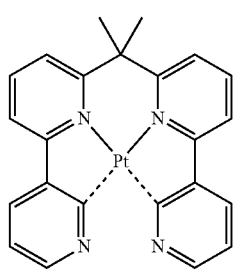
PD46
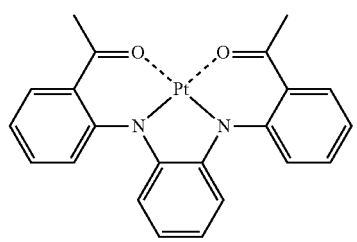
PD47
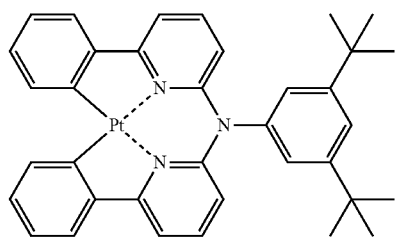
PD48
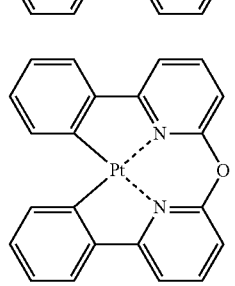
PD49
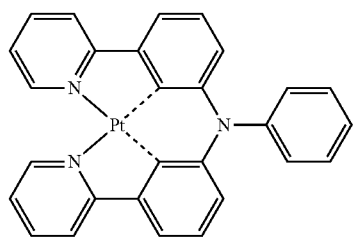
PD50
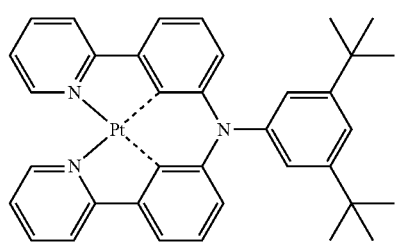

PD51 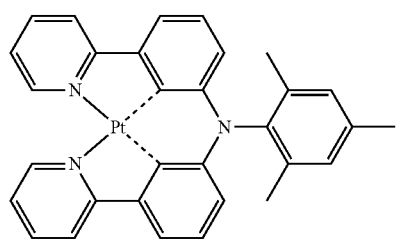
PD57 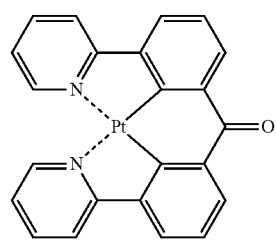
PD52 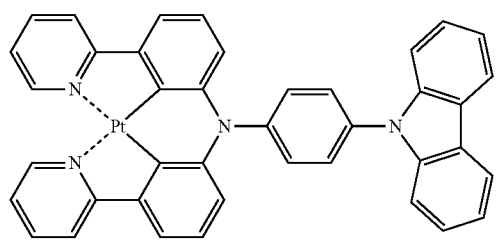
PD58 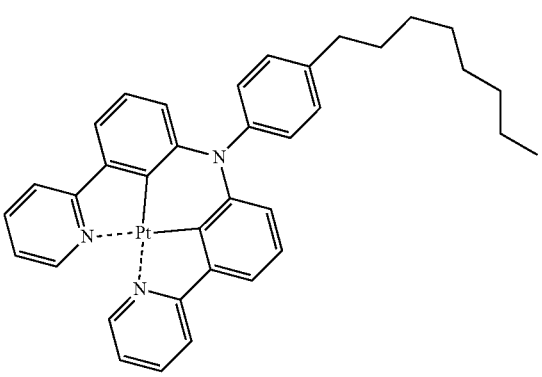
PD53 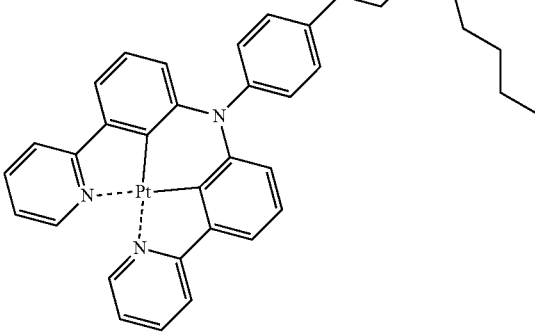
PD54 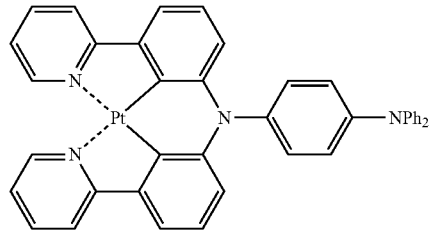
PD59 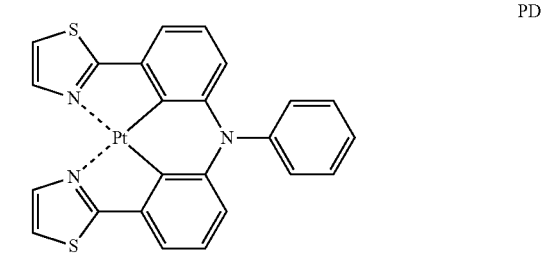
PD55 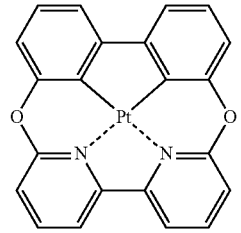
PD60 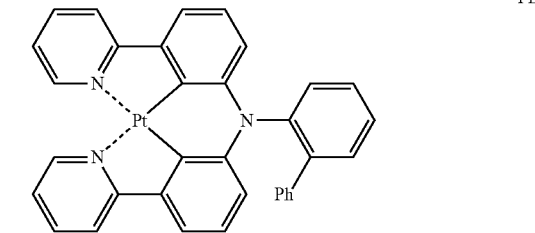
PD56 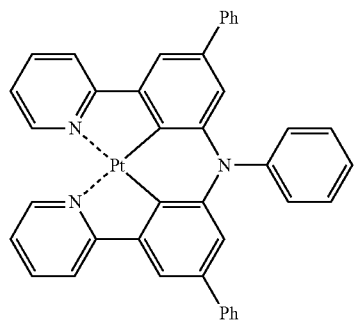
PD61 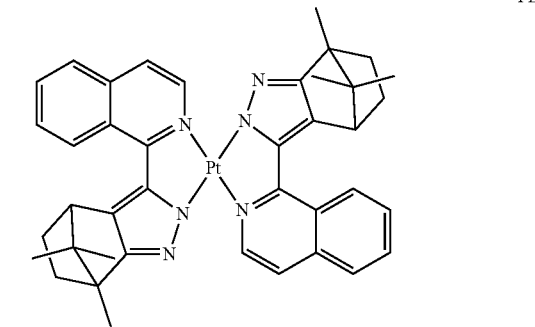

-continued
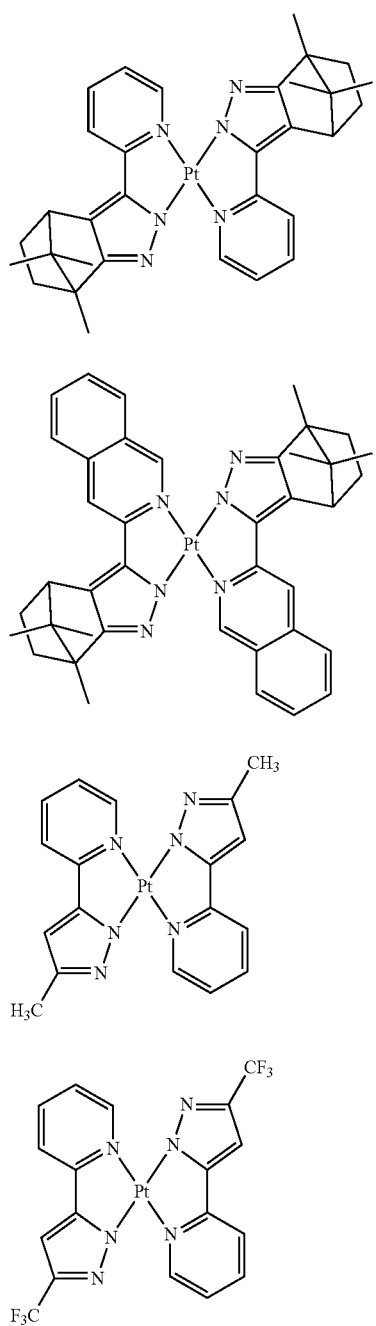
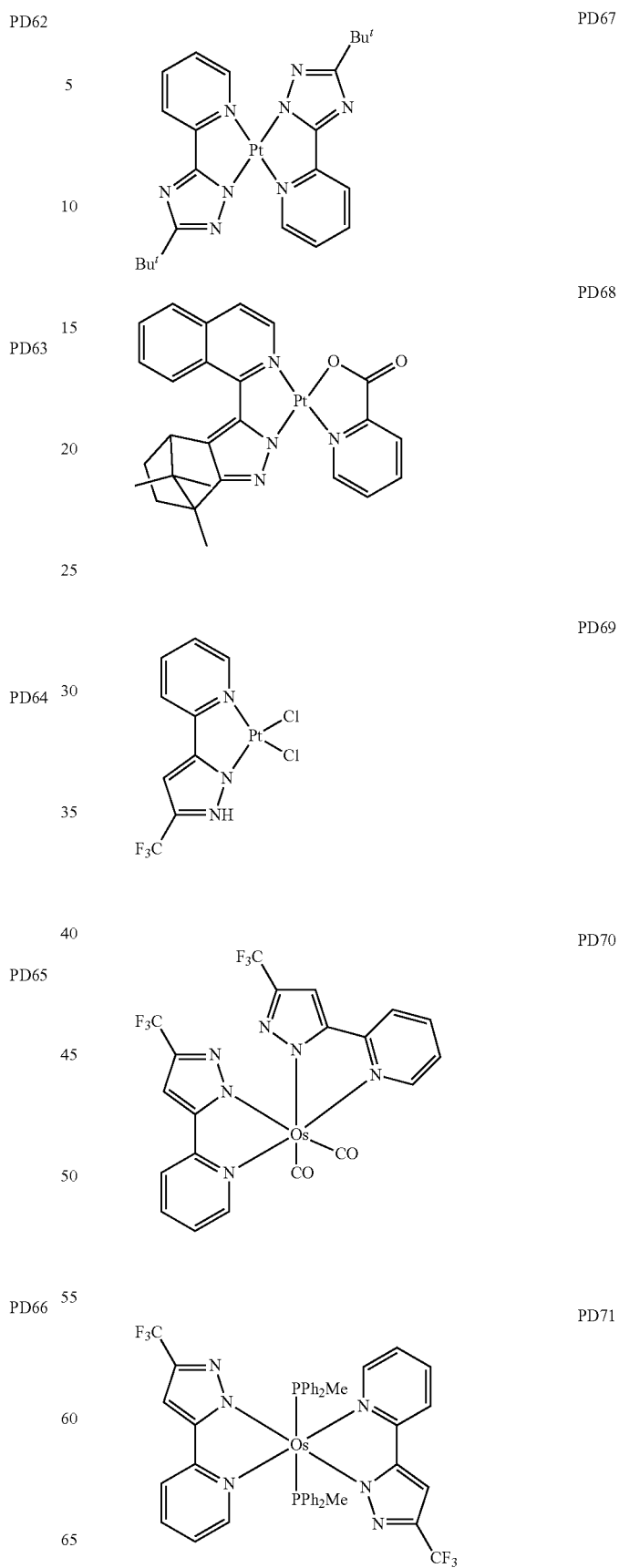

PD72

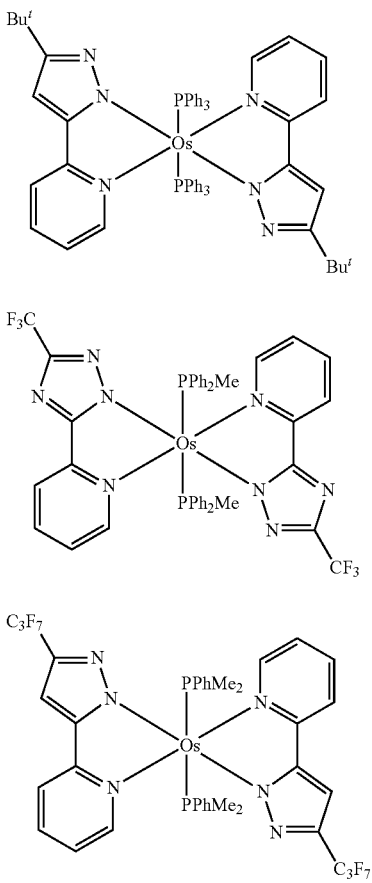

PD73

PD74

In some embodiments, the phosphorescent dopant may include PtOEP or PhGD:

PtOEP

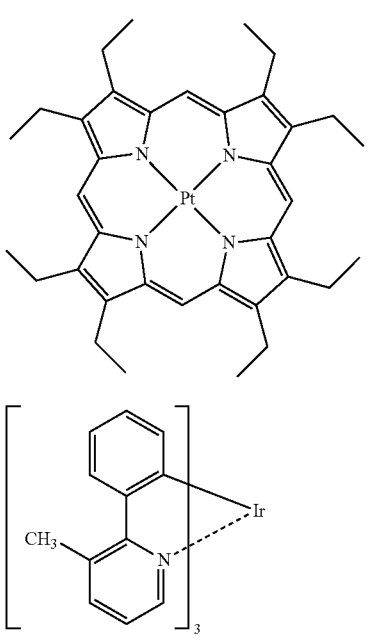

PhGD

In some other embodiments, the EML may include a host and a dopant. The dopant may be the at least one of the condensed cyclic compound of Formula 1, and the host may be any suitable host that may be used in an emission layer of an organic light-emitting device. In this case, the condensed cyclic compound of Formula 1 may serve as a TADF emitter. The host may be selected from an anthracene host, a carbazole host, an indolocarbazole host, and a pyrene host. However, embodiments of the present disclosure are not limited thereto.

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1,000 Å, and in some embodiments, may be from about 200 Å to about 600 Å. When the thickness of the EML is within these ranges, the EML may have improved light emitting ability without a substantial increase in driving voltage.

Next, the electron transport region may be disposed on the EML.

The electron transport region may include at least one of a HBL, an ETL, and an EIL.

In some embodiments, the electron transport region may have a structure including a HBL/ETL/EIL, or an ETL/EIL, wherein the layers forming the structure of the electron transport region may be sequentially stacked on the EML in the stated order. However, embodiments of the present disclosure are not limited thereto. The ETL may have a single-layer structure or a multi-layer structure including at least two different materials.

Conditions for forming the HBL, ETL, and EIL of the electron transport region may be defined based on the above-described formation conditions for the HIL.

When the electron transport region includes an HBL, the HBL may include at least one of BCP, Bphen, and BAlq. However, embodiments of the present disclosure are not limited thereto.

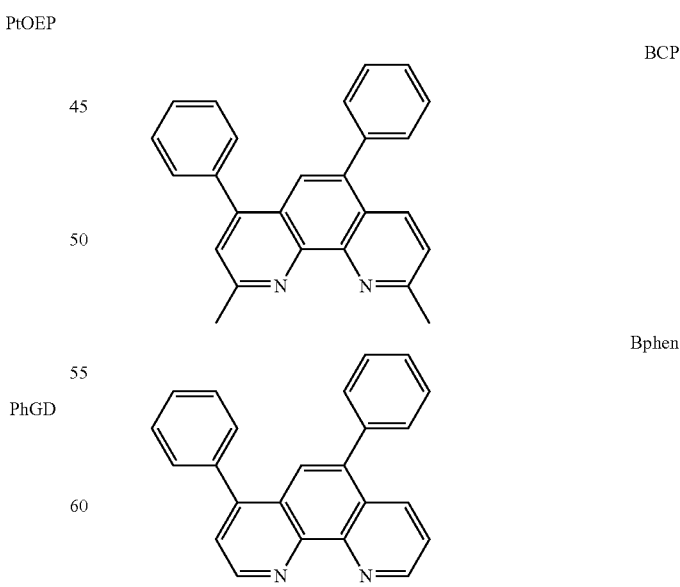

The thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The ETL may further include at least one of Alq$_3$, Balq, TAZ, NTAZ, BCP, and Bphen.

Alq$_3$

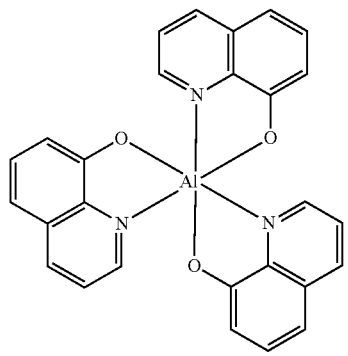

BAlq

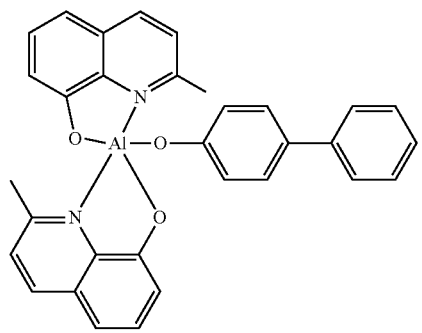

TAZ

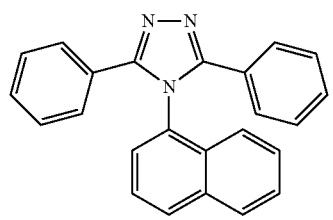

NTAZ

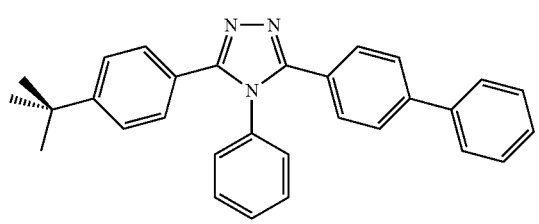

In some embodiments, the ETL may include at least one of Compounds ET1 and ET2 represented below, but is not limited thereto.

ET1

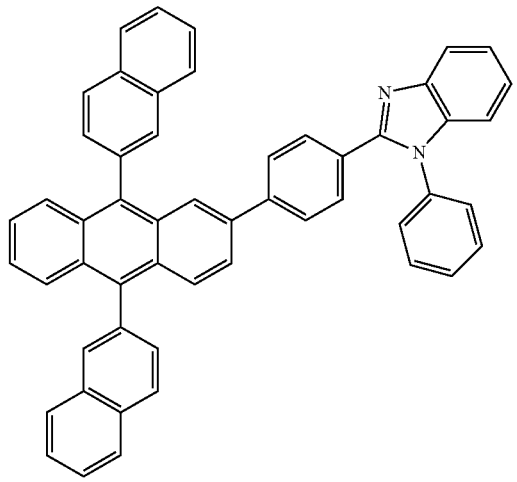

ET2

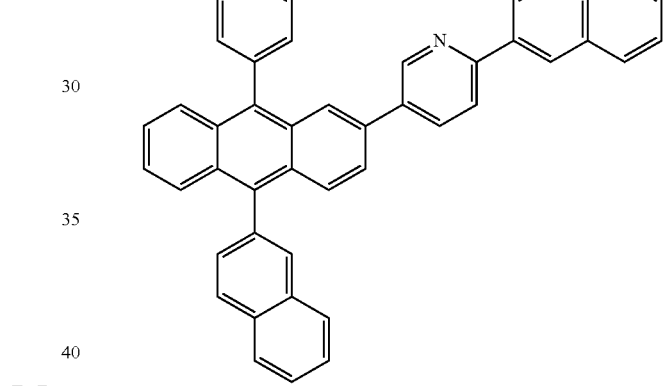

A thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex are compound ET-D1 (lithium quinolate (LiQ)), or compound ET-D2.

ET-D1

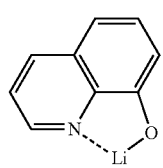

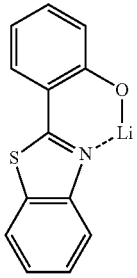

ET-D2

The electron transport region may include an EIL that may facilitate injection of electrons from the second electrode 19. The EIL may include at least one selected from LiF, NaCl, CsF, $Li_2O$, and BaO. The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

The second electrode 19 is disposed on the organic layer 15. The second electrode 19 may be a cathode. A material for the second electrode 19 may be a metal, an alloy, or an electrically conductive compound that have a low work function, or a combination thereof. Non-limiting examples of the material for the second electrode 19 are lithium (Li), magnesium (Mg), aluminum (Al), aluminum (AD-lithium (Li), calcium (Ca), magnesium (Mg)-indium (In), and magnesium (Mg)-silver (Ag), or the like. In some embodiments, to manufacture a top-emission light-emitting device, the second electrode 19 may be formed as a transmissive electrode from, for example, indium tin oxide (ITO) or indium zinc oxide (IZO).

Although the organic light-emitting device of FIG. 1 is described above, embodiments of the present disclosure are not limited thereto.

As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group a methyl group, an ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$ alkyl group as described above. Non-limiting examples of the $C_1$-$C_{60}$ alkoxy group are a methoxy group, an ethoxy group, and an isopropyloxy group.

As used herein, a $C_2$-$C_{60}$ alkenyl group refers to a structure including at least one carbon double bond in the middle or at the terminal of the $C_2$-$C_{60}$ alkyl group. Non-limiting examples of the $C_2$-$C_{60}$ alkenyl group are an ethenyl group, a propenyl group, and a butenyl group. A $C_2$-$C_{60}$ alkylene group refers to a divalent group having the same structure as the $C_2$-$C_{60}$ alkenyl group.

As used herein, a $C_2$-$C_{60}$ alkynyl group refers to a structure including at least one carbon triple bond in the middle or at the terminal of the $C_2$-$C_{60}$ alkyl group. Non-limiting examples of the $C_2$-$C_{60}$ alkynyl group are an ethynyl group and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_2$-$C_{10}$ heterocycloalkyl group refers to a monovalent monocyclic group having 2 to 10 carbon atoms in which at least one hetero atom selected from N, O, P, and S is included as a ring-forming atom. Non-limiting examples of the $C_2$-$C_{10}$ heterocycloalkyl group are a tetrahydrofuranyl group and a tetrahydrothiophenyl group. A $C_2$-$C_{10}$ heterocycloalkylene group refers to a divalent group having the same structure as the $C_2$-$C_{10}$ heterocycloalkyl group.

As used herein, a $C_3$-$C_{10}$ cycloalkenyl group refers to a monovalent monocyclic group having 3 to 10 carbon atoms that includes at least one double bond in the ring but does not have aromaticity. Non-limiting examples of the $C_3$-$C_{10}$ cycloalkenyl group are a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_2$-$C_{10}$ heterocycloalkenyl group used herein refers to a monovalent monocyclic group having 2 to 10 carbon atoms that includes at least one double bond in the ring and in which at least one hetero atom selected from N, O, P, and S is included as a ring-forming atom. Non-limiting examples of the $C_2$-$C_{10}$ heterocycloalkenyl group are a 2,3-dihydrofuranyl group and a 2,3-dihydrothiophenyl group. A $C_2$-$C_{10}$ heterocycloalkenylene group used herein refers to a divalent group having the same structure as the $C_3$-$C_{10}$ heterocycloalkenyl group.

As used herein, a $C_6$-$C_{60}$ aryl group refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include at least two rings, the rings may be fused to each other.

As used herein, a $C_2$-$C_{60}$ heteroaryl group refers to a monovalent, aromatic carbocyclic aromatic group having 2 to 60 carbon atoms in which at least one hetero atom selected from N, O, P, and S is included as a ring-forming atom, and 2 to 60 carbon atoms. A $C_2$-$C_{60}$ heteroarylene group refers to a divalent, aromatic carbocyclic group having 2 to 60 carbon atoms in which at least one hetero atom selected from N, O, P, and S is included as a ring-forming atom. Non-limiting examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl and the $C_2$-$C_{60}$ heteroarylene include at least two rings, the rings may be fused to each other.

As used herein, a $C_6$-$C_{60}$ aryloxy group indicates —$OA_{102}$ (where $A_{102}$ is a $C_6$-$C_{60}$ aryl group as described above), and a $C_6$-$C_{60}$ arylthio group indicates —$SA_{103}$ (where $A_{103}$ is a $C_6$-$C_{60}$ aryl group as described above).

As used herein, a monovalent non-aromatic condensed polycyclic group refers to a monovalent group having at least two rings condensed to each other, in which only carbon atoms (for example, 8 to 60 carbon atoms) are exclusively included as ring-forming atoms, wherein the entire molecule is non-aromatic. A non-limiting example of the monovalent non-aromatic condensed polycyclic group is a fluorenyl group. A divalent non-aromatic condensed polycyclic group refers to a divalent group having the same structure as the monovalent non-aromatic condensed polycyclic group.

As used herein, at least one of substituents of the substituted $C_1$-$C_6$ alkylene group, the substituted $C_2$-$C_6$ alkenylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_2$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_1$)($Q_2$), —Si($Q_3$)($Q_4$)($Q_5$), and —B($Q_6$)($Q_7$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

For example, at least one of substituents of the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclooctyl group, a cyclopentenyl group a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group;

a cyclopentyl group, a cyclohexyl group, a cycloheptyl group, a cyclooctyl group, a cyclopentenyl group a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, monovalent non-aromatic condensed polycyclic group, monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclooctyl group, a cyclopentenyl group a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group. However, embodiments of the present disclosure are not limited thereto.

One or more embodiments of the present disclosure, which include condensed cyclic compounds, and organic light-emitting devices including the same, will now be described in detail with reference to the following examples. However, these examples are only for illustrative purposes and are not intended to limit the scope of the one or more embodiments of the present disclosure. In the following synthesis examples, the expression that "'B' instead of 'A' was used" means that the amounts of 'B' and 'A' were the same in equivalent amounts.

EXAMPLES

Synthesis Example 1

Compound 1 was synthesized according to the following reaction scheme:

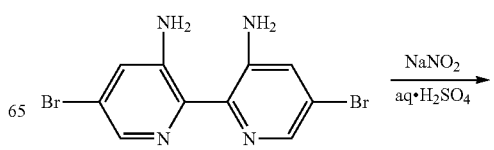

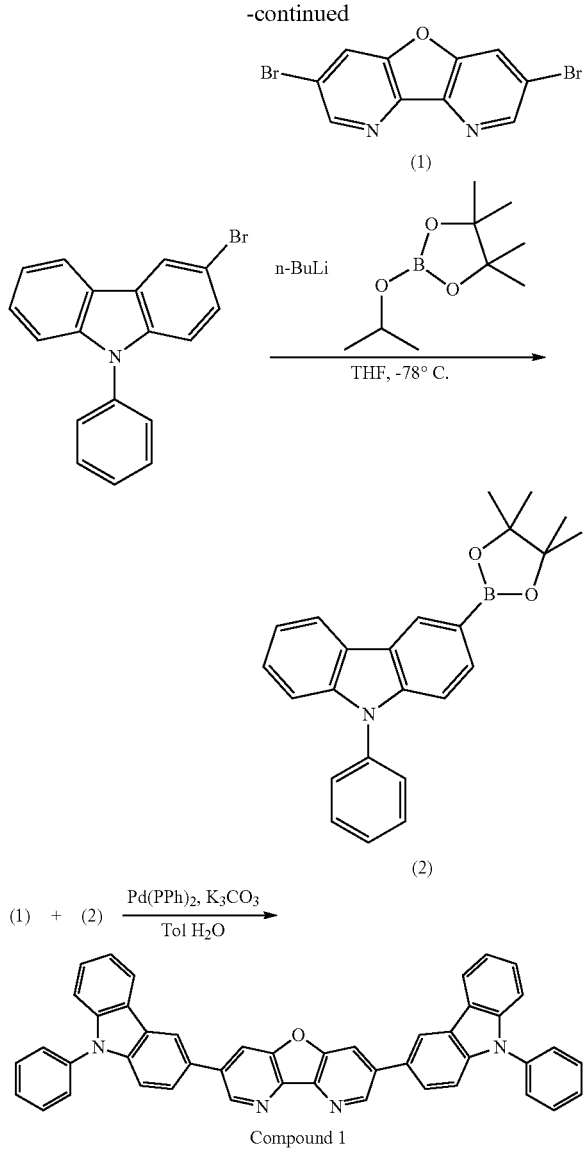

Compound 1

Synthesis of Intermediate (1)

A mixture of 10.0 g (29.1 mmol) of 3,3'-diamino-5,5'-dibromo-2,2'-bipyridyl with a 80% formic acid was slowly dropwise added to a solution of 3.0 g (43.5 mmol) of sodium nitrite dissolved in conc. sulfuric acid while maintaining the temperature at about 0° C. to about 5° C., and stirred for about 30 minutes, followed by a temperature increase to about 90° C. and then stirring at about 90° C. for about 30 minutes. After a resulting reaction product was cooled down to room temperature, water was added thereto, followed by extraction under alkali conditions, and removing water with magnesium sulfate ($MgSO_4$). A resulting product was filtered under a reduced pressure to obtain a filtrate, which was then concentrated under a reduced pressure, followed by separation using silica gel column chromatography to obtain 2.9 g of Intermediate (1) (Yield: 30%).

LC-Mass (calcd.: 327.96 g/mol. found: M+1=329 g/mol).

Synthesis of Intermediate (2)

After a mixed solution of 10 g (31.0 mmol) of 3-bromo-9-phenyl-9H-carbazole with anhydrous tetrahydrofuran (THF) was cooled down to −78° C., about 3 equivalents of n-butyllithium (n-BuLi) was slowly dropwise added thereto and stirred at −78° C. for about 2 hours. Then, about 3 equivalents of 2-isopropoxy-4,4,5,5-tetramethyl-[1,3,2]-dioxaborolane was dropwise added to the solution and stirred at room temperature overnight. A resulting product was extracted with an organic solvent, followed by removing water with magnesium sulfate ($MgSO_4$) and filtration through a filter under a reduced pressure to obtain a filtrate, which was then concentrated under a reduced pressure, and recrystallized (using methanol and THF) to obtain 7.5 g of Intermediate (2) (Yield: 65%).

LC-Mass (calcd.: 369.26 g/mol. found: M+1=370 g/mol).

Synthesis of Compound 1

3.0 g (1 equivalent) of Intermediate (1), 7.5 g (2.2 equivalents) of Intermediate (2), 2.1 g (0.2 equivalents) of $Pd(PPh_3)_4$, and 7.6 g (6 equivalents) of potassium carbonate ($K_2CO_3$) were added to toluene and water, and heated under reflux while stirring. After termination of the reaction, a resulting product was cooled down to room temperature, and extracted using an organic solution. A resulting extract solution was concentrated under a reduced pressure, and recrystalized using ethyl acetate to obtain 2.5 g of Compound 1 (Yield: 42%).

MALDI-TOF Mass (calcd.: 652.23 g/mol. found: 651.83 g/mol).

Synthesis Example 2

Compound 2 (2.8 g, Yield 45%) was obtained in the same manner as in Synthesis Example 1, except that 3.2 g (1 equivalent) of 3,7-dibromothieno[3,2-b:4,5-b]dipyridine, instead of Intermediate (1), was used.

MALDI-TOF Mass (calcd.: 668.20 g/mol. found: 668.17 g/mol).

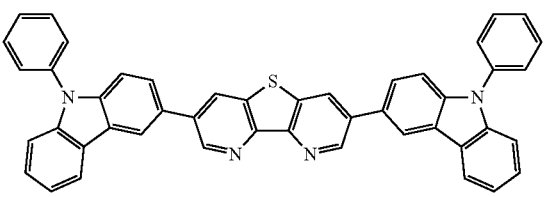 [SMILES: c1ccc(-n2c3ccccc3c3cc(-c4cnc5c(c4)sc4cc(-c6ccc7c(c6)c6ccccc6n7-c6ccccc6)cnc45)ccc32)cc1]

Synthesis Example 3

Compound 17 (2.2 g, Yield 39%) was obtained in the same manner as in Example 1, except that in synthesizing Intermediate (1) 2-(3-amino-6-bromopyridin-2-yl)-6-bromopyridin-3-amine, instead of 3,3'-diamino-5,5'-dibromo-2,2'-bipyridyl was used, and in synthesizing Intermediate (2) 2-bromo-9-phenyl-9H-carbazole, instead of 3-bromo-9-phenyl-9H-carbazole was used.

MALDI-TOF Mass (calcd.: 652.23 g/mol. found: 651.87 g/mol).

17

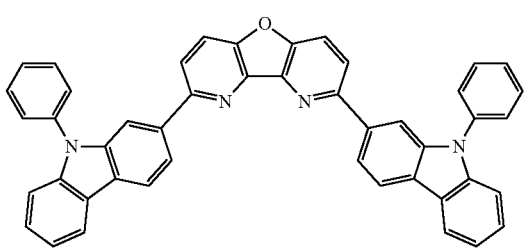

Synthesis Example 4

Compound 21 (2.4 g, Yield 40%) was obtained in the same manner as in Example 1, except that in synthesizing Intermediate (1) 3-(4-amino-5-bromopyridin-3-yl)-5-bromopyridin-4-amine, instead of 3,3'-diamino-5,5'-dibromo-2,2'-bipyridyl was used.

MALDI-TOF Mass (calcd.: 652.23 g/mol. found: 651.87 g/mol).

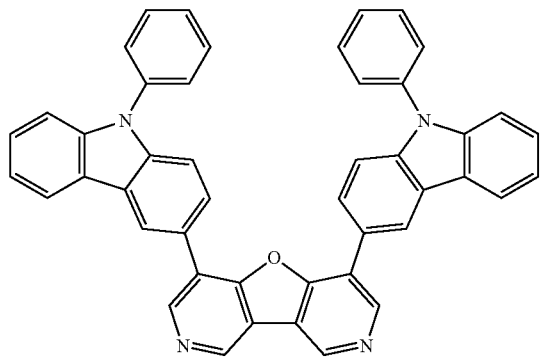

21

Synthesis Example 5

Compound 22 (3.2 g, Yield 51%) was obtained in the same manner as in Synthesis Example 1, except that 3.2 g (1 equivalent) of 4,6-dibromothieno[3,2-c:4,5-c']dipyridine, instead of Intermediate (1), was used.

MALDI-TOF Mass (calcd.: 668.20 g/mol. found: 668.17 g/mol).

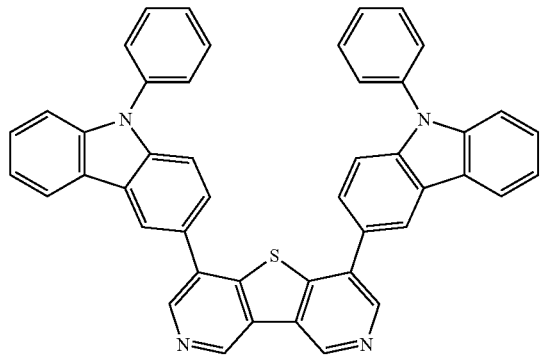

22

Synthesis Example 6

Compound 29 (3.0 g, Yield 50%) was obtained in the same manner as in Example 1, except that in synthesizing Intermediate (1) 3-(2-amino-5-bromopyridin-3-yl)-5-bromopyridin-2-amine, instead of 3,3'-diamino-5,5'-dibromo-2,2'-bipyridyl was used.

MALDI-TOF Mass (calcd.: 652.23 g/mol. found: 651.89 g/mol).

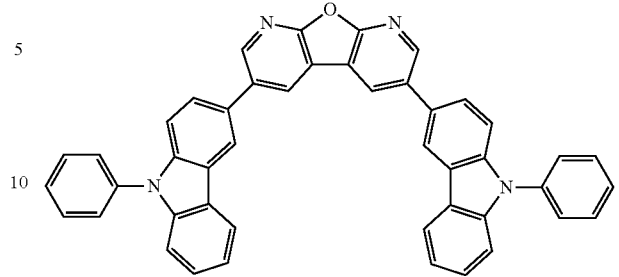

29

Synthesis Example 7

Compound 30 (2.9 g, Yield 47%) was obtained in the same manner as in Synthesis Example 1, except that 3.2 g (1 equivalent) of 3,6-dibromothieno[2,3-b:4,5-b']dipyridine, instead of Intermediate (1), was used.

MALDI-TOF Mass (calcd.: 668.20 g/mol. found: 668.17 g/mol).

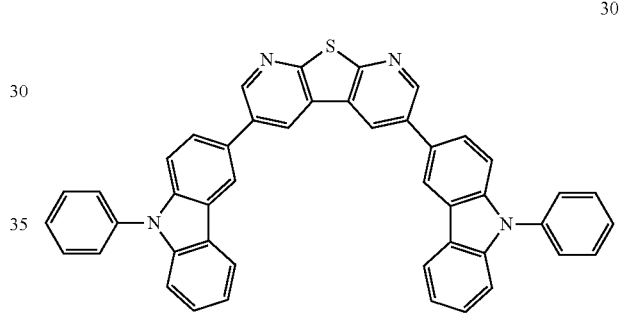

30

Synthesis Example 8

Compound 54 (1.9 g, Yield: 31%) was obtained in the same manner as in Synthesis Example 1, except that 3.2 g (1 equivalent) of 3,5-dibromothieno[2,3-b:5,4-c']dipyridine, instead of Intermediate (1), was used.

MALDI-TOF Mass (calcd.: 668.20 g/mol. found: 668.18 g/mol).

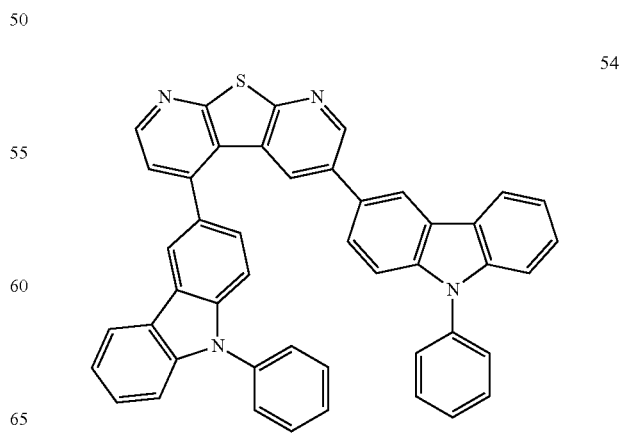

54

Synthesis Example 9

Compound 73 (1.0 g, Yield 30%) was obtained in the same manner as in Example 1, except that in synthesizing Intermediate (1) 3-(3-amino-5-bromopyridin-2-yl)-6-bromopyrazin-2-amine, instead of 3,3'-diamino-5,5'-dibromo-2,2'-bipyridyl was used.

MALDI-TOF Mass (calcd.: 653.22 g/mol. found: 653.19 g/mol).

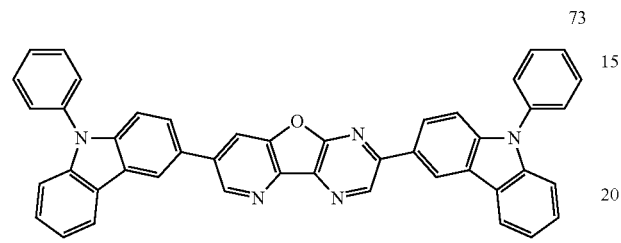

73

Synthesis Example 10

Compound 178 (1.7 g, Yield 32%) was obtained in the same manner as in Example 2, except that in synthesizing Intermediate (2) 7-bromo-9-phenyl-9H-pyrido[2,3-b]indole, instead of 3-bromo-9-phenyl-9H-carbazole was used.

MALDI-TOF Mass (calcd.: 654.22 g/mol. found: 654.20 g/mol)

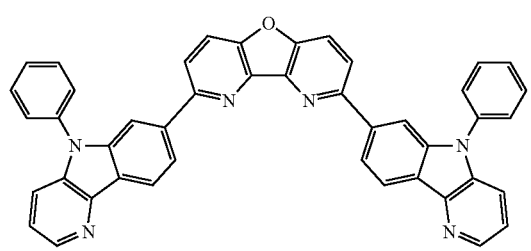

178

Synthesis Example 11

Compound 308 (2.5 g, Yield 40%) was obtained in the same manner as in Example 2, except that in synthesizing Intermediate (2) 2-bromo-10-phenyl-10H-phenoxazine, instead of 3-bromo-9-phenyl-9H-carbazole was used.

MALDI-TOF Mass (calcd.: 684.22 g/mol. found: 684.20 g/mol).

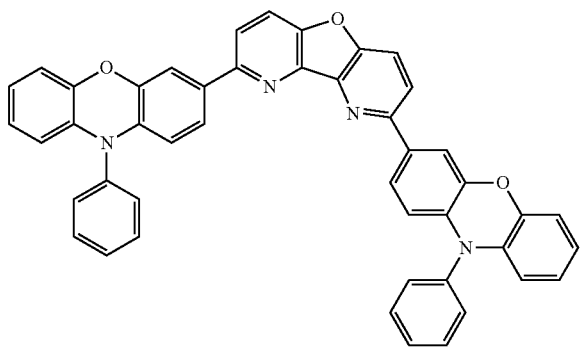

308

Evaluation Example 1

Evaluation of HOMO, LUMO, Triplet (T1), and Singlet (S1). Energy Levels

The highest occupied molecular orbital (HOMO), lowest unoccupied molecular orbital (LUMO), triplet (T1) energy levels, and singlet (S1) energy levels of Compounds 1, 2, 17, 21, 22, 29, 30, 54, 73, 178, and Compounds A, B, and C were evaluated according to the methods described in Table 1. The results are shown in Table 2.

TABLE 1

| | |
|---|---|
| HOMO energy level evaluation method | Each of the compounds was diluted in toluene to a concentration of $1 \times 10^{-5}$M, and then UV absorption spectra thereof were measured at room temperature using a UV-Vis-NIR spectrophotometer (Varian Cary 5000). A HOMO energy level of the compound was calculated based on the optical band gap (Eg) of the absorption spectrum edge. |
| LUMO energy level evaluation method | A potential (V)-current (A) plot of each of the compounds was obtained using cyclic voltammetry (CV) (Electrolyte: 0.1M $Bu_4NClO_4$/Solvent: THF/ Electrode: 3-electrode system (working electrode: GC, reference electrode: Ag/AgCl, auxiliary electrode: Pt)), and a LUMO energy level of the compound was calculated based on the reduction onset potential in the potential-current plot. |
| T1 energy level evaluation method | A mixture of each of the compounds and 2-MeTHF (prepared by dissolving 1 mg of the compound in 3 cubic centimeters (cc) of toluene) was put in a quartz cell, which was then placed in liquid nitrogen (77K) for photoluminescence spectroscopy. Photoluminescence spectra of the compounds were measured using a photoluminescence spectrometer and then compared with those at room temperature to analyze only peaks appearing at low temperature. A T1 energy level of each of the compounds was calculated based on the low-temperature peaks. |
| S1 energy level evaluation method | A mixture of each of the compounds and 2-MeTHF (prepared by dissolving 1 mg of the compound in 3 cc of toluene) was put in a quartz cell, which was then placed in a photoluminescence spectrometer at room temperature to obtain photoluminescence spectra of the compound. Only main peaks appearing in the photoluminescent spectra were analyzed to calculate singlet energy levels of the compounds. |

TABLE 2

| Compound No. | HOMO (eV) (absolute value) | LUMO (eV) (absolute value) | T1 energy level (eV) | S1 energy level (eV) |
|---|---|---|---|---|
| Compound 1 | 5.41 | 2.41 | 2.68 | 2.88 |
| Compound 2 | 5.57 | 2.19 | 2.87 | 2.88 |
| Compound 17 | 5.50 | 2.39 | 2.68 | 2.81 |
| Compound 21 | 5.42 | 2.37 | 2.65 | 2.87 |
| Compound 22 | 5.60 | 2.10 | 2.81 | 2.89 |
| Compound 29 | 5.54 | 2.34 | 2.86 | 2.99 |
| Compound 30 | 5.51 | 2.27 | 2.85 | 3.00 |
| Compound 54 | 5.57 | 2.36 | 2.86 | 3.04 |
| Compound 73 | 5.45 | 2.83 | 2.63 | 2.82 |
| Compound 178 | 5.69 | 2.46 | 2.70 | 2.88 |
| Compound 308 | 5.26 | 2.21 | 2.71 | 2.86 |
| Compound A | 5.35 | 2.93 | 2.28 | 2.42 |
| Compound B | 5.28 | 2.02 | 2.65 | 2.98 |
| Compound C | 5.48 | 2.33 | 2.64 | 2.97 |

Compound A

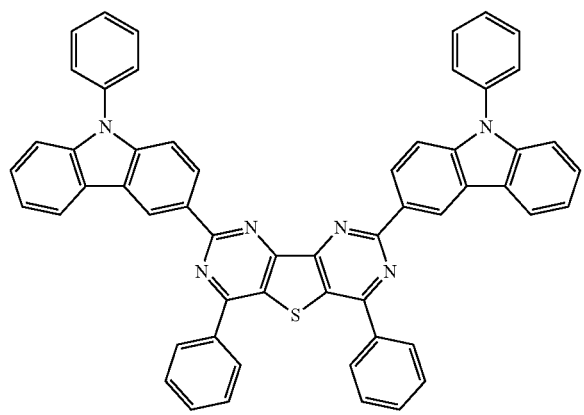

Compound B

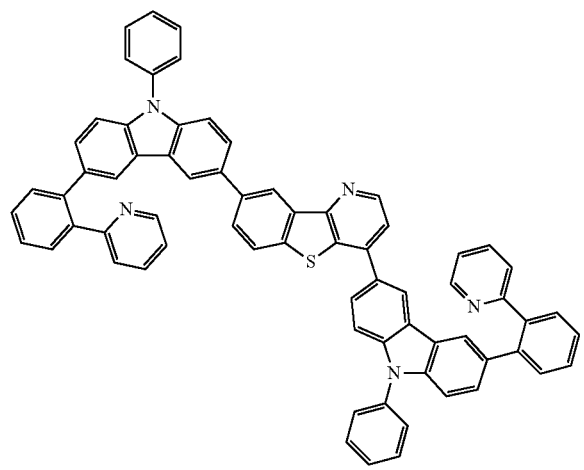

Compound C

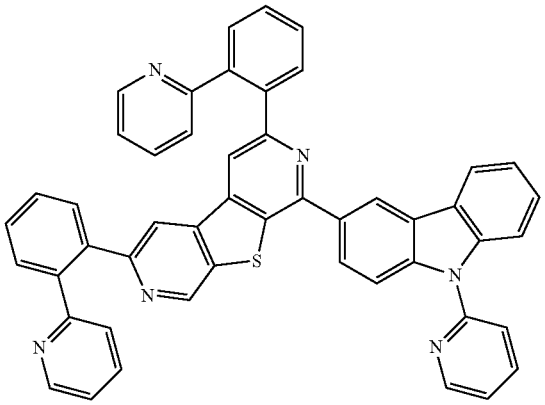

Referring to Table 2, Compounds 1 to 2, 17, 21, 22, 29, 30, 54, 73, 178, and 308 were found to have higher triplet energy levels and wider band gaps compared to those of Compound A, B, or C, and thus to have electrical characteristics suitable for use as materials for organic light-emitting devices, indicating that Compounds 1 to 2, 17, 21, 22, 29, 30, 54, 73, 178, and 308 may be used as TADF emitters due to having a small gap of about 0.3 eV or less between T1 and S1 energy levels.

Evaluation Example 2: Thermal Stability Evaluation

Figure 2:
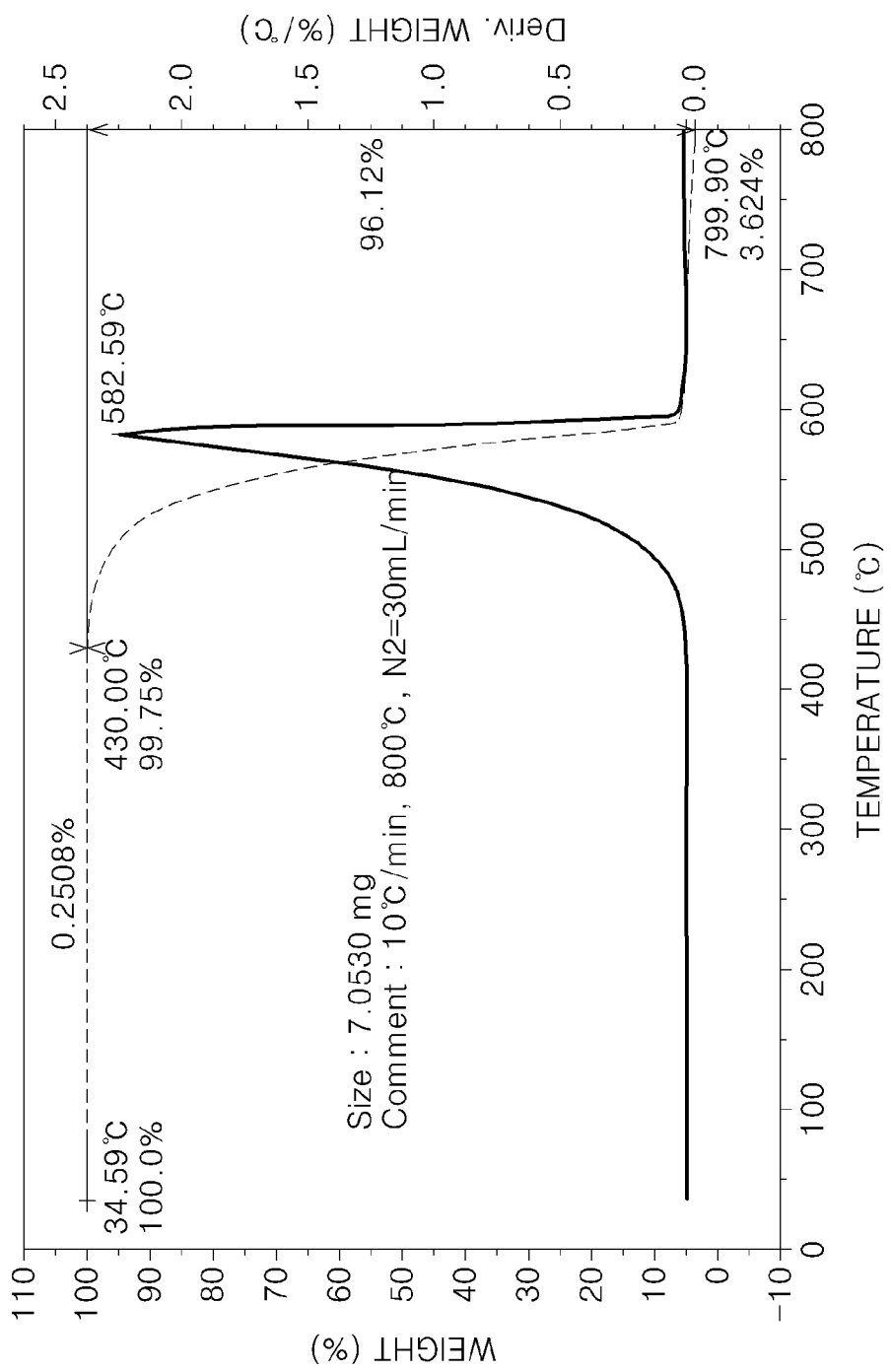
FIG. 2 is a graph of weight (percent, %) and derivative weight (percent per degree Centigrade, %/° C.) versus temperature (degrees Centigrade, ° C.) illustrating thermogravimetric analysis (TGA) data of Compound 1.
Figure 3:
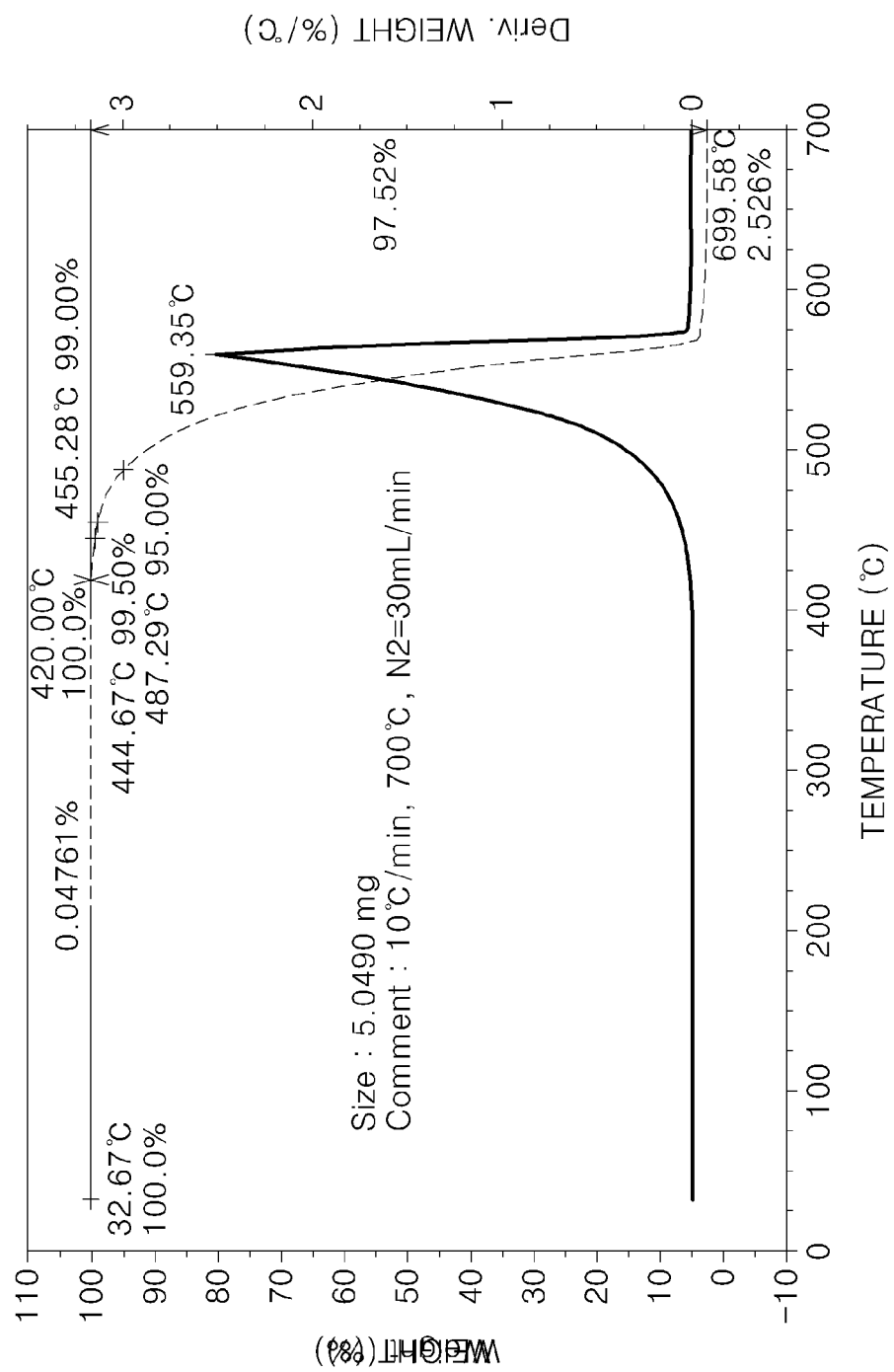
FIG. 3 is a graph of weight (percent, %) and derivative weight (percent per degree Centigrade, %/° C.) versus temperature (degrees Centigrade, ° C.) illustrating TGA data of Compound 178.
Figure 4:
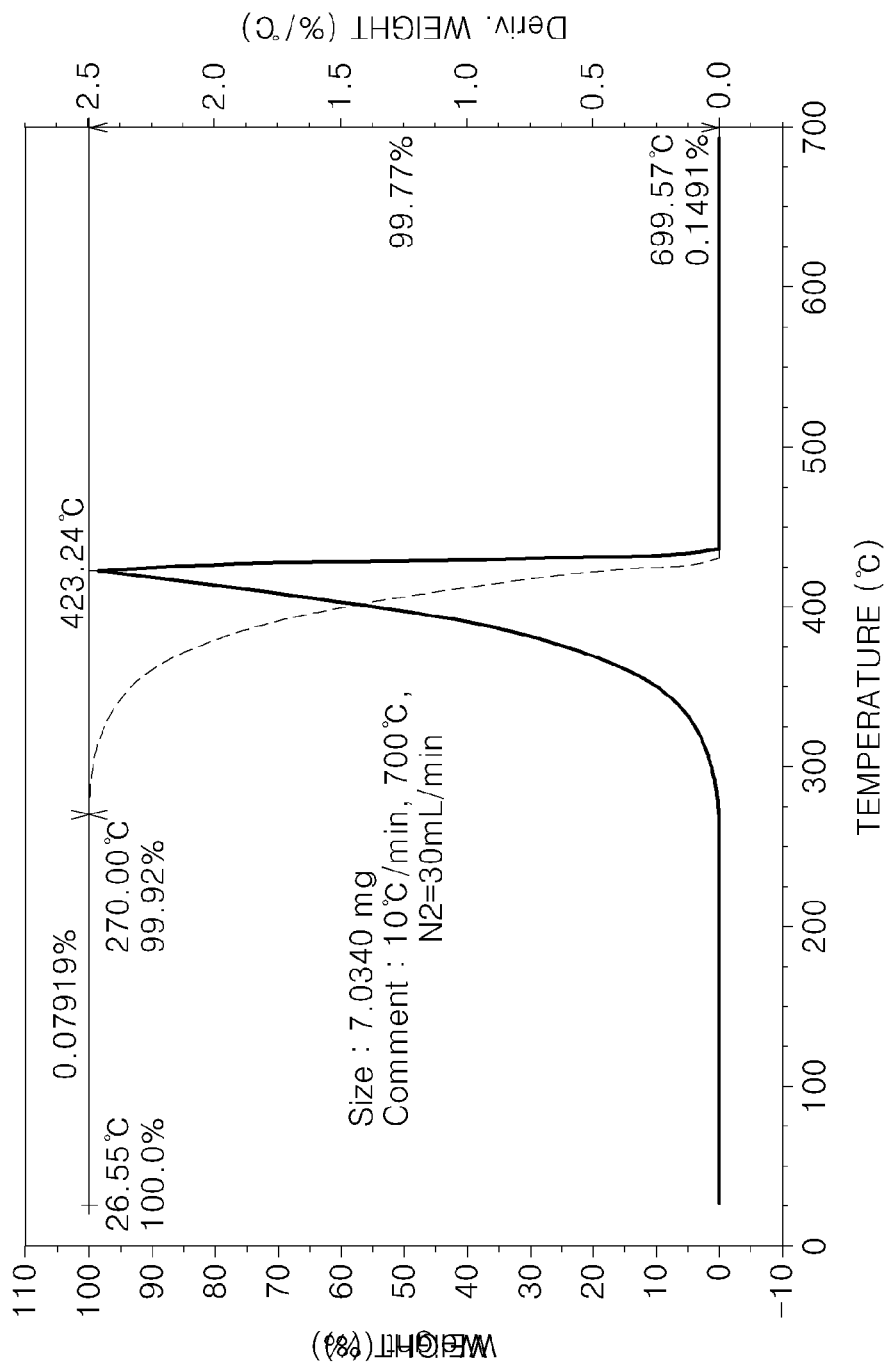
FIG. 4 is a graph of weight (percent, %) and derivative weight (percent per degree Centigrade, %/° C.) versus temperature (degrees Centigrade, ° C.) illustrating TGA data of Compound D.

Thermal analysis was performed on Compounds 1 and 178, and Compound D by thermo gravimetric analysis (TGA) and differential scanning calorimetry (DSC) ($N_2$ atmosphere, Temperature ranges: from room temperature to 700° C. or 800° C. (10° C./min) (for TGA), and from room temperature to 400° C. (for DSC), Pan Type: Pt Pan in disposable Al Pan (for TGA), disposable Al pan (for DSC)). The results are shown in FIGS. 2 to 4. The decomposition temperatures of Compounds 1 and 178, and Compound D, which were obtained based on the plots of FIGS. 2 to 4, respectively, are shown in Table 3. Referring to FIGS. 2 to 4 and Table 3, Compounds 1 and 178 were found to have improved thermal stabilities compared to Compound D.

TABLE 3

| | Compound 1 | Compound 178 | Compound D |
|---|---|---|---|
| Decomposition onset temperature | 430° C. | 445° C. | 270° C. |

Example 1

An ITO glass substrate (having an ITO layer as an anode) having a sheet resistance of about 15 ohms per square centimeter ($\Omega/cm^2$) was cut to a size of 50 mm×50 mm×0.7 mm, washed by sonication in acetone, isopropyl alcohol and then in pure water each for 15 minutes, and washed with UV ozone for 30 minutes.

N,N'-di(1-naphthyl)-N,N'-diphenylbenzidine (NPB) was deposited on the ITO layer anode at a vacuum level of about 650×10$^{-7}$ Pascals (Pa) and a deposition rate of about 0.1 to 0.3 nanometers per second (nm/s) to form an HIL having a thickness of about 70 nanometers (nm), followed by depositing 4,4',4"-tri(N-carbazolyl)triphenylamine (TCTA) on the HIL to form an HTL having a thickness of about 10 nm, thereby forming a hole transport region having a total thickness of about 80 nm.

Next, Compound 1 (host) and $Ir(ppy)_3$ (dopant) were co-deposited in a weight ratio of about 90:10 on the HTL to form an EML having a thickness of about 300 Å, and bis(8-hydroxy-2-methylquinolinato)-aluminum biphenoxide (BAlq) was then deposited on the EML to form a HBL layer having a thickness of about 50 Å.

Next, $Alq_3$ was deposited on the HBL to form an ETL having a thickness of about 200 Å, LiF was deposited on the ETL to form an EIL having a thickness of about 1 nm, and then an Al layer having a thickness of about 100 nm on the EIL to form a cathode, thereby completing the manufacture of an organic light-emitting device having a structure including ITO/NPB(70 nm)/TCTA(10 nm)/EML(Compound 1(90 wt %):$Ir(PPy)_3$(10 wt %), 30 nm)/Balq (5 nm)/$Alq_3$(20 nm)/LiF (1 nm)/Al(100 nm).

Example 2

An organic light-emitting device was manufactured in the same manner as in Example 1, except that Compound 2, instead of Compound 1, was used as a host to form the EML.

Example 3

An organic light-emitting device was manufactured in the same manner as in Example 1, except that Compound 17, instead of Compound 1, was used as a host to form the EML.

Example 4

An organic light-emitting device was manufactured in the same manner as in Example 1, except that Compound 21, instead of Compound 1, was used as a host to form the EML.

Example 5

An organic light-emitting device was manufactured in the same manner as in Example 1, except that Compound 22, instead of Compound 1, was used as a host to form the EML.

Example 6

An organic light-emitting device was manufactured in the same manner as in Example 1, except that Compound 29, instead of Compound 1, was used as a host to form the EML.

Example 7

An organic light-emitting device was manufactured in the same manner as in Example 1, except that Compound 30, instead of Compound 1, was used as a host to form the EML.

Example 8

An organic light-emitting device was manufactured in the same manner as in Example 1, except that Compound 54, instead of Compound 1, was used as a host to form the EML.

Example 9

An organic light-emitting device was manufactured in the same manner as in Example 1, except that Compound 73, instead of Compound 1, was used as a host to form the EML.

Example 10

An organic light-emitting device was manufactured in the same manner as in Example 1, except that Compound 178, instead of Compound 1, was used as a host to form the EML.

Example 11

An organic light-emitting device was manufactured in the same manner as in Example 1, except that Compound 308, instead of Compound 1, was used as a host to form the EML.

Comparative Example 1

An organic light-emitting device was manufactured in the same manner as in Example 1, except that Compound A, instead of Compound 1, was used as a host to form the EML.

Comparative Example 2

An organic light-emitting device was manufactured in the same manner as in Example 1, except that Compound B, instead of Compound 1, was used as a host to form the EML.

Comparative Example 3

An organic light-emitting device was manufactured in the same manner as in Example 1, except that Compound C, instead of Compound 1, was used as a host to form the EML.

Comparative Example 4

An organic light-emitting device was manufactured in the same manner as in Example 1, except that Compound D, instead of Compound 1, was used as a host to form the EML.

Evaluation Example 3: Characteristics Evaluation of Organic Light-Emitting Devices Changes in current density and luminance with respect to voltage, and emission efficiencies of the organic light-emitting devices of Examples 1 to 4 and Comparative Examples 1 to 4 were measured according to the following methods. The results are shown in Table 5.

(1) Measurement of Current Density Charges with Respect to Voltage Changes

A current value flowing through each of the organic light-emitting devices was measured while increasing a voltage from 0 volts (V) to about 10 V by using a current-voltage source meter (Keithley 2400), and then was divided by the area of the corresponding light-emitting device to obtain a current density.

(2) Measurement of Luminance Changes with Respect to Voltage Changes

The luminance values of the organic light-emitting devices were measured while increasing a voltage from about 0 V to about 10 V by using a Minolta CS-1000A spectroradiometer.

(3) Measurement of Emission Efficiencies

Current efficiencies at a certain current density of 10 milliAmperes per square centimeter ($mA/cm^2$) of the organic light-emitting devices were calculated based on the current densities, voltages, and luminance values obtained from the above-described measurements (1) and (2).

TABLE 4

| Example | Host | Driving voltage (V) | Current efficiency (cd/A) | Power efficiency (lm/W) | Emission color |
|---|---|---|---|---|---|
| Example 1 | Compound 1 | 4.0 | 40.0 | 31.3 | Green |
| Example 2 | Compound 2 | 4.1 | 35.2 | 27.3 | Green |
| Example 3 | Compound 17 | 4.3 | 23.6 | 17.3 | Green |
| Example 4 | Compound 21 | 4.2 | 33.2 | 24.7 | Green |
| Example 5 | Compound 22 | 4.2 | 29.4 | 22.0 | Green |
| Example 6 | Compound 29 | 4.1 | 34.6 | 26.8 | Green |
| Example 7 | Compound 30 | 4.1 | 32.7 | 24.8 | Green |
| Example 8 | Compound 54 | 4.2 | 23.9 | 18.0 | Green |
| Example 9 | Compound 73 | 4.3 | 28.6 | 21.0 | Green |
| Example 10 | Compound 178 | 4.2 | 36.9 | 27.4 | Green |
| Example 11 | Compound 308 | 4.5 | 31.5 | 21.2 | Green |
| Comparative Example A | Compound A | 5.4 | 22.8 | 13.3 | Green |
| Comparative Example B | Compound B | 5.9 | 15.8 | 8.4 | Green |
| Comparative Example C | Compound C | 5.4 | 15.0 | 8.8 | Green |
| Comparative Example D | Compound D | 4.7 | 21.5 | 14.3 | Green |

Referring to Table 3, the organic light-emitting devices of Examples 1 to 11 were found to have improved emission efficiencies and improved driving voltage characteristics, compared to those of the organic light-emitting devices of Comparative Examples 1 to 4.

As described above, according to the one or more of the above embodiments, a condensed cyclic compound represented by Formula 1 may have improved electrical and thermally stable characteristics. Thus, an organic light-emitting device including the condensed cyclic compound of Formula 1 may have a low driving voltage, a high efficiency, a high luminance, and long lifetime characteristics.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present inventive concept as defined by the following claims.

What is claimed is:

1. A condensed cyclic compound represented by Formula 1:

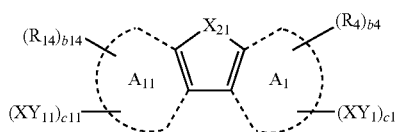

Formula 1

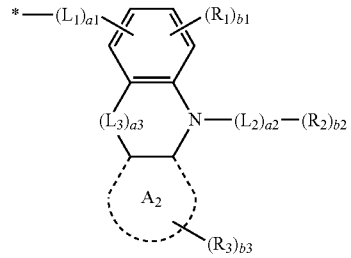

Formula 2-1

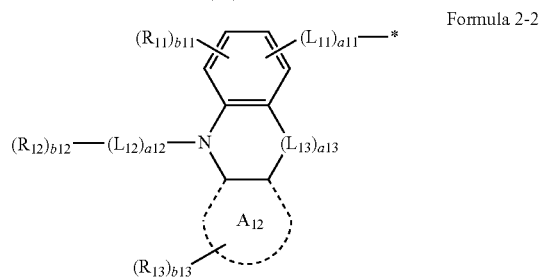

Formula 2-2 wherein, in Formula 1, $XY_1$ is a group represented by Formula 2-1;

$XY_{11}$ is a group represented by Formula 2-2;

wherein, in Formulae 1, 2-1, and 2-2, $X_{21}$ is selected from O, S, Se, and $Si(R_{21})(R_{22})$;

c1 and c11 are each independently an integer from 1 to 3;

$A_1$ is a 6-membered ring comprising at least one N as a ring-member atom;

$A_{11}$ is pyridine;

$A_2$ and $A_{12}$ are each independently selected from a benzene, a naphthalene, a pyridine, a pyrimidine, a pyrazine, a pyridazine, and a triazine;

$L_1$ and $L_{11}$ are each independently selected from a phenylene group, a naphthylene group, a pyridinylene group, a pyrimidinylene group, a pyrazinylene group, a pyridazinylene group, and a triazinylene group; and a phenylene group, a naphthylene group, a pyridinylene group, a pyrimidinylene group, a pyrazinylene group, a pyridazinylene group, and a triazinylene group, each substituted with at least one of a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a pyridinyl group, a pyrimidinyl group, a pyrazinyl group, a pyridazinyl group, and a triazinyl group;

$L_2$ and $L_{12}$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;

$L_3$ and $L_{13}$ are each independently selected from O, S, a substituted or unsubstituted $C_1$-$C_5$ alkylene group, and a substituted or unsubstituted $C_2$-$C_5$ alkenylene group;

a1 to a3, and a11 to a13 are each independently an integer selected from 0 to 3;

$R_1$ to $R_4$, $R_{11}$ to $R_{14}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b1, b2, b11, and b12 are each independently 1, 2, or 3;

b3 and b13 are each independently an integer selected from 1 to 6;

b4 is 1 or 2; and b14 is 0, 1, or 2, wherein at least one of substituents of the substituted $C_1$-$C_5$ alkylene group, the substituted $C_2$-$C_5$ alkenylene group, the substituted $C_3$-$C_{10}$ cycloalkylene group, the substituted $C_2$-$C_{10}$ heterocycloalkylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalk-enyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

2. The condensed cyclic compound of claim 1, wherein $A_1$ is selected from a pyridine, a pyrimidine, a pyrazine, a pyridazine, and a triazine.

3. The condensed cyclic compound of claim 1, wherein $A_2$ and $A_{12}$ are each independently a benzene, a naphthalene, or a pyridine.

4. The condensed cyclic compound of claim 1, wherein the condensed cyclic compound of Formula 1 is represented by one of Formulae 1(1) to 1(28):

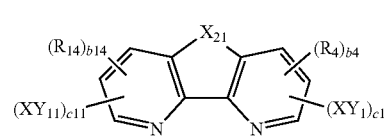

Formula 1(1)

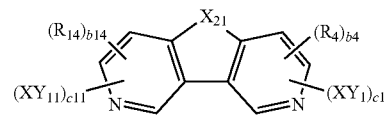

Formula 1(2)

-continued

Formula 1(3)
Formula 1(4)
Formula 1(5)
Formula 1(6)
Formula 1(7)
Formula 1(8)
Formula 1(9)
Formula 1(10)
Formula 1(11)
Formula 1(12)
Formula 1(13)
Formula 1(14)

-continued

Formula 1(15)
Formula 1(16)
Formula 1(17)
Formula 1(18)
Formula 1(19)
Formula 1(20)
Formula 1(21)
Formula 1(22)
Formula 1(23)
Formula 1(24)
Formula 1(25)

-continued

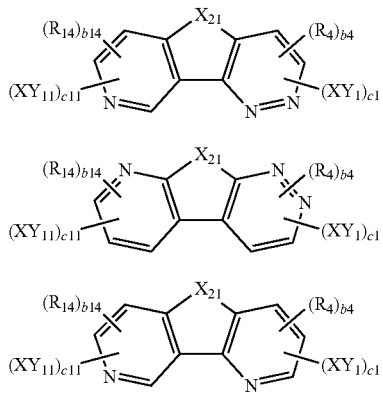

Formula 1(26)

Formula 1(27)

Formula 1(28)

wherein, in Formulae 1(1) to 1(28), $X_{21}$, $XY_1$, $XY_{11}$, $L_1$ to $L_3$, $L_{11}$ to $L_{13}$, a1 to a3, a11 to a13, $R_1$ to $R_4$, $R_{11}$ to $R_{14}$, b1 to b4, and b11 to b14 are the same as in claim 1.

5. The condensed cyclic compound of claim 1, wherein the condensed cyclic compound of Formula 1 is represented by one of Formulae 1-1 to 1-10:

Formula 1-1

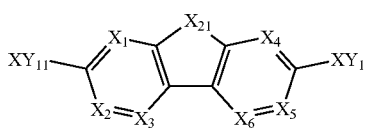

Formula 1-2

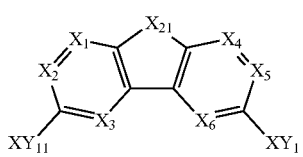

Formula 1-3

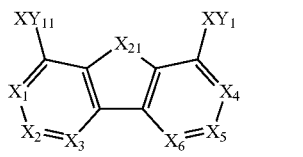

Formula 1-4

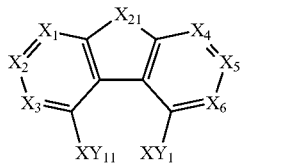

Formula 1-5

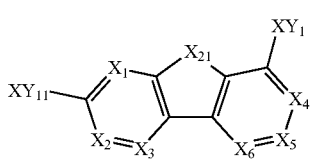

Formula 1-6

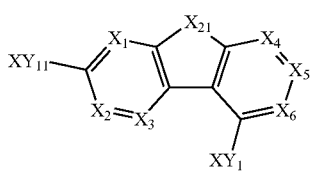

Formula 1-7

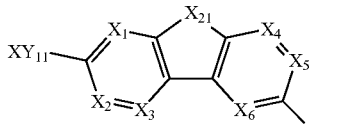

Formula 1-8

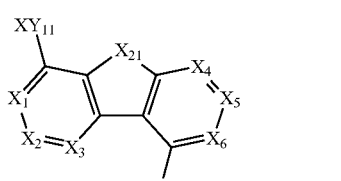

Formula 1-9

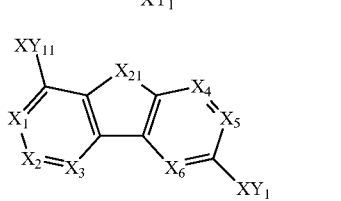

Formula 1-10

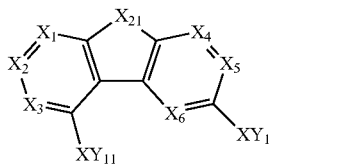

wherein, in Formulae 1-1 to 1-10,
$X_{21}$, $XY_1$, and $XY_{11}$ are the same as in claim 1;
$X_1$ is N or $C(R_{14a})$,
$X_2$ is N or $C(R_{14b})$;
$X_3$ is N or $C(R_{14c})$;
$X_4$ is N or $C(R_{4a})$;
$X_5$ is N or $C(R_{4b})$;
$X_6$ is N or $C(R_{4c})$,
provided that one of $X_1$ to $X_3$ is N, and at least one of $X_4$ to $X_6$ is N;
$R_{14a}$ to $R_{14c}$ are the same as $R_{14}$ in claim 1; and
$R_{4a}$ to $R_{4c}$ are the same as $R_4$ in claim 1.

6. The condensed cyclic compound of claim 1, wherein a1 and a11 are 0.

7. The condensed cyclic compound of claim 1, wherein $L_2$ and $L_{12}$ are each independently selected from
a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, a $C_2$-$C_{60}$ heteroaryl group, a monovalent non-aromatic condensed polycyclic group, and a monovalent non-aromatic condensed heteropolycyclic group.

8. The condensed cyclic compound of claim 1, wherein $L_2$ and $L_{12}$ are each independently selected from a phenylene group, a naphthylene group, a phenalenylene group, a phenanthrylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group; and a phenylene group, a naphthylene group, a phenalenylene group, a phenanthrylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

9. The condensed cyclic compound of claim 1, wherein $L_3$ and $L_{13}$ are each independently selected from O, S, a $C_1$-$C_5$ alkylene group, and a $C_2$-$C_5$ alkenylene group; and a $C_1$-$C_5$ alkylene group and a $C_2$-$C_5$ alkenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

10. The condensed cyclic compound of claim 1, wherein a3 and a13 are each independently 0 or 1.

11. The condensed cyclic compound of claim 1, wherein -$(L_3)_{a3}$- and -$(L_{13})_{a13}$- are each independently selected from a single bond, —O—, —S—, a $C_1$-$C_2$ alkylene group, and a $C_2$-$C_3$ alkenylene group; and a $C_1$-$C_2$ alkylene group and a $C_2$-$C_3$ alkenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{20}$ alkyl group.

12. The condensed cyclic compound of claim 1, wherein $R_2$ and $R_{12}$ are each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, and a substituted or unsubstituted monovalent non-aromatic condensed heteropolycyclic group.

13. The condensed cyclic compound of claim 1, wherein $R_1$ to $R_4$, $R_{11}$ to $R_{14}$, and $R_{21}$ to $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, and a $C_1$-$C_{20}$ alkoxy group;

a $C_1$-$C_{20}$ alkyl group, a $C_2$-$C_{20}$ alkenyl group, a $C_2$-$C_{20}$ alkynyl group, and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a triazinyl group, a quinolinyl group, an isoquinolinyl group, and a quinazolinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzofuranyl group, a dibenzothiophenyl group, a benzocarbazolyl group, a dibenzocarbazolyl group, an imidazopyrimidinyl group, and an imidazopyridinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{33}$)($Q_{34}$)($Q_{35}$); and —Si($Q_3$)($Q_4$)($Q_5$), wherein $Q_3$ to $Q_5$, and $Q_{33}$ to $Q_{35}$ are each independently a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

14. The condensed cyclic compound of claim 1, wherein $R_2$ and $R_{12}$ are each independently selected from groups represented by Formulae 5-1 to 5-36; and $R_1$, $R_3$, $R_4$, $R_{11}$, $R_{13}$, $R_{14}$, $R_{21}$, and $R_{22}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and the groups represented by Formulae 5-1 to 5-36:

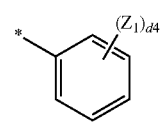

Formula 5-1

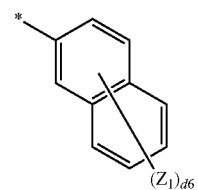

Formula 5-2

-continued
Formula 5-3
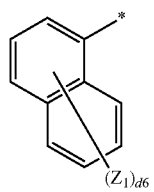
Formula 5-4
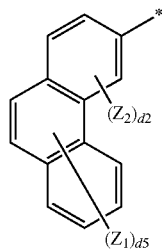
Formula 5-5
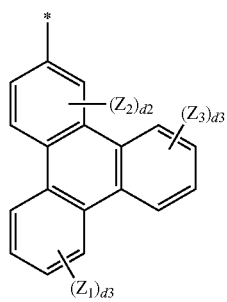
Formula 5-6
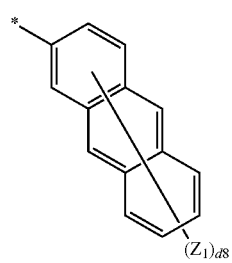
Formula 5-7
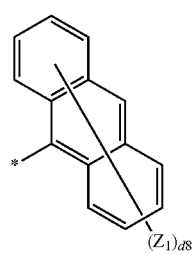
Formula 5-8
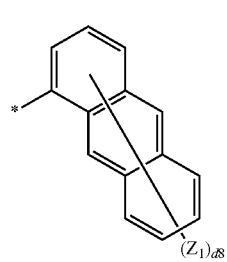
-continued
Formula 5-9
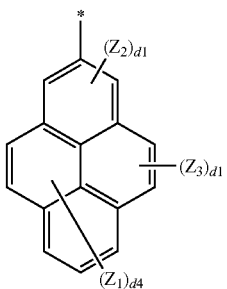
Formula 5-10
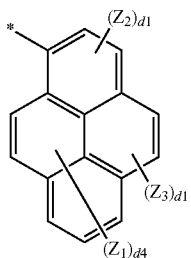
Formula 5-11
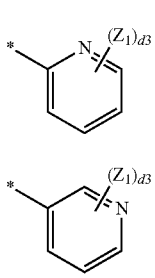
Formula 5-12
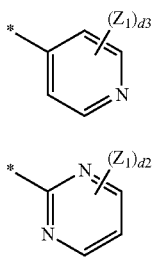
Formula 5-13
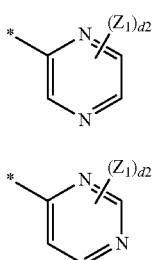
Formula 5-14
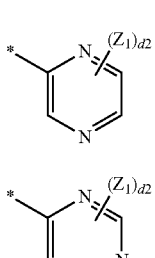
Formula 5-15
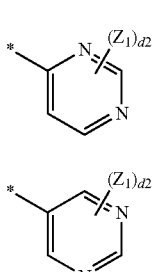
Formula 5-16
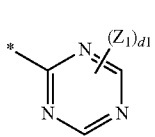
Formula 5-17
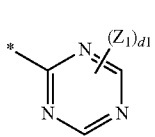
Formula 5-18
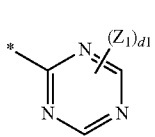

-continued
Formula 5-19
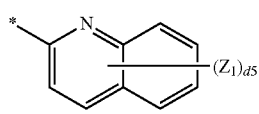
Formula 5-20
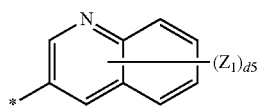
Formula 5-21
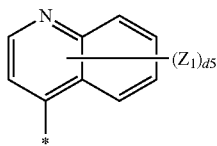
Formula 5-22
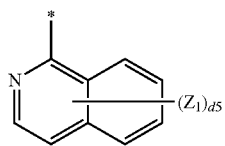
Formula 5-23
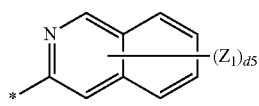
Formula 5-24
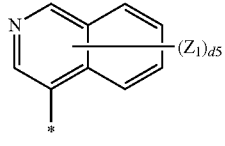
Formula 5-25
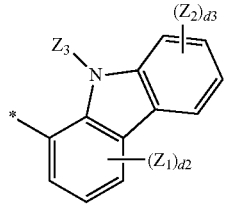
Formula 5-26
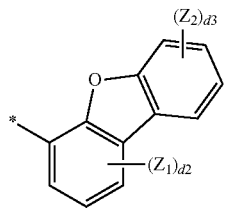
Formula 5-27
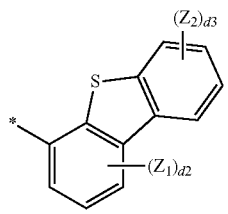
-continued
Formula 5-28
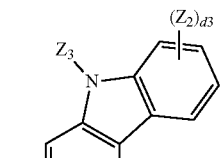
Formula 5-29
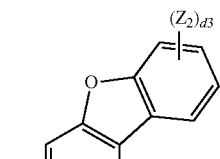
Formula 5-30
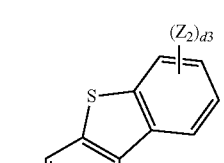
Formula 5-31
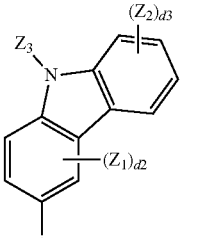
Formula 5-32
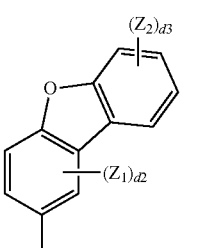
Formula 5-33
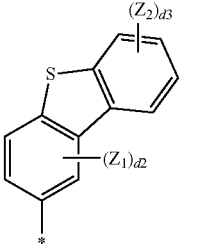
Formula 5-34
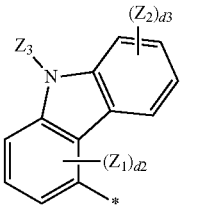

-continued

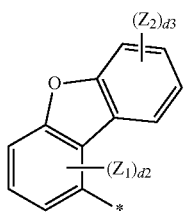

Formula 5-35

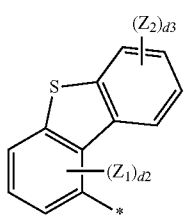

Formula 5-36 wherein, in Formulae 5-1 to 5-36, $Z_1$ to $Z_3$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 is 1 or 2;
d2 is an integer selected from 1 to 3;
d3 is an integer selected from 1 to 4;
d4 is an integer selected from 1 to 8;
d5 is an integer selected from 1 to 6;
d6 is an integer selected from 1 to 4;
d7 is an integer selected from 1 to 8;
d8 is an integer selected from 1 to 9; and
* indicates a binding site to an adjacent atom.

15. The condensed cyclic compound of claim 1, wherein $R_2$ and $R_{12}$ are each independently selected from a phenyl group, a naphthyl group, an anthracenyl group, a pyrenyl group, a phenanthrenyl group, and a triphenylenyl group, and a phenyl group, a naphthyl group, an anthracenyl group, a pyrenyl group, a phenanthrenyl group, and a triphenylenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group; and $R_1$, $R_3$, $R_4$, $R_{11}$, $R_{13}$, $R_{14}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group.

16. The condensed cyclic compound of claim 1, wherein XYZ is represented by one of Formulae 2-1(1) to 2-1(6), and $XY_{11}$ is represented by one of Formulae 2-2(1) to 2-2(6):

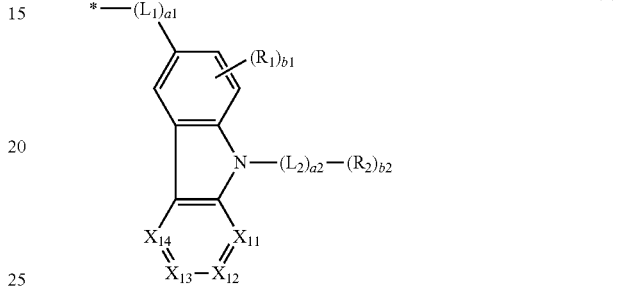

Formula 2-1(1)

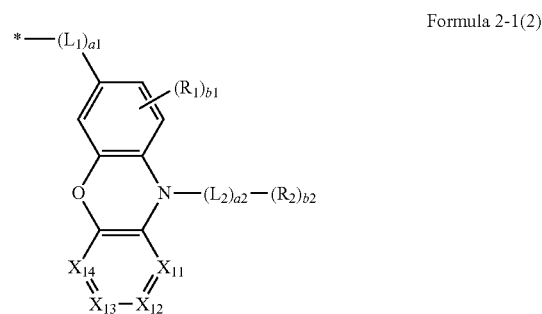

Formula 2-1(2)

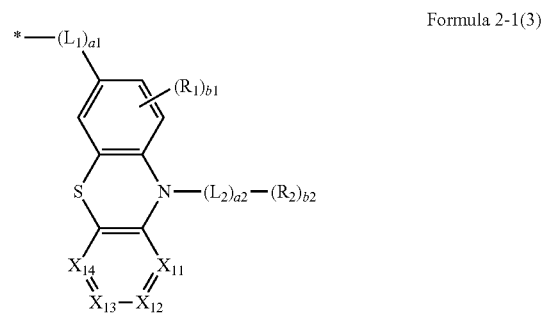

Formula 2-1(3)

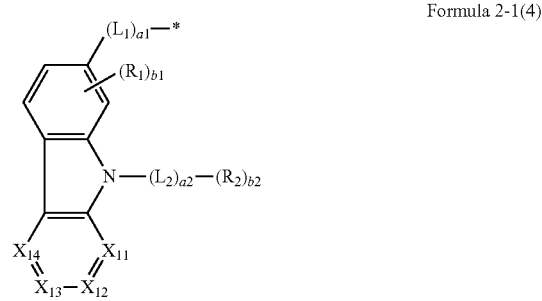

Formula 2-1(4)

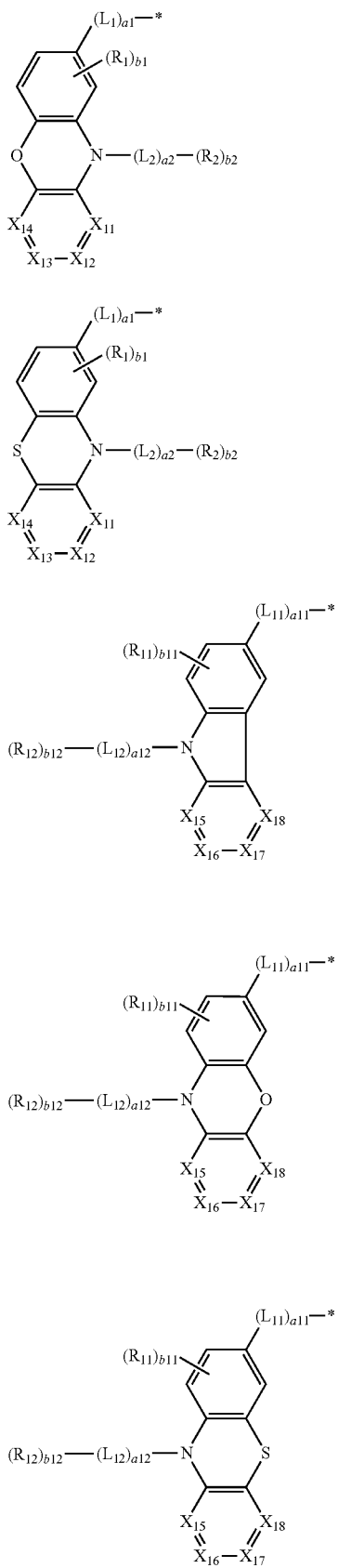

Formula 2-1(5)

Formula 2-1(6)

Formula 2-2(1)

Formula 2-2(2)

Formula 2-2(3)

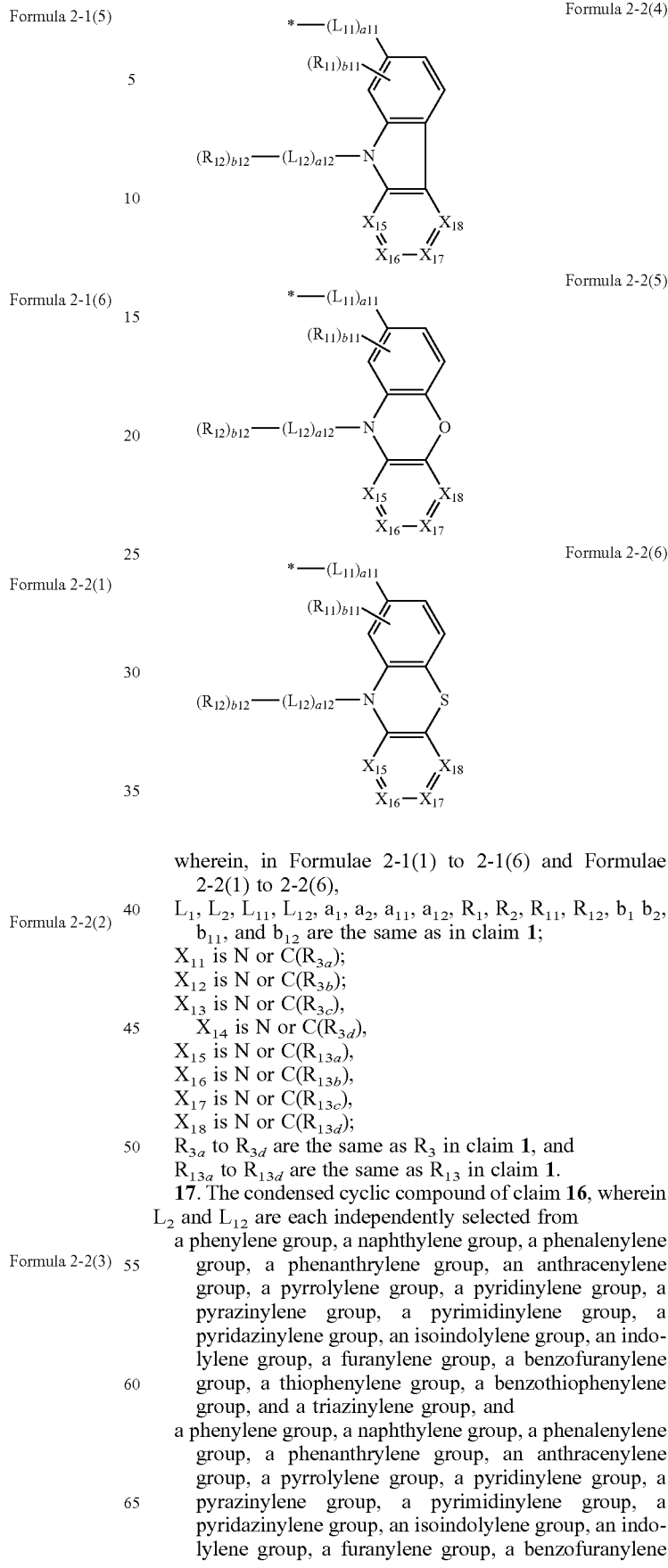

Formula 2-2(4)

Formula 2-2(5)

Formula 2-2(6)

wherein, in Formulae 2-1(1) to 2-1(6) and Formulae 2-2(1) to 2-2(6), $L_1$, $L_2$, $L_{11}$, $L_{12}$, $a_1$, $a_2$, $a_{11}$, $a_{12}$, $R_1$, $R_2$, $R_{11}$, $R_{12}$, $b_1$ $b_2$, $b_{11}$, and $b_{12}$ are the same as in claim 1;

$X_{11}$ is N or $C(R_{3a})$;
$X_{12}$ is N or $C(R_{3b})$;
$X_{13}$ is N or $C(R_{3c})$,
$X_{14}$ is N or $C(R_{3d})$,
$X_{15}$ is N or $C(R_{13a})$,
$X_{16}$ is N or $C(R_{13b})$,
$X_{17}$ is N or $C(R_{13c})$,
$X_{18}$ is N or $C(R_{13d})$;
$R_{3a}$ to $R_{3d}$ are the same as $R_3$ in claim 1, and
$R_{13a}$ to $R_{13d}$ are the same as $R_{13}$ in claim 1.

17. The condensed cyclic compound of claim 16, wherein $L_2$ and $L_{12}$ are each independently selected from
a phenylene group, a naphthylene group, a phenalenylene group, a phenanthrylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, and
a phenylene group, a naphthylene group, a phenalenylene group, a phenanthrylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

a2 and a12 are each independently 0 or 1;

$R_2$ and $R_{12}$ are each independently selected from a phenyl group, a naphthyl group, an anthracenyl group, a pyrenyl group, a phenanthrenyl group, and a triphenylenyl group, and a phenyl group, a naphthyl group, an anthracenyl group, a pyrenyl group, a phenanthrenyl group, and a triphenylenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group; and $R_1$, $R_{3a}$ to $R_{3d}$, $R_{11}$, and $R_{13a}$ to $R_{13d}$ are each independently selected from a hydrogen, a deuterium, —F, —Cl, —Br, —I, a hydroxyl group, a cyano group, a nitro group, an amino group, an amidino group, a hydrazine group, a hydrazine group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, and a triphenylenyl group.

18. The condensed cyclic compound of claim 1, wherein the condensed cyclic compound of Formula 1 is one of Compounds 1 to 312:

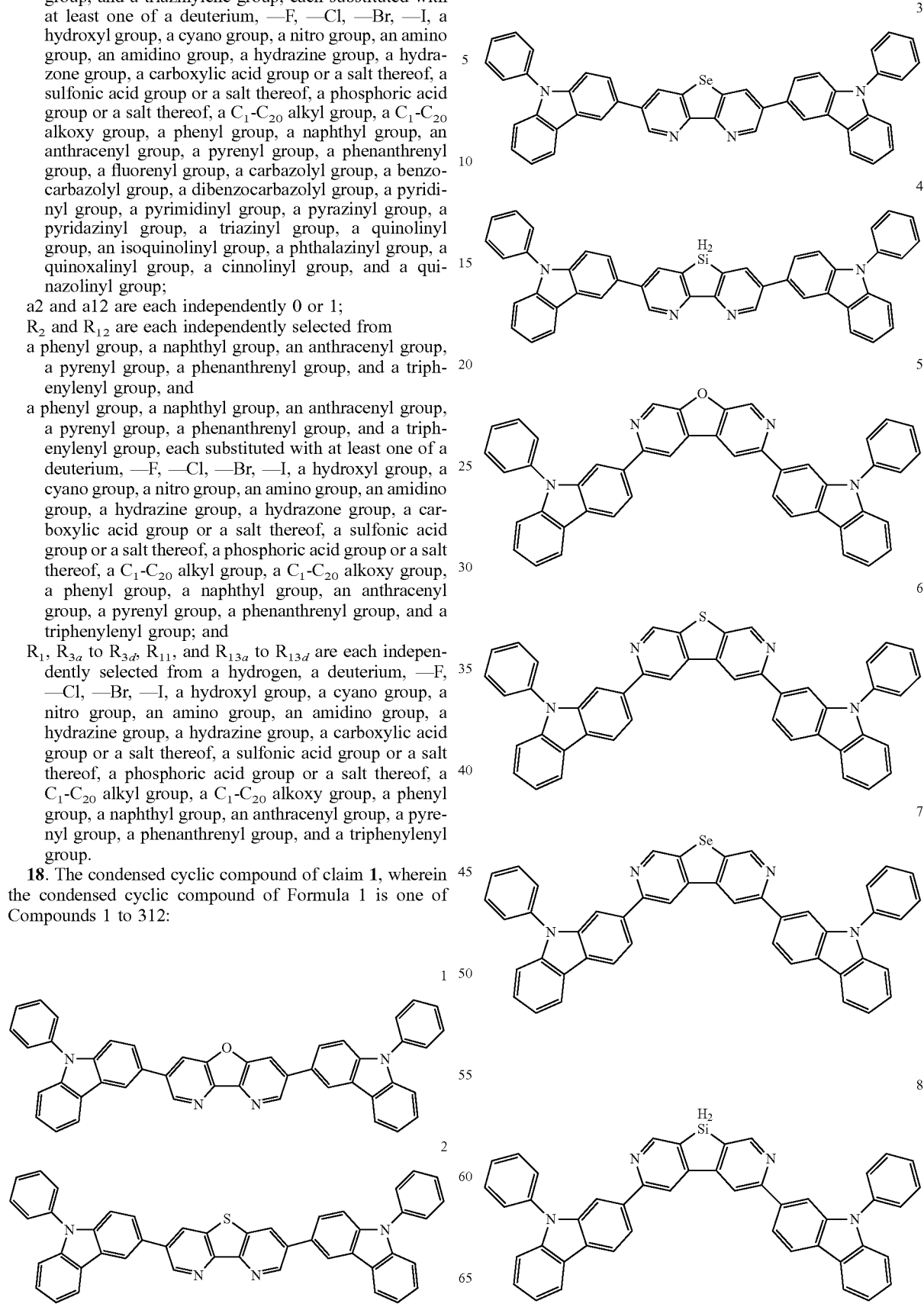

-continued
9
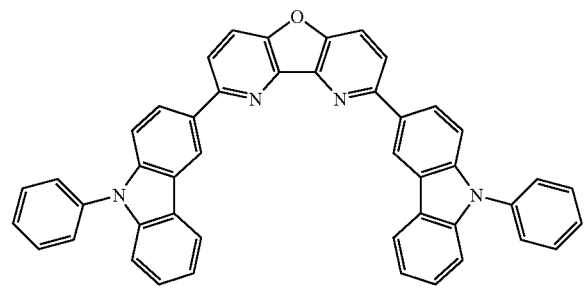
10
11
12
13
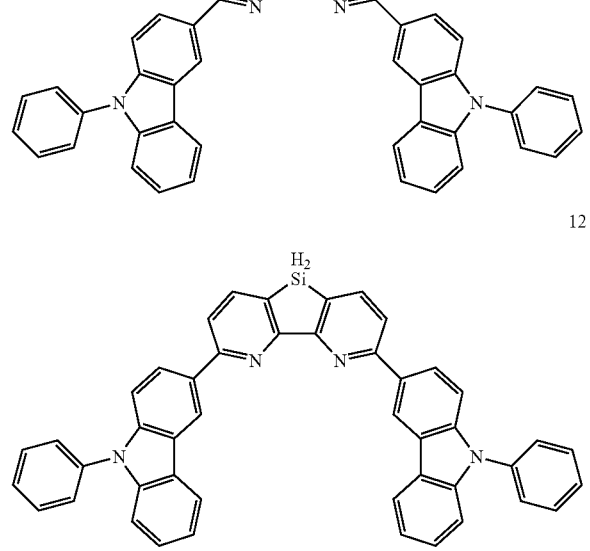
14
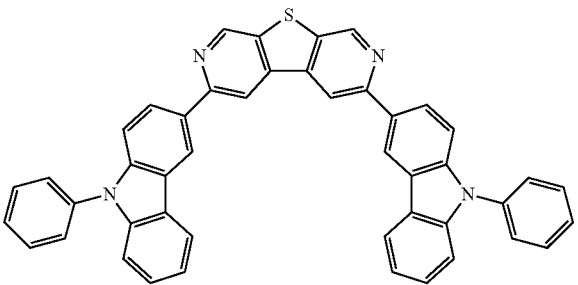
15
16
17
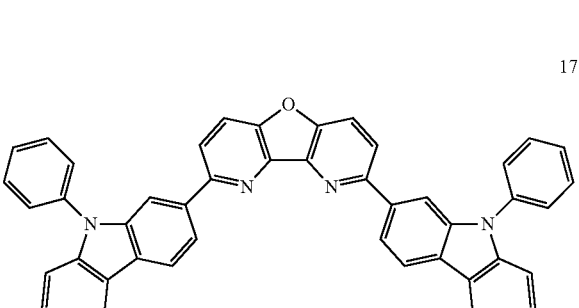
18
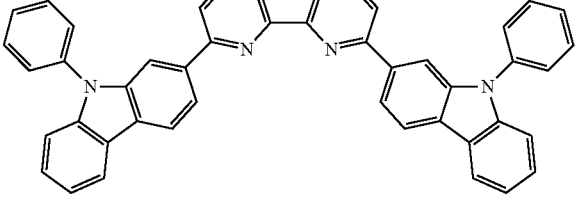

19
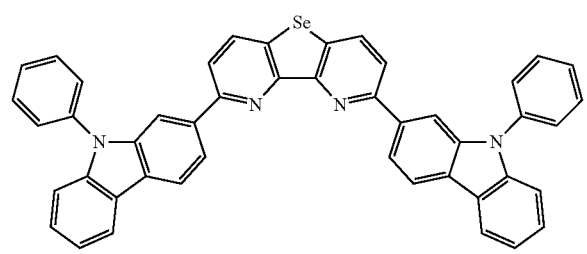
20
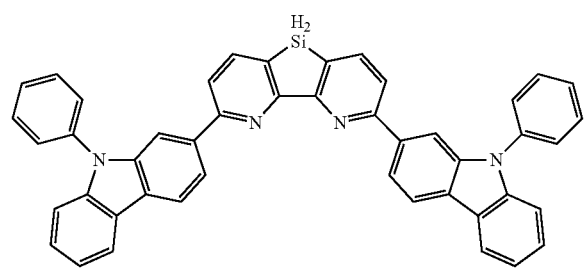
21
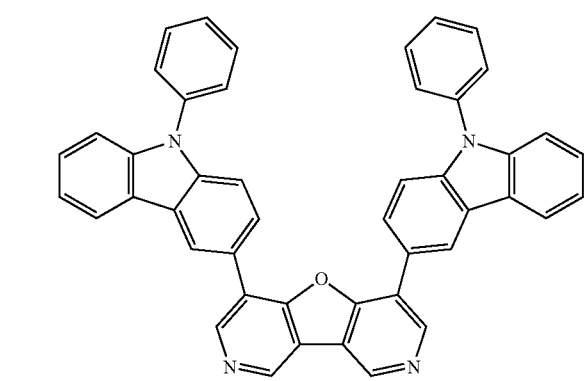
22
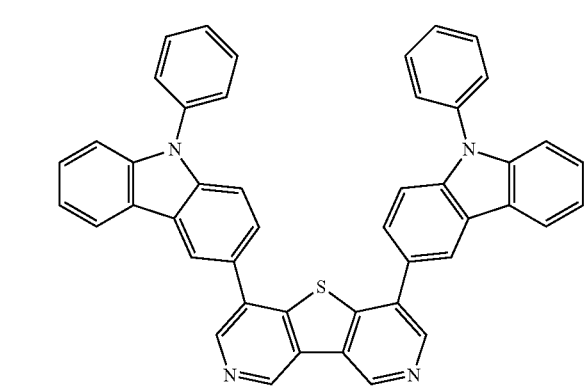
23
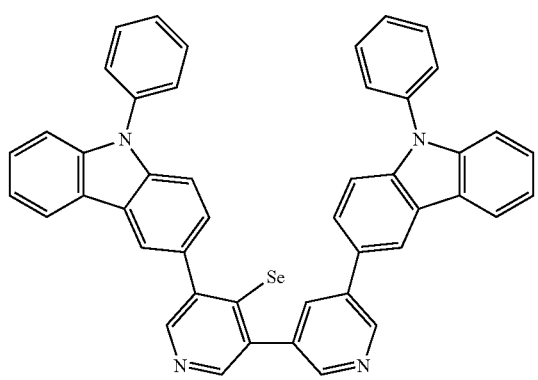
24
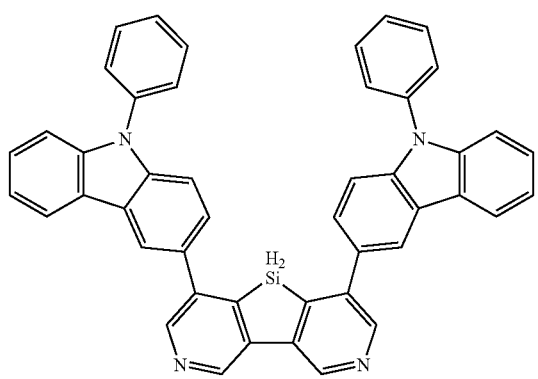
25
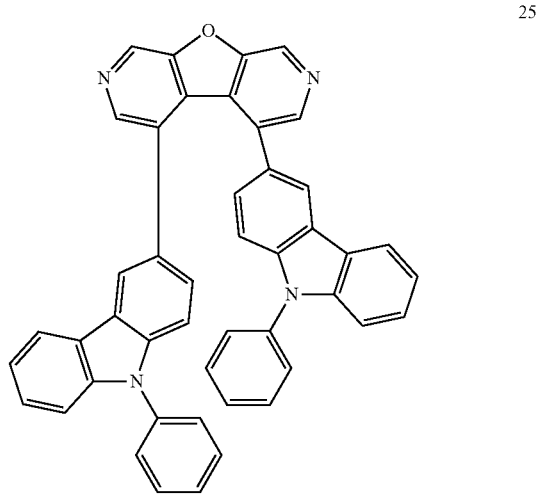

26
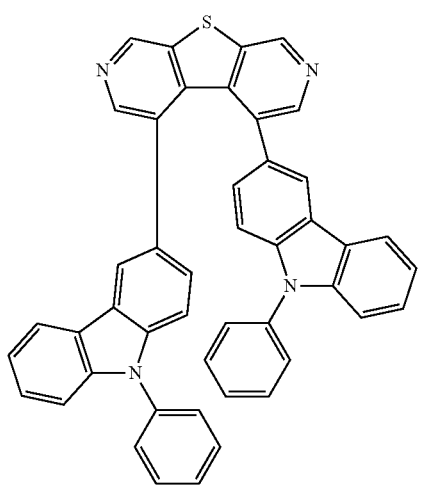
27
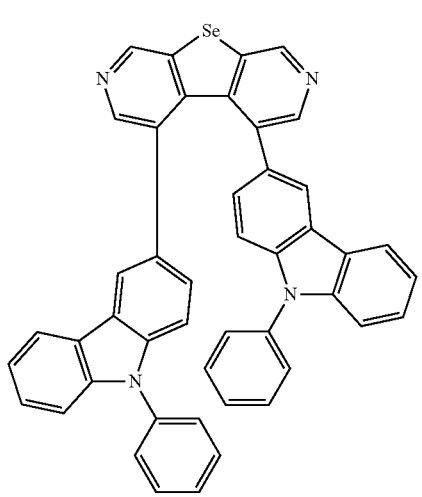
28
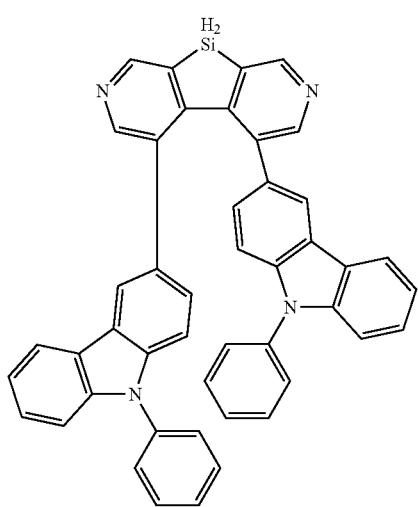
29
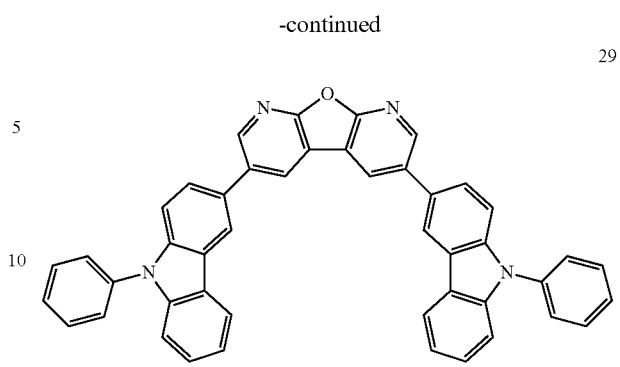
30
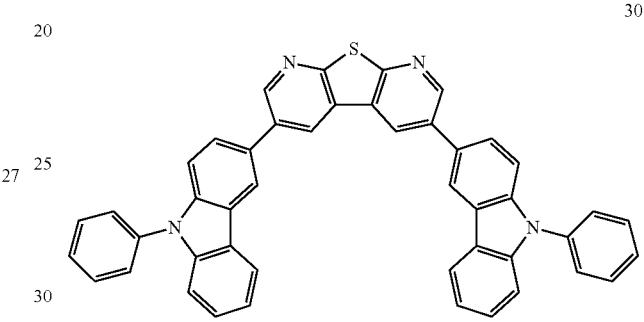
31
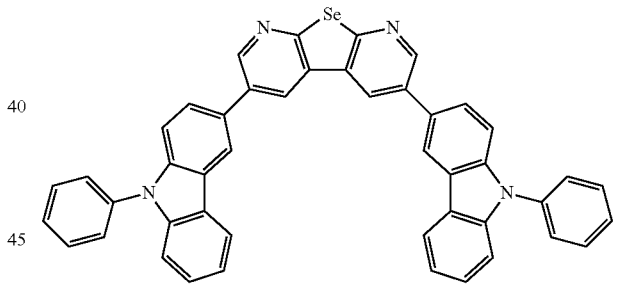
32
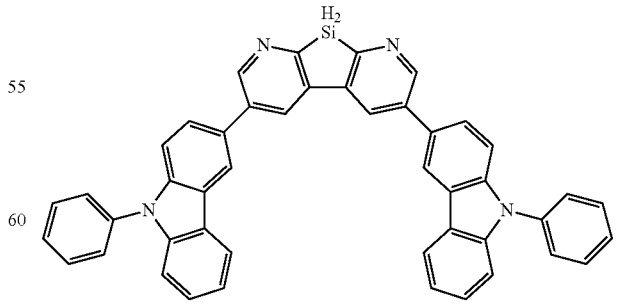

33
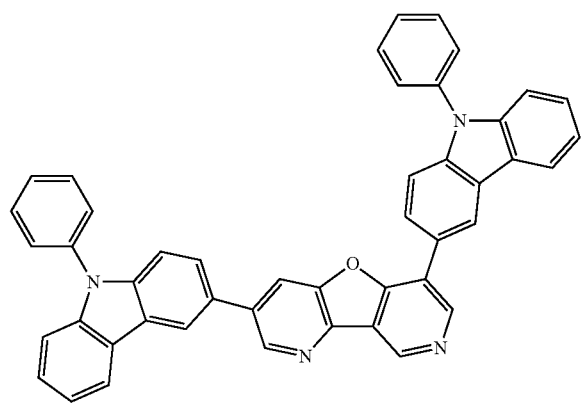
34
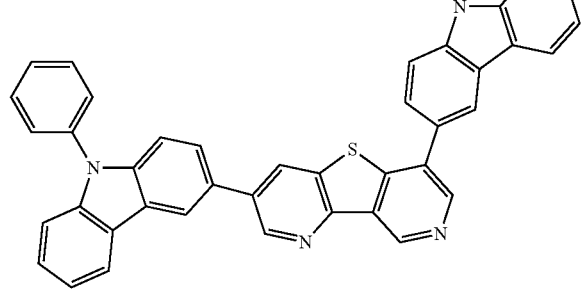
35
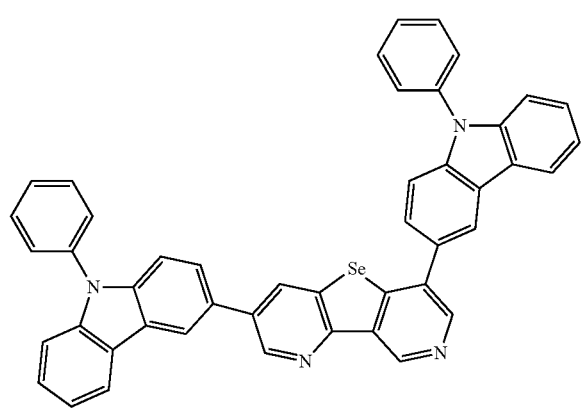
36
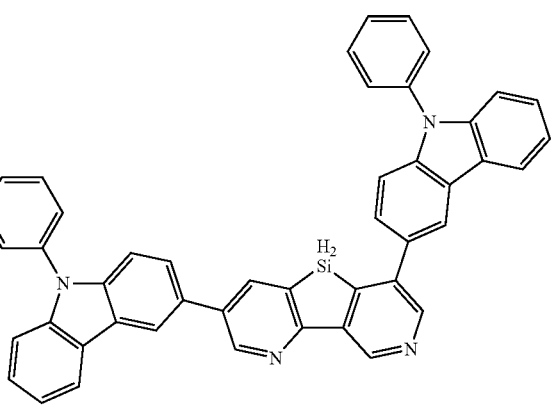
37
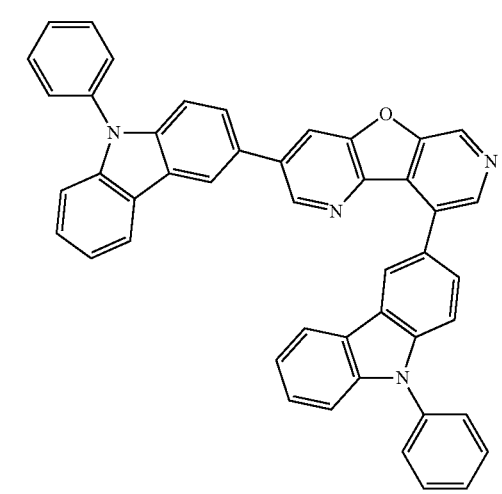
38
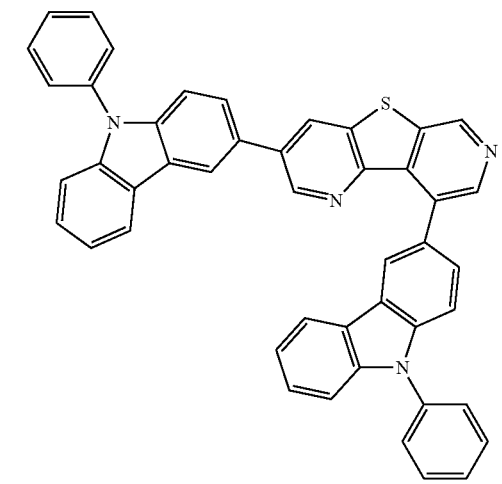

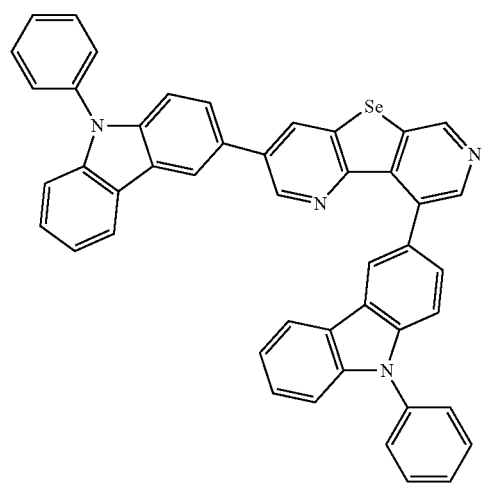
39
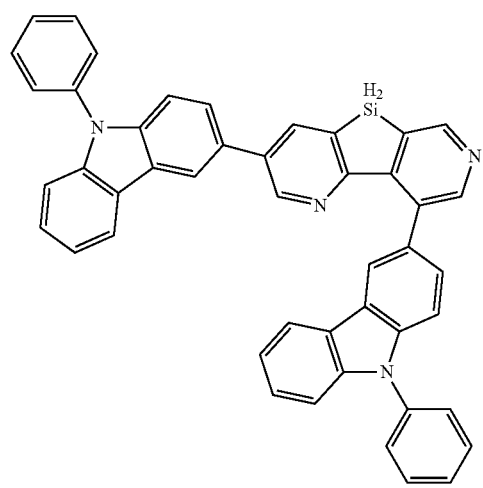
40
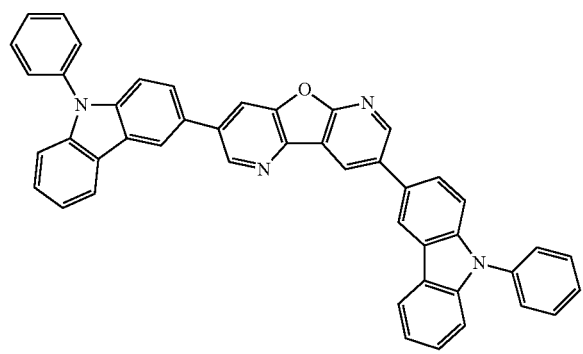
41
42
43
44
45

-continued
46
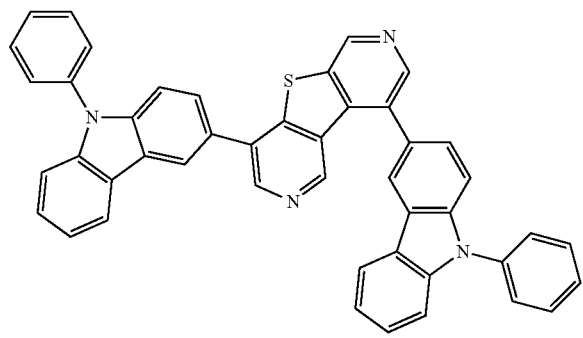
47
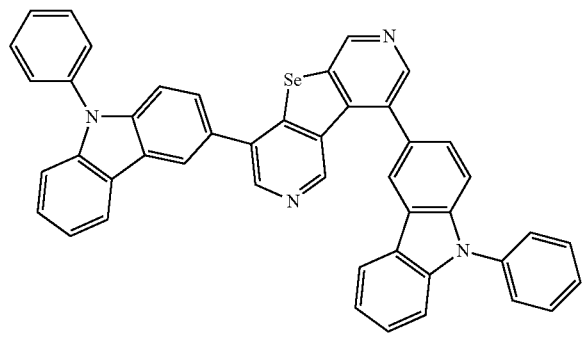
48
49
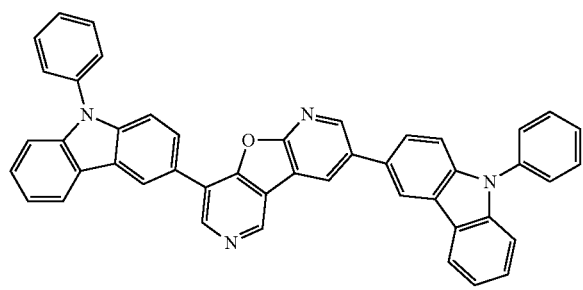
-continued
50
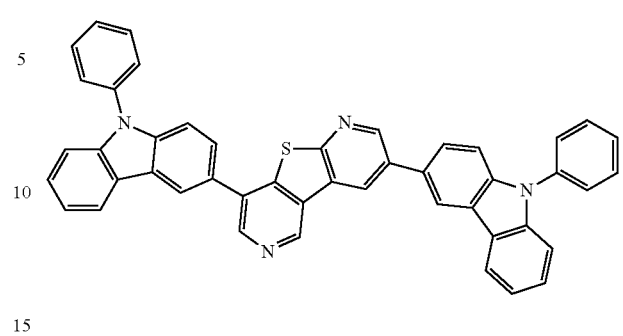
51
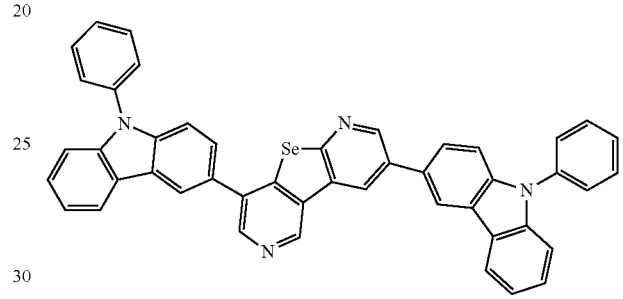
52
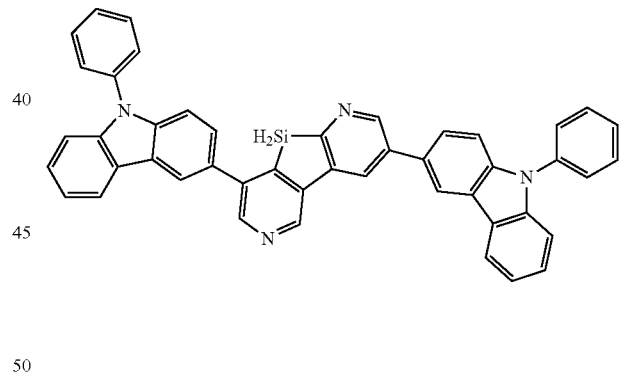
53
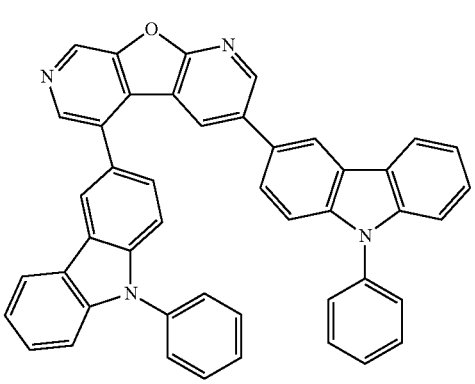

54
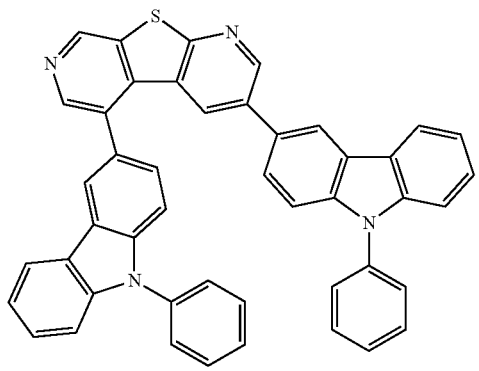
55
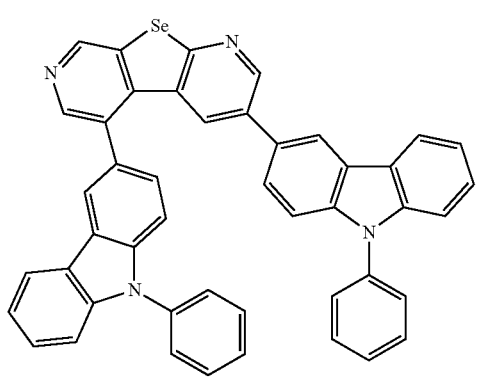
56
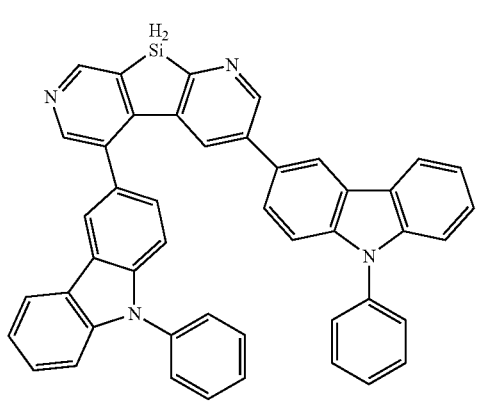
57
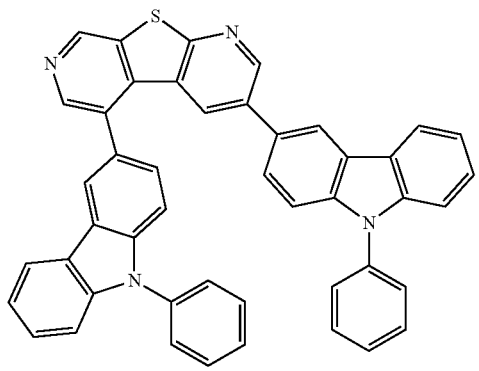
58
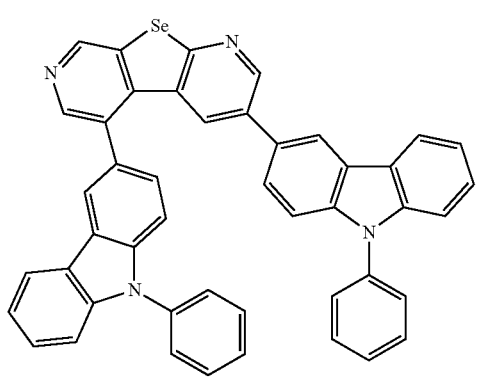
59
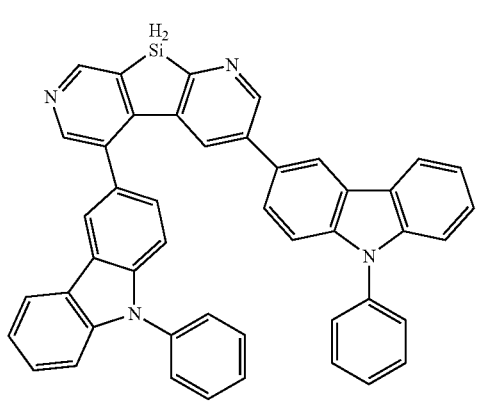
60
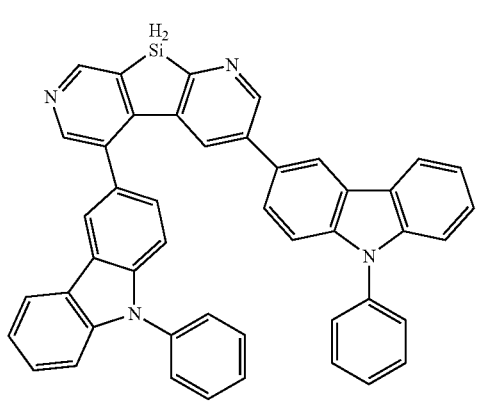
61
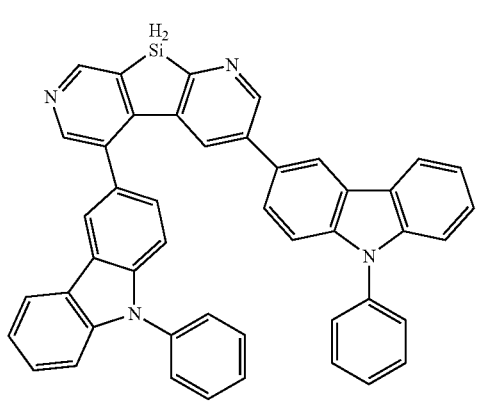
62
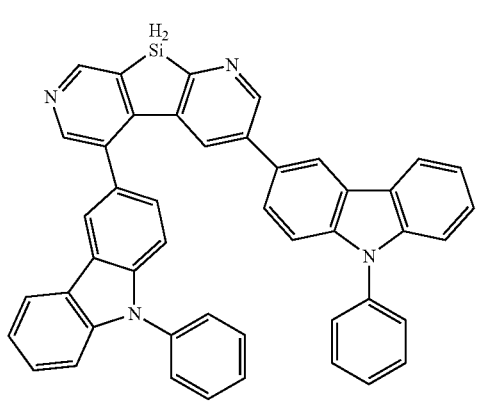

63
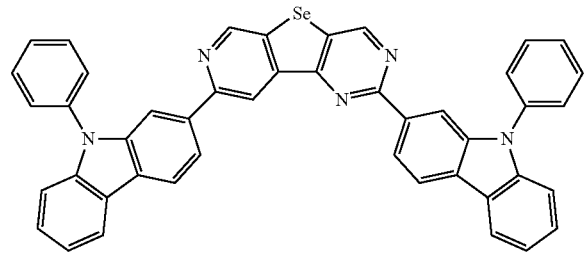
64
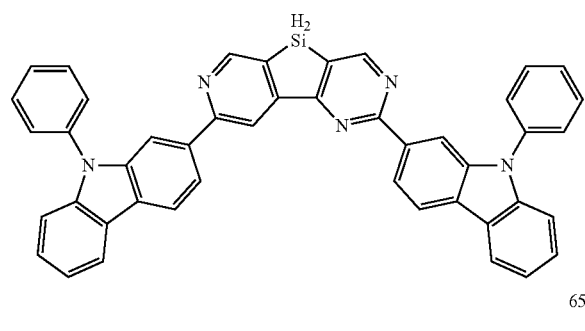
65
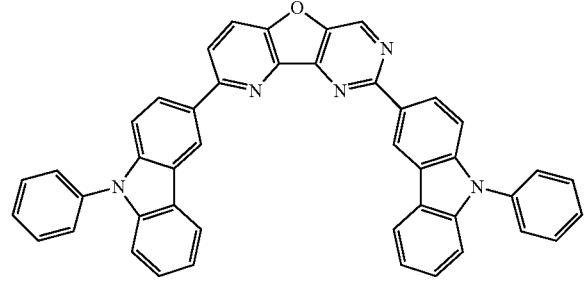
66
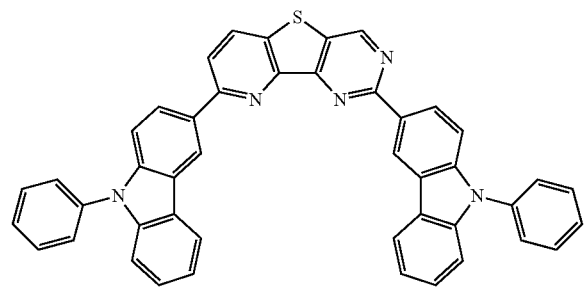
67
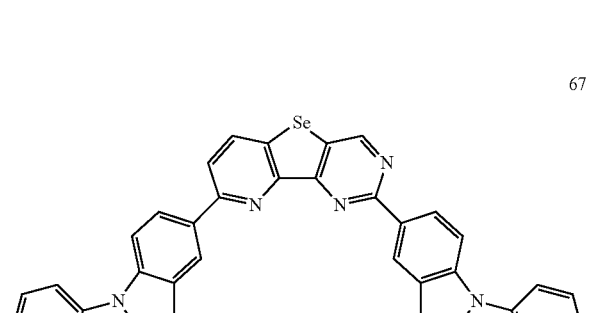
68
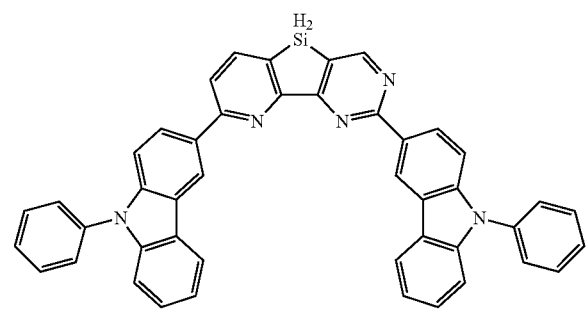
69
70
71
72

-continued
73
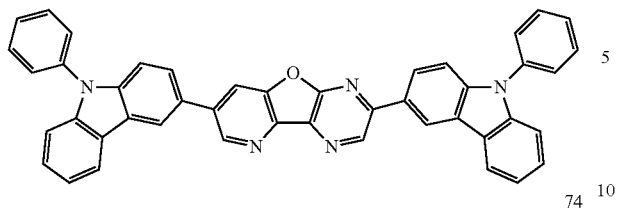
74
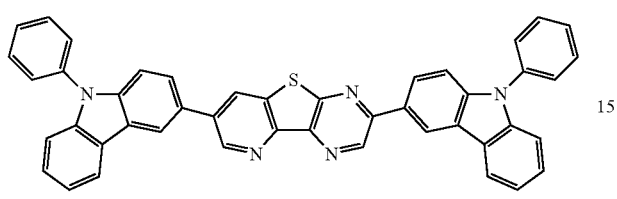
75
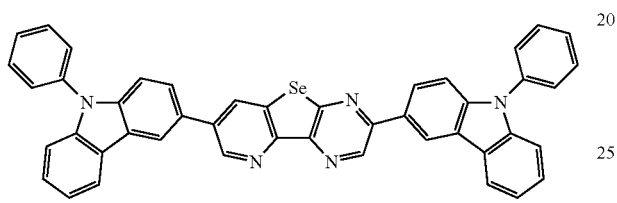
76
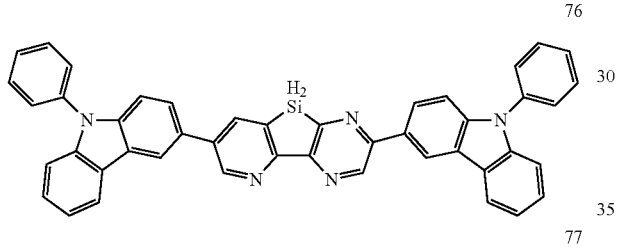
77
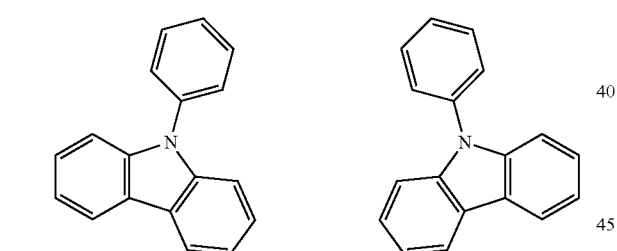
78
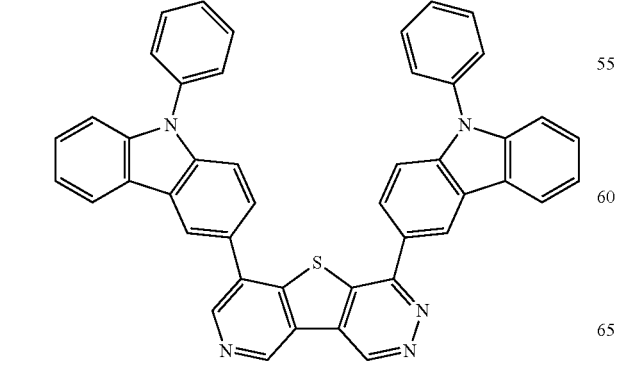
-continued
79
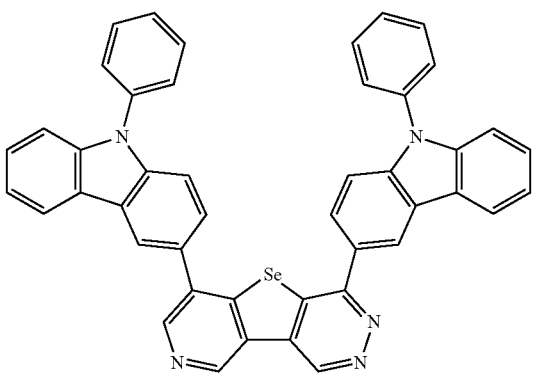
80
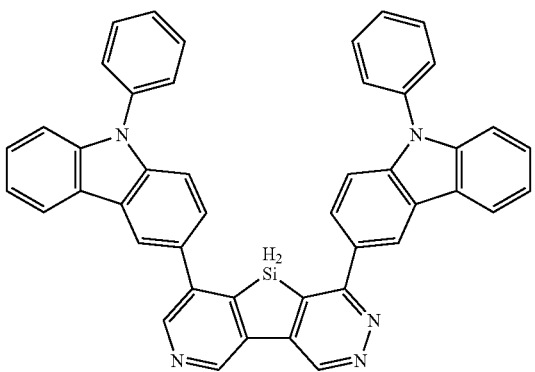
81
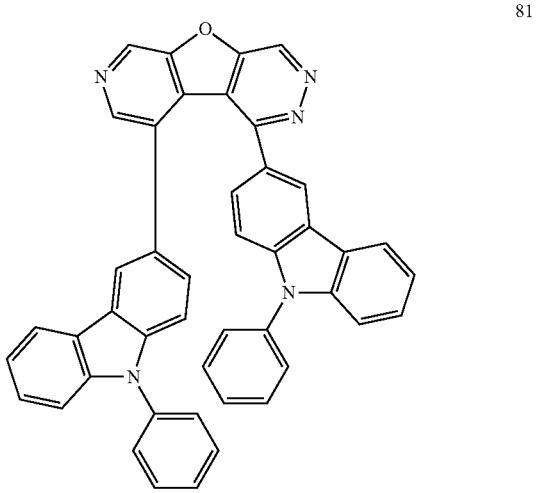

82
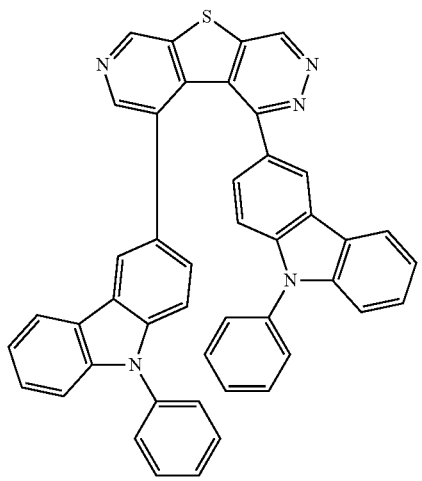
85
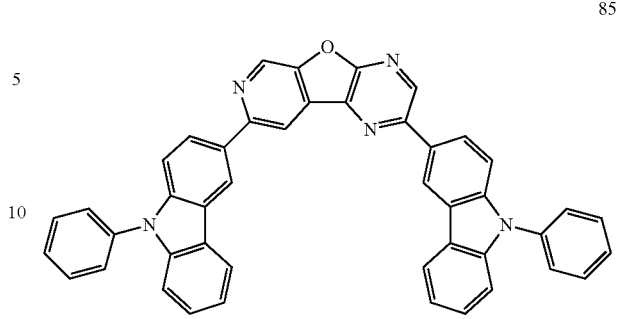
83
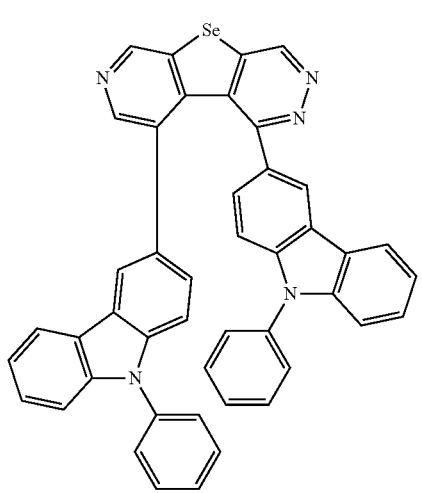
86
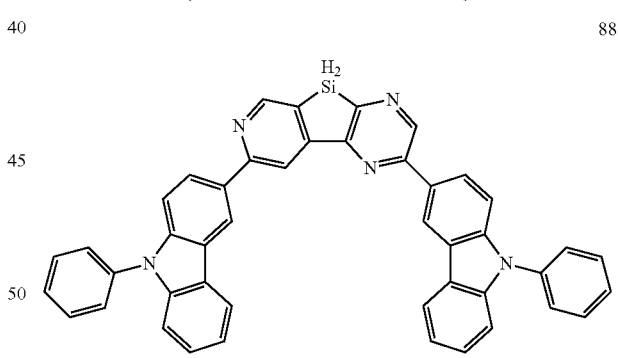
87
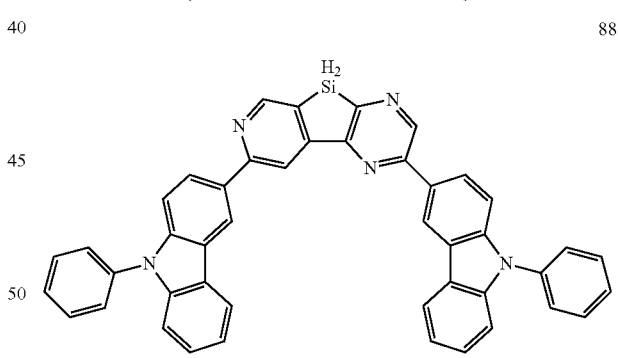
84
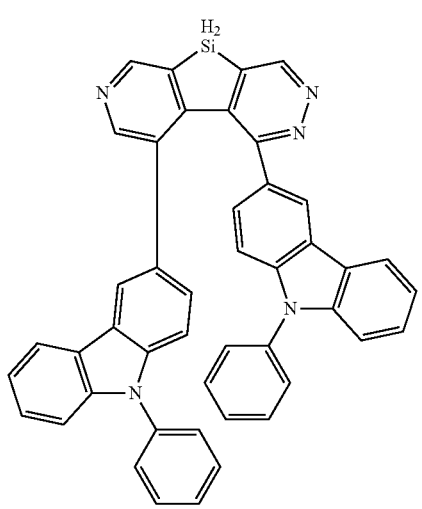
88
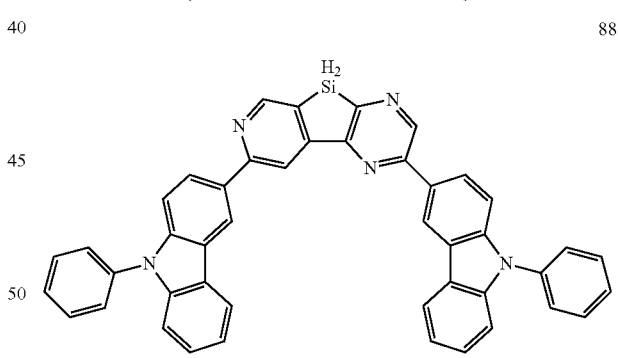
89
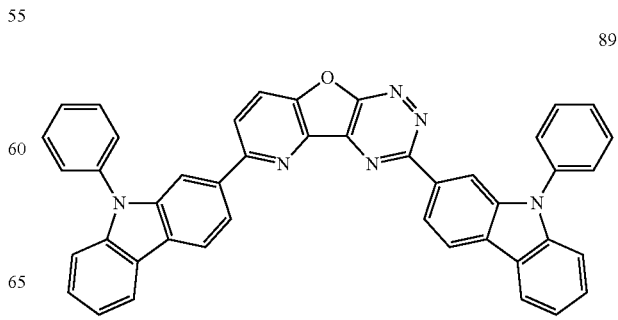

187
-continued
90
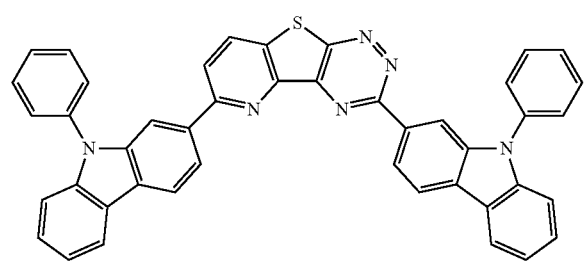
91
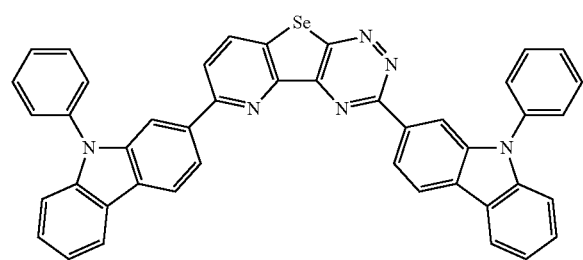
92
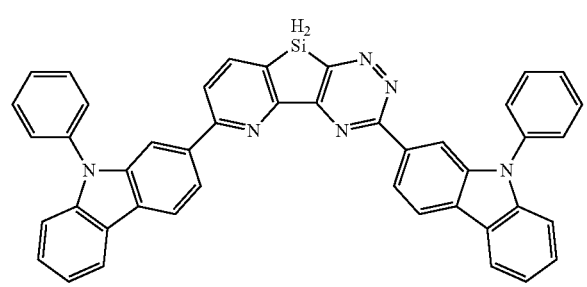
93
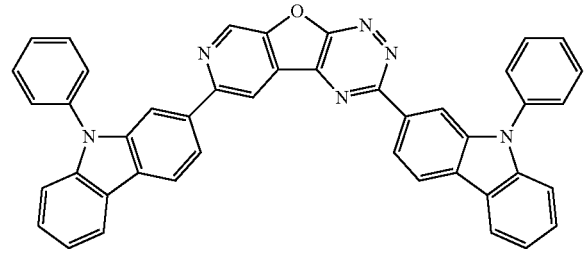
94
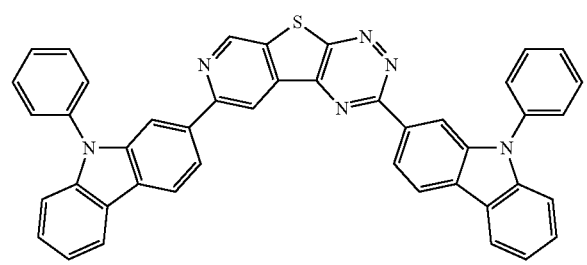
188
-continued
95
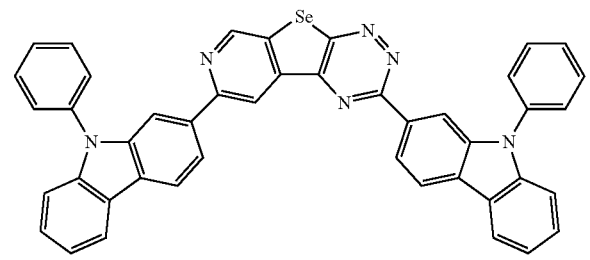

-continued
100
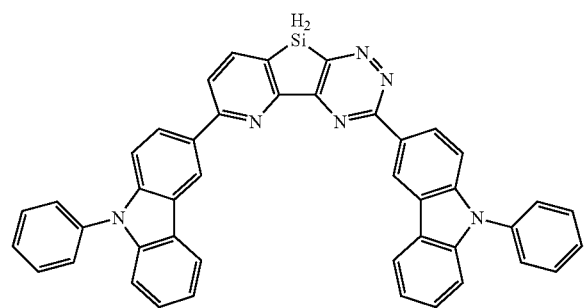
101
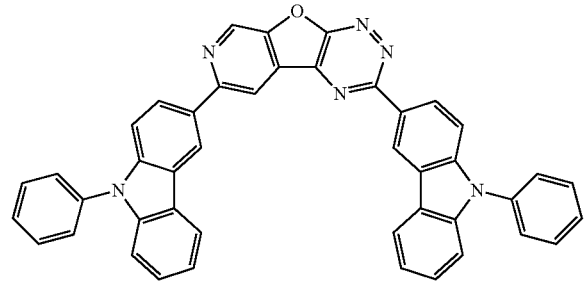
102
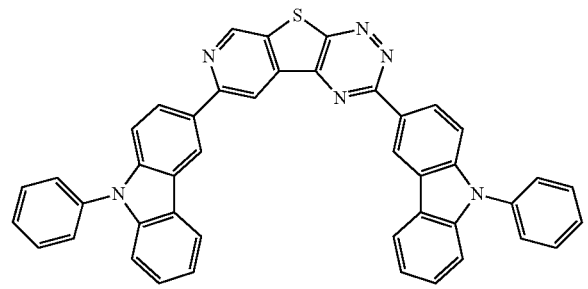
103
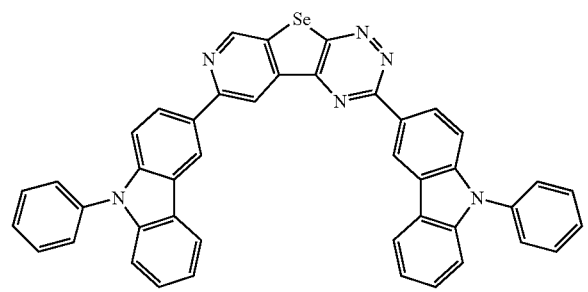
104
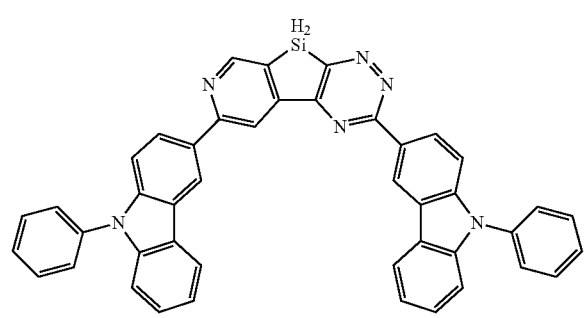
-continued
105
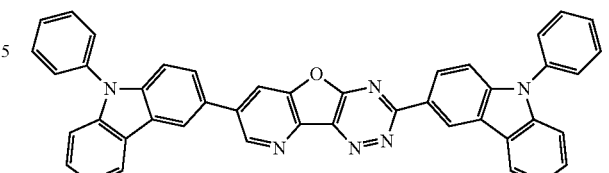
106
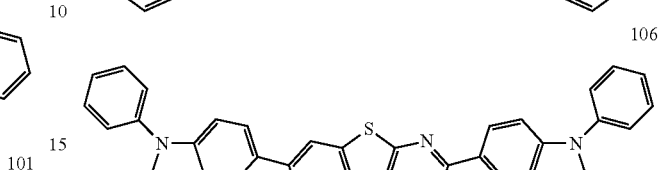
107
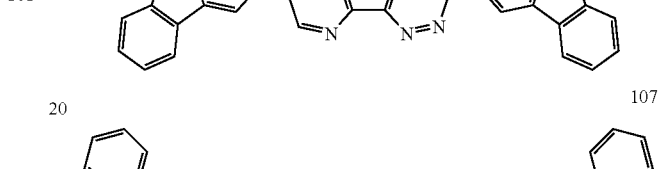
108
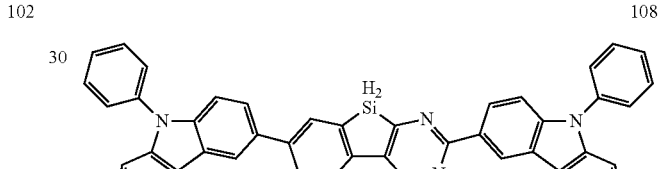
109
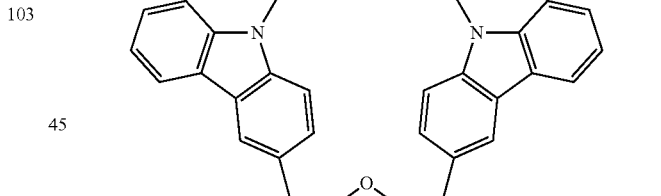
110
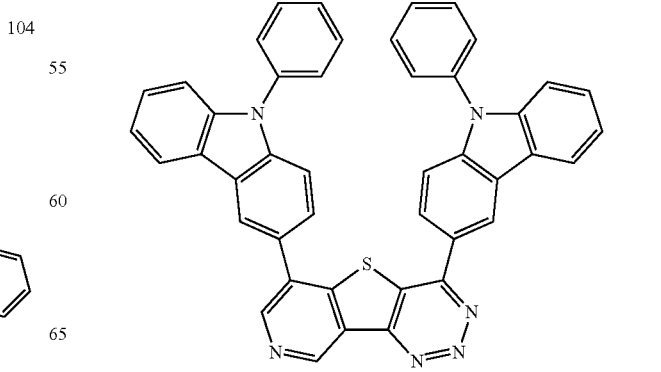

-continued
111
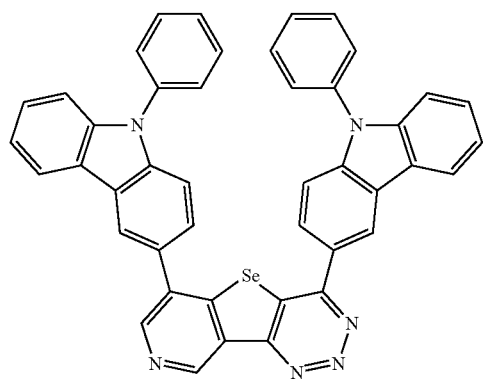
112
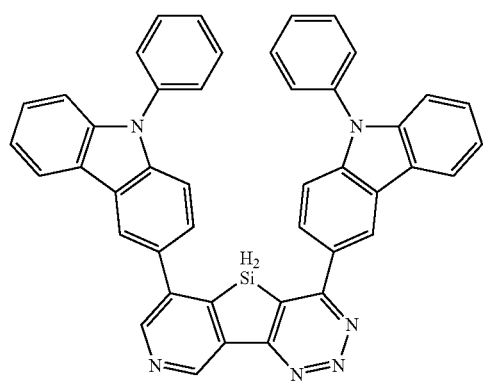
113
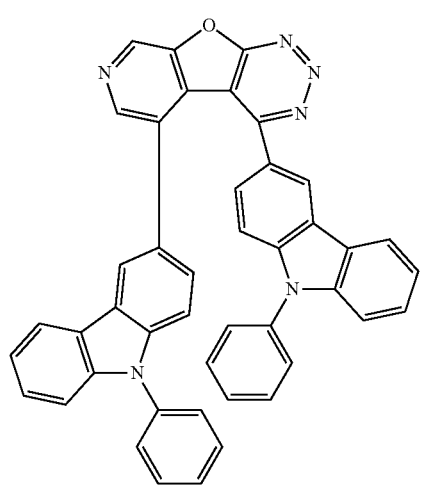
-continued
114
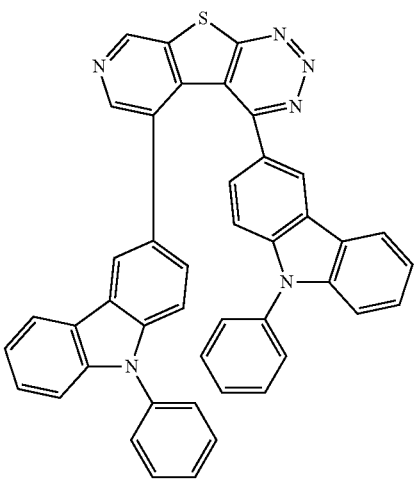
115
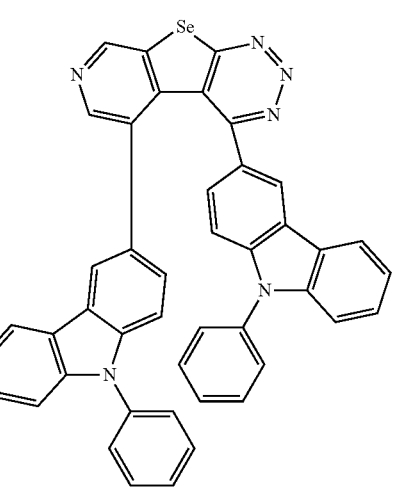
116
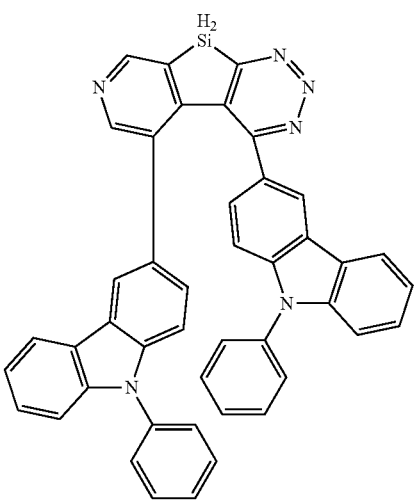

117
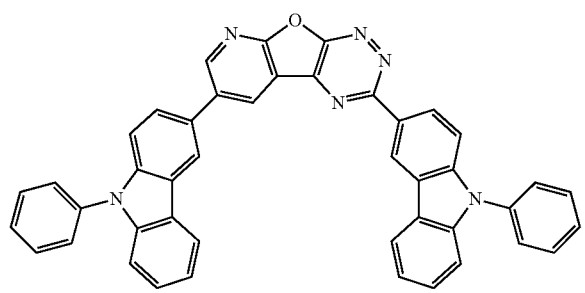
118
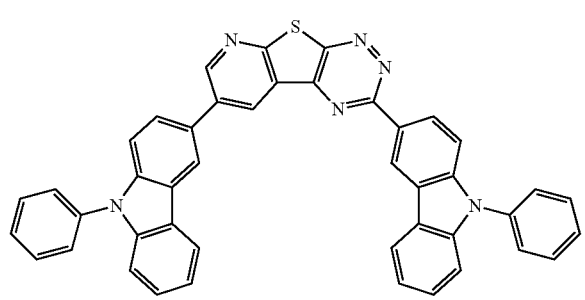
119
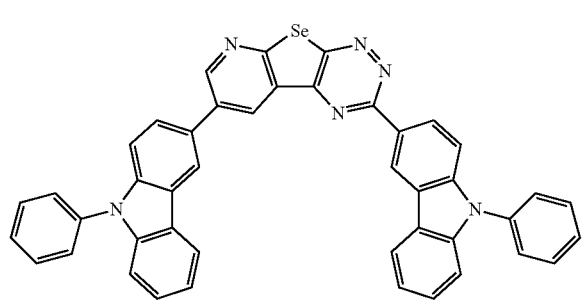
120
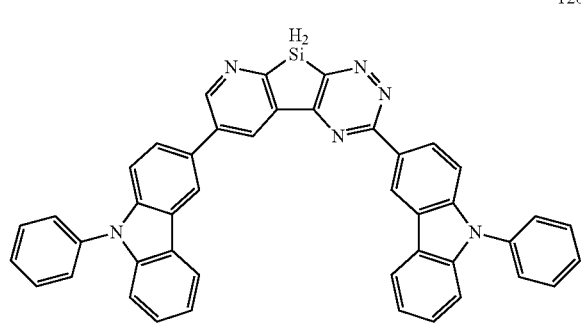
121
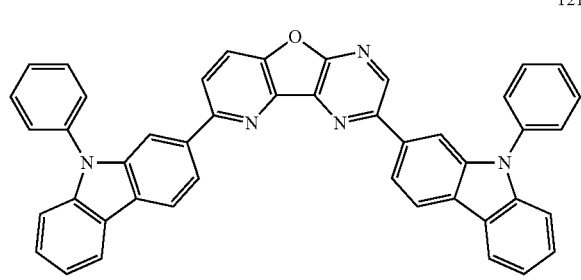
122
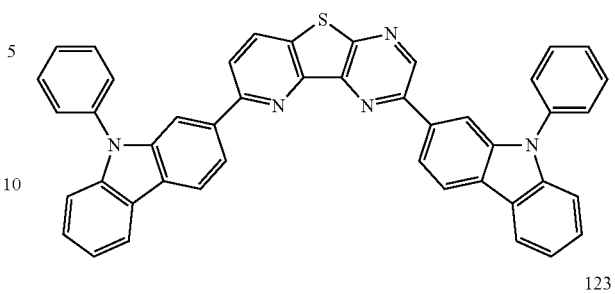
123
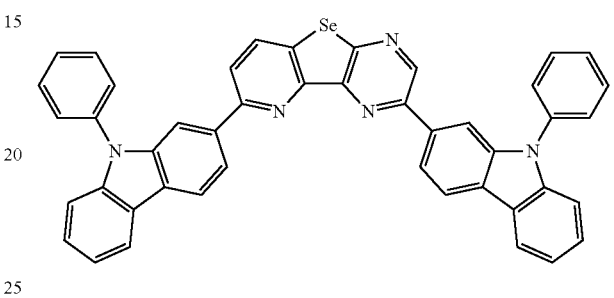
124
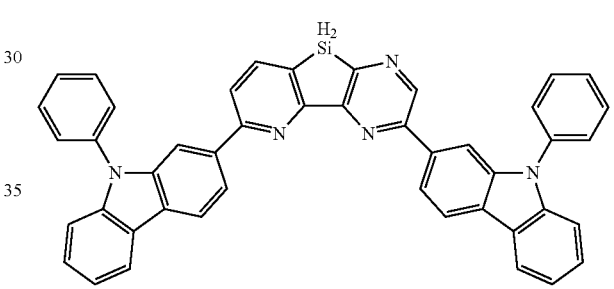
125
126
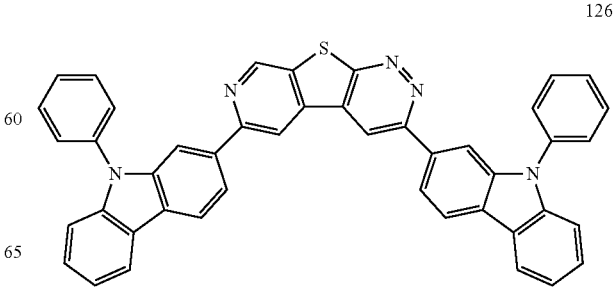

127
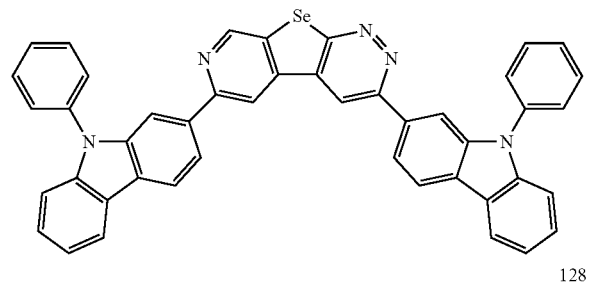
128
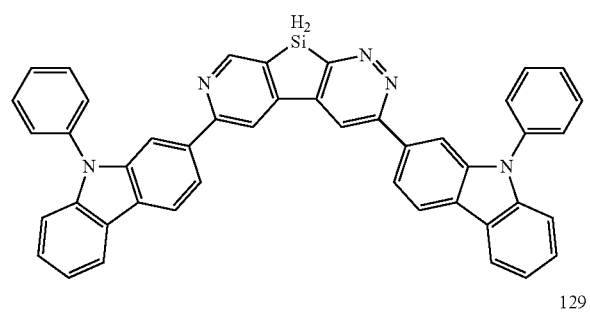
129
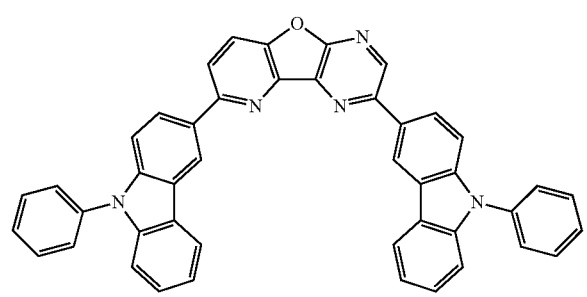
130
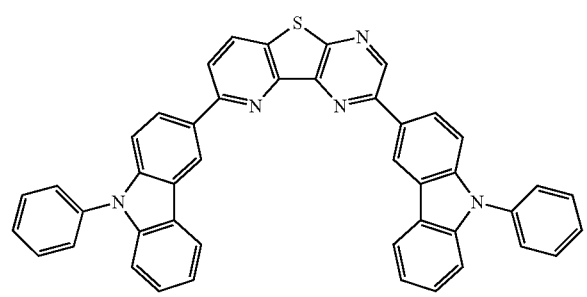
131
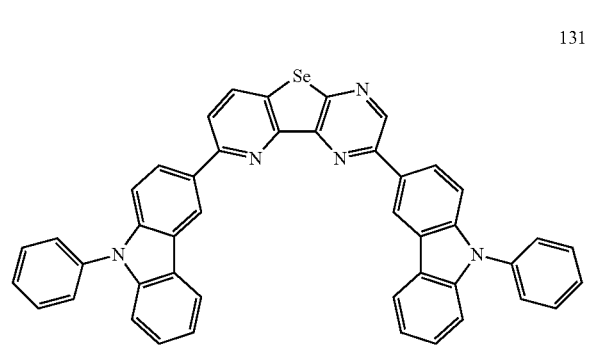
132
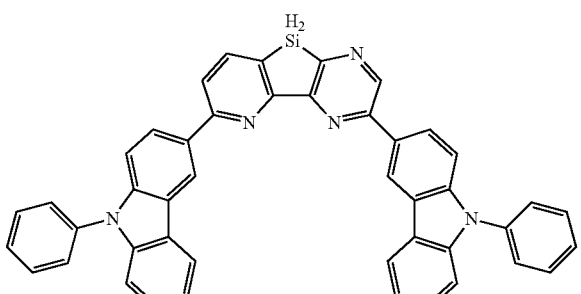
133
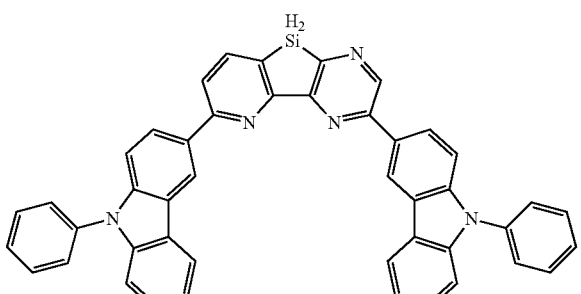
134
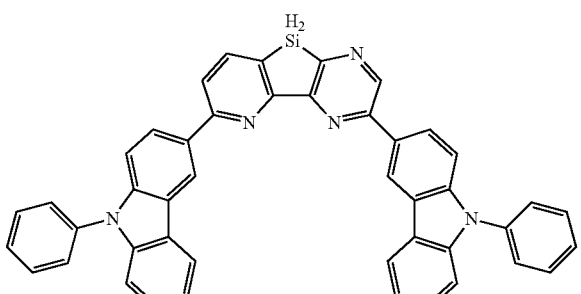
135
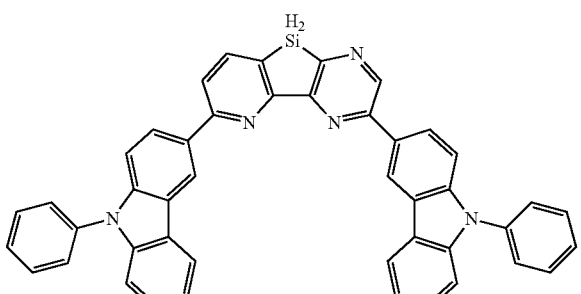
136

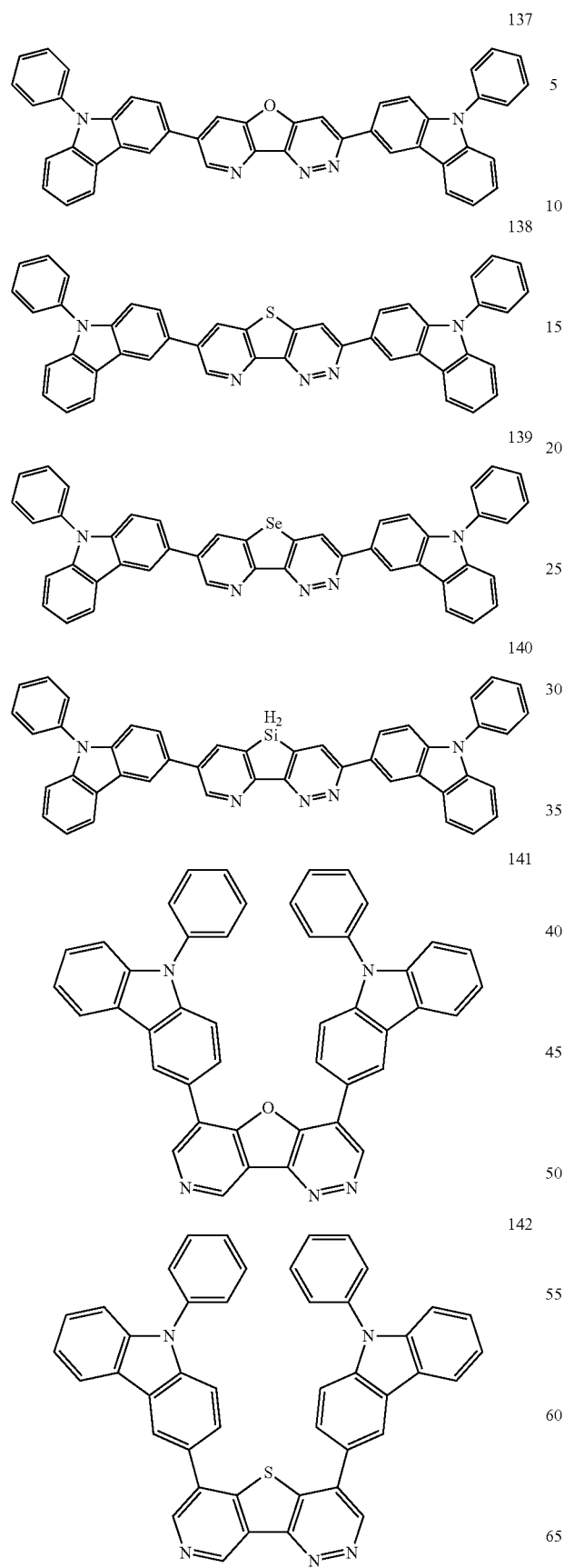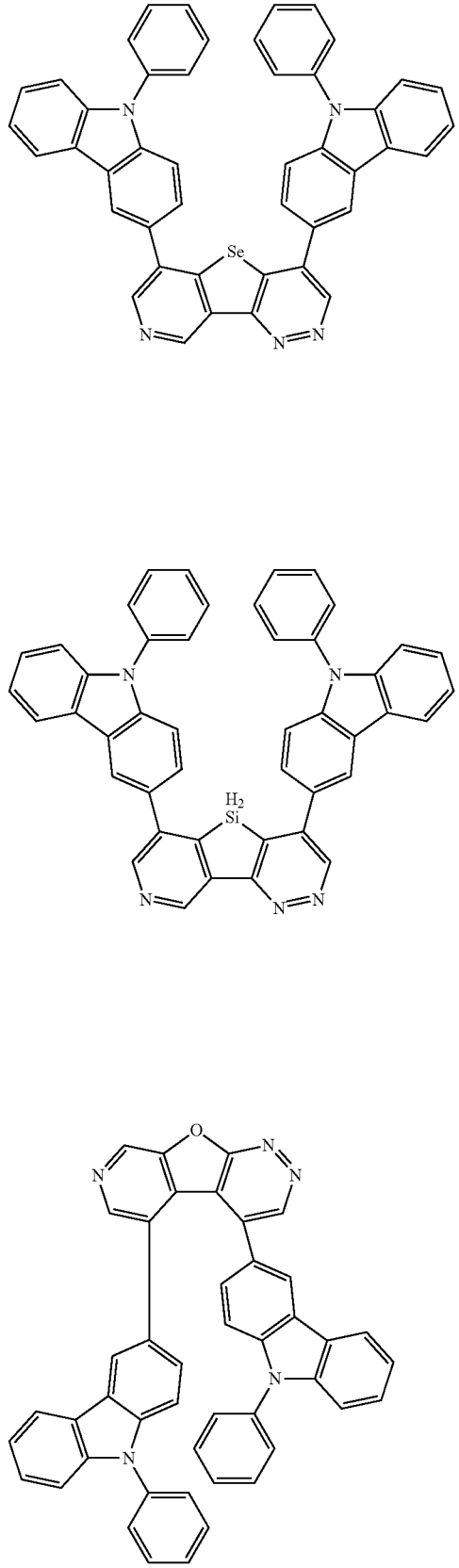

146
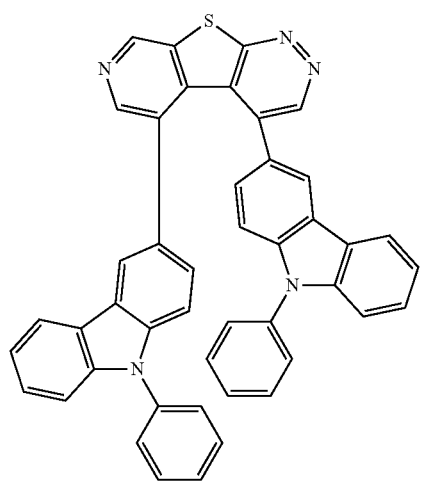
147
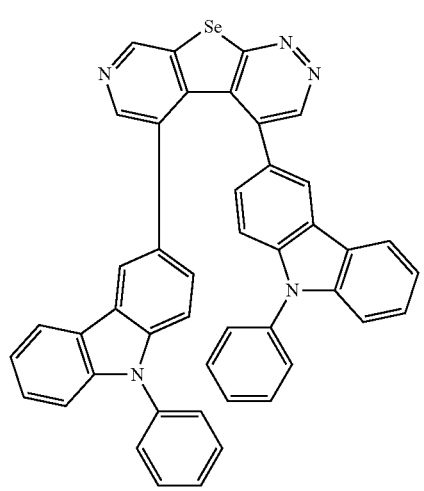
148
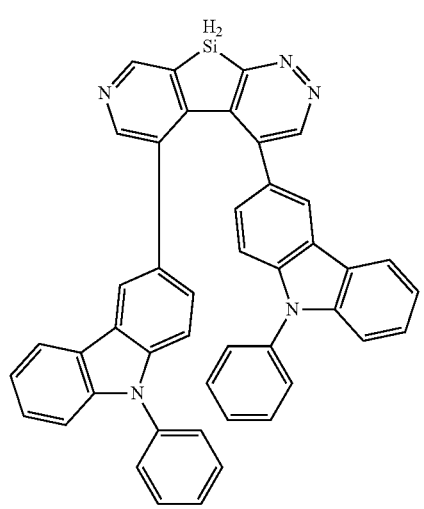
149
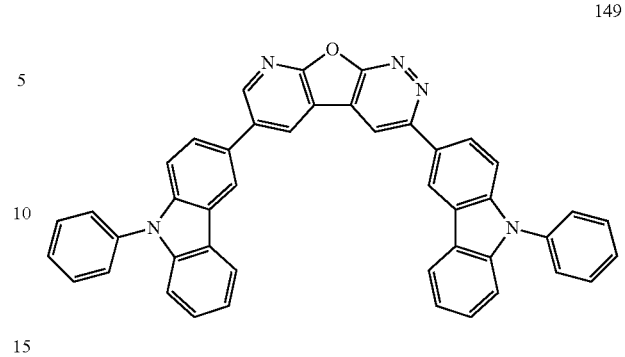
150
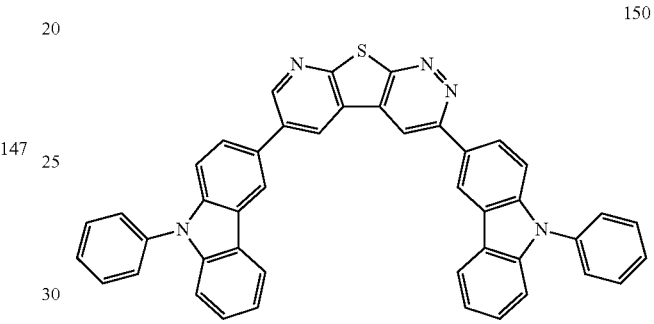
151
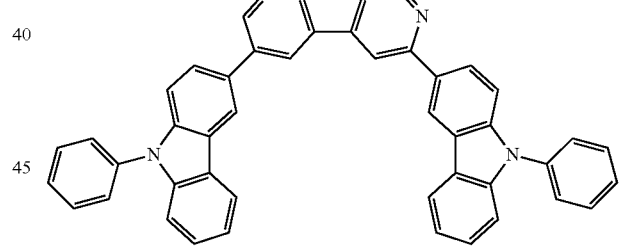
152
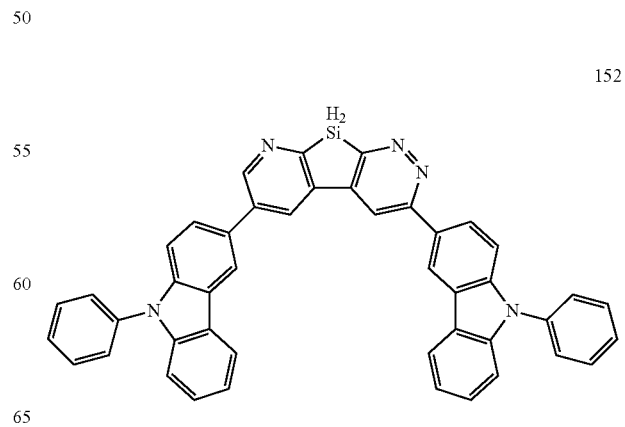

153
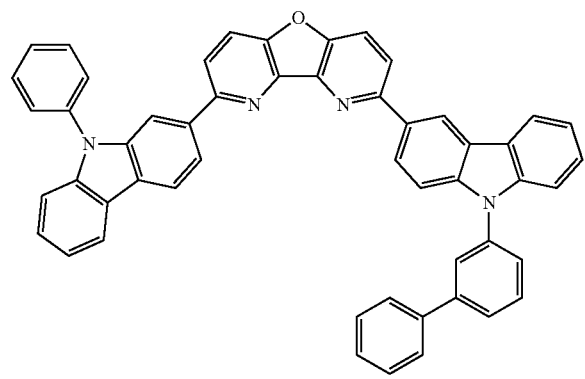
154
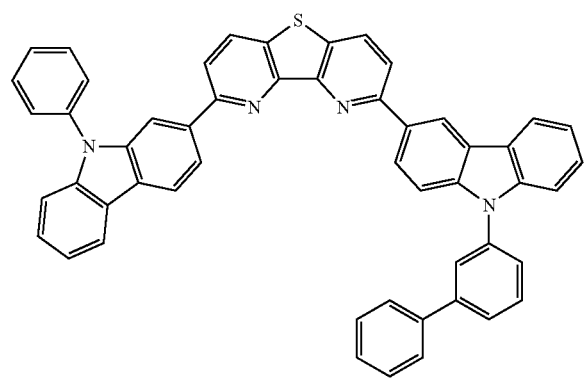
155
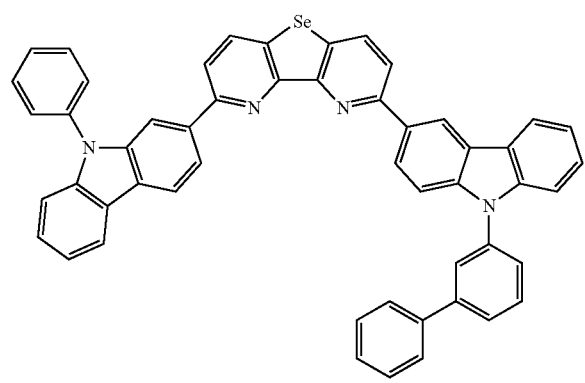
156
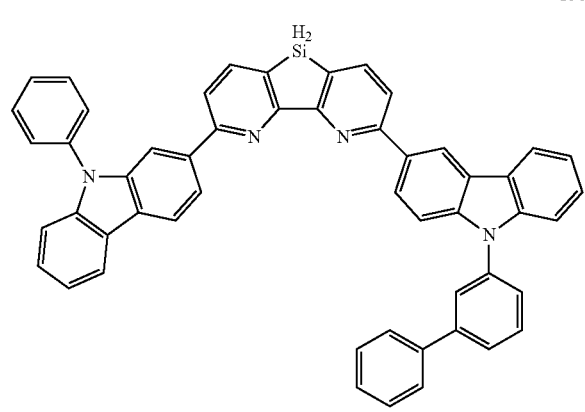
157
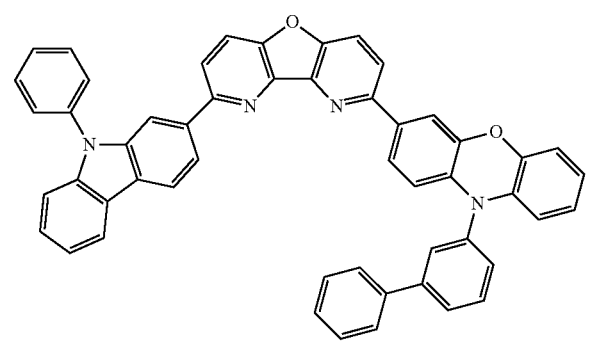
158
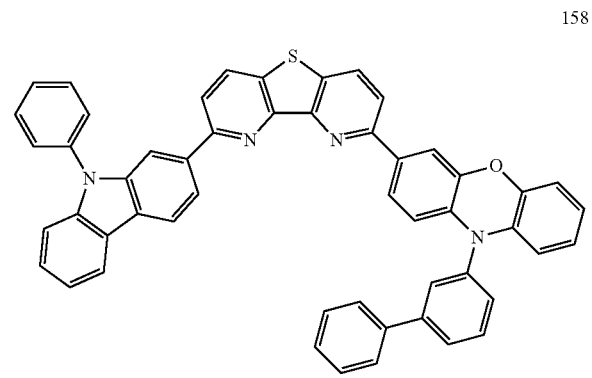
159
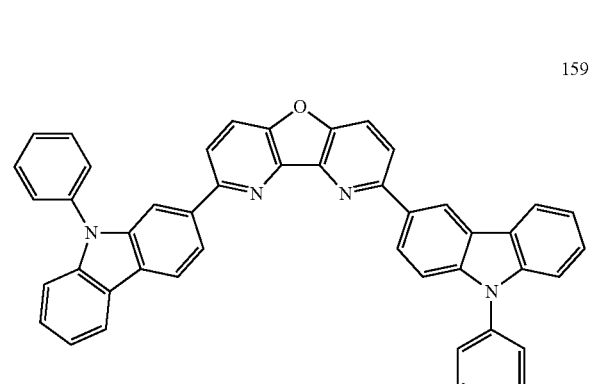
160
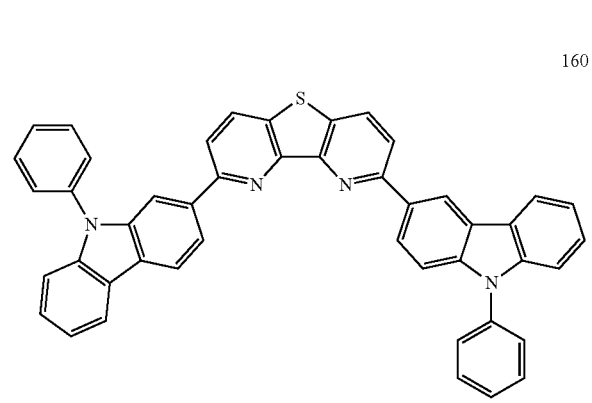

161
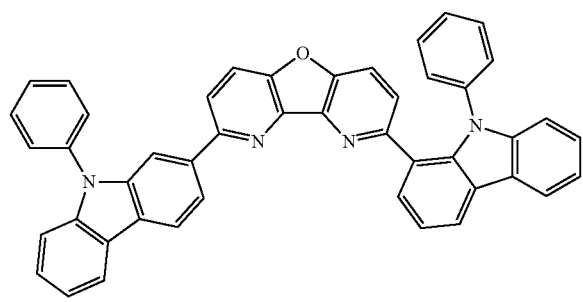
162
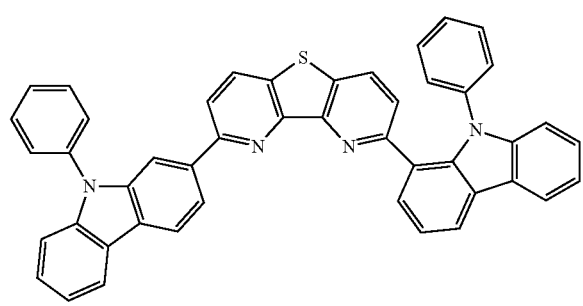
163
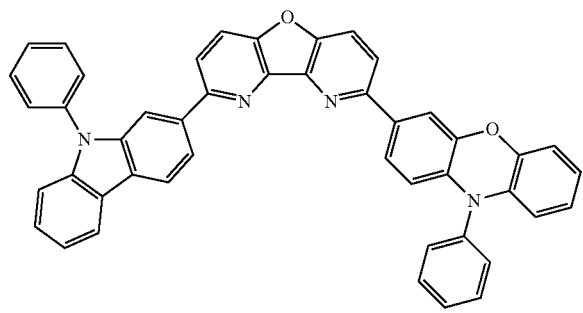
164
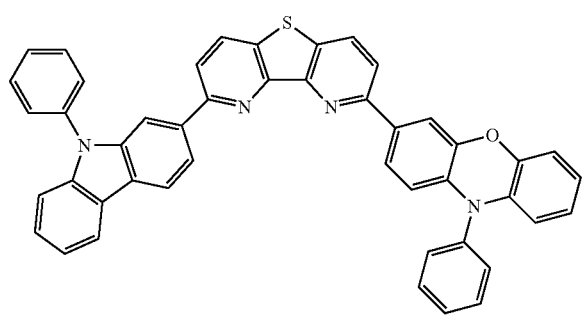
165
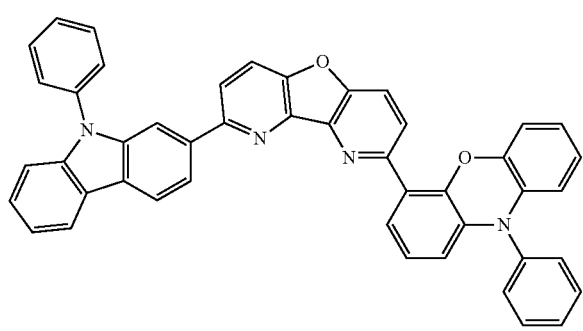
166
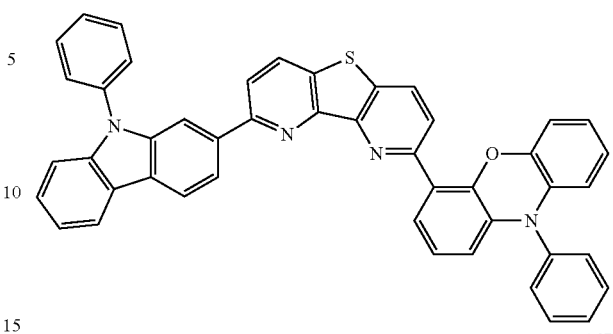
167
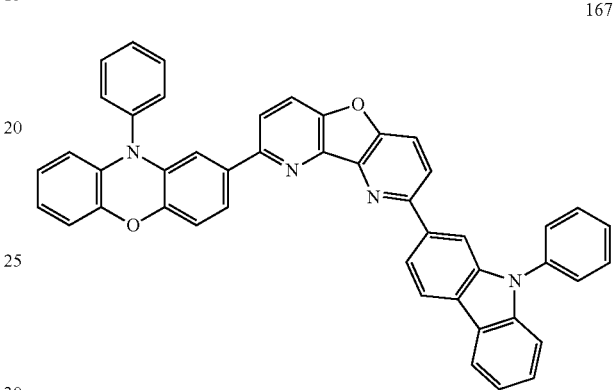
168
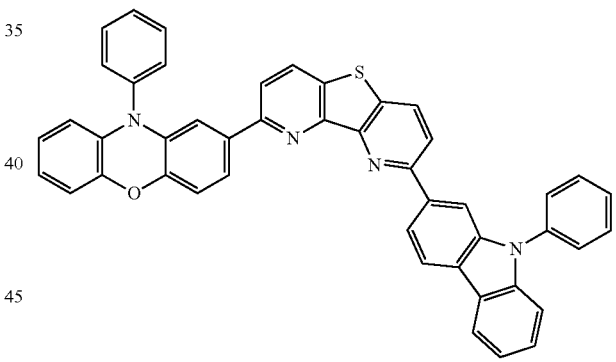
169
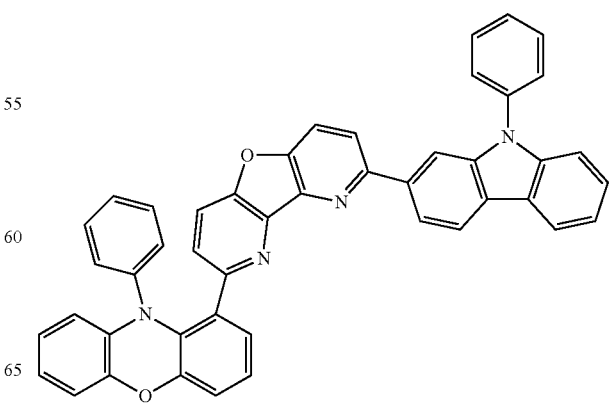

-continued
170
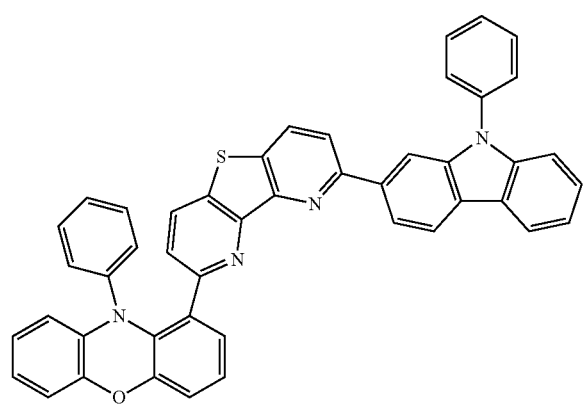
171
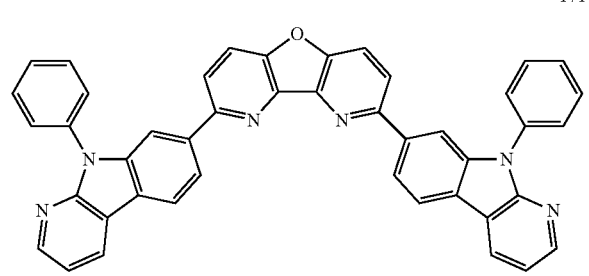
172
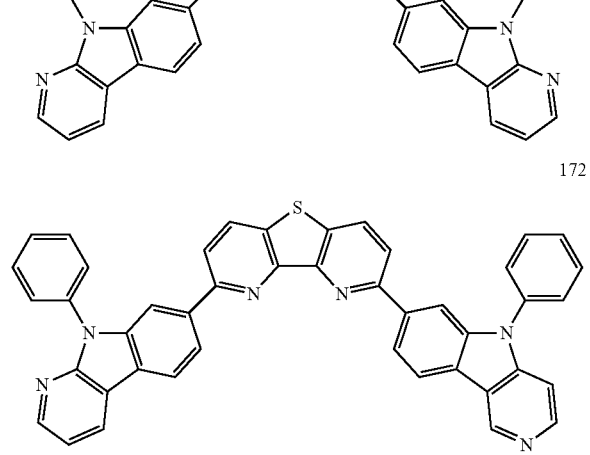
173
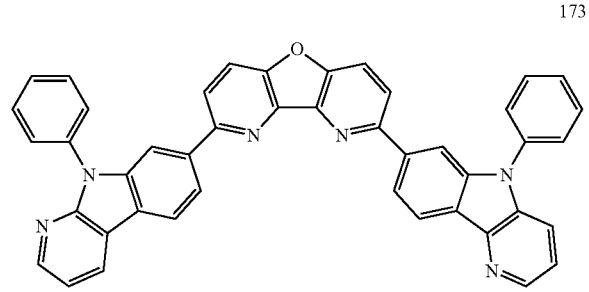
174
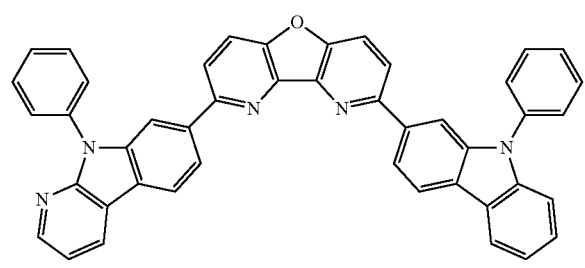
-continued
175
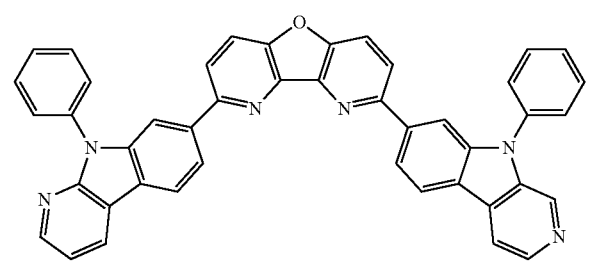
176
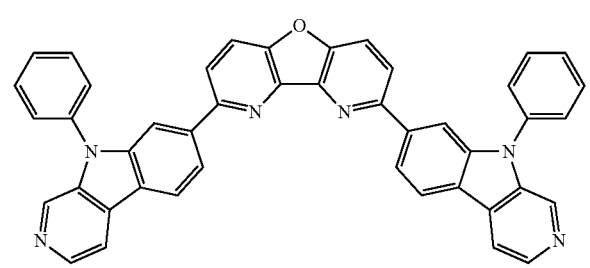
177
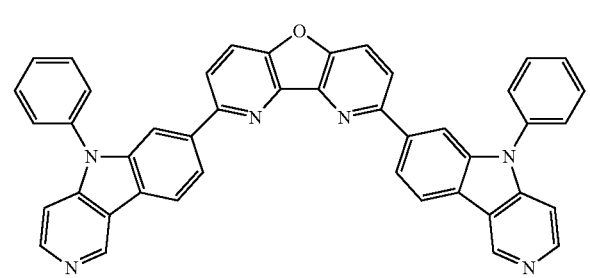
178
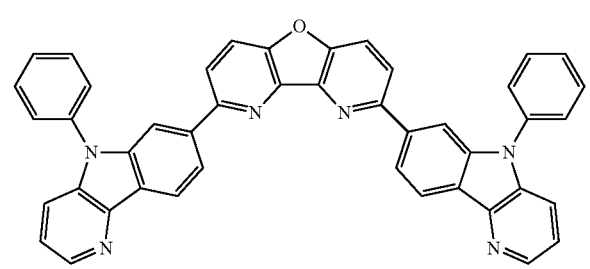
179
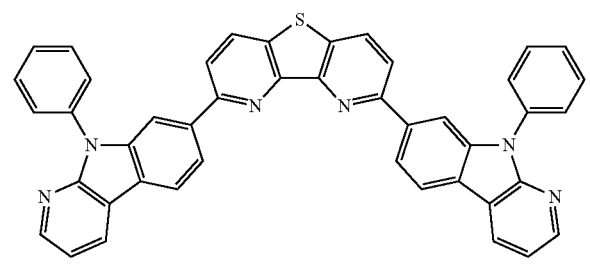

207
-continued
180
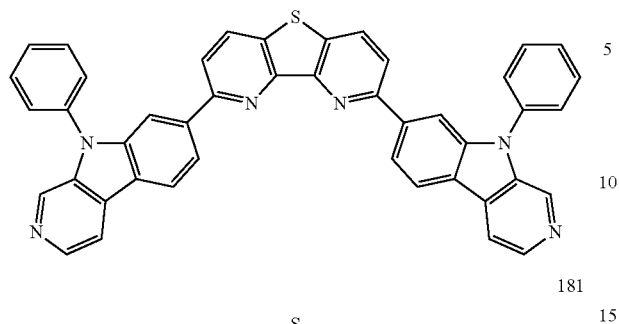
181
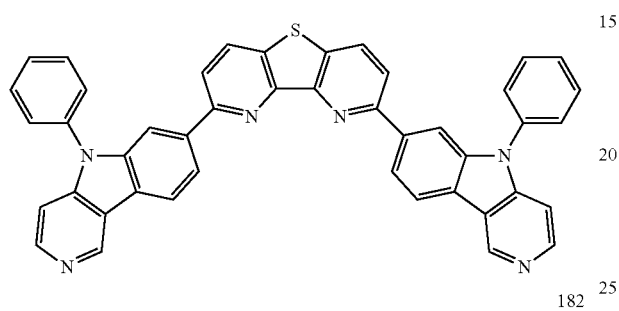
182
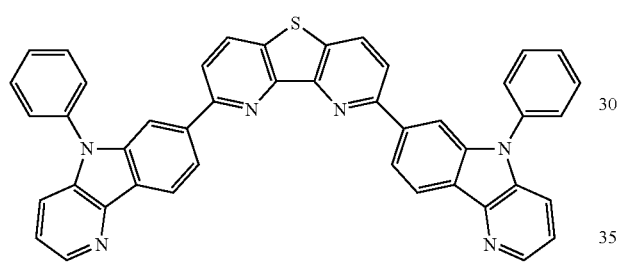
183
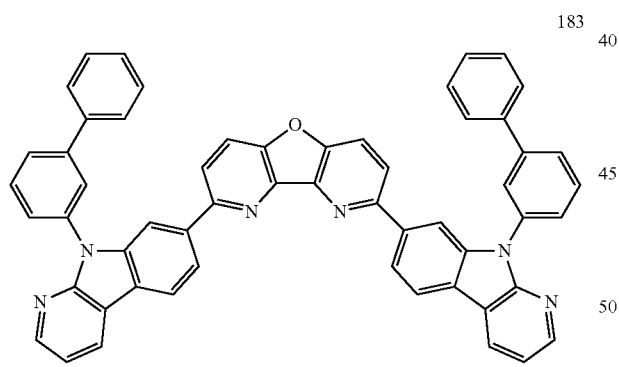
184
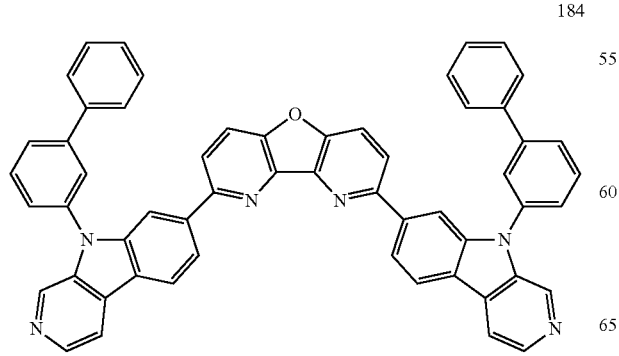
208
-continued
185
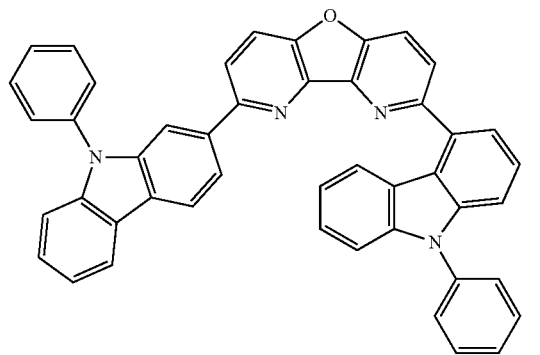
186
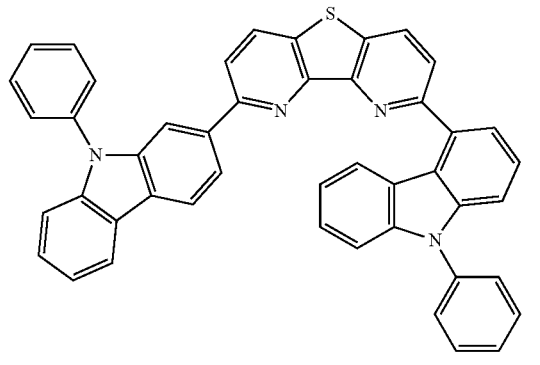
187
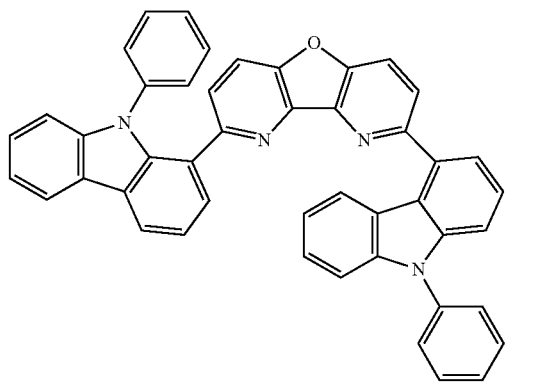
188
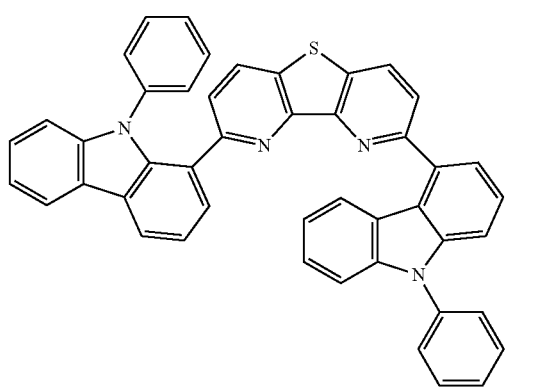

189
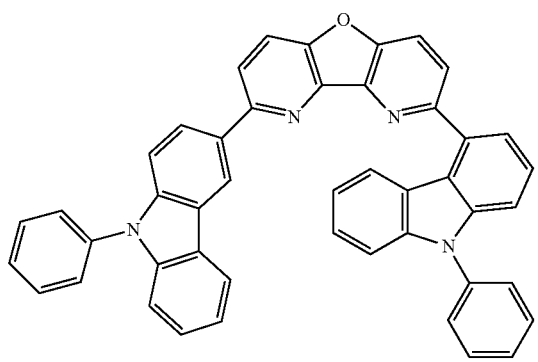
190
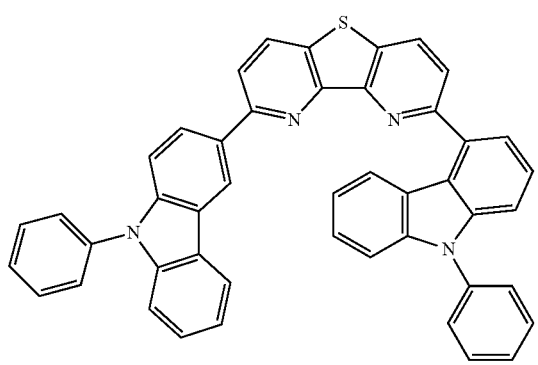
191
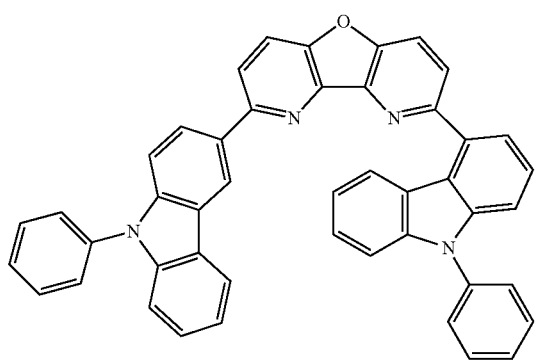
192
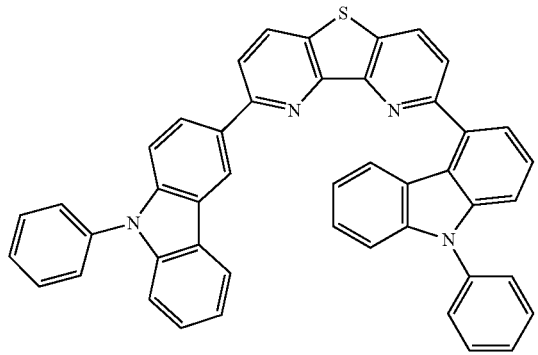
193
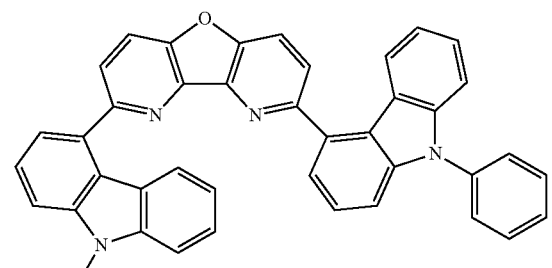
194
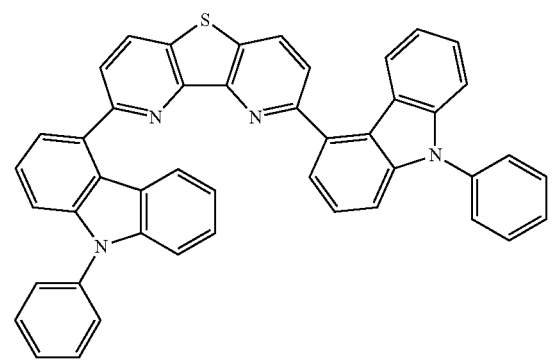
195
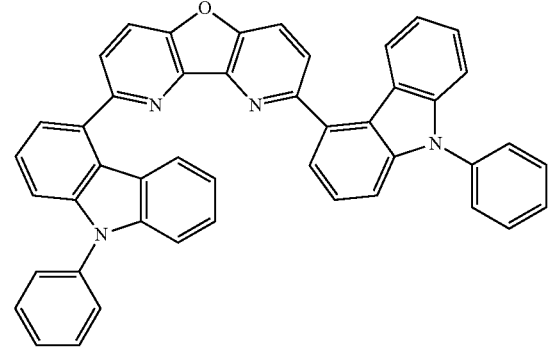
196
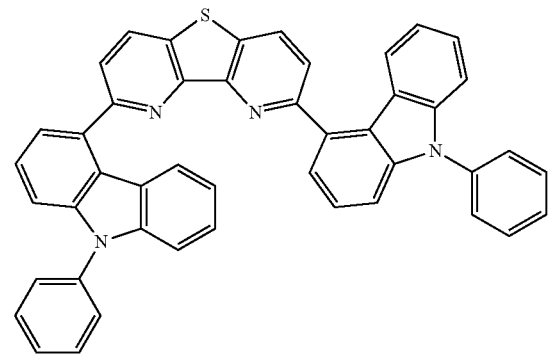

US 9,850,253 B2
211 -continued
197
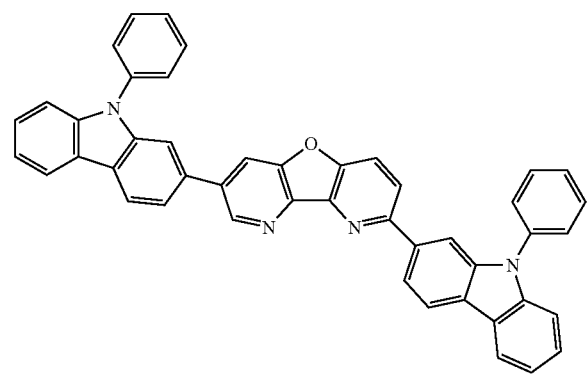
198
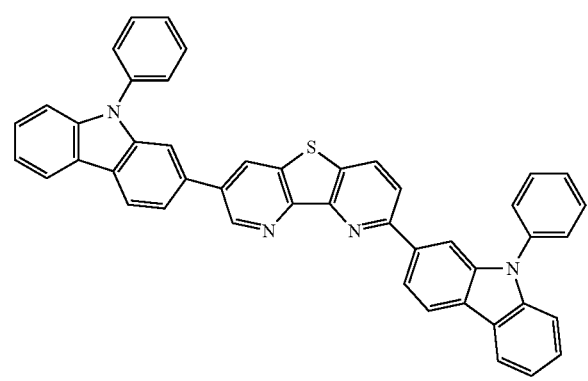
199
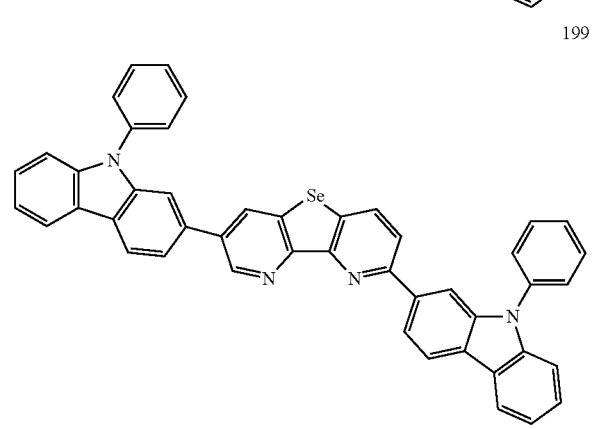
200
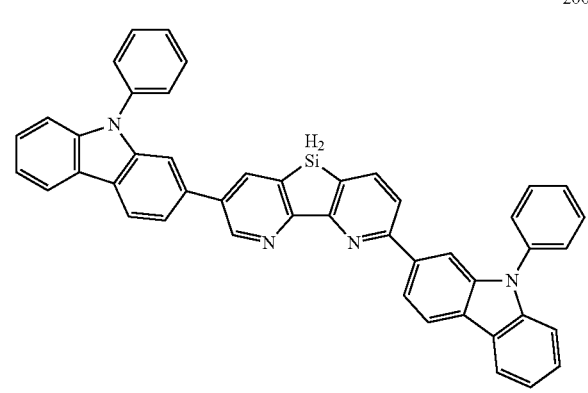
212 -continued
201
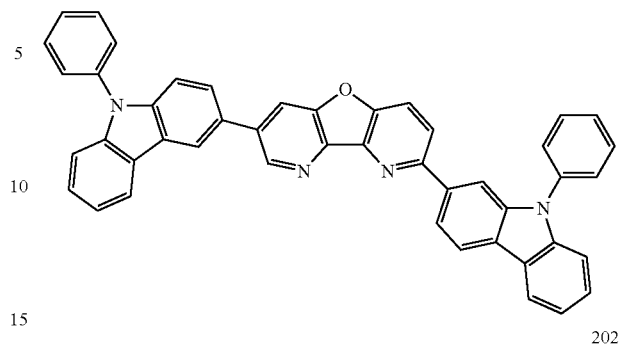
202
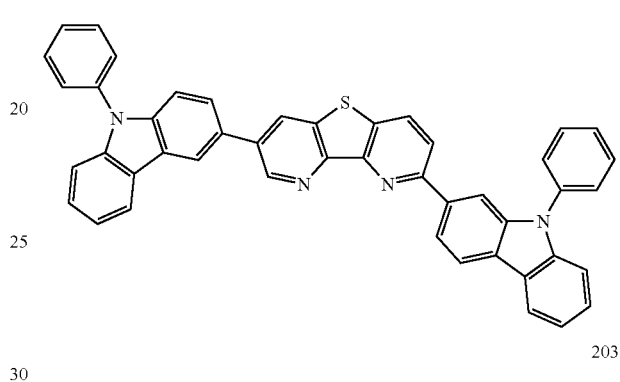
203
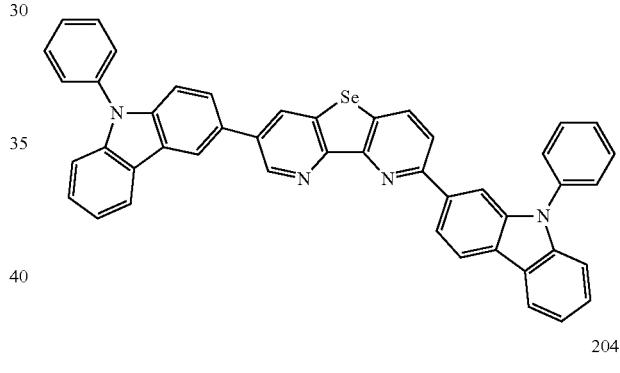
204
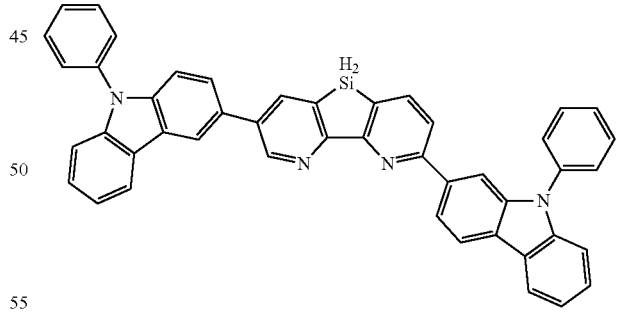
205
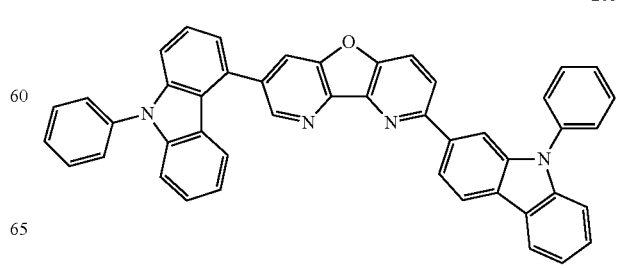

-continued
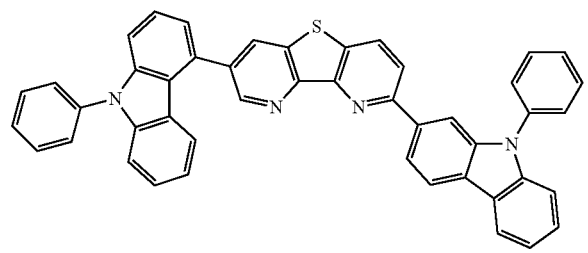
206
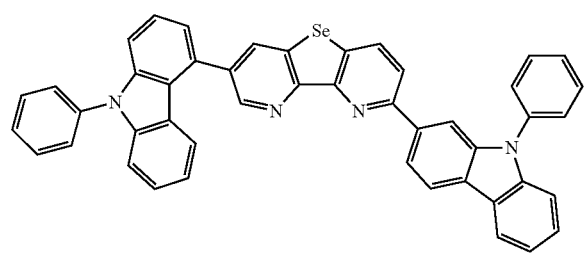
207
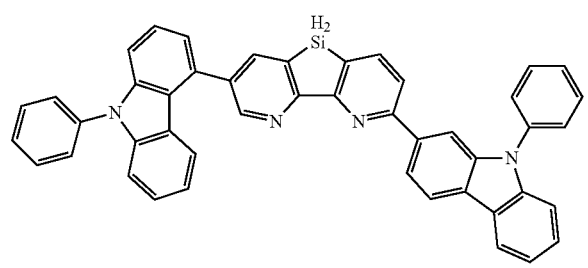
208
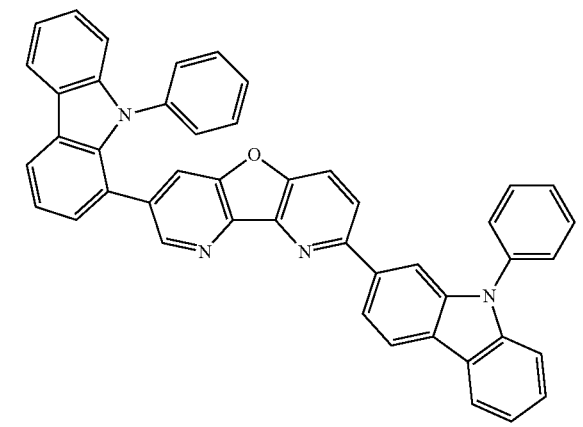
209
-continued
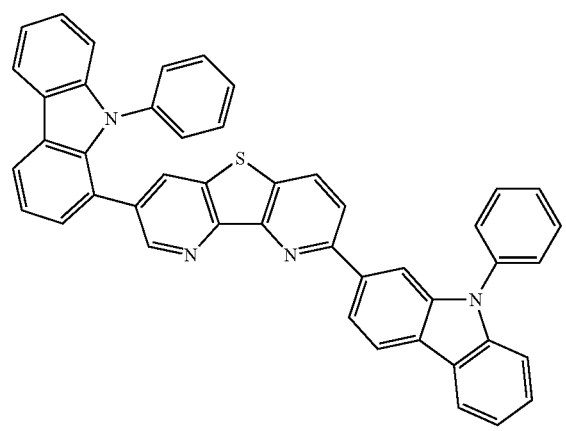
210
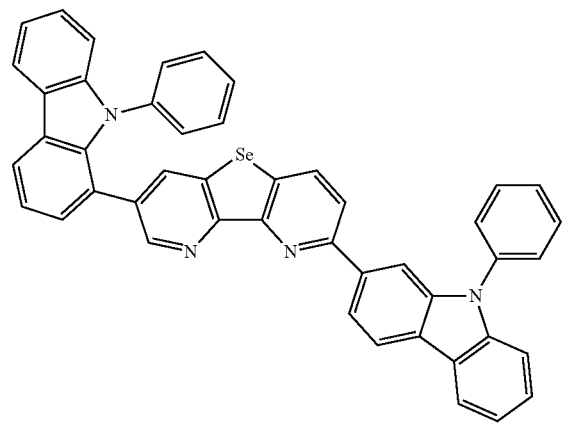
211
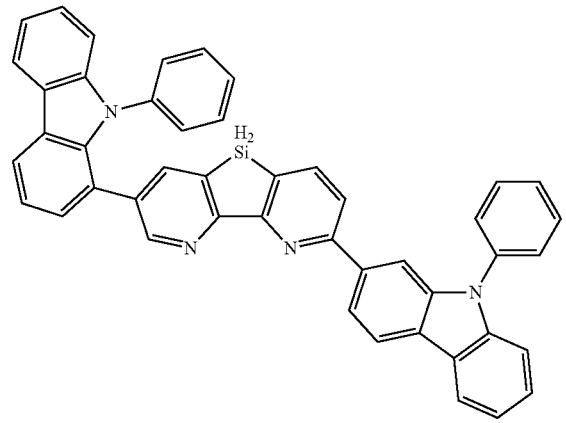
212

213
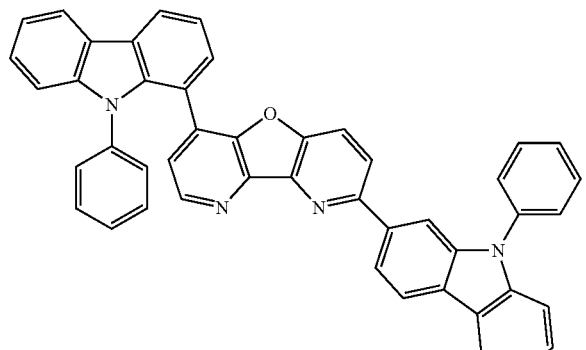
214
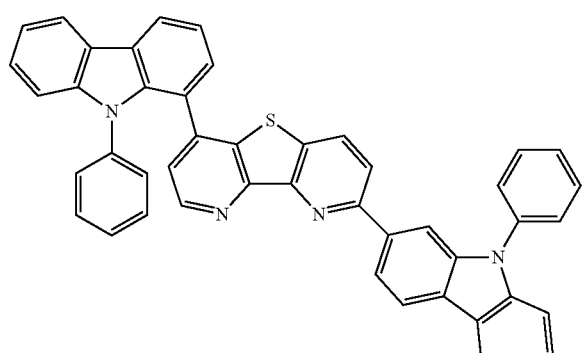
215
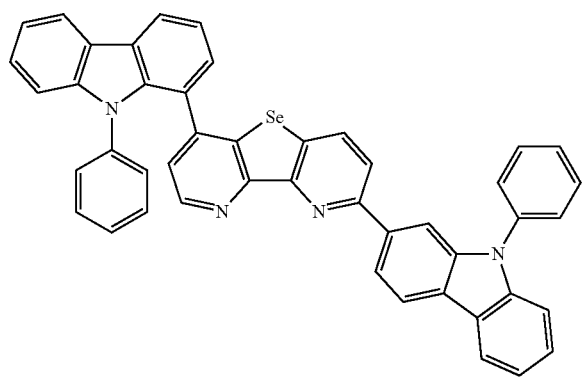
216
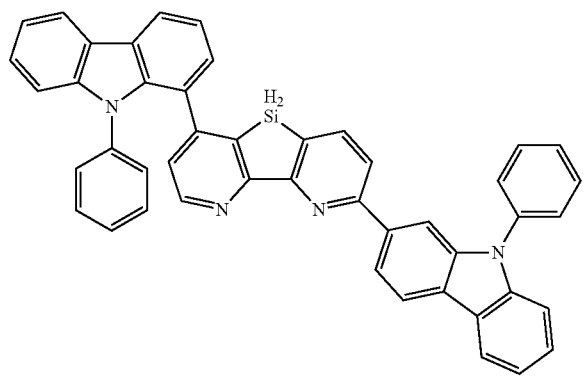
217
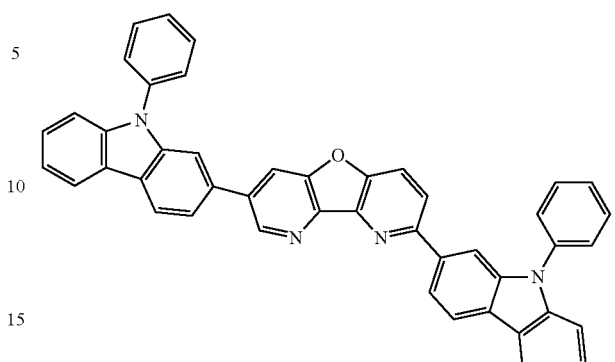
218
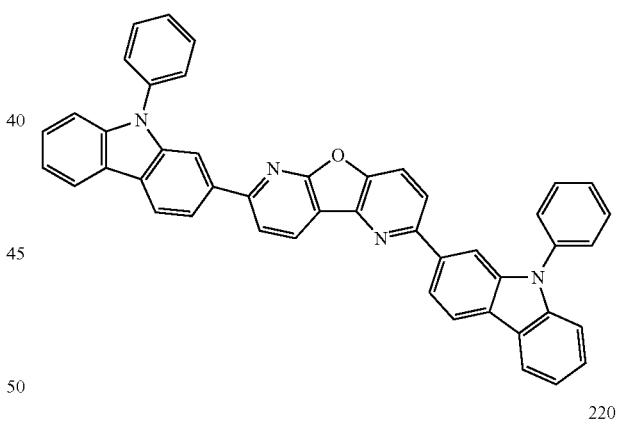
219
220
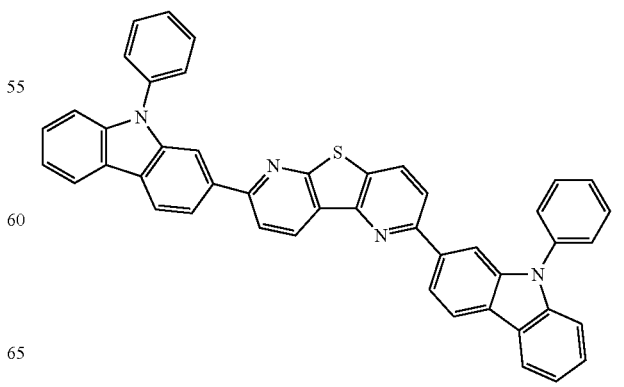

217
-continued
221
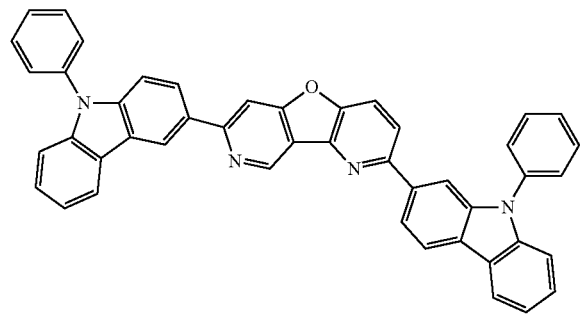
222
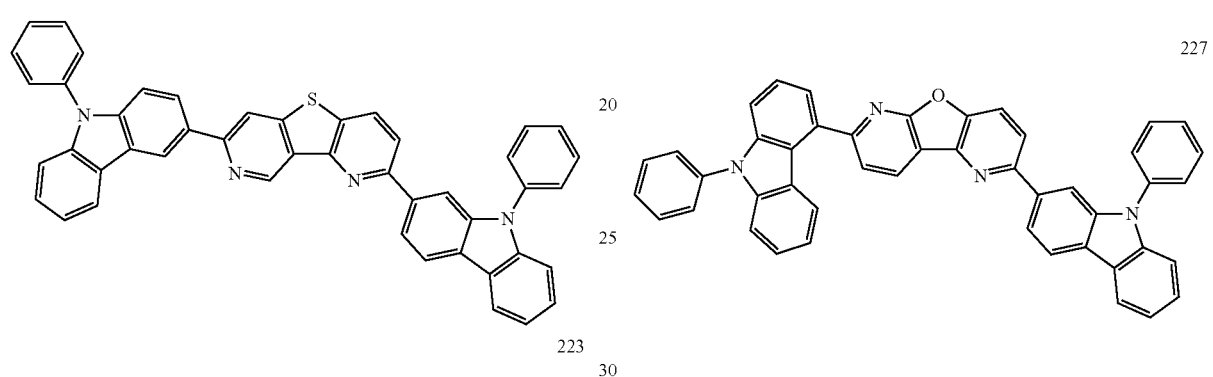
223
224
225
218
-continued
226
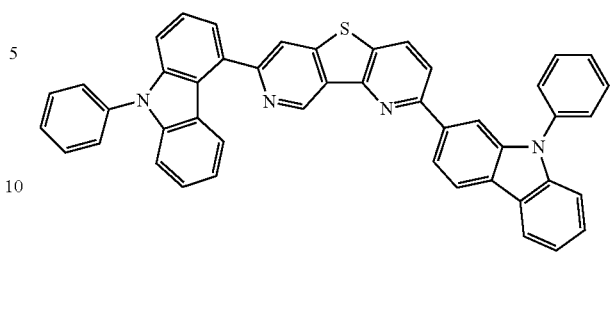
227
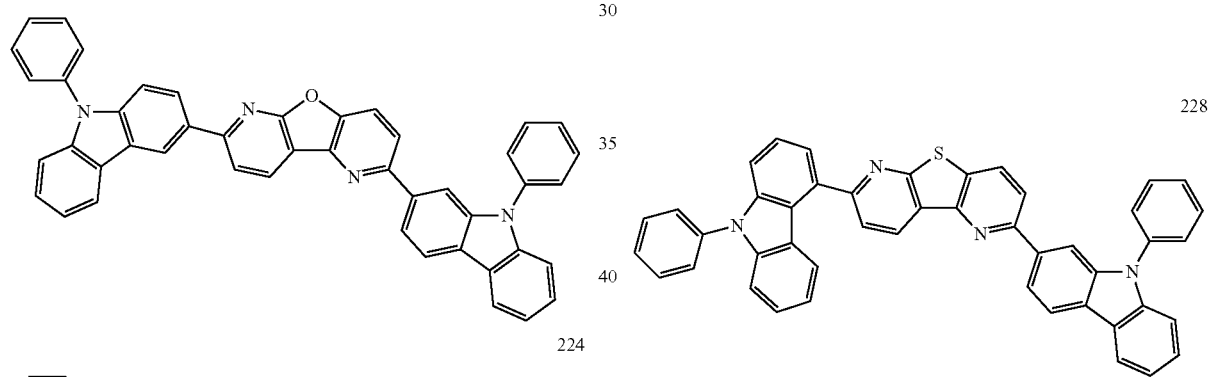
228
229
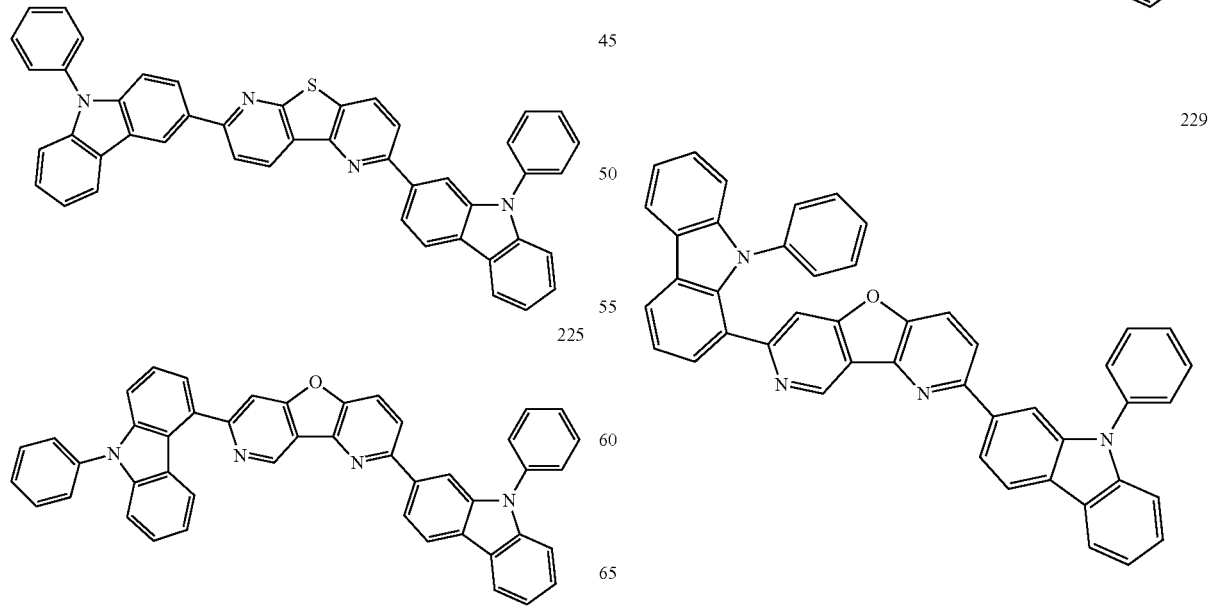

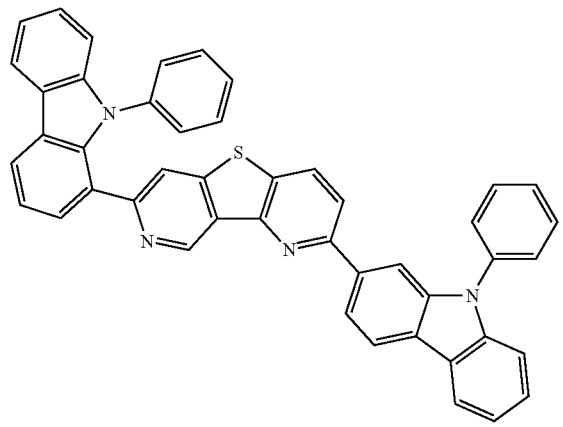
230
231
232
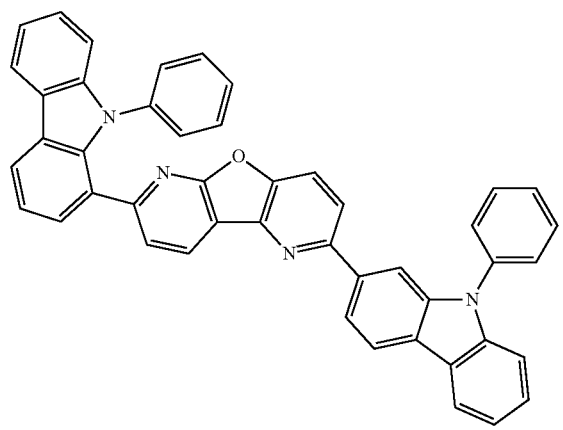
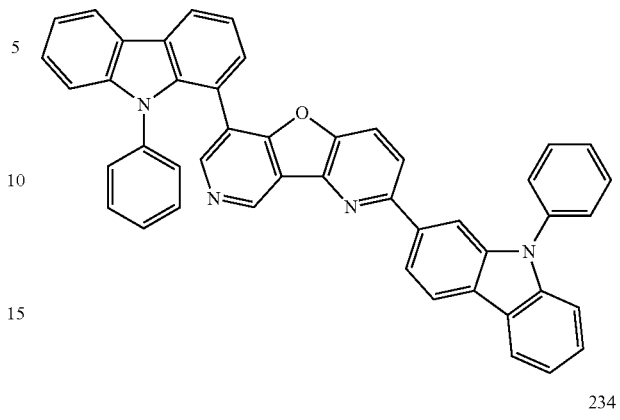
233
234
235
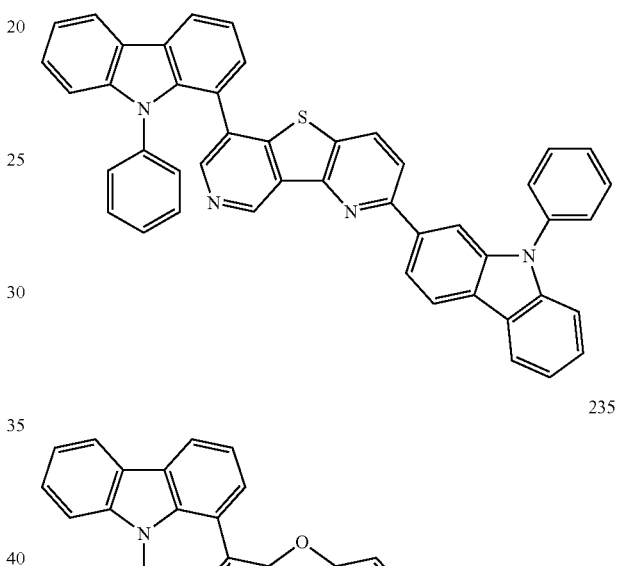
236

221
-continued
237
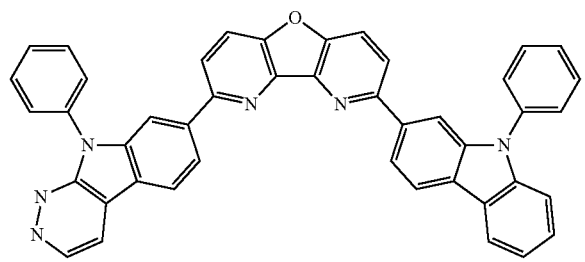
238
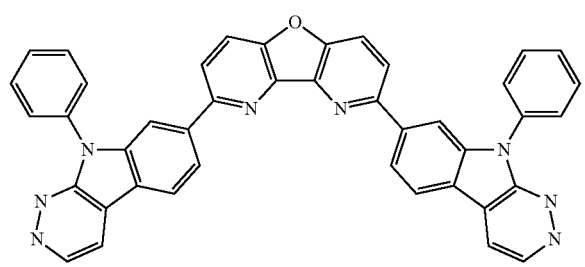
239
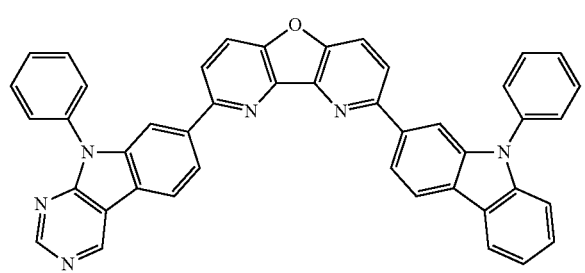
240
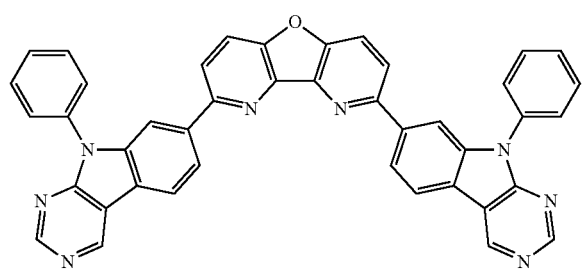
241
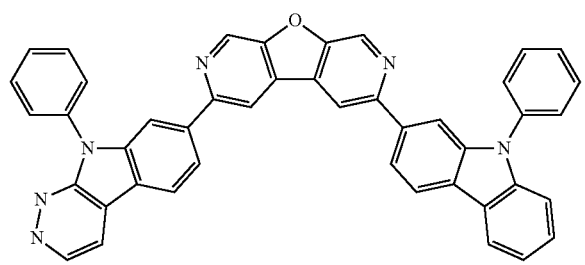
222
-continued
242
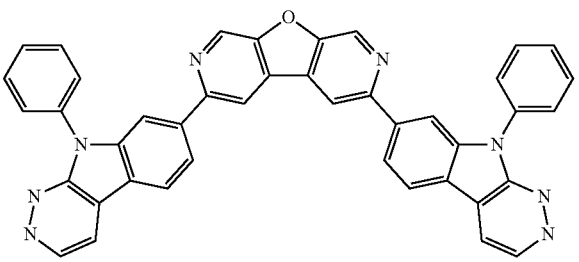
243
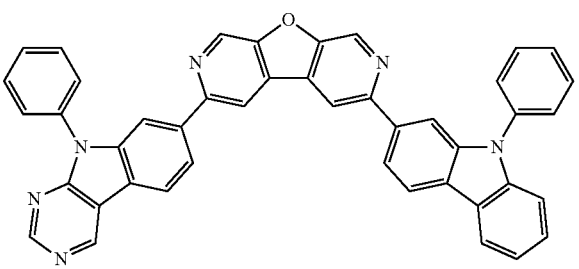
244
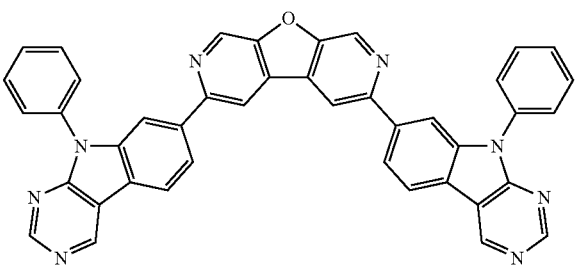
245
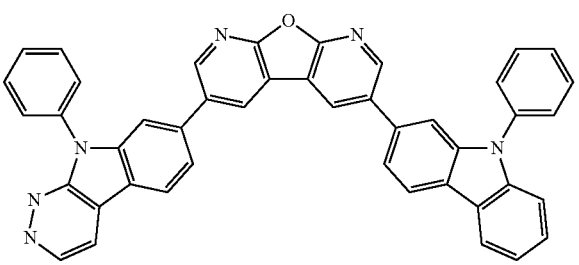
246
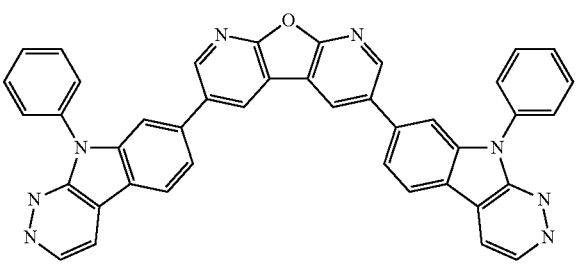

223
-continued
247
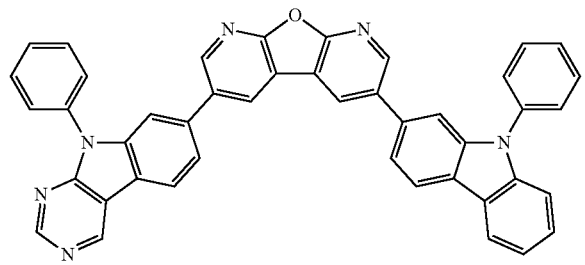
248
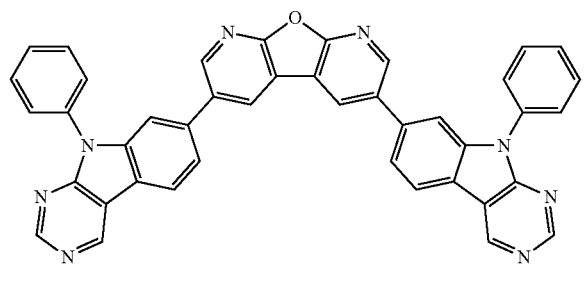
249
250
251
224
-continued
252
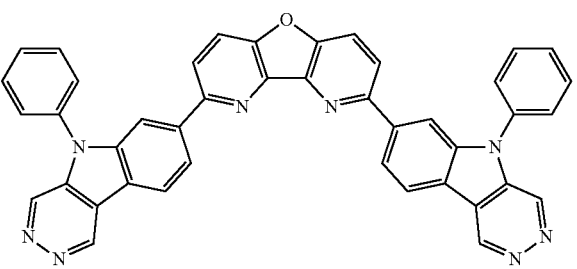
253
254
255
256

-continued
257
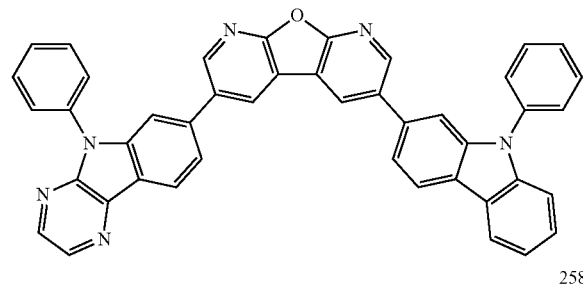
258
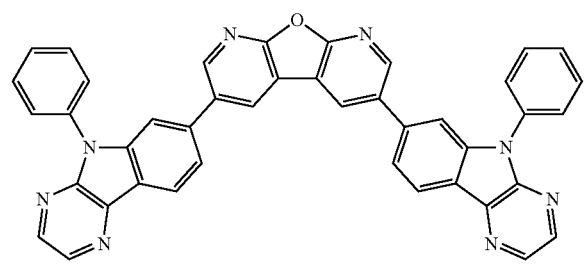
259
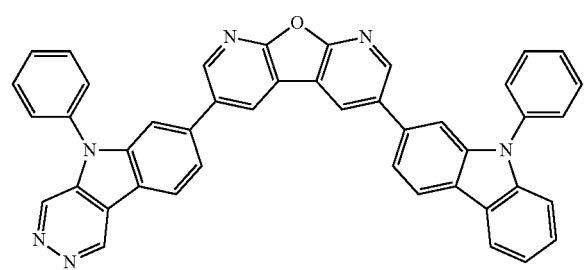
260
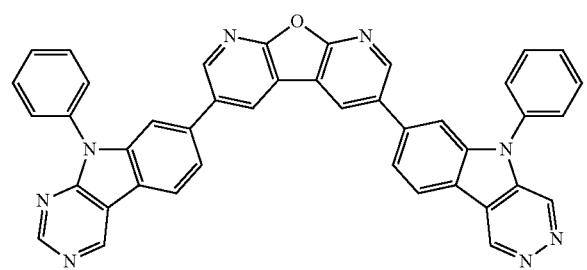
261
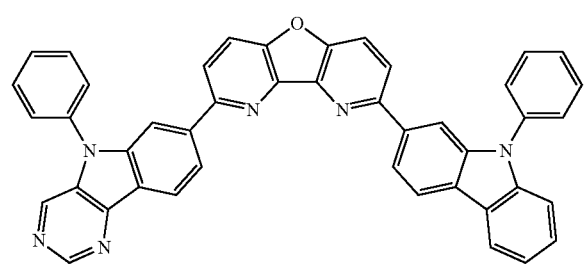
-continued
262
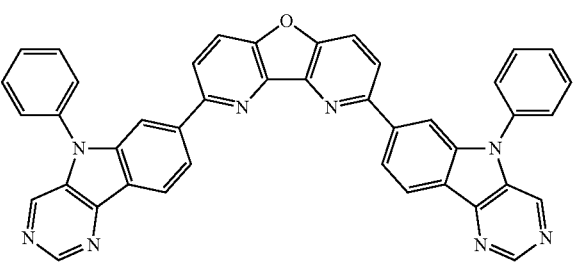
263
264
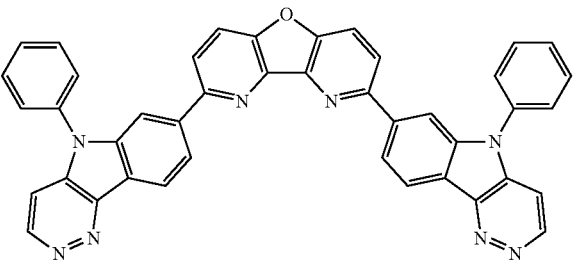
265
266
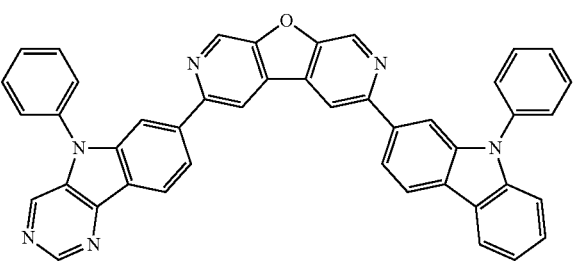

227
-continued
267
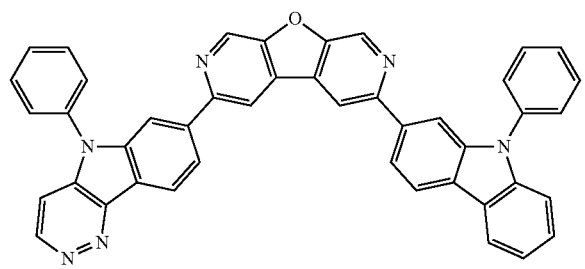
268
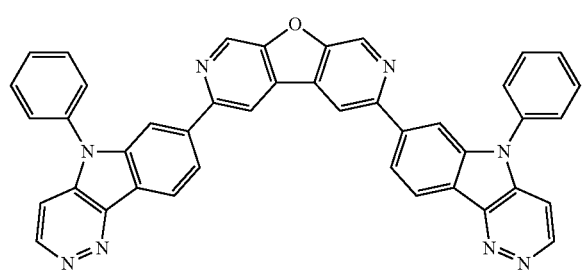
269
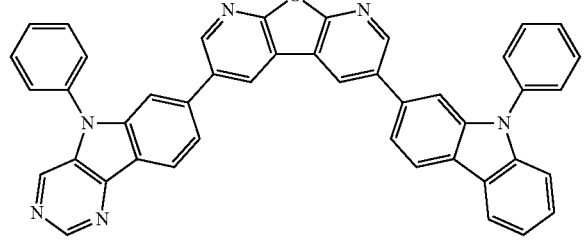
270
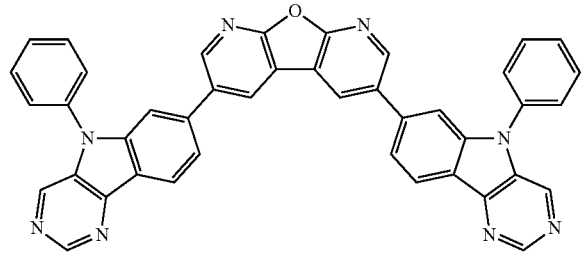
271
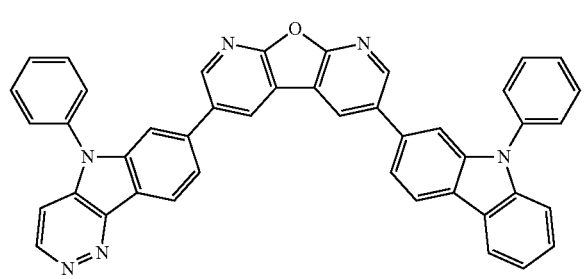
228
-continued
272
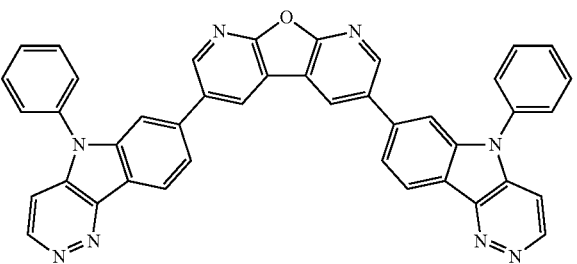
273
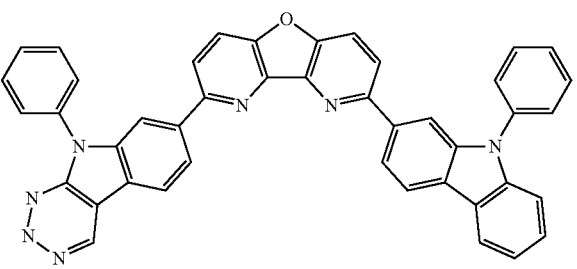
274
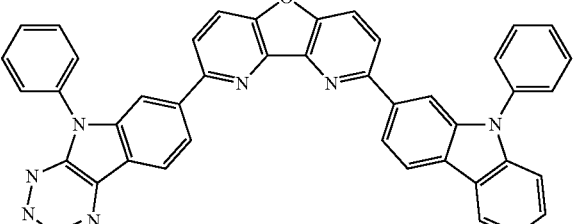
275
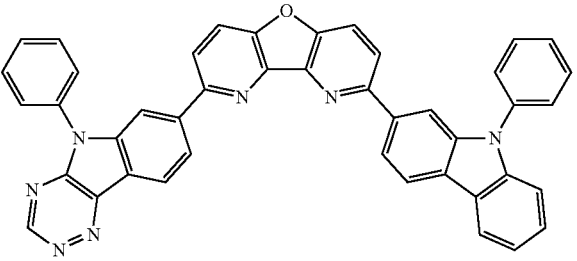
276
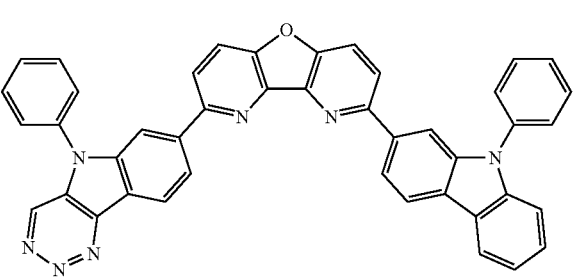

229
-continued
277
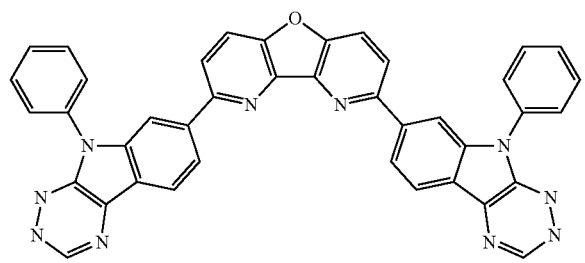
277
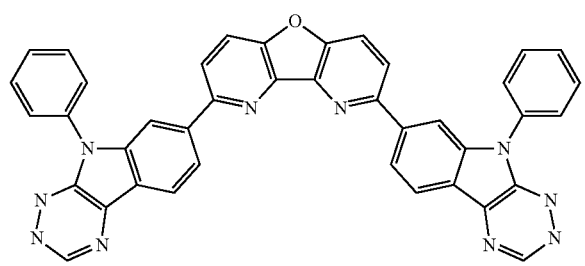
278
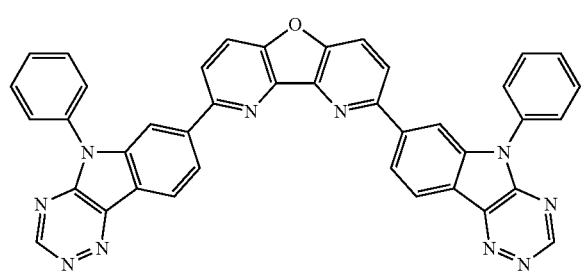
280
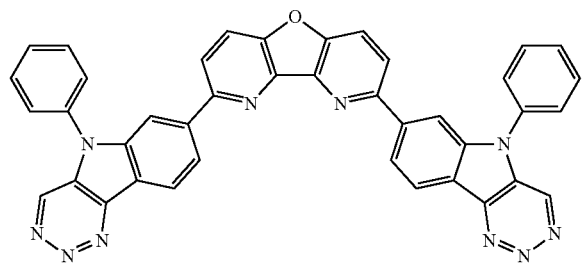
281
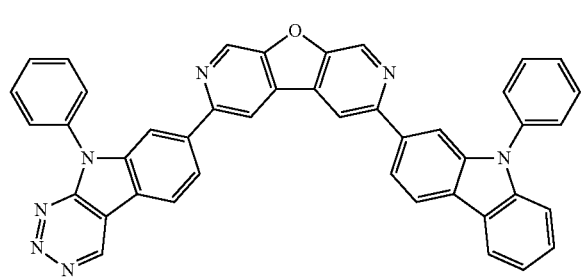
230
-continued
282
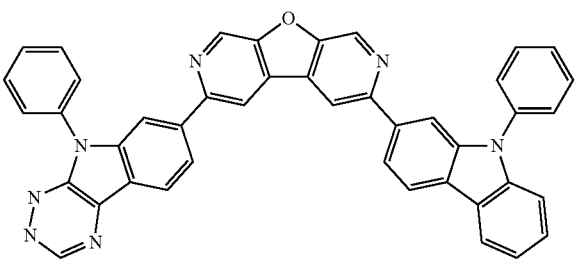
283
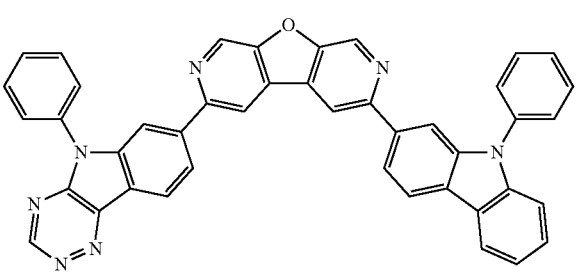
284
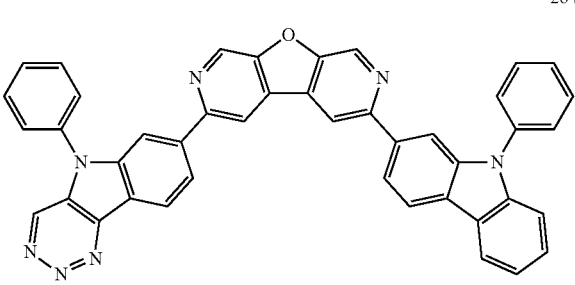
285
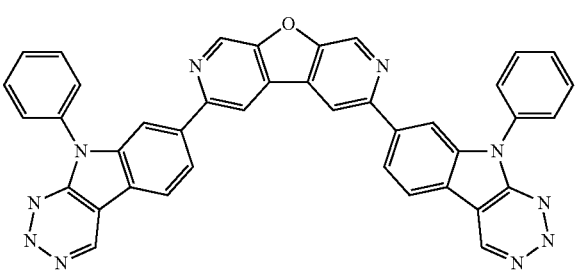
286
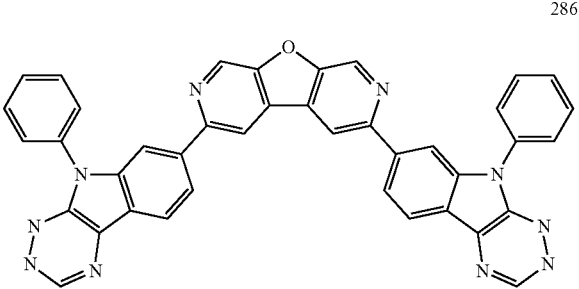

231
-continued
287
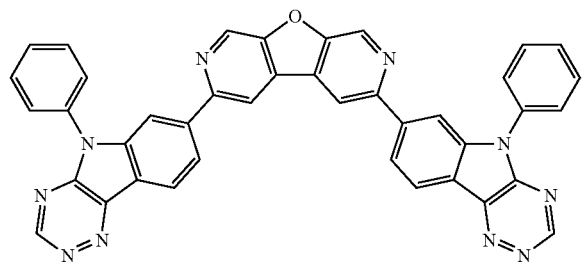
288
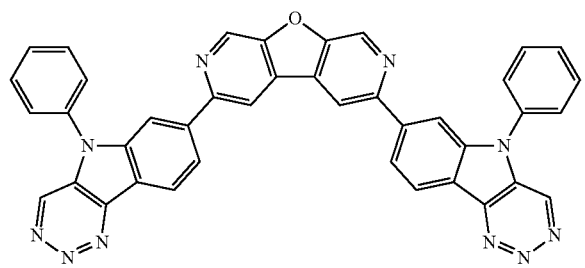
289
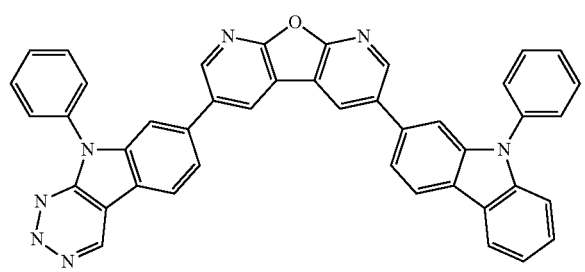
290
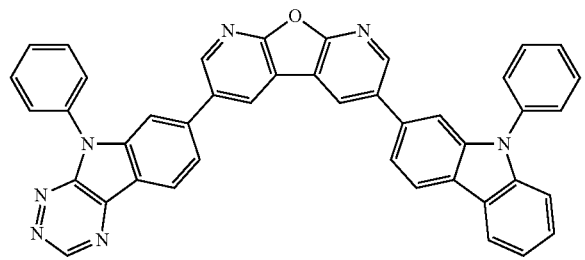
291
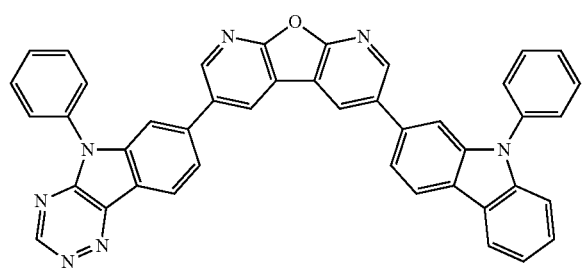
232
-continued
292
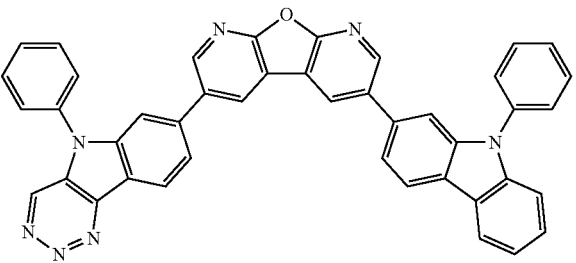
293
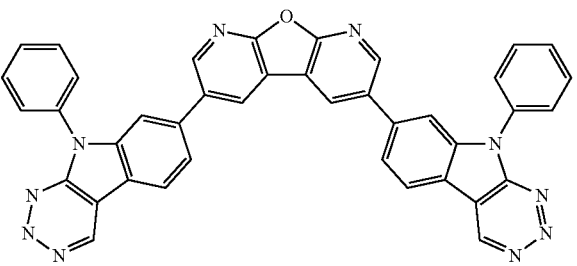
294
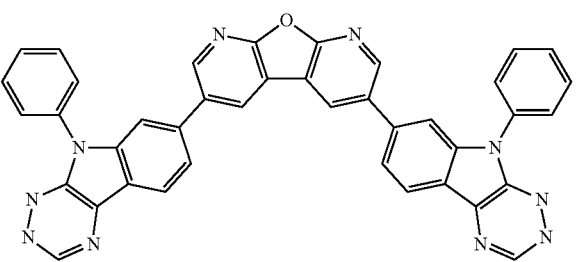
295
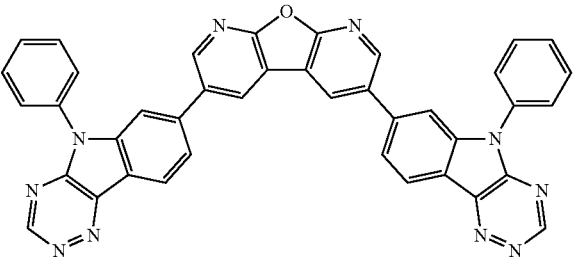
296
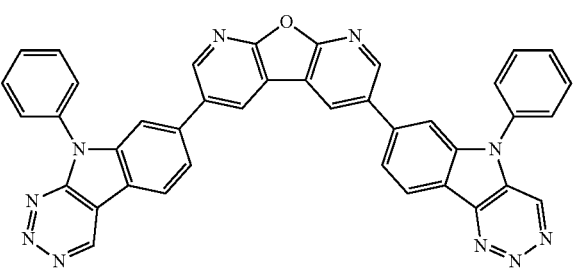

297
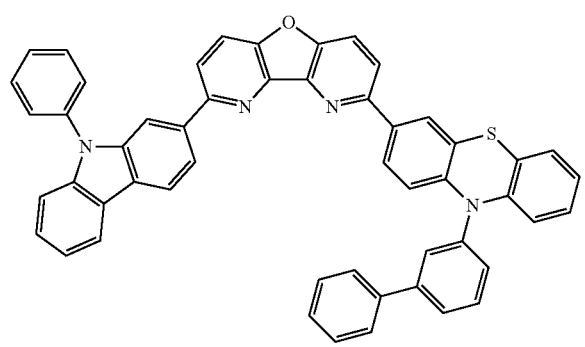
298
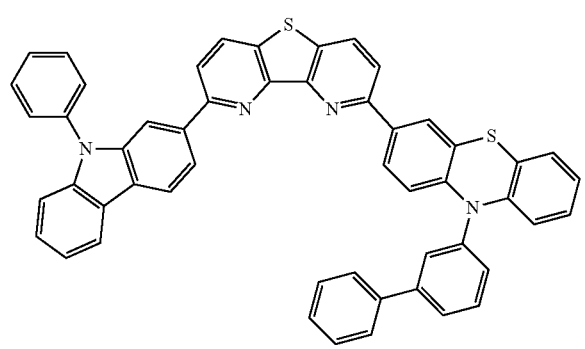
299
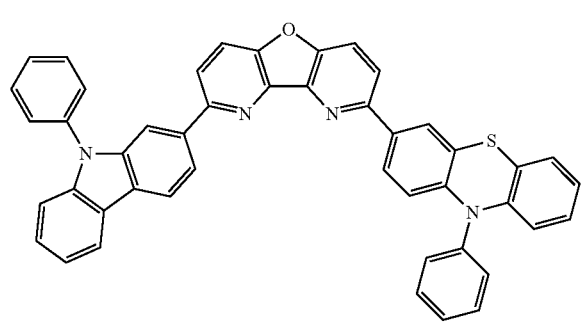
300
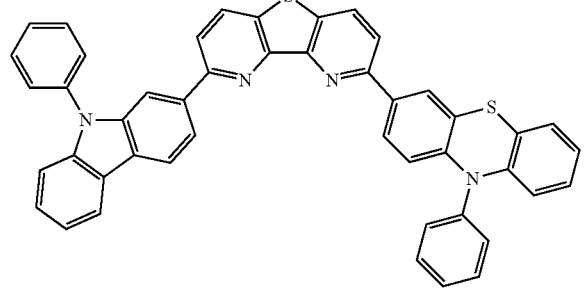
301
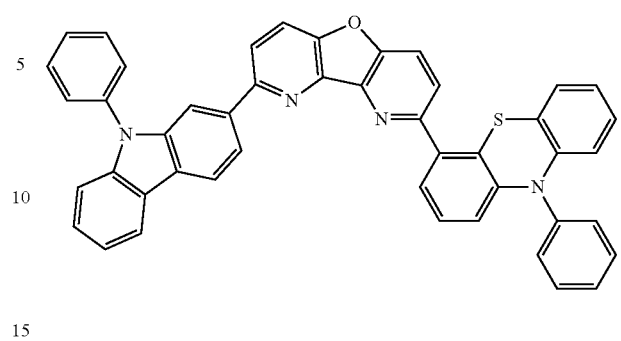
302
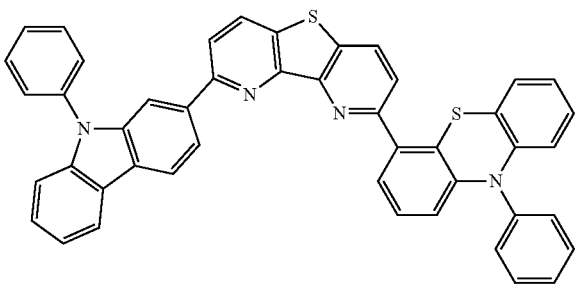
303
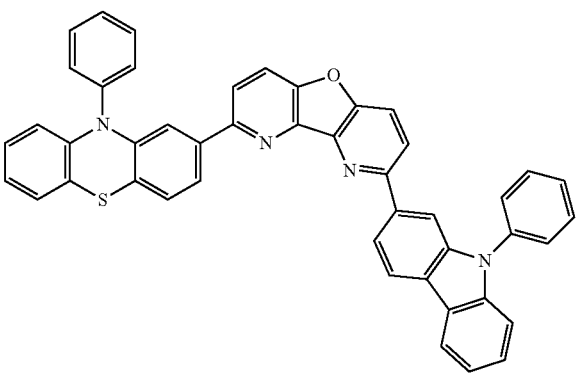
304
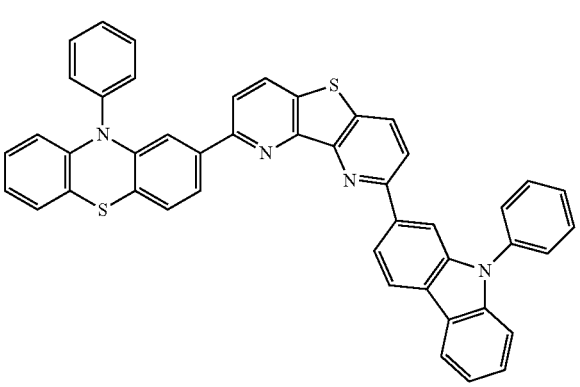

305
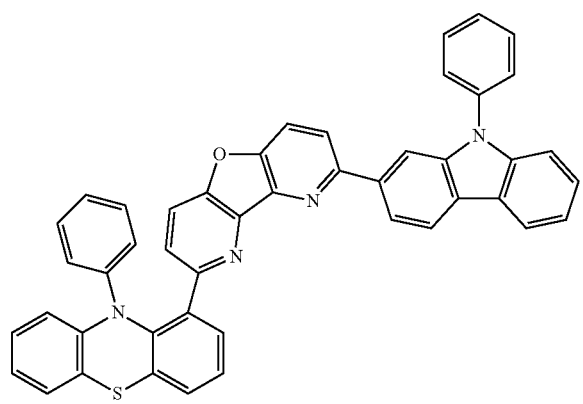
306
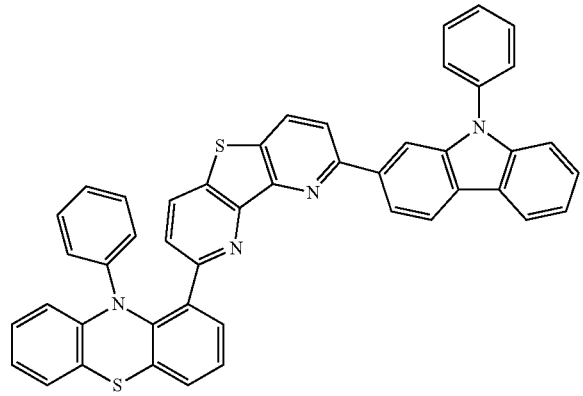
307
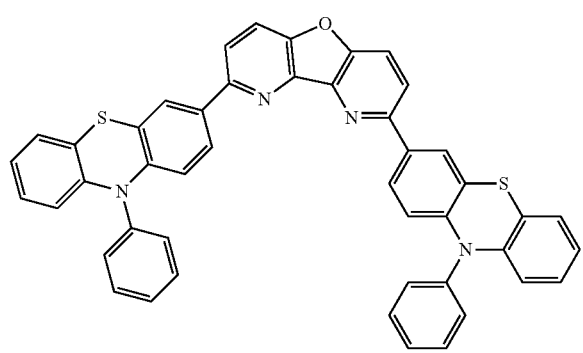
308
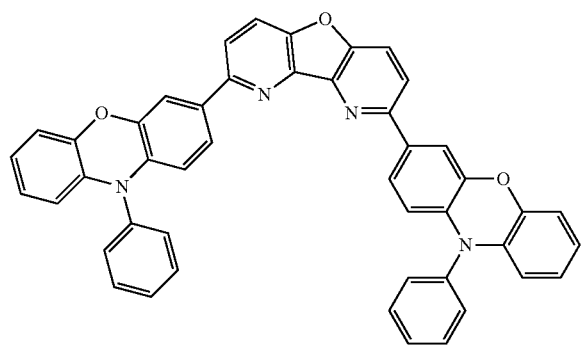
309
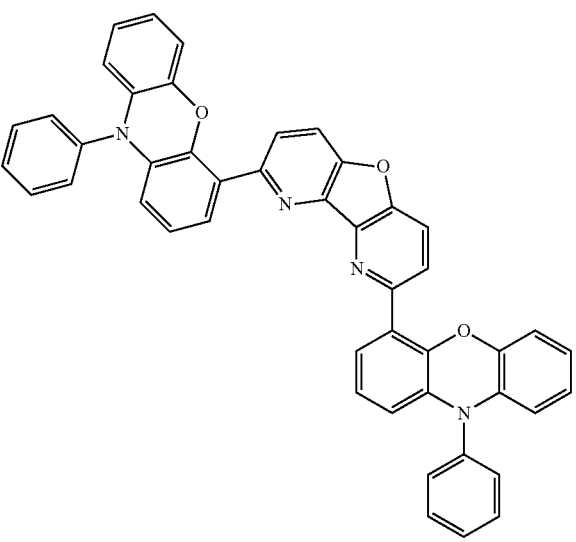
310
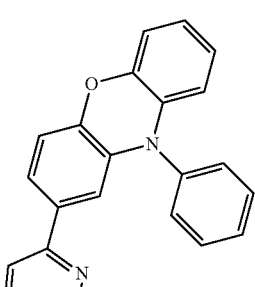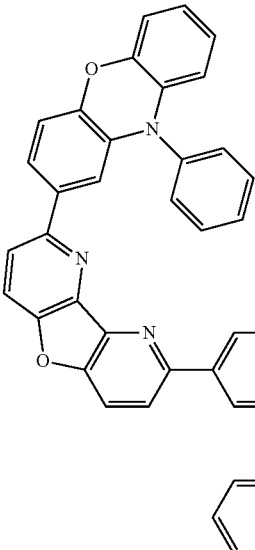

-continued

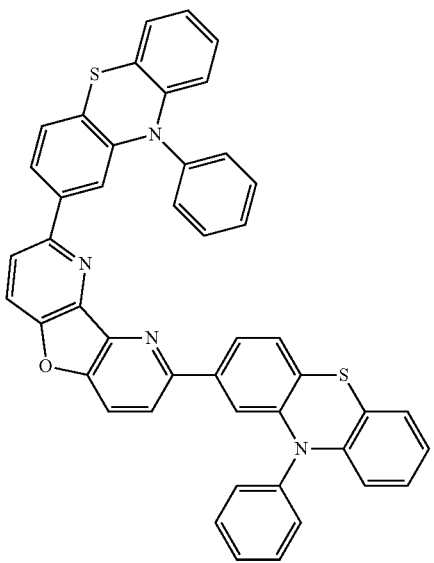

311

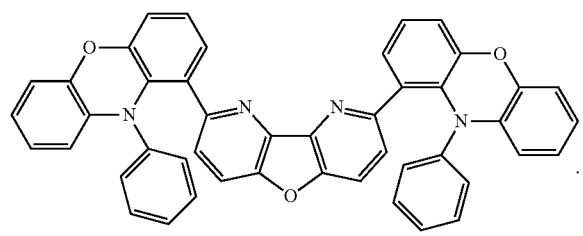

312

19. The condensed cyclic compound of claim 1, wherein a gap between singlet ($S_1$) and triplet ($T_1$) energy levels is about 0.3 electron volt or less.

20. An organic light-emitting device comprising:
a first electrode;
a second electrode; and
an organic layer disposed between the first electrode and the second electrode, wherein the organic layer comprises an emission layer and at least one cyclic compound represented by Formula 1 of claim 1.

21. The organic light-emitting device of claim 20, wherein the first electrode is an anode,
the second electrode is a cathode, and
the organic layer comprises
i) a hole transport region disposed between the first electrode and the emission layer, wherein the hole transport region comprises at least one of a hole injection layer, a hole transport layer, and an electron blocking layer; and
ii) an electron transport region disposed between the emission layer and the second electrode, wherein the electron transport layer comprises at least one of a hole blocking layer, an electron transport layer, and an electron injection layer.

22. The organic light-emitting device of claim 20, wherein the emission layer comprises the at least one condensed cyclic compound represented by Formula 1.

23. The organic light-emitting device of claim 20, wherein the emission layer comprises the at least one condensed cyclic compound of Formula 1 and an organometallic compound.

24. The organic light-emitting device of claim 20, wherein the at least one condensed cyclic compound represented by Formula 1 included in the emission layer is a thermally activated delayed fluorescence emitter.

25. The organic light-emitting device of claim 24, wherein the at least one condensed cyclic compound of Formula 1 included in the emission layer is a thermally activated delayed fluorescence emitter, and wherein the emission layer further comprises a host.

* * * * *